(12) United States Patent
Pirozzi et al.

(10) Patent No.: US 10,137,193 B2
(45) Date of Patent: Nov. 27, 2018

(54) METHODS FOR TREATING OR PREVENTING ASTHMA BY ADMINISTERING AN IL-4R ANTAGONIST

(71) Applicants: Sanofi Biotechnology, Paris OT (FR); Regeneron Pharmaceuticals, Inc., Tarrrytown, NY (US)

(72) Inventors: Gianluca Pirozzi, Berkeley Heights, NJ (US); Franck Skobieranda, Flourtown, PA (US); Yongtao Li, Springfield, NJ (US); Neil Graham, Croton-on-Hudson, NY (US); Steven P. Weinstein, Hartsdale, NY (US)

(73) Assignees: Sanofi Biotechnology (FR); Regeneron Pharmaceuticals, Inc., Tarrytown, NY (US)

( * ) Notice: Subject to any disclaimer, the term of this patent is extended or adjusted under 35 U.S.C. 154(b) by 350 days.

(21) Appl. No.: 14/627,728

(22) Filed: Feb. 20, 2015

(65) Prior Publication Data
US 2015/0246119 A1  Sep. 3, 2015

Related U.S. Application Data

(60) Provisional application No. 61/943,019, filed on Feb. 21, 2014, provisional application No. 62/077,669, filed on Nov. 10, 2014.

(30) Foreign Application Priority Data

Sep. 15, 2014 (EP) .................................. 14306413

(51) Int. Cl.
| | | |
|---|---|---|
| A61K 39/395 | (2006.01) | |
| A61K 31/137 | (2006.01) | |
| A61K 31/00 | (2006.01) | |
| A61K 31/167 | (2006.01) | |
| A61K 31/56 | (2006.01) | |
| A61K 31/569 | (2006.01) | |
| A61K 31/58 | (2006.01) | |
| C07K 16/28 | (2006.01) | |
| A61K 39/00 | (2006.01) | |

(52) U.S. Cl.
CPC .......... *A61K 39/3955* (2013.01); *A61K 31/00* (2013.01); *A61K 31/137* (2013.01); *A61K 31/167* (2013.01); *A61K 31/56* (2013.01); *A61K 31/569* (2013.01); *A61K 31/58* (2013.01); *C07K 16/2866* (2013.01); *A61K 2039/54* (2013.01); *A61K 2039/545* (2013.01); *C07K 2317/21* (2013.01)

(58) Field of Classification Search
None
See application file for complete search history.

(56) References Cited

U.S. PATENT DOCUMENTS

| | | |
|---|---|---|
| 5,599,905 A | 2/1997 | Mosley et al. |
| 5,714,146 A | 2/1998 | Lewis et al. |
| 5,717,072 A | 2/1998 | Mosley et al. |
| 5,856,296 A | 1/1999 | Mosley et al. |
| 5,985,280 A | 11/1999 | Ritter et al. |
| 6,156,877 A | 12/2000 | Ritter et al. |
| 6,391,581 B1 | 5/2002 | Mosley et al. |
| 6,596,541 B2 | 7/2003 | Murphy et al. |
| 6,716,587 B2 | 4/2004 | Mosley et al. |
| 6,927,044 B2 | 8/2005 | Stahl et al. |
| 7,186,809 B2 | 3/2007 | Pluenneke et al. |
| 7,317,090 B2 | 1/2008 | Mosley et al. |
| 7,582,298 B2 | 9/2009 | Stevens et al. |
| 7,605,237 B2 | 10/2009 | Gustafson et al. |
| 7,608,693 B2 | 10/2009 | Stevens et al. |
| 7,794,717 B2 | 9/2010 | Stevens et al. |
| 8,075,887 B2 | 12/2011 | Martin et al. |
| 8,092,802 B2 | 1/2012 | Stevens et al. |
| 8,178,098 B2 | 5/2012 | Lahn et al. |
| 8,337,839 B2 | 12/2012 | Rawlings et al. |
| 8,338,135 B2 | 12/2012 | Stevens et al. |
| 8,735,095 B2 | 5/2014 | Martin et al. |
| 8,945,559 B2 | 2/2015 | Dix et al. |
| 9,238,692 B2 | 1/2016 | Dix et al. |
| 9,574,004 B2 * | 2/2017 | Ardeleanu ......... A61K 39/3955 |
| 2003/0124121 A1 | 7/2003 | Pluenneke |
| 2005/0118176 A1 | 6/2005 | Mosley et al. |
| 2005/0255532 A1 | 11/2005 | Ruben et al. |
| 2005/0282181 A1 | 12/2005 | Yan et al. |

(Continued)

FOREIGN PATENT DOCUMENTS

| | | |
|---|---|---|
| EP | 0 367 566 A1 | 5/1990 |
| EP | 0 604 693 A1 | 7/1994 |

(Continued)

OTHER PUBLICATIONS

Brummell et al, Biochemistry; 1993; vol. 32, pp. 1180-1187.*

(Continued)

*Primary Examiner* — Bridget E Bunner
*Assistant Examiner* — Fozia Hamud
(74) *Attorney, Agent, or Firm* — Lathrop Gage LLP; James H. Velema, Esq.; Judith Stone-Hulslander

(57) ABSTRACT

The invention provides methods for treating or preventing asthma and associated conditions in a patient. The methods featured in the invention comprise administering to a subject in need thereof a therapeutic composition comprising an interleukin-4 receptor (IL-4R) antagonist, such as an anti-IL-4R antibody.

30 Claims, 71 Drawing Sheets
(63 of 71 Drawing Sheet(s) Filed in Color)
Specification includes a Sequence Listing.

(56) References Cited

U.S. PATENT DOCUMENTS

| | | |
|---|---|---|
| 2007/0041976 A1 | 2/2007 | Pluenneke et al. |
| 2007/0274996 A1 | 11/2007 | Carter et al. |
| 2008/0160035 A1 | 7/2008 | Stevens et al. |
| 2009/0074793 A1 | 3/2009 | Martin et al. |
| 2009/0098142 A1 | 4/2009 | Kassalan et al. |
| 2010/0021476 A1 | 1/2010 | Stevens et al. |
| 2010/0047254 A1 | 2/2010 | Martin et al. |
| 2010/0291107 A1 | 11/2010 | Stevens et al. |
| 2012/0004205 A1 | 1/2012 | Rothenberg |
| 2012/0052072 A1 | 3/2012 | Martin et al. |
| 2012/0088814 A1 | 4/2012 | Gregory |
| 2012/0097565 A1 | 4/2012 | Dix et al. |
| 2012/0135010 A1 | 5/2012 | Stevens et al. |
| 2013/0052190 A1 | 2/2013 | Collins et al. |
| 2013/0078675 A1 | 3/2013 | Martin et al. |
| 2014/0056920 A1 | 2/2014 | Ardeleanu et al. |
| 2014/0072583 A1 | 3/2014 | Ardeleanu et al. |
| 2014/0271681 A1 | 9/2014 | Martin et al. |
| 2015/0017182 A1 | 1/2015 | Mannent et al. |
| 2016/0102147 A1 | 4/2016 | Dix et al. |
| 2016/0185866 A1 | 6/2016 | Mannent et al. |

FOREIGN PATENT DOCUMENTS

| | | |
|---|---|---|
| EP | 2 022 507 A1 | 2/2009 |
| WO | 2001092340 A2 | 12/2001 |
| WO | 2005047331 A2 | 5/2005 |
| WO | 2005085284 A1 | 9/2005 |
| WO | 2006072564 A1 | 7/2006 |
| WO | 2008054606 A2 | 5/2008 |
| WO | 2010053751 A1 | 5/2010 |
| WO | 2010120524 A2 | 10/2010 |
| WO | 2012047954 A1 | 4/2012 |
| WO | 2014/031610 A1 | 2/2014 |
| WO | 2014039461 A1 | 3/2014 |
| WO | 2014/205365 A1 | 12/2014 |
| WO | 2015/127229 A1 | 8/2015 |
| WO | 2016/077675 A1 | 5/2016 |

OTHER PUBLICATIONS

Kobayashi et al. Protein Engineering; 1999; vol. 12, pp. 879-844.*

Brorson et al. J. Immunol; 1999; vol. 163, pp. 6694-6701.*

Coleman Research in Immunol; 1994; vol. 145; pp. 33-36.*

Giembycz et al, British Journal of Pharmacology, 2008; vol. 153, pp. 1090-1104.*

Frois et al Clinical Therapeutics, 2009, vol. 31, No. 12, pp. 2779-2802.*

National Heart, Lung, and Blood Institute (NHLBI) guidelines; 2007; 2 pages.*

Al-Lazikani et al. (1997) "Standard conformations for the canonical structures of immunoglobulins," J. Mol. Biol. 273:927-948.

Angal et al. (1993) "A single amino acid substitution abolishes the heterogeneity of chimeric mouse/human (IgG4) antibody," Molecular Immunology. 30:105.

Arron et al. (May 18, 2009) "Peripheral Biomarkers of an IL-13 Induced Bronchial Epithelial Gene Signature in Asthma," Am. J. Respir. Crit. Care Med. Online Abstracts Issue. B21 Airway Inflammation: New Information about Mediators and Biomarkers. Poster Discussion. 1 page.

Bachert (2005) et al. "Pharmacological management of nasal polyposis," Drugs. 65(11):1537-1552.

Bateman et al. (2004) "Can guideline-defined asthma control be achieved?" Am. J. Respir. Crit. Care Med. 170:836-844.

Burmeister-Getz et al. (2009) "Human pharmacokinetics/pharmacodynamics of an interleukin-4 and interleukin-13 dual antagonist in asthma," J. Clin. Pharmacol. 49:1025-1036.

Corren et al. (Jan. 7, 2010) "A Randomized, Controlled, Phase 2 Study of AMG 317, an IL-4R Antagonist, in Patients with Asthma," Am. J. Res. Crit. Care Med. 181(8):788-796.

Davies et al. (1996) "Affinity improvement of single antibody VH domains: residues in all three hypervariable regions affect binding," Immunotechnol. 2:169-179.

Gavett et al. (1997) "Interleukin-4 receptor blockade prevents airway responses induced by antigen challenge in mice," Am. J. Physiol. 272:L253-261.

Gevaert et al. (2006) "Nasal IL-5 levels determine the response to anti-IL-5 treatment in patients with nasal polyps," Journal of allergy and clinical immunology. 118(5):1133-1141.

Groves et al. (2007) "Inhibition of IL-4 and IL-13 with an IL-4 mutein (Aeroderm) protects against flares in atopic eczema," in AD Poster at St. John's Institute of Dermatology. J. Investig. Dermatol. 127:S54.

Grunewald, et al., "An antagonistic IL-4 Mutant Prevents Type I Allergy in the Mouse: Inhibition of the IL-4/1L-13 Receptor System completely Abrogates Humoral Immune Response to Allergen and Development of Allergic Symptoms in Vivo." The Journal of Immunology. 1998, 160(8):4004-4009.

Holt et al. (2003) "Domain antibodies: Proteins for Therapy," Trends Biotechnol. 21:484-490.

Hopkins et al. (2007) "The Lund-Mackay staging system for chronic rhinosinusitis: how is it used and what does it predict?" Otolaryngology—Head and Neck Surgery. 137(4):555-561.

Hopkins et al. (2009) "Psychometric validity of the 22-item Sinonasal Outcome Test," Clinical Otolaryngology. 34(5):447-454.

Jia et al. (Aug. 1, 2012) "Periostin is a systemic biomarker of eosinophilic airway inflammation in asthmatic patients," J. Allergy Clin. Immunol. 130:647-654.

Junittila et al. (2008) "Tuning sensitivity to IL-4 and IL-13: differential expression of IL-4Ra, IL-13Ra1, and gamma c regulates cytokine sensitivity," J. Exp. Med. 205(11):2595-2608.

Kakkar et al. (Oct. 2011) "Population PK and IgE pharmacodynamic analysis of a fully human monoclonal antibody against IL4 receptor," Pharmaceutical Research. 28(10):2530-2542.

Kopf et al. (1993) "Disruption of the murine IL-4 gene blocks Th2 cytokine responses," Letters to Nature. 362:245-248.

Kostic et al. (2010) "A Fully Human IL4Ra Antibody for Inhibition of IL-4/IL-13-driven TH2 Responses in Allergic Disease," Immunology. 135:S105-S106.

Langer (1990) "New methods of drug delivery," Science. 249:1527-1533.

Lezcano-Meza et al. (2003) "Interleukin (IL)-4 and to a lesser extent either IL-13 or interferon-gamma regulate the production of eotaxin-2/CCL24 in nasal polyps," Allergy 58(10): 1011-1017.

Lilly et al. (1999) "Elevated plasma eotaxin levels in patients with acute asthma," J. Allergy Clin. Immunol. 104:786-790.

Ludmila Kelly et al. (Feb. 3, 2014) "Poster 1013: IL-4R alpha antibody inhibits IgE production and airway remodeling in the mouse of house dust mite-induced eosinophilic asthma," World Allergy Organization Journal. 7(1): P8.

Maliszewski et al. (1994) "In Vivo Biological Effects of Recombinant Soluble Interleukin-4 Receptor," Proc. Soc. Exp. Biol. Med. 206:233-237.

Martin et al. (1989) "Modeling antibody hypervariable loops: a combined algorithm," Proc. Natl. Acad. Sci. USA. 86:9268-9272.

Molfino et al. (2012) "Molecular and clinical rationale for therapeutic targeting of interleukin-5 and its receptor," Clin. Exp. Allergy. 42(5):712-737.

Mordenti et al. (1991) "Interspecies scaling of clearance and volume of distribution data for five therapeutic proteins," Pharma. Res. 8:1351.

Morioka et al. (2009) "IL-4/IL-13 antagonist DNA vaccination successfully suppresses Th2 type chronic dermatitis," British Journal of Dermatology. 160(6):1172-1179.

Niranjan et al. (Jul. 2013) "Pathogenesis of allergen-induced eosinophilic esophagitis is independent of interleukin (IL)-13," Immunology and Cell Biology. 91(6):408-415.

Oh et al. (2010) "Investigational therapeutics targeting the IL-4/IL-13/STAT-6 pathway for the treatment of asthma," Eur. Respir Rev. 19:46-54.

Otulana et al. (May 18, 2011) "A Phase 2b Study of Inhaled Pitrakinra, An IL-4R/IL-13 Antagonist, Successfully Identified

(56) References Cited

OTHER PUBLICATIONS

Responder Subpopulations of Patients with Uncontrolled Asthma," Am. J. Respir. Crit. Care Med. 183: A6179.
Sanofi With Regeneron Pharmaceuticals (2013) "Sanofi and Regeneron Report Positive Proof-of-Concept Data for Dupilumab, and IL-4R alpha Antibody, in Atopic Dermatitis." 71st Annual Meeting of the American Academy of Dermatology. Retrieved from the Internet URL:http://files.shareholder.com/downloads/REGN/2689212012x0x640531/794a7e54-6904-416-ba38-a4ccc1726852/REGN_News_2013_3_2_Gneral_Releases.pdf.
Sanofi With Regeneron Pharmaceuticals (Jun. 2014) "An Evaluation of Dupilumab in Patients with Nasal Polyposis and Chronic Symptoms of Sinusitis," Trial in Progress. ClinicalTrials.gov Identifier: NCT01920893. Retrieved from the Internet URL:http://clinicaltrials.gov/show/NCT01920893. [Last Accessed on Sep. 29, 2014].
Sato et al. (1993) "Recombinant Soluble Murine IL-4 Receptor Can Inhibit or Enhance IgE Responses in Vivo," J. Immunol. 150:2717-2723.
Scavuzzo et al. (2005) "Inflammatory mediators and eosinophilia in atopic and non-atopic patients with nasal polyposis," Biomedicine & Pharmacotherapy. 59(6):323-329.
Schmidt-Weber (Mar. 13, 2012) "Anti-IL-4 as a New Strategy in Allergy," Chem. Immunol. Allergy. 96:120-125.
Sekiya et al. (2002) "Increased levels of a TH2-type CC chemokine thymus and activation-regulated chemokine (TARC) in serum and induced sputumm of asthmatics," Allergy. 57:173-177.
Slager et al. (Apr. 26, 2012) "IL-4 Receptor Polymorphisms Predict Reduction in Asthma Exacerbations During Response to an Anti IL-4 Receptor Antagonist," J. Allergy Clin. Immunol. 13(2):516-522.
Taylor et al. (1992) "A transgenic mouse that expresses a diversity of human sequence heavy and light chain immunoglobulins," Nucl. Acids Res. 20:6287-6295.
Tazawa et al. (2004) "Relative importance of IL-4 and IL-13 in lesional skin of atopic dermatitis," Arch. Dermatol. Res. 295:459-464.
Tomkinson et al. (2001) "A Murine IL-4 Receptor Antagonist That Inhibits IL-4- and IL-13-Induced Responses Prevents Antigen-Induced Airway Eosinophilia and Airway Hyperresponsiveness," J. Immunol. 166:5792-5800.
Virchow et al. (1994) "Cellular and immunological markers of allergic and intrinsic bronchial asthma," Lung. 172:313-334.
Walker et al. (1993) "Atopic dermatitis: correlation of peripheral blood T cell activation, eosinophilia and serum factors with clinical severity," Clinical and Experimental Allergy. 23:145-153.
Wenzel et al. (2007) "Effect of an interleukin-4 variant on late phase asthmatic response to allergen challenge in asthmatic patients: results of two phase 2a studies," Lancet. 370:1422-1431.
Wenzel et al. (2010) "ERS—Programme," European Respiratory Society, Annual Congress 2010. pp. 3980.
Wenzel et al. (May 21, 2013) "Dupilumab in Persistent Asthma with Elevated Eosiniphil Levels," New England Journal of Medicine. 368(26):2455-2466.
Wils-Karp et al. (2008) "Untangling the Complex Web of IL-4 and IL-13 Mediated Signaling Pathways," Science Signaling. 1(51):1-5.
Woodruff et al. (2009) "T-helper Type 2-driven Inflammation Defines Major Subphenotypes of Asthma," Am. J. Respir. Crit. Care Med. 180:388-395.
Wu et al. (1987) "Receptor-mediated in vitro gene transformation by a soluble DNA carrier system," J. Biol. Chem. 262:4429-4432.
Yamanaka et al. (May 12, 2011) "The Role of Cytokines/Chemokines in the Pathogenesis of Atopic Dermatitis," Curr. Probl. Dermatol. 41:80-92.
Zuo et al. (2010) "IL-13 Induced Esophageal Remodeling and Gene Expression by an Eosinophil-Independent, IL-13Ra2-Inhibited Pathway," Journal of Immunology. 185:660-669.
Zurawski et al. (1995) "The primary binding subunit of the human interleukin-4 receptor is also a component of the Interleukin-13 Receptor," J. Biol. Chem. 270:13869-13878.

International Preliminary Report on Patentability corresponding to International Patent Application No. PCT/US2013/055747, dated Feb. 24, 2015.
International Search Report corresponding to International Patent Application No. PCT/US2013/055747, dated Feb. 13, 2014.
International Search Report with Written Opinion corresponding to International Patent Application No. PCT/US2014/043440, dated Oct. 6, 2014.
International Search Report with Written Opinion corresponding to International Patent Application No. PCT/US2015/016852, dated May 11, 2015.
Borish et al. (2001) "Efficacy of soluble IL-4 receptor for the treatment of adults with asthma," J. Clin. Allergy Clin. Immunol. 107:963-970.
Newton et al. (2008) "A Review of Nasal Polyposis," Therapeutic and Clinical Risk Management. 4(2):507-512.
Walker et al. (2008) "Use of biologicals as immunotherapy in asthma and related diseases," Expert Review of Clinical Immunology. 4(6):743-756.
Wenzel et al. (Apr. 27, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
American Academy of Allergy, Asthma & Immunology. "Rhinitis (Hay Fever)" American Academy of Allergy, Asthma & Immunology. Accessible on the Internet at URL: http://www.aaaai.org/conditions-and-treatments/allergies/rhinitis. [Last Accessed May 7, 2016].
Basic Local Alignment Search Tool. Search Results: "Alignment Heavy Chain Dupilumab with Seq ID No. 10," National Center for Biotechnology Information. [Retrieved on Jan. 12, 2016].
Basic Local Alignment Search Tool. Search Results: "Alignment Heavy Chain Dupilumab with Seq ID No. 9," National Center for Biotechnology Information. [Retrieved on Jan. 12, 2016].
Cho et al. (Apr. 11, 2012) "Spontaneous Eosinophilic Nasal Inflammation in a Genetically-Mutant Mouse: Comparative Study with an Allergic Inflammation Model," PLoS One. 7(4):e35114. pp. 1-8.
Clackson et al. (1991) "Making antibody fragments using phage display libraries," Nature. 352:624-628.
Figueiredo et al. (2008) "Inflammatory genes in nasal polyposis," Curr. Opin. Otolaryngol. Head Neck Surg. 16:18-21.
Getz et al. (2009) "Human Pharmacokinetics|Pharmacodynamics of an Interleukin-4 and Interleukin-13 Dual Antagonist in Asthma," The Journal of Clinical Pharmacology. 49(9):1025-1036.
Gevaert et al. (Nov. 2011) "Mepolizumab, a humanized anti-IL-5 mAb, as a treatment option for severe nasal polyposis," J. Allergy Clin. Immunol. 128(5):989-995.
Glare et al. (1999) "Asthmatic airway biopsy specimens are more likely to express the IL-4 alternative splice variant IL-4δ2," J. Allergy Clin. Immunol. 104:978-982.
Gu et al. (Feb. 2011) "Expression and role of acidic mammalian chitinase and eotaxin-3 in chronic rhinosinusitis with nasal polyps," Journal of Otolaryngology—Head and Neck Surgery. 40(1):64-69.
KEGG: Kyoto Encyclopedia of Genes and Genomes. "Drug: D10354," KEGG Drug Entry No. D10354. Kanehisa Laboratories. Accessible on the Internet at URL: http://www.genomajp/dbget-bin/www_bget?dr:D10354. [Last Accessed on Jan. 12, 2016].
Kimura et al. (Jul. 2011) "Increased expression and role of thymic stromal lymphopoietin in nasal polyposis," Allergy Asthma Immunol. Res. 3(3):186-193.
Knappik et al. (2000) "Fully synthetic human combinatorial antibody libraries (HuCAL) based on modular consensus frameworks and CDRs randomized with trinucleotides," J. Mol. Biol. 296(1):57-86.
Portolano et al. (1993) "Lack of promiscuity in autoantigen-specific H and L chain combinations as revealed by human H and L chain roulette," J. Immunol. 150(3):880-887.
PubChem Database [online] (Feb. 2, 2014) "CAS Registry No. 1190264-60-8," PubChem SID No. 172232447. National Center for Biotechnology Information. Accessible on the Internet at URL: http://pubchem.ncbi.nlm.nih.gov/substance/172232447#section=Top. [Mar. 14, 2016].

(56) References Cited

OTHER PUBLICATIONS

Regeneron Pharmaceuticals, Inc. (Sep. 30, 2014) "Regeneron and Sanofi Announce Positive Phase 2 Top-Line Dupilumab Results in Patients with Chronic Sinusitis with Nasal Polyps," Acquire Media.
Schubert et al. (1998) "Evaluation and treatment of allergic fungal sinusitis. I. Demographics and diagnosis," J. Allergy Clin. Immunol. 102(3):387-394.
Schubert et al. (1998) "Evaluation and treatment of allergic fungal sinusitis. II. Treatment and follow-up," J. Allergy Clin. Immunol. 102(3):395-402.
Sheahan et al. (Feb. 2010) "Local IgE production in nonatopic nasal polyposis," Journal of Otolaryngology—Head and Neck Surgery. 39(1):45-51.
Small et al. (2005) "Efficacy and safety of mometasone furoate nasal spray in nasal polyposis," J. Allergy Clin. Immunol. 116:1275-1281.
Trangsrud et al. (2002) "Intranasal Corticosteroids for Allergic Rhinitis," Pharmacotherapy. 22(11):1458-1467.—Abstract only.
Van Zele et al. (2006) "Differentiation of chronic sinus diseases by measurement of inflammatory mediators," Allergy. 61:1280-1289.
Van Zele et al. (2010) "Oral steroids and doxycycline: two different approaches to treat nasal polyps," J. Allergy Clin. Immunol. 125(5):1069-1076.
Vlaminck et al. (May 2014) "The importance of local eosinophilia in the surgical outcome of chronic rhinosinusitis: a 3-year prospective observational study," Am. J. Rhinol. Allergy. 28(3):260-264.
World Health Organization (Jan. 1, 2012) "International Nonproprietary Names for Pharmaceutical Substances (INN)," WHO Drug Information. 26(4):401-471.
International Search Report with Written Opinion corresponding to International Patent Application No. PCT/US2015/060540, dated Feb. 17, 2016.

\* cited by examiner

Figure iii

| | Placebo All comers n=158 | Placebo HEOS n=68 | 200 mg q2w All comers n=154 | 200 mg q2w HEOS n=62 | 300 mg q2w All comers n=157 | 300 mg q2w HEOS n=66 | 200 mg q2w All Comers n=158 | 200 mg q2w HEOS n=65 | 300 mg q2w All Comers n=157 | 300 mg q2w HEOS n=64 | All Total n=776 | All HEOS n=325 |
|---|---|---|---|---|---|---|---|---|---|---|---|---|
| Mean age (yr) | 49 | 45.8 | 47.9 | 47 | 47.9 | 48.8 | 51 | 50.8 | 47.5 | 47.8 | 48.6 | 48 |
| Male sex (%) | 34.2 | 35.8 | 43.5 | 40.3 | 36.3 | 42.4 | 36 | 44.6 | 34.4 | 32.2 | 36.9 | 39.4 |
| Race (%) White | 75.3 | 72.1 | 81.2 | 74.2 | 76.4 | 77.3 | 76 | 78.5 | 82.2 | 73.1 | 78.2 | 76 |
| Mean Weight (kg) | 78.7 | 75.97 | 81.3 | 77.07 | 79.86 | 83.34 | 80.66 | 79.96 | 80.15 | 79.21 | 80.12 | 79.12 |
| BMI >30 (%) | 38 | 30.9 | 39.9 | 29.5 | 39.5 | 40.9 | 43.3 | 41.5 | 40.1 | 35.9 | 40.1 | 35.8 |
| Age of onset of Asthma (years) | 27.82 | 25.57 | 24.12 | 26.18 | 27.39 | 30.38 | 27.14 | 27.08 | 27.01 | 29.29 | 26.54 | 27.69 |
| Atopic Medical History (%) | 77.3 | 82.4 | 76.2 | 80.3 | 80.6 | 76.9 | 79.2 | 81.5 | 73.4 | 79.4 | 77.3 | 80.1 |
| Baseline FEV1 (L) | 1.83 | 1.95 | 1.88 | 1.80 | 1.86 | 1.87 | 1.79 | 1.80 | 1.85 | 1.77 | 1.84 | 1.83 |
| Baseline %pred FEV1 | 60.86 | 59.57 | 60.29 | 58.18 | 60.73 | 59.92 | 61.26 | 59.65 | 60.76 | 58.67 | 60.80 | 59.22 |
| Baseline FEV1 Reversibility | 27.94 | 26.31 | 26.44 | 27.47 | 25.81 | 24.59 | 25.66 | 23.90 | 27.37 | 27.96 | 26.85 | 25.71 |
| Mean number of asthma exacerbations in last year | 1.94 | 1.93 | 1.78 | 1.79 | 1.90 | 2.06 | 1.75 | 1.94 | 1.96 | 2.16 | 1.87 | 1.98 |
| Baseline ACQ | 2.69 | 2.55 | 2.72 | 2.76 | 2.70 | 2.69 | 2.72 | 2.65 | 2.80 | 2.98 | 2.74 | 2.73 |
| ICS/LABA High dose (%) | 49.4 | 50.7 | 54.2 | 53.7 | 54.2 | 59.4 | 50.7 | 59.7 | 51 | 52.5 | 50.5 | 54.8 |

Dupilumab Asthma DRI 125344 interim

Figure 24

| | Dupilumab PoC study: ACT11457 | | Lebrikizumab Phase 2 Study (Corren et al., NEJM 2011) | | | | | |
|---|---|---|---|---|---|---|---|---|
| | | | Placebo | | | Lebrikizumab | | |
| Marker | Placebo | Dupilumab | All ITT | Periostin High | Periostin Low | All ITT | Periostin High | Periostin Low |
| FeNO | 35 | -28.7 | 10.1 | 13.8 | 7.9 | 19.2 | 34.4 | 4.3 |
| Total Serum IgE | -5.5 | -36.8 | 3.7 | 9.4 | -2.1 | 16 | 19.1 | 12.9 |
| TARC (CCL17) | 7.6 | -26 | 5 | -0.8 | 10.9 | 12.4 | 8.7 | 15.5 |

Figure 48

|  | DRI12544: 12 Week Interim | | | | | Lebrikizumab Phase 2 Study (Corren et al., NEJM 2011) | | | | | | |
|---|---|---|---|---|---|---|---|---|---|---|---|---|
|  | Placebo + ICS/LABA | | | Dupilumab + ICS/LABA 300 mg q2w | | | Placebo + ICS/LABA | | | Lebrikizumab + ICS/LABA | | |
| Marker | All ITT | Heos (>0.3 Gi/L) | Low Eos (<0.2 Gi/L) | All ITT | Heos (>0.3 Gi/L) | Low Eos (<0.2 Gi/L) | All ITT | Periostin High | Periostin Low | All ITT | Periostin High | Periostin Low |
| FeNO | 10.22 | 11.82 | 5.06 | 26.75 | 33.83 | 3.44 | 10.1 | 13.8 | 7.9 | 19.2 | 34.4 | 4.9 |
| Total Serum IgE | 20.20 | 21.68 | 9.90 | 33.55 | 34.17 | 31.55 | 3.7 | 9.4 | 2.1 | 16 | 19.1 | 12.9 |
| TARC (CCL17) | 9.85 | 10.08 | 17.40 | 32.27 | 37.03 | 28.85 | 5 | 0.8 | 10.9 | 12.3 | 6.7 | 15.5 |

Figure 49

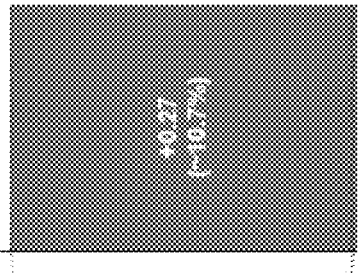
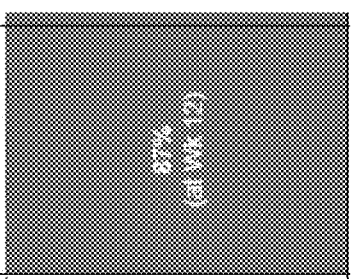
Figure 50

|  | Placebo (N=158) | Dupilumab | | | |
|---|---|---|---|---|---|
|  |  | 300 mg q4w (N=154) | 300 mg q4w (N=157) | 200 mg q2w (N=150) | 300 mg q2w (N=157) |
| Randomized and not treated | 0 | 4 (2.6%) | 0 | 2 (1.3%) | 1 (0.6%) |
| Patient's request for not treated | 0 | 1 (0.6%) | 0 | 0 | 0 |
| Reason for not treated |  |  |  |  |  |
| Adverse event | 0 | 0 | 0 | 0 | 0 |
| Lack of efficacy | 0 | 0 | 0 | 0 | 0 |
| Poor compliance to protocol | 0 | 0 | 0 | 0 | 0 |
| Other reason | 0 | 4 (2.6%) | 0 | 2 (1.3%) | 1 (0.6%) |
| Randomized and treated | 158 (100%) | 150 (97.4%) | 157 (100%) | 148 (98.7%) | 156 (99.4%) |
| Completed the 12-week study treatment period | 153 (96.8%) | 143 (92.9%) | 145 (92.4%) | 141 (94.0%) | 149 (94.9%) |
| Completed the study treatment period | 111 (70.3%) | 102 (66.2%) | 103 (65.6%) | 110 (73.3%) | 117 (74.5%) |
| Discontinued from the study treatment period | 12 (7.6%) | 13 (8.4%) | 15 (9.6%) | 9 (6.0%) | 7 (4.5%) |
| Patient's request for treatment discontinuation | 2 (1.3%) | 8 (5.2%) | 10 (6.4%) | 2 (1.3%) | 5 (3.2%) |
| Reason for treatment discontinuation |  |  |  |  |  |
| Adverse event | 6 (3.8%) | 6 (3.9%) | 10 (6.4%) | 5 (3.3%) | 3 (1.9%) |
| Lack of efficacy | 1 (0.6%) | 0 | 1 (0.6%) | 0 | 0 |
| Poor compliance to protocol | 3 (1.9%) | 0 | 0 | 2 (1.3%) | 1 (0.6%) |
| Other reason | 2 (1.3%) | 7 (4.5%) | 4 (2.5%) | 2 (1.3%) | 3 (1.9%) |
| Completed the study period | 44 (27.8%) | 48 (31.2%) | 48 (30.6%) | 44 (29.3%) | 46 (29.3%) |
| Discontinued from the study period | 5 (3.2%) | 6 (3.9%) | 9 (5.7%) | 3 (2.0%) | 10 (6.4%) |

Figure 51

| | | | | | |
|---|---|---|---|---|---|
| Patient's request for study discontinuation | 4 (2.5%) | 5 (3.2%) | 8 (5.1%) | 3 (2.0%) | 6 (3.8%) |
| Reason for study discontinuation | | | | | |
| Adverse event | 1 (0.6%) | 1 (0.6%) | 3 (1.9%) | 1 (0.7%) | 4 (2.5%) |
| Lack of efficacy | 0 | 0 | 0 | 0 | 0 |
| Poor compliance to protocol | 0 | 0 | 0 | 0 | 0 |
| Other reason | 4 (2.5%) | 5 (3.2%) | 6 (3.8%) | 2 (1.3%) | 6 (3.8%) |
| Status at last study contact | | | | | |
| Alive | 35 (22.2%) | 47 (30.5%) | 45 (28.7%) | 42 (28.0%) | 43 (27.4%) |
| Dead | 0 | 0 | 1 (0.6%) | 0 | 0 |
| Lost to follow-up | 0 | 0 | 0 | 0 | 0 |

Figure 51 (Cont.)

|  | Placebo | Dupilumab | | | | All |
|---|---|---|---|---|---|---|
|  |  | 300 mg q4w | 300 mg q4w | 200 mg q2w | 300 mg q2w |  |
| Randomized population | 158 (100%) | 154 (100%) | 157 (100%) | 150 (100%) | 157 (100%) | 776 (100%) |
| Efficacy population |  |  |  |  |  |  |
| Intent-to-Treat (ITT) | 158 (100%) | 154 (100%) | 157 (100%) | 150 (100%) | 157 (100%) | 776 (100%) |
| HEos ITT | 68 (43.0%) | 62 (40.3%) | 66 (42.0%) | 65 (43.3%) | 64 (40.8%) | 325 (41.9%) |
| PK Population | 158 | 150 | 157 | 148 | 156 | 769 |
| Safety population | 158 | 150 | 157 | 148 | 156 | 769 |
| HEos Safety | 68 | 59 | 66 | 64 | 64 | 321 |

Figure 52

|  | Placebo (N=158) | Dupilumab | | | |
|---|---|---|---|---|---|
|  |  | 200 mg q4w (N=150) | 300 mg q4w (N=157) | 200 mg q2w (N=148) | 300 mg q2w (N=156) |
| Cumulative exposure to treatment (patient years) | 65.3 | 61.4 | 62.9 | 61.5 | 64.4 |
| Duration of study treatment (Day) | | | | | |
| Number | 158 | 150 | 157 | 148 | 156 |
| Mean (SD) | 151.0 (30.2) | 149.5 (32.6) | 146.4 (36.0) | 151.7 (31.6) | 150.9 (33.5) |
| Median | 167.0 | 167.0 | 167.0 | 167.0 | 168.0 |
| Min : Max | 14 : 174 | 14 : 188 | 14 : 197 | 14 : 176 | 14 : 176 |
| Duration of study treatment by category [n(%)] | | | | | |
| >0 and <=2 weeks | 2 (1.3%) | 3 (2.0%) | 1 (0.6%) | 1 (0.7%) | 3 (1.9%) |
| >2 and <=4 weeks | 2 (1.3%) | 1 (0.7%) | 2 (1.3%) | 1 (0.7%) | 0 |
| >4 and <=8 weeks | 0 | 0 | 5 (3.2%) | 4 (2.7%) | 4 (2.6%) |
| >8 and <=12 weeks | 1 (0.6%) | 2 (1.3%) | 3 (1.9%) | 1 (0.7%) | 0 |
| >12 and <=16 weeks | 11 (7.0%) | 17 (11.3%) | 14 (8.9%) | 7 (4.7%) | 9 (5.8%) |
| >16 and <=20 weeks | 23 (14.6%) | 17 (11.3%) | 22 (14.0%) | 17 (11.5%) | 23 (14.7%) |
| >20 and <=24 weeks | 86 (54.4%) | 80 (53.3%) | 76 (48.4%) | 89 (60.1%) | 89 (57.1%) |
| >24 weeks | 33 (20.9%) | 30 (20.0%) | 34 (21.7%) | 28 (18.9%) | 28 (17.9%) |

Figure 53

| Number of patients with duration of study treatment by category [n(%)] | Placebo | 300mg q4w | 300mg q4w | 200mg q2w | 300mg q2w |
|---|---|---|---|---|---|
| ≥ 0 week | 158 (100%) | 150 (100%) | 157 (100%) | 148 (100%) | 156 (100%) |
| ≥ 2 week | 156 (98.7%) | 147 (98.0%) | 156 (99.4%) | 147 (99.3%) | 153 (98.1%) |
| ≥ 4 weeks | 154 (97.5%) | 146 (97.3%) | 154 (98.1%) | 146 (98.6%) | 153 (98.1%) |
| ≥ 8 weeks | 154 (97.5%) | 146 (97.3%) | 149 (94.9%) | 142 (95.9%) | 149 (95.5%) |
| ≥ 12 weeks | 153 (96.8%) | 144 (96.0%) | 146 (93.0%) | 141 (95.3%) | 149 (95.5%) |
| ≥ 16 weeks | 142 (89.9%) | 127 (84.7%) | 132 (84.1%) | 134 (90.5%) | 140 (89.7%) |
| ≥ 20 weeks | 119 (75.3%) | 110 (73.3%) | 110 (70.1%) | 117 (79.1%) | 117 (75.0%) |
| ≥ 24 weeks | 33 (20.9%) | 30 (20.0%) | 34 (21.7%) | 28 (18.9%) | 28 (17.9%) |

| Blood EOS | | 200mg q4w | 300mg q4w | 200mg q2w | 300mg q2w |
|---|---|---|---|---|---|
| ≥300 | FEV1 | 0.08 (n=62) | 0.17* (n=66) | 0.25*** (n=65) | 0.20** (n=64) |
| | ACQ-5 | -0.24 | -0.28 | -0.35* | -0.48** |
| | Exacerbations (%) | -74.3* | -26.1 | -64.4* | -74.6* |
| ≥275 | FEV1 | 0.04 (n=69) | 0.15* (n=72) | 0.23** (n=68) | 0.18** (n=75) |
| | ACQ-5 | -0.21 | -0.26 | -0.36* | -0.42** |
| | Exacerbations (%) | -66.9* | -17.3 | -63.8* | -78** |
| ≥250 | FEV1 | 0.09 (n=82) | 0.16* (n=84) | 0.24*** (n=75) | 0.17** (n=88) |
| | ACQ-5 | -0.25 | -0.27 | -0.42** | -0.47** |
| | Exacerbations (%) | -68.6* | -13.5 | -62* | -74.6** |
| ≥225 | FEV1 | 0.10 (n=83) | 0.15* (n=93) | 0.23*** (n=86) | 0.18** (n=94) |
| | ACQ-5 | -0.23 | -0.28 * | -0.42** | -0.44** |
| | Exacerbations (%) | -76.2** | -39.4 | -71.9** | -81.9*** |
| ≥200 | FEV1 | 0.11 (n=94) | 0.16** (n=102) | 0.23*** (n=99) | 0.18** (n=104) |
| | ACQ-5 | -0.24 | -0.28* | -0.40** | -0.39** |
| | Exacerbations (%) | -67** | -41.3 | -69.7** | -78.2*** |
| ≥175 | FEV1 | 0.12 * (n=101) | 0.17** (n=107) | 0.24*** (n=104) | 0.18*** (n=110) |
| | ACQ-5 | -0.18 | -0.23 | -0.35** | -0.37** |
| | Exacerbations (%) | -70.8** | -43.8 | -67.9** | -75.9*** |
| ≥150 | FEV1 | 0.12 * (n=112) | 0.15** (n=116) | 0.23*** (n=120) | 0.17*** (n=129) |
| | ACQ-5 | -0.25 | -0.22 | -0.34** | -0.33** |
| | Exacerbations (%) | -68.2** | -42.3 | -68.2** | -70.7*** |
| ITT pop | FEV1 | 0.09* (n=154) | 0.12** (n=157) | 0.19*** (n=150) | 0.16*** (n=157) |
| | ACQ-5 | -0.10 | -0.17 | -0.22* | -0.19 |
| | Exacerbations (%) | -57.3** | -38.4 | -66.6** | -66.9*** |

Figure 54

| | Placebo (N=158) | 200 mg q4w (N=154) | 300 mg q4w (N=157) | 200 mg q2w (N=150) | 300 mg q2w (N=157) |
|---|---|---|---|---|---|
| FEV1 (L) Total ITT Population | | | | | |
| Percent change from baseline | | | | | |
| Number | 130 | 134 | 135 | 136 | 146 |
| LS Mean (SE) [a] | 6.20 (1.89) | 13.54 (1.90) | 14.09 (1.86) | 18.00 (1.89) | 17.75 (1.84) |
| LS Mean Diff, 95% CI [a] | | 7.34 (2.16, 12.51) | 7.88 (2.77, 13.00) | 11.79 (6.62, 16.96) | 11.55 (6.45, 16.65) |
| P-value vs placebo [a] | | 0.0055 | 0.0026 | <.0001 | <.0001 |
| | Placebo (N=68) | 200 mg q4w (N=62) | 300 mg q4w (N=66) | 200 mg q2w (N=65) | 300 mg q2w (N=64) |
| FEV1 (L) EOS ≥ 300 | | | | | |
| Percent change from baseline | | | | | |
| Number | 59 | 53 | 55 | 57 | 59 |
| LS Mean (SE) [a] | 10.44 (3.31) | 17.98 (3.43) | 21.58 (3.32) | 25.92 (3.32) | 25.81 (3.35) |
| LS Mean Diff, 95% CI [a] | | 7.54 (-1.77, 16.84) | 11.14 (2.03, 20.26) | 15.48 (6.36, 24.60) | 15.37 (6.21, 24.53) |
| P-value vs placebo [a] | | 0.1119 | 0.0168 | 0.0009 | 0.0011 |
| | Placebo (N=90) | 200 mg q4w (N=92) | 300 mg q4w (N=91) | 200 mg q2w (N=85) | 300 mg q2w (N=93) |
| FEV1 (L) EOS < 300 | | | | | |
| Percent change from baseline | | | | | |
| Number | 71 | 81 | 80 | 79 | 87 |
| LS Mean (SE) [a] | 4.83 (2.16) | 11.03 (2.14) | 10.14 (2.07) | 13.63 (2.14) | 12.57 (2.06) |
| LS Mean Diff, 95% CI [a] | | 6.21 (0.37, 12.04) | 5.31 (-0.49, 11.11) | 8.80 (2.92, 14.69) | 7.74 (1.98, 13.50) |
| P-value vs placebo [a] | | 0.0371 | 0.0729 | 0.0034 | 0.0086 |

Figure 55

| | | Placebo | 300mg q4w | 300mg qlw | 200mg q2w | 300mg q2w | All |
|---|---|---|---|---|---|---|---|
| HEos≥300 | Baseline Eosinophil | 0.56 | 0.7 | 0.5 | 0.61 | 0.53 | 0.59 |
| | Baseline Total IgE | 582.97 | 649.15 | 722.76 | 477.95 | 359.39 | 558.93 |
| | IgE>100 & EoS>0.14 | 52 (76.5%) | 48 (77.4%) | 54 (81.8%) | 52 (80.0%) | 46 (71.9%) | 252 (77.5%) |
| | IgE<100 or EoS<=0.14 | 16 (23.5%) | 14 (22.6%) | 12 (18.2%) | 13 (20.0%) | 18 (28.1%) | 73 (22.5%) |
| | Baseline ECP | 38.62 | 41.9 | 33.95 | 38.42 | 38.22 | 37.35 |
| | Baseline Periostin | 54881.75 | 58828.85 | 51731.95 | 58382.14 | 52068.91 | 55016.13 |
| | Baseline Eotaxin | 133.08 | 86.62 | 85.55 | 83.61 | 72.42 | 92.47 |
| | Baseline TARC | 68 | 62 | 66 | 65 | 64 | 325 |
| | Baseline FeNo | 59 | 57 | 60 | 59 | 59 | 298 |
| Eos≥200-299 | Baseline Eosinophil | 0.25 | 0.25 | 0.25 | 0.23 | 0.25 | 0.24 |
| | Baseline Total IgE | 284.24 | 400.53 | 215.22 | 320.62 | 467.23 | 338.64 |
| | IgE>100 & EoS>0.14 | 26 (68.4%) | 21 (65.6%) | 22 (61.1%) | 22 (64.7%) | 21 (52.5%) | 112 (63.2%) |
| | IgE<100 or EoS<=0.14 | 12 (31.6%) | 11 (34.4%) | 14 (38.9%) | 12 (35.3%) | 19 (47.5%) | 69 (37.8%) |
| | Baseline ECP | 14.24 | 18.77 | 16.83 | 14.59 | 17.67 | 16.38 |
| | Baseline Periostin | 48355.58 | 51821.43 | 49857.14 | 46958.62 | 50147.06 | 49545.01 |
| | Baseline Eotaxin | 52.79 | 55.19 | 46.76 | 41.86 | 58.05 | 53.11 |
| | Baseline TARC | 357.71 | 479.47 | 520.87 | 428.49 | 423.45 | 439.96 |
| | Baseline FeNo | 30.81 | 40.9 | 34.72 | 33.5 | 36.82 | 35.28 |
| Eos<200 | Baseline Eosinophil | 0.12 | 0.13 | 0.13 | 0.13 | 0.13 | 0.12 |
| | Baseline Total IgE | 303.86 | 281.78 | 467.62 | 401.25 | 303 | 336.2 |
| | IgE>100 & EoS>0.14 | 12 (23.5%) | 11 (18.3%) | 7 (12.7%) | 15 (28.3%) | 15 (28.9%) | 60 (22.2%) |
| | IgE<100 or EoS<=0.14 | 39 (76.5%) | 49 (76.5%) | 48 (87.3%) | 38 (70.6%) | 38 (71.7%) | 210 (77.8%) |
| | Baseline ECP | 8.75 | 11.55 | 9.15 | 12.18 | 16.6 | 11.53 |
| | Baseline Periostin | 44670.45 | 45224 | 53697.92 | 71215.91 | 46600 | 52074.57 |
| | Baseline Eotaxin | 40.49 | 48.56 | 49.17 | 42.53 | 42.05 | 44.71 |
| | Baseline TARC | 436.98 | 416.77 | 567.99 | 536.27 | 410.89 | 472.68 |
| | Baseline FeNo | 24.84 | 29.56 | 22.26 | 27.47 | 25.91 | 26.01 |
| Total Pop | Baseline Eosinophil | 0.34 | 0.38 | 0.33 | 0.36 | 0.32 | 0.35 |
| | Baseline Total IgE | 419.31 | 454.36 | 517.07 | 416.21 | 367.83 | 435.05 |
| | IgE>100 & EoS>0.14 | 90 (42.7%) | 80 (51.3%) | 83 (52.8%) | 89 (59.3%) | 82 (52.2%) | 424 (54.7%) |
| | IgE<100 or EoS<=0.14 | 67 (42.7%) | 74 (48.1%) | 74 (47.1%) | 61 (40.7%) | 75 (47.8%) | 351 (45.3%) |
| | Baseline ECP | 22.04 | 25.2 | 21.34 | 24 | 24.97 | 23.49 |
| | Baseline Periostin | 50074.83 | 52006.92 | 51684.72 | 60510.65 | 49837.23 | 52720.56 |
| | Baseline Eotaxin | 63.49 | 65.23 | 63.91 | 59.01 | 58.42 | 66.11 |
| | Baseline TARC | 602.27 | 694.43 | 565.18 | 616.41 | 471.93 | 589.43 |
| | Baseline FeNo | 38.95 | 42.03 | 38.13 | 39.35 | 37.16 | 39.1 |

Dupilumab

Figure 56

| Mean score | PBO (N=158) | DUPI 300mg Q2W (N=157) | LS means Diff (95% CI) |
|---|---|---|---|
| ACQ Total | | | |
| Baseline mean(sd) | 2.69 (0.80) | 2.80 (0.83) | |
| Week12 mean(se) | -1.14 (0.08) | -1.34 (0.08) | -0.20 (-0.41, 0.01) |

| Responder pMCID=0.6 | PBO (N=158) | DUPI 300mg Q2W (N=157) | OR (95% CI) |
|---|---|---|---|
| ACQ Total | | | |
| Responders | 91 (57.6%) | 116 (73.9%) | 1.68 (0.96, 2.96) |
| Non responders | 67 (42.4%) | 41 (26.1%) | |

Figure 57

| | PBO (N=158) | DUPI 300mg Q2W (N=157) | LS means Diff (95% CI) |
|---|---|---|---|
| ACQ1 (awoken) | | | |
| Baseline mean(sd) | 2.28 (1.19) | 2.35 (1.22) | |
| Week12 mean(se) | -0.98 (0.09) | -1.25 (0.09) | -0.27 (-0.51, -0.03) |
| ACQ2 (morning symptom) | | | |
| Baseline mean(sd) | 2.68 (0.80) | 2.82 (0.92) | |
| Week12 mean(se) | -1.02 (0.09) | -1.27 (0.09) | -0.25 (-0.49, -0.01) |
| ACQ3 (activity) | | | |
| Baseline mean(sd) | 2.66 (1.10) | 2.69 (0.95) | |
| Week12 mean(se) | -1.22 (0.10) | -1.32 (0.09) | -0.10 (-0.36, 0.16) |
| ACQ4 (shortness of breath) | | | |
| Baseline mean(sd) | 2.94 (0.93) | 3.09 (0.99) | |
| Week12 mean(se) | -1.19 (0.10) | -1.33 (0.09) | -0.14 (-0.40, 0.12) |
| ACQ5 (time wheeze) | | | |
| Baseline mean(sd) | 2.87 (1.21) | 3.04 (1.31) | |
| Week12 mean(se) | -1.32 (0.11) | -1.51 (0.10) | -0.19 (-0.47, 0.09) |

Figure 58

| AQLQ Total | PBO (N=158) | DUPI 300mg Q2W (N=157) | LS Mean Diff, 95% CI a |
|---|---|---|---|
| Baseline mean (sd) | 4.12 (1.10) | 3.91 (1.13) | |
| Week 12 mean (se) | 0.83 (0.08) | 1.14 (0.08) | 0.31 (0.09, 0.53) |

| pMCID=0.6 | PBO (N=158) | DUPI 300mg Q2W (N=157) | OR (95% CI) |
|---|---|---|---|
| AQLQ Total | | | |
| Responders | 77 (48.7%) | 95 (60.5%) | 1.38 (0.82, 2.33) |
| Non responders | 81 (51.3%) | 62 (39.5%) | |

Figure 59

| | PBO (N=158) | DUPI 300mg Q2W (N=157) | LS Mean Diff, 95% CI a |
|---|---|---|---|
| AQLQ Activity Limitation | | | |
| Baseline mean (sd) | 4.25 (1.15) | 4.12 (1.13) | |
| Week 12 mean (se) | 0.69 (0.08) | 0.96 (0.08) | 0.27 (0.06, 0.49) |
| AQLQ Emotional Function | | | |
| Baseline mean (sd) | 4.14 (1.43) | 3.85 (1.50) | |
| Week 12 mean (se) | 0.84 (0.10) | 1.15 (0.10) | 0.31 (0.03, 0.59) |
| AQLQ Environmental Stimuli | | | |
| Baseline mean (sd) | 3.80 (1.50) | 3.61 (1.54) | |
| Week 12 mean (se) | 0.71 (0.10) | 1.07 (0.10) | 0.36 (0.08, 0.64) |
| AQLQ Symptoms | | | |
| Baseline mean (sd) | 4.09 (1.11) | 3.83 (1.17) | |
| Week 12 mean (se) | 1.01 (0.09) | 1.31 (0.08) | 0.30 (0.07, 0.54) |

Figure 60

| EQ5D Total | PBO (N=158) | DUPI 300mg Q2W (N=157) | LS Mean Diff, 95% CI a |
|---|---|---|---|
| Baseline mean (sd) | 0.78 (0.20) | 0.78 (0.19) | |
| Week 12 mean (se) | 0.05 (0.01) | 0.07 (0.01) | 0.03 (-0.01, 0.07) |

Figure 61

|  | PBO (N=158) | DUPI 300mg Q2W (N=157) | LS Mean Diff, 95% CI a |
|---|---|---|---|
| EQ5D Mobility | | | |
| Baseline mean (sd) | 1.38 (0.49) | 1.39 (0.49) | |
| Week12 mean (se) | -0.14 (0.03) | -0.17 (0.03) | -0.03 (-0.12, 0.06) |
| EQ5D Self care | | | |
| Baseline mean (sd) | 1.08 (0.28) | 1.14 (0.34) | |
| Week12 mean (se) | -0.05 (0.02) | -0.06 (0.02) | -0.01 (-0.07, 0.05) |
| EQ5D Usual Activities | | | |
| Baseline mean (sd) | 1.48 (0.53) | 1.43 (0.51) | |
| Week12 mean (se) | -0.19 (0.04) | -0.18 (0.04) | 0.01 (-0.09, 0.11) |
| EQ5D Pain Discomfort | | | |
| Baseline mean (sd) | 1.54 (0.56) | 1.55 (0.50) | |
| Week12 mean (se) | -0.08 (0.04) | -0.21 (0.04) | -0.13 (-0.24, -0.01) |
| EQ5D Anxiety Depression | | | |
| Baseline mean (sd) | 1.30 (0.49) | 1.39 (0.55) | |
| Week12 mean (se) | -0.07 (0.04) | -0.10 (0.04) | -0.03 (-0.13, 0.06) |

Figure 62

| | PBO (N=158) | DUPI 300mg Q2W (N=157) | LS Mean Diff, 95% CI a |
|---|---|---|---|
| HADS anxiety | | | |
| Baseline mean (sd) | 7.24 (4.41) | 7.69 (4.41) | |
| Week12 mean (se) | -1.43 (0.26) | -1.71 (0.25) | -0.28 (-0.97, 0.42) |
| HADS Depression | | | |
| Baseline mean (sd) | 5.07 (3.67) | 5.08 (4.12) | |
| Week12 mean (se) | -0.44 (0.25) | -1.18 (0.24) | -0.74 (-1.41, -0.06) |

| | PBO (N=158) | DUPI 300mg Q2W (N=157) | OR (95% CI) |
|---|---|---|---|
| pMCID=4 / anxiety | | | |
| HADS Total | | | |
| Responders | 26 (16.5%) | 33 (21.0%) | 1.22 (0.64, 2.33) |
| Non responders | 132 (83.5%) | 124 (79.0%) | |
| pMCID=4 / depression | | | |
| HADS Total | | | |
| Responders | 17 (10.8%) | 26 (16.6%) | 1.75 (0.81, 3.79) |
| Non responders | 141 (89.2%) | 131 (83.4%) | |

Figure 63

|  | PBO (N=158) | DUPI 300mg Q2W (N=157) | LS Mean Diff, 95% CI a |
| --- | --- | --- | --- |
| HADS Total | | | |
| Baseline mean (sd) | 12.31 (7.46) | 12.78 (7.85) | |
| Week 12 mean (se) | -1.87 (0.45) | -2.87 (0.44) | -1.01 (-2.22, 0.20) |

|  | PBO (N=158) | DUPI 300mg Q2W (N=157) | OR (95% CI) |
| --- | --- | --- | --- |
| (pMCID=-2)/ total | | | |
| HADS Total | | | |
| Responders | 70 (44.3%) | 83 (52.9%) | 1.32 (0.79, 2.20) |
| Non responders | 88 (55.7%) | 74 (47.1%) | |

Figure 64

| ITT HEDS | Placebo (N=68) | 200 mg q4w (N=63) | 300 mg q4w (N=66) | 200 mg q2w (N=65) | 300 mg q2w (N=64) |
|---|---|---|---|---|---|
| N | | | | | |
| Total score - Baseline | 12.56 (7.68) | 12.03 (6.50) | 12.31 (7.10) | 12.83 (6.68) | 14.03 (8.55) |
| Total score - LS means change from Baseline-Week 12 | -1.40 (0.66) | -3.92 (0.71) | -2.02 (0.68) | -4.33 (0.68)* | -4.87 (0.68)* |
| Anxiety - Baseline | 7.47 (4.48) | 6.77 (4.05) | 7.23 (4.20) | 7.50 (4.24) | 8.08 (4.57) |
| Anxiety-LS means change from Baseline-Week 12 | -1.15 (0.38) | -1.78 (0.41) | -1.15 (0.39) | -2.44 (0.39)* | -2.68 (0.39)* |
| Depression - Baseline | 5.09 (3.83) | 5.27 (3.18) | 5.08 (3.47) | 5.33 (3.36) | 5.95 (4.58) |
| Depression - LS means change from Baseline-Week 12 | -0.25 (0.36) | -2.13 (0.39)* | -0.89 (0.37) | -1.87 (0.38)* | -2.13 (0.37)* |

Figure 65

| ITT | Placebo (N=158) | 200 mg q4w (N=154) | 300 mg q4w (N=157) | 200 mg q2w (N=150) | 300 mg q2w (N=157) |
|---|---|---|---|---|---|
| Total score - Baseline | 12.31 (7.46) | 12.03 (6.52) | 12.24 (7.03) | 12.47 (7.07) | 12.78 (7.85) |
| Total score -LS means change from Baseline-Week 12 | -1.87 (0.45) | -2.15 (0.45) | -1.61 (0.44) | -3.30 (0.45)* | -2.87 (0.44) |
| Anxiety - Baseline | 7.24 (4.41) | 7.10 (4.00) | 7.25 (4.31) | 7.34 (4.14) | 7.69 (4.41) |
| Anxiety-LS means change from Baseline-Week 12 | -1.43 (0.26) | -1.21 (0.26) | -0.99 (0.25) | -1.94 (0.26) | -1.71 (0.25) |
| Depression- Baseline | 5.07 (3.67) | 4.93 (3.24) | 4.99 (3.40) | 5.13 (3.66) | 5.08 (4.12) |
| Depression -LS means change from Baseline-Week 12 | -0.44 (0.25) | -0.96 (0.25) | -0.62 (0.25) | -1.36 (0.25)* | -1.18 (0.24)* |

Figure 66

| | PBO (N=158) | DUPI 300mg Q2W (N=157) | LS Mean Diff, 95% CI a |
|---|---|---|---|
| SNOT 22 Total | | | |
| Baseline mean (sd) | 35.11 (20.71) | 36.39 (18.89) | |
| Week 12 mean (se) | -7.46 (1.24) | -12.65 (1.22) | -5.18 (-8.53, -1.83) |

| | PBO (N=158) | DUPI 300mg Q2W (N=157) | OR (95% CI) |
|---|---|---|---|
| (pMCID=-10) SNOT 22 Total | | | |
| Responders | 50 (31.6%) | 73 (46.5%) | 2.22 (1.28, 3.84) |
| Non responders | 108 (68.4%) | 84 (53.5%) | |

Figure 67

| | PBO (N=158) | DUPI 300mg Q2W (N=157) | LS Mean Diff, 95% CI a |
|---|---|---|---|
| SNOT 22 nasal score | | | |
| Baseline mean (sd) | 10.38 (6.66) | 10.80 (6.63) | |
| Week 12 mean (se) | -1.75 (0.43) | -4.23 (0.42) | -2.48 (-3.64, -1.33) |
| SNOT 22 ear score | | | |
| Baseline mean (sd) | 2.49 (2.95) | 2.65 (3.03) | |
| Week 12 mean (se) | -0.40 (0.19) | -0.60 (0.19) | -0.20 (-0.71, 0.32) |
| SNOT 22 sleep score | | | |
| Baseline mean (sd) | 7.42 (5.20) | 8.09 (4.67) | |
| Week 12 mean (se) | -2.04 (0.32) | -3.08 (0.31) | -1.04 (-1.90, -0.19) |
| SNOT 22 general and practical score | | | |
| Baseline mean (sd) | 10.75 (5.68) | 11.02 (5.28) | |
| Week 12 mean (se) | -2.50 (0.39) | -3.82 (0.38) | -1.32 (-2.38, -0.27) |
| SNOT 22 emotional score | | | |
| Baseline mean (sd) | 4.07 (3.48) | 3.83 (3.45) | |
| Week 12 mean (se) | -0.86 (0.21) | -0.95 (0.21) | -0.08 (-0.65, 0.48) |

Figure 68

| | Placebo (N=16) | 200 mg q4w (N=17) | 300 mg q4w (N=20) | Dupilumab 200 mg q2w (N=10) | 300 mg q2w (N=16) | All (N=79) |
|---|---|---|---|---|---|---|
| With atopic dermatitis medical history [n] | | | | | | |
| Number | 154 | 151 | 155 | 149 | 153 | 762 |
| Yes | 16 (10.4%) | 17 (11.3%) | 20 (12.9%) | 10 (6.7%) | 16 (10.5%) | 79 (10.4%) |
| Ongoing | 12 (7.8%) | 13 (8.6%) | 17 (11.0%) | 7 (4.7%) | 13 (8.5%) | 62 (8.1%) |
| With concomitant immunosuppressant medication [n (%)] | | | | | | |
| Number | 16 | 17 | 20 | 10 | 16 | 79 |
| Yes | 1 (6.3%) | 0 | 0 | 0 | 0 | 1 (1.3%) |

Figure 69

SEQUENCE LISTING

```
<160> NUMBER OF SEQ ID NOS: 8

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      HCVR polypeptide

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

```
<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      LCVR polypeptide

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Tyr Ser
            20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR1 peptide

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR2 peptide

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      HCDR3 peptide

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      LCDR1 peptide

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      LCDR2 peptide

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      LCDR3 peptide

<400> SEQUENCE: 8

Met Gln Ala Leu Gln Thr Pro Tyr Thr
1               5
```

METHODS FOR TREATING OR PREVENTING ASTHMA BY ADMINISTERING AN IL-4R ANTAGONIST

RELATED APPLICATIONS

This application claims the benefit of priority of U.S. Provisional Application No. 61/943,019, filed Feb. 21, 2014, and U.S. Provisional Application No. 62/077,669, filed Nov. 10, 2014 and EP Application No. 14306413.7, filed Sep. 15, 2014. The contents of the aforementioned applications are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Feb. 20, 2015, is named 565200-SA9-134_SL.txt and is 4,167 bytes in size.

FIELD OF THE INVENTION

The invention relates to the treatment and/or prevention of asthma and related conditions. More specifically, the invention relates to the administration of an interleukin-4 receptor (IL-4R) antagonist to treat or prevent asthma in a patient in need thereof.

BACKGROUND

Asthma is a chronic inflammatory disease of the airways characterized by airway hyper responsiveness, acute and chronic bronchoconstriction, airway edema, and mucus plugging. The inflammation component of asthma is thought to involve many cell types, including mast cells, eosinophils, T lymphocytes, neutrophils, and epithelial cells, and their biological products. Patients with asthma most often present with symptoms of wheezing, shortness of breath, cough, and chest tightness. For most asthma patients, a regimen of controller therapy and bronchodilator therapy provides adequate long-term control. Inhaled corticosteroids (ICS) are considered the "gold standard" in controlling asthma symptoms, and inhaled beta2-agonists are the most effective bronchodilators currently available. Studies have shown that combination therapy of an ICS with an inhaled long-acting beta2-agonist (LABA) provides better asthma control than high doses of ICS alone. Consequently, combination therapy has been the recommended treatment for subjects who are not controlled on low doses of ICS alone.

Nonetheless, it is estimated that 5% to 10% of the population with asthma has symptomatic disease despite maximum recommended treatment with combinations of anti-inflammatory and bronchodilator drugs. Furthermore, this severe asthma population accounts for up to 50% of the total health cost through hospital admissions, use of emergency services, and unscheduled physician visits. There is an unmet need for a new therapy in this severe asthma population as many of these patients are poorly responsive to ICS due to a number of cellular and molecular mechanisms. In addition, the long term adverse effects of systemic and inhaled corticosteroids on bone metabolism, adrenal function, and growth in children lead to attempts to minimize the amount of corticosteroid usage. Although a large portion of asthma patients are managed reasonably well with current treatments, patients with severe corticosteroid-refractory asthma have few therapeutic treatment options that can adequately control the disease. The consequence of unresponsiveness to therapy or lack of compliance with therapy is loss of asthma control and ultimately asthma exacerbation.

Accordingly, a need exists in the art for novel targeted therapies for the treatment and/or prevention of asthma.

BRIEF SUMMARY OF THE INVENTION

According to one aspect, methods are provided for treating asthma in a subject in need thereof.

In another aspect, methods are provided for increasing the forced expiratory volume in 1 second (FEV1) in liters in a subject in need thereof.

In another aspect, methods are provided for reducing asthma-related exacerbation events in a subject in need thereof.

In yet another aspect, methods are provided for improving one or more asthma-associated parameter(s) in a subject in need thereof.

In a further aspect, methods are provided for reducing or eliminating an asthma patient's dependence on inhaled corticosteroids and/or long-acting beta-agonists for the treatment of one or more asthma exacerbations.

The methods featured in the invention comprise administering to a subject a therapeutically effective amount of a pharmaceutical composition comprising an interleukin-4 receptor IL-4R antagonist. According to certain embodiments, the IL-4R antagonist is an antibody or antigen-binding fragment thereof that specifically binds IL-4R. Exemplary anti-IL-4R antibodies that can be used in the context of the methods featured in the invention are described elsewhere herein. For example, in one embodiment, the IL-4R antagonist is an antibody or antigen-binding fragment thereof that specifically binds to an IL-4R, and comprises the heavy chain and light chain (Complementarity Determining Region) CDR sequences from the Heavy Chain Variable Region (HCVR) and Light Chain Variable Region (LCVR) of SEQ ID NOs:1 and 2, respectively.

The invention also includes an IL-4R antagonist as disclosed herein for use in the manufacture of a medicament for the treatment and/or prevention of asthma or for treating any of the other indications or conditions disclosed herein.

The invention also includes an IL-4R antagonist as disclosed herein for use in the treatment and/or prevention of asthma or for treating and/or prevention of any of the other indications or conditions disclosed herein.

An embodiment includes a method for treating moderate to severe uncontrolled asthma in a subject in need thereof comprising administering to the subject a combination therapy comprising: i) one or more maintenance doses of an inhaled corticosteroid (ICS), ii) one or more maintenance doses of a long-acting beta$_2$-adrenergic agonist (LABA), iii) a loading dose of about 400 to about 600 mg of an interleukin-4 receptor IL-4R antagonist, and iv) one or more maintenance doses of about 200 to about 300 mg of the IL-4R antagonist, wherein the ICS and LABA are administered for the duration of administration of the IL-4R antagonist.

In certain aspects, the IL-4R antagonist is an antibody or an antigen-binding fragment thereof that specifically binds to IL-4R. In further certain aspects, the antibody or antigen-binding fragment thereof that specifically binds to IL-4R comprises heavy and light chain CDR sequences from the HCVR/LCVR sequence pair comprising SEQ ID NOs: 1/2. In further certain aspects, the antibody or antigen-binding fragment thereof that specifically binds to IL-4R comprises three heavy chain complementarity determining region (HCDR) sequences comprising SEQ ID NOs: 3, 4, and 5, respectively, and three light chain complementarity determining (LCDR) sequences comprising SEQ ID NOs: 6, 7, and 8, respectively. In further certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In yet further certain aspects, the antibody is dupilumab. In yet further certain aspects, the antibody has the CAS number 1190264-60-8.

In certain aspects, the one or more maintenance doses are administered every other week (q2w). In other aspects, the one or more maintenance doses are administered every fourth week (q4w).

In certain aspects, the loading dose comprises 600 mg of the antibody or antigen-binding fragment thereof, and the one or more maintenance doses comprises 300 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 400 mg of the antibody or antigen-binding fragment thereof, and the one or more maintenance dose comprises 200 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 600 mg of the antibody or antigen-binding fragment thereof, and the one or more maintenance doses comprises 300 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 400 mg of the antibody or antigen-binding fragment thereof, and the one or more maintenance doses comprises 200 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the antibody or antigen-binding fragment thereof is administered to the subject systemically, subcutaneously, intravenously, or intranasally.

In certain aspects, the subject has a blood eosinophil count selected from the group consisting of: greater than or equal to 300 cells/μL, 200 to 299 cells/μL; and less than 200 cells/μL.

In certain aspects, the ICS is selected from the group consisting of: mometasone furoate, budesonide, and fluticasone propionate. In certain aspects, the LABA is selected from the group consisting of: formoterol and salmeterol. In further aspects, the ICS is mometasone furoate, and the LABA is formoterol. In yet further aspects, the ICS is budesonide, and the LABA is formoterol. In even yet further aspects, the ICS is fluticasone propionate, and the LABA is salmeterol.

In certain aspects, the subject is selected from the group consisting of: a subject age 18 years of age or older, a subject age 12 to <18 years old, a subject age 6 to <12 years old, and a subject age 2 to <6 years old.

In certain aspects, the subject has moderate to severe, uncontrolled asthma for greater than or equal to 12 months, based on the Global Initiative for Asthma (GINA) 2009 Guidelines, and one or more of the following criteria: i) Existing treatment with moderate- or high-dose ICS/LABA (2 fluticasone propionate 250 μg twice daily or equipotent ICS daily dosage) with a stable dose of ICS/LABA for greater than or equal to 1 month prior to administration of the loading dose of IL-4R antagonist; ii) Forced expiratory volume (FEV1) 40 to 80% predicted normal prior to administration of the loading dose of IL-4R antagonist; iii) Juniper Asthma Control Questionnaire, 5-question version (ACQ-5) score greater than or equal to 1.5 prior to administration of the loading dose of IL-4R antagonist; iv) Reversibility of at least 12% and 200 mL in FEV1 after 200 μg to 400 μg (2 to 4 inhalations) of salbutamol/albuterol prior to administration of the loading dose of IL-4R antagonist; or v) Has experienced, within 1 year prior to administration of the loading dose of IL-4R antagonist, any of the following events: a) Treatment with greater than or equal to 1 systemic (oral or parenteral) steroid bursts for worsening asthma, b) Hospitalization or an emergency/urgent medical care visit for worsening asthma.

In certain aspects, the antibody or an antigen-binding fragment thereof that specifically binds to IL-4R is administered in a formulation comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or an antigen-binding fragment thereof that specifically binds to IL-4R is administered in a formulation comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or antigen-binding fragment thereof comprises an HCVR comprising the amino acid sequence of SEQ ID NO: 1 and an LCVR comprising the amino acid sequence of SEQ ID NO: 2.

An embodiment includes a method for increasing the forced expiratory volume in 1 second (FEV1) in liters in a subject in need thereof comprising administering to the subject a combination therapy comprising: i) one or more maintenance doses of an ICS, ii) one or more maintenance doses of a LABA, iii) a loading dose of about 400 to about 600 mg of an IL-4R antagonist, and iv) one or more maintenance doses of about 200 to about 300 mg of the IL-4R antagonist, wherein the ICS and LABA are administered for the duration of administration of the IL-4R antagonist.

In certain aspects, the IL-4R antagonist is an antibody or an antigen-binding fragment thereof that specifically binds to IL-4R. In further certain aspects, the antibody or antigen-binding fragment thereof that specifically binds to IL-4R comprises heavy and light chain CDR sequences from the HCVR/LCVR sequence pair comprising SEQ ID NOs: 1/2. In further certain aspects, the antibody or antigen-binding fragment thereof that specifically binds to IL-4R comprises three HCDR sequences comprising SEQ ID NOs: 3, 4, and 5, respectively, and three light chain complementarity determining (LCDR) sequences comprising SEQ ID NOs: 6, 7, and 8, respectively. In further certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In yet further certain aspects, the antibody is dupilumab.

In certain aspects, the one or more maintenance doses are administered every other week (q2w). In other aspects, the one or more maintenance doses are administered every fourth week (q4w).

In certain aspects, the loading dose comprises 600 mg of the antibody or antigen-binding fragment thereof, and the one or more maintenance doses comprises 300 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the loading dose comprises 400 mg of the antibody or antigen-binding fragment thereof, and the one or more maintenance dose comprises 200 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the loading dose comprises 600 mg of the antibody or antigen-binding fragment thereof, and the one or more maintenance doses comprises 300 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the loading dose comprises 400 mg of the antibody or antigen-binding fragment thereof, and the one or more maintenance doses comprises 200 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the antibody or antigen-binding fragment thereof is administered to the subject systemically, subcutaneously, intravenously, or intranasally.

In certain aspects, the subject has a blood eosinophil count selected from the group consisting of: greater than or equal to 300 cells/µL, 200 to 299 cells/µL; and less than 200 cells/µL.

In certain aspects, the ICS is selected from the group consisting of: mometasone furoate, budesonide, and fluticasone propionate. In certain aspects, the LABA is selected from the group consisting of: formoterol and salmeterol. In further aspects, the ICS is mometasone furoate, and the LABA is formoterol. In yet further aspects, the ICS is budesonide, and the LABA is formoterol. In yet even further aspects, the ICS is fluticasone propionate, and the LABA is salmeterol.

In certain aspects, the subject is selected from the group consisting of: a subject age 18 years of age or older, a subject age 12 to <18 years old, a subject age 6 to <12 years old, and a subject age 2 to <6 years old.

In certain aspects, the subject has moderate to severe, uncontrolled asthma for greater than or equal to 12 months, based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of IL-4R antagonist; ii) FEV1 40 to 80% predicted normal prior to administration of the loading dose of IL-4R antagonist; iii) ACQ-5 score greater than or equal to 1.5 prior to administration of the loading dose of IL-4R antagonist; iv) Reversibility of at least 12% and 200 mL in FEV1 after 200 µg to 400 µg (2 to 4 inhalations) of salbutamol/albuterol prior to administration of the loading dose of IL-4R antagonist; or v) Has experienced, within 1 year prior to administration of the loading dose of IL-4R antagonist, any of the following events: a) Treatment with greater than or equal to 1 systemic (oral or parenteral) steroid bursts for worsening asthma, b) Hospitalization or an emergency/urgent medical care visit for worsening asthma.

In certain aspects, the antibody or an antigen-binding fragment thereof that specifically binds to IL-4R is administered in a formulation comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or an antigen-binding fragment thereof that specifically binds to IL-4R is administered in a formulation comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or antigen-binding fragment thereof comprises an HCVR comprising the amino acid sequence of SEQ ID NO: 1 and an LCVR comprising the amino acid sequence of SEQ ID NO: 2.

An embodiment includes a method for improving one or more asthma-associated parameter(s) in a subject in need thereof comprising administering to the subject a combination therapy comprising: i) one or more maintenance doses of an ICS, ii) one or more maintenance doses of a LABA, iii)

a loading dose of about 400 to about 600 mg of an IL-4R antagonist, and iv) one or more maintenance doses of about 200 to about 300 mg of the IL-4R antagonist, wherein the ICS and LABA are administered for the duration of administration of the IL-4R antagonist.

In certain aspects, the IL-4R antagonist is an antibody or an antigen-binding fragment thereof that specifically binds to IL-4R. In further certain aspects, the antibody or antigen-binding fragment thereof that specifically binds to IL-4R comprises heavy and light chain CDR sequences from the HCVR/LCVR sequence pair comprising SEQ ID NOs: 1/2. In further certain aspects, the antibody or antigen-binding fragment thereof that specifically binds to IL-4R comprises three HCDR sequences comprising SEQ ID NOs: 3, 4, and 5, respectively, and three light chain complementarity determining (LCDR) sequences comprising SEQ ID NOs: 6, 7, and 8, respectively. In further certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In yet further certain aspects, the antibody is dupilumab.

In certain aspects, the one or more maintenance doses are administered every other week (q2w). In other aspects, the one or more maintenance doses are administered every fourth week (q4w).

In certain aspects, the loading dose comprises 600 mg of the antibody or antigen-binding fragment thereof, and the one or more maintenance doses comprises 300 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the loading dose comprises 400 mg of the antibody or antigen-binding fragment thereof, and the one or more maintenance dose comprises 200 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the loading dose comprises 600 mg of the antibody or antigen-binding fragment thereof, and the one or more maintenance doses comprises 300 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the loading dose comprises 400 mg of the antibody or antigen-binding fragment thereof, and the one or more maintenance doses comprises 200 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/µL, 200 to 299 cells/µL; and less than 200 cells/µL.

In certain aspects, the antibody or antigen-binding fragment thereof is administered to the subject systemically, subcutaneously, intravenously, or intranasally.

In certain aspects, the subject has a blood eosinophil count selected from the group consisting of: greater than or equal to 300 cells/µL, 200 to 299 cells/µL; and less than 200 cells/µL.

In certain aspects, the ICS is selected from the group consisting of: mometasone furoate, budesonide, and fluticasone propionate. In certain aspects, the LABA is selected from the group consisting of: formoterol and salmeterol. In further aspects, the ICS is mometasone furoate, and the LABA is formoterol. In yet further aspects, the ICS is budesonide, and the LABA is formoterol. In yet even further aspects, the ICS is fluticasone propionate, and the LABA is salmeterol.

In certain aspects, the subject is selected from the group consisting of: a subject age 18 years of age or older, a subject age 12 to <18 years old, a subject age 6 to <12 years old, and a subject age 2 to <6 years old.

In certain aspects, the subject has moderate to severe, uncontrolled asthma for greater than or equal to 12 months, based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of IL-4R antagonist; ii) FEV1 40 to 80% predicted normal prior to administration of the loading dose of IL-4R antagonist; iii) ACQ-5 score greater than or equal to 1.5 prior to administration of the loading dose of IL-4R antagonist; iv) Reversibility of at least 12% and 200 mL in FEV1 after 200 µg to 400 µg (2 to 4 inhalations) of salbutamol/albuterol prior to administration of the loading dose of IL-4R antagonist; or v) Has experienced, within 1 year prior to administration of the loading dose of IL-4R antagonist, any of the following events: a) Treatment with greater than or equal to 1 systemic (oral or parenteral) steroid bursts for worsening asthma, b) Hospitalization or an emergency/urgent medical care visit for worsening asthma.

In certain aspects, the antibody or an antigen-binding fragment thereof that specifically binds to IL-4R is administered in a formulation comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or an antigen-binding fragment thereof that specifically binds to IL-4R is administered in a formulation comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or antigen-binding fragment thereof comprises an HCVR comprising the amino acid sequence of SEQ ID NO: 1 and an LCVR comprising the amino acid sequence of SEQ ID NO: 2.

In certain aspects, the one or more asthma-associated parameter(s) is selected from the group consisting of: (1)

relative percent change from baseline at week 12 in forced expiratory volume in 1 second (FEV1); (2) annualized rate of loss of asthma control events during the treatment period; (3) annualized rate of severe exacerbation events during the treatment period; (4) time to loss of asthma control events during the treatment period; (5) time to severe exacerbation events during the treatment period; (6) time to loss of asthma control events during overall study period; (7) time to severe exacerbation events during overall study period; (8) health care resource utilization; (9) change from baseline at week 12 in: i) morning and evening asthma symptom scores,
  ii) ACQ-5 score, iii) AQLQ score, iv) morning and evening PEF, v) number of inhalations/day of salbutamol/albuterol or levosalbutamol/levalbuterol for symptom relief, vi) nocturnal awakenings; (10) change from baseline at week 12 and week 24 in: i) 22-item Sino Nasal Outcome Test (SNOT-22), ii) Hospital Anxiety and Depression Score (HADS), iii) EuroQual questionnaire (EQ-5D-3L or EQ-5D-5L).

In certain aspects, the loss of asthma control (LOAC) event is defined as: i) greater than or equal to 6 additional reliever puffs of salbutamol/albuterol or levosalbutamol/levalbuterol in a 24 hour period compared to baseline on 2 consecutive days, or ii) an increase in corticosteroid greater than or equal to 4 times the dose at visit 2, or iii) use of systemic corticosteroids for greater than or equal to 3 days, or iv) hospitalization or emergency room visit because of asthma, requiring systemic corticosteroids.

In certain aspects, the severe exacerbation event is defined as: i) use of systemic corticosteroids for greater than or equal to 3 days, or ii) hospitalization or emergency room visit because of asthma, requiring systemic corticosteroids.

An embodiment includes a method for reducing an asthma patient's dependence on inhaled corticosteroids (ICS) and/or long-acting beta-agonists (LABA) for the treatment of one or more asthma exacerbations comprising: (a) selecting a patient who has moderate-to-severe asthma that is uncontrolled with a background asthma therapy comprising an ICS, a LABA, or a combination thereof; and (b) administering to the patient a combination therapy comprising: i) one or more maintenance doses of an ICS, ii) one or more maintenance doses of a LABA, iii) a loading dose of about 400 to about 600 mg of an IL-4R antagonist, and iv) one or more maintenance doses of about 200 to about 300 mg of the IL-4R antagonist, wherein the ICS and LABA are administered for the duration of administration of the IL-4R antagonist.

In certain aspects, the IL-4R antagonist is an antibody or an antigen-binding fragment thereof that specifically binds to IL-4R. In further certain aspects, the antibody or antigen-binding fragment thereof that specifically binds to IL-4R comprises heavy and light chain CDR sequences from the HCVR/LCVR sequence pair comprising SEQ ID NOs: 1/2. In further certain aspects, the antibody or antigen-binding fragment thereof that specifically binds to IL-4R comprises three HCDR sequences comprising SEQ ID NOs: 3, 4, and 5, respectively, and three light chain complementarity determining (LCDR) sequences comprising SEQ ID NOs: 6, 7, and 8, respectively. In further certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In yet further certain aspects, the antibody is dupilumab.

In certain aspects, the one or more maintenance doses are administered every other week (q2w). In other aspects, the one or more maintenance doses are administered every fourth week (q4w).

In certain aspects, the loading dose comprises 600 mg of the antibody or antigen-binding fragment thereof, and the one or more maintenance doses comprises 300 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 400 mg of the antibody or antigen-binding fragment thereof, and the one or more maintenance dose comprises 200 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 600 mg of the antibody or antigen-binding fragment thereof, and the one or more maintenance doses comprises 300 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 400 mg of the antibody or antigen-binding fragment thereof, and the one or more maintenance doses comprises 200 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the antibody or antigen-binding fragment thereof is administered to the subject systemically, subcutaneously, intravenously, or intranasally.

In certain aspects, the subject has a blood eosinophil count selected from the group consisting of: greater than or equal to 300 cells/μL, 200 to 299 cells/μL; and less than 200 cells/μL.

In certain aspects, the ICS is selected from the group consisting of: mometasone furoate, budesonide, and fluticasone propionate. In certain aspects, the LABA is selected from the group consisting of: formoterol and salmeterol. In further aspects, the ICS is mometasone furoate, and the LABA is formoterol. In yet further aspects, the ICS is budesonide, and the LABA is formoterol. In even yet further aspects, the ICS is fluticasone propionate, and the LABA is salmeterol.

In certain aspects, the patient is selected from the group consisting of: a subject age 18 years of age or older, a subject age 12 to <18 years old, a subject age 6 to <12 years old, and a subject age 2 to <6 years old.

In certain aspects, the patient has moderate to severe, uncontrolled asthma for greater than or equal to 12 months, based on the Global Initiative for Asthma (GINA) 2009

Guidelines, and one or more of the following criteria: i) Existing treatment with moderate- or high-dose ICS/LABA (2 fluticasone propionate 250 μg twice daily or equipotent ICS daily dosage) with a stable dose of ICS/LABA for greater than or equal to 1 month prior to administration of the loading dose of IL-4R antagonist; ii) FEV1 40 to 80% predicted normal prior to administration of the loading dose of IL-4R antagonist; iii) ACQ-5 score greater than or equal to 1.5 prior to administration of the loading dose of IL-4R antagonist; iv) Reversibility of at least 12% and 200 mL in FEV1 after 200 μg to 400 μg (2 to 4 inhalations) of salbutamol/albuterol prior to administration of the loading dose of IL-4R antagonist; or v) Has experienced, within 1 year prior to administration of the loading dose of IL-4R antagonist, any of the following events: a) Treatment with greater than or equal to 1 systemic (oral or parenteral) steroid bursts for worsening asthma, b) Hospitalization or an emergency/urgent medical care visit for worsening asthma.

In certain aspects, the antibody or an antigen-binding fragment thereof that specifically binds to IL-4R is administered in a formulation comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or an antigen-binding fragment thereof that specifically binds to IL-4R is administered in a formulation comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or antigen-binding fragment thereof comprises an HCVR comprising the amino acid sequence of SEQ ID NO: 1 and an LCVR comprising the amino acid sequence of SEQ ID NO: 2.

An embodiment includes a method for treating moderate to severe uncontrolled asthma in a subject in need thereof comprising administering to the subject a combination therapy comprising: i) one or more maintenance doses of an ICS, ii) one or more maintenance doses of a LABA, iii) a loading dose of about 400 to about 600 mg of an IL-4R antagonist, and iv) one or more maintenance doses of about 200 to about 300 mg of the IL-4R antagonist, wherein the ICS and LABA are administered for the duration of administration of the IL-4R antagonist, wherein the subject has a blood eosinophil count selected from the group consisting of: greater than or equal to 300 cells/μL, 200 to 299 cells/μL; and less than 200 cells/μL.

In certain aspects, the IL-4R antagonist is an antibody or an antigen-binding fragment thereof that specifically binds to IL-4R. In further certain aspects, the antibody or antigen-binding fragment thereof that specifically binds to IL-4R comprises heavy and light chain CDR sequences from the HCVR/LCVR sequence pair comprising SEQ ID NOs: 1/2. In further certain aspects, the antibody or antigen-binding fragment thereof that specifically binds to IL-4R comprises three HCDR sequences comprising SEQ ID NOs: 3, 4, and 5, respectively, and three light chain complementarity determining (LCDR) sequences comprising SEQ ID NOs: 6, 7, and 8, respectively. In further certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In yet further certain aspects, the antibody is dupilumab.

In certain aspects, the one or more maintenance doses are administered every other week (q2w). In other aspects, the one or more maintenance doses are administered every fourth week (q4w).

In certain aspects, the loading dose comprises 600 mg of the antibody or antigen-binding fragment thereof, and the one or more maintenance doses comprises 300 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 400 mg of the antibody or antigen-binding fragment thereof, and the one or more maintenance dose comprises 200 mg of the antibody or antigen-binding fragment thereof administered every other week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 600 mg of the antibody or antigen-binding fragment thereof, and the one or more maintenance doses comprises 300 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the loading dose comprises 400 mg of the antibody or antigen-binding fragment thereof, and the one or more maintenance doses comprises 200 mg of the antibody or antigen-binding fragment thereof administered every fourth week. In further aspects, the one or more maintenance doses are administered for at least 24 weeks. In yet further aspects, the subject has a blood eosinophil count selected from the group consisting of: greater than or equal to 300 cells/μL, 200 to 299 cells/μL; and less than 200 cells/μL.

In certain aspects, the antibody or antigen-binding fragment thereof is administered to the subject systemically, subcutaneously, intravenously, or intranasally.

In certain aspects, the ICS is selected from the group consisting of: mometasone furoate, budesonide, and fluticasone propionate. In certain aspects, the LABA is selected from the group consisting of: formoterol and salmeterol. In further aspects, the ICS is mometasone furoate, and the LABA is formoterol. In yet further aspects, the ICS is budesonide, and the LABA is formoterol. In even yet further aspects, the ICS is fluticasone propionate, and the LABA is salmeterol.

In certain aspects, the subject is selected from the group consisting of: a subject age 18 years of age or older, a subject age 12 to <18 years old, a subject age 6 to <12 years old, and a subject age 2 to <6 years old.

In certain aspects, the subject has moderate to severe, uncontrolled asthma for greater than or equal to 12 months, based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of IL-4R antagonist; ii) FEV1 40 to 80% predicted normal prior to administration of the loading dose of IL-4R antagonist; iii) ACQ-5 score greater than or equal to 1.5 prior to administration of the loading dose of IL-4R antagonist; iv) Reversibility of at least 12% and 200 mL in FEV1 after 200 µg to 400 µg (2 to 4 inhalations) of salbutamol/albuterol prior to administration of the loading dose of IL-4R antagonist; or v) Has experienced, within 1 year prior to administration of the loading dose of IL-4R antagonist, any of the following events: a) Treatment with greater than or equal to 1 systemic (oral or parenteral) steroid bursts for worsening asthma, b) Hospitalization or an emergency/urgent medical care visit for worsening asthma.

In certain aspects, the antibody or an antigen-binding fragment thereof that specifically binds to IL-4R is administered in a formulation comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or an antigen-binding fragment thereof that specifically binds to IL-4R is administered in a formulation comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, and wherein the pH of the formulation is about 5.9. In further aspects, the viscosity of the formulation is about 8.5 cPoise.

In certain aspects, the antibody or antigen-binding fragment thereof comprises an HCVR comprising the amino acid sequence of SEQ ID NO: 1 and an LCVR comprising the amino acid sequence of SEQ ID NO: 2.

An embodiment includes an IL-4R antagonist for use in the treatment and/or prevention of asthma and related conditions.

An embodiment includes a pharmaceutical composition comprising an anti-IL4R antibody antagonist or an antigen binding fragment thereof for use in the treatment and/or prevention of asthma and related conditions.

An embodiment includes a formulation comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, and wherein the pH of the formulation is about 5.9. In certain aspects, the viscosity of the formulation is about 8.5 cPoise. In certain aspects, the antibody or antigen-binding fragment thereof comprises an HCVR comprising the amino acid sequence of SEQ ID NO: 1 and an LCVR comprising the amino acid sequence of SEQ ID NO: 2.

An embodiment includes a formulation comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, and wherein the pH of the formulation is about 5.9. In certain aspects, the viscosity of the formulation is about 8.5 cPoise. In certain aspects, the antibody or antigen-binding fragment thereof comprises an HCVR comprising the amino acid sequence of SEQ ID NO: 1 and an LCVR comprising the amino acid sequence of SEQ ID NO: 2.

An embodiment includes a method for treating moderate to severe uncontrolled asthma in a subject in need thereof, wherein said subject has a low or moderate blood eosinophil level, comprising administering to the subject a therapy comprising a loading dose of about 400 to about 600 mg of an IL-4R antagonist, and one or more maintenance doses of about 200 to about 300 mg of the IL-4R antagonist.

In certain aspects, the subject has a blood eosinophil count between about 200 cells/µL and about 299 cells/µL or the subject has a blood eosinophil count of less than about 200 cells/µL.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, one or more maintenance doses are administered q2w or q4w. In certain aspects, the loading dose comprises 600 mg of the antibody or antigen-binding fragment thereof, and the one or more maintenance doses comprises 300 mg of the antibody or antigen-binding fragment thereof administered q4w. In certain aspects, the loading dose comprises 600 mg of the antibody or antigen-binding fragment thereof, and the one or more maintenance doses comprises 300 mg of the antibody or antigen-binding fragment thereof administered q2w. In certain aspects, the loading dose comprises 400 mg of the antibody or antigen-binding fragment thereof, and the one or more maintenance doses comprises 200 mg of the antibody or antigen-binding fragment thereof administered q4w. In certain aspects, the loading dose comprises 400 mg of the antibody or antigen-binding fragment thereof, and the one or more maintenance doses comprises 200 mg of the antibody or antigen-binding fragment thereof administered q2w. In certain aspects, one or more maintenance doses are administered for at least 24 weeks.

In certain aspects, a subject has an elevated level of one or more biomarkers selected from the group consisting of: periostin, *thymus* and Activation Regulated Chemokine (TARC), Dipeptidyl Peptidase 4 (DPP4), Eosinophil Cationic Protein (ECP), Eotaxin-3, total IgE, antigen-specific IgE, and Fractional exhaled Nitric Oxide (FeNO).

An embodiment includes a method for treating moderate to severe uncontrolled asthma in a subject in need thereof, wherein said subject is between about 12 and about 75 years of age, comprising administering to the subject a therapy comprising a loading dose of about 400 to about 600 mg of an IL-4R antagonist, and one or more maintenance doses of about 200 to about 300 mg of the IL-4R antagonist.

In certain aspects, the subject has a blood eosinophil count between about 200 cells/μL and about 299 cells/μL or has a blood eosinophil count of less than about 200 cells/μL.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, one or more maintenance doses are administered q2w or q4w. In certain aspects, the loading dose comprises 600 mg of the antibody or antigen-binding fragment thereof, and the one or more maintenance doses comprises 300 mg of the antibody or antigen-binding fragment thereof administered q4w. In certain aspects, the loading dose comprises 600 mg of the antibody or antigen-binding fragment thereof, and the one or more maintenance doses comprises 300 mg of the antibody or antigen-binding fragment thereof administered q2w. In certain aspects, the loading dose comprises 400 mg of the antibody or antigen-binding fragment thereof, and the one or more maintenance doses comprises 200 mg of the antibody or antigen-binding fragment thereof administered q4w. In certain aspects, the loading dose comprises 400 mg of the antibody or antigen-binding fragment thereof, and the one or more maintenance doses comprises 200 mg of the antibody or antigen-binding fragment thereof administered q2w. In certain aspects, one or more maintenance doses are administered for at least 24 weeks.

In certain aspects, a subject has an elevated level of one or more biomarkers selected from the group consisting of: eosinophil (Eos), periostin, TARC, DPP4, ECP, Eotaxin-3, total IgE, antigen-specific IgE, and FeNO.

An embodiment includes a method for treating moderate to severe uncontrolled asthma in a subject in need thereof, comprising administering to the subject a combination therapy comprising one or more oral doses of prednisone, a loading dose of about 400 to about 600 mg of an IL-4R antagonist, and one or more maintenance doses of about 200 to about 300 mg of the IL-4R antagonist.

In certain aspects, one or more oral doses of up to about 10 mg prednisone each are administered. In certain aspects, one or more oral doses of up to about 5 mg prednisone each are administered. In certain aspects, one or more oral doses of prednisone are daily doses. In certain aspects, the subject has a blood eosinophil count between about 200 and about 299 cells/μL. In certain aspects, the subject has a blood eosinophil count of less than about 200 cells/μL.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, one or more maintenance doses are administered q2w or q4w. In certain aspects, the loading dose comprises 600 mg of the antibody or antigen-binding fragment thereof, and the one or more maintenance doses comprises 300 mg of the antibody or antigen-binding fragment thereof administered q4w. In certain aspects, the loading dose comprises 600 mg of the antibody or antigen-binding fragment thereof, and the one or more maintenance doses comprises 300 mg of the antibody or antigen-binding fragment thereof administered q2w. In certain aspects, the loading dose comprises 400 mg of the antibody or antigen-binding fragment thereof, and the one or more maintenance doses comprises 200 mg of the antibody or antigen-binding fragment thereof administered q4w. In certain aspects, the loading dose comprises 400 mg of the antibody or antigen-binding fragment thereof, and the one or more maintenance doses comprises 200 mg of the antibody or antigen-binding fragment thereof administered q2w. In certain aspects, one or more maintenance doses are administered for at least 24 weeks.

In certain aspects, a subject has an elevated level of one or more biomarkers selected from the group consisting of: Eos, periostin, TARC, DPP4, ECP, Eotaxin-3, total IgE, antigen-specific IgE, and FeNO.

An embodiment includes a method for reducing the incidence of one or more asthma exacerbations in a subject in need thereof, comprising administering to the subject a combination therapy comprising one or more maintenance doses of an ICS, one or more maintenance doses of a second controller, a loading dose of about 400 to about 600 mg of an IL-4R antagonist, and one or more maintenance doses of about 200 to about 300 mg of the IL-4R antagonist, wherein the ICS and second asthma controller are administered for the duration of administration of the IL-4R antagonist.

In certain aspects, the asthma exacerbation is selected from the group consisting of a 30% or greater reduction from baseline in morning peak expiratory flow (PEF) on two consecutive days, six or more additional reliever puffs of albuterol or levalbuterol in a 24 hour period (compared to baseline) on two consecutive days, and a deterioration of asthma requiring systemic (oral and/or parenteral) steroid treatment, or an increase in inhaled corticosteroids to at least 4 times the last dose received prior to discontinuation, or hospitalization.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

An embodiment includes a method for improving FEV1 in a subject in need thereof, comprising administering to the subject a therapeutically effective amount of a pharmaceutical composition comprising a loading dose of about 400 to about 600 mg of an IL-4R antagonist, and a pharmaceutical composition comprising one or more maintenance doses of about 200 to about 300 mg of the IL-4R antagonist.

In certain aspects, the improvement in an asthma-associated parameter is an increase of FEV1 from baseline of at least 0.10 L.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

An embodiment includes a method for reducing the incidence of one or more asthma exacerbations in a subject in need thereof, wherein said subject has a low or moderate blood eosinophil level and/or wherein said subject is between about 12 and about 75 years of age, comprising administering to the subject a therapy comprising a loading dose of about 400 to about 600 mg of an IL-4R antagonist, and one or more maintenance doses of about 200 to about 300 mg of the IL-4R antagonist.

In certain aspects, the asthma exacerbation is selected from the group consisting of a 30% or greater reduction from baseline in morning peak expiratory flow (PEF) on two consecutive days, six or more additional reliever puffs of albuterol or levalbuterol in a 24 hour period (compared to baseline) on two consecutive days, and a deterioration of asthma requiring systemic (oral and/or parenteral) steroid treatment, or an increase in inhaled corticosteroids to at least 4 times the last dose received prior to discontinuation, or hospitalization.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

An embodiment includes a method for improving FEV1 in a subject in need thereof, wherein said subject has a low or moderate blood eosinophil level and/or wherein said subject is between 12-75 year of age, comprising administering to the subject a therapeutically effective amount of a pharmaceutical composition comprising a loading dose of about 400 to about 600 mg of an IL-4R antagonist, and a pharmaceutical composition comprising one or more maintenance doses of about 200 to about 300 mg of the IL-4R antagonist.

In certain aspects, the improvement in an asthma-associated parameter is an increase of FEV1 from baseline of at least 0.10 L.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

An embodiment includes a method for treating moderate to severe uncontrolled asthma in a subject in need thereof, wherein said subject has a low or moderate blood eosinophil level and/or wherein said subject is between 12-75 year of age, comprising administering to the subject a combination therapy comprising one or more maintenance doses of an ICS, one or more maintenance doses of a second asthma controller, a loading dose of about 400 to about 600 mg of an IL-4R antagonist, and one or more maintenance doses of about 200 to about 300 mg of the IL-4R antagonist, wherein the ICS and second asthma controller are administered for the duration of administration of the IL-4R antagonist.

In certain aspects, the one or more maintenance doses of ICS are medium-to-high doses. In certain aspects, the subject has a blood eosinophil count between about 200 and about 299 cells/µL. In certain aspects, subject has a blood eosinophil count of less than about 200 cells/µL.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

An embodiment includes a method for treating moderate to severe uncontrolled asthma in a subject in need thereof, comprising administering to the subject a combination therapy comprising one or more oral doses of prednisone, one or more maintenance doses of an ICS, one or more maintenance doses of a second inhaled asthma controller, a loading dose of about 400 to about 600 mg of an IL-4R antagonist, and one or more maintenance doses of about 200 to about 300 mg of the IL-4R antagonist, wherein the ICS and second inhaled asthma controller are administered for the duration of administration of the IL-4R antagonist.

In certain aspects, the one or more maintenance doses of ICS are medium-to-high doses. In certain aspects, one or more oral doses of up to about 10 mg prednisone each are administered. In certain aspects, one or more oral doses of up to about 5 mg prednisone each are administered. In certain aspects, one or more oral doses of prednisone are daily doses.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

An embodiment includes a method for treating moderate to severe uncontrolled asthma in a subject in need thereof, wherein said subject is between about 12 and about 17 years of age, comprising administering to the subject a therapy comprising a loading dose of about 400 to about 600 mg of an IL-4R antagonist, and one or more maintenance doses of about 200 to about 300 mg of the IL-4R antagonist.

In certain aspects, the subject has a blood eosinophil count between about 200 cells/µL and about 299 cells/µL, or less than about 200 cells/µL.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, the one or more maintenance doses are administered q4w. In certain aspects, the one or more maintenance doses are administered for at least 24 weeks. In certain aspects, the loading dose comprises 600 mg of the antibody or antigen-binding fragment thereof, and the one or more maintenance doses comprises 300 mg of the antibody or antigen-binding fragment thereof administered q4w, and, optionally, the one or more maintenance doses are administered for at least 24 weeks. In certain aspects, the loading dose comprises 600 mg of the antibody or antigen-binding fragment thereof, and the one or more maintenance doses comprises 300 mg of the antibody or antigen-binding fragment thereof administered q2w and, optionally, the one or more maintenance doses are administered for at least 24 weeks. In certain aspects, the loading dose comprises 400 mg of the antibody or antigen-binding fragment thereof, and the one or more maintenance doses comprises 200 mg of the antibody or antigen-binding fragment thereof administered q4w and, optionally, the one or more maintenance doses are administered for at least 24 weeks. In certain aspects, the loading dose comprises 400 mg of the antibody or antigen-binding fragment thereof, and the one or more maintenance doses comprises 200 mg of the antibody or antigen-binding fragment thereof administered q2w and, optionally, the one or more maintenance doses are administered for at least 24 weeks.

In certain aspects, the subject has an elevated level of one or more biomarkers selected from the group consisting of: eosinophil (Eos), periostin, TARC, DPP4, ECP, Eotaxin-3, total IgE, antigen-specific IgE, and FeNO.

An embodiment includes a method for treating moderate to severe uncontrolled asthma in a subject in need thereof comprising administering to the subject a combination therapy comprising one or more maintenance doses of an inhaled corticosteroid (ICS), one or more maintenance doses of a long-acting beta$_2$-adrenergic agonist (LABA), a loading dose of about 4 mg/kg of an interleukin-4 receptor (IL-4R) antagonist, and one or more maintenance doses of about 2 mg/kg of the IL-4R antagonist, wherein the ICS and LABA are administered for the duration of administration of the IL-4R antagonist.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the Heavy Chain variable region (HCVR)/Light Chain Variable Region (LCVR) sequence pair comprising SEQ ID NOs: 1/2. In certain aspects, the antibody or antigen-binding fragment thereof that specifically binds to IL-4R comprises three Heavy chain Complementarity Determining Region (HCDR) sequences comprising SEQ ID NOs: 3, 4, and 5, respectively, and three Light chain Complementarity determining Region (LCDR) sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, the one or more maintenance doses are administered every other week (q2w) or are administered every fourth week (q4w).

An embodiment includes a method for treating moderate to severe uncontrolled asthma in a subject in need thereof, wherein said subject has a low or moderate blood eosinophil level, comprising administering to the subject a therapy comprising a loading dose of about 4 mg/kg of an IL-4R antagonist, and one or more maintenance doses of about 2 mg/kg of the IL-4R antagonist.

In certain aspects, the subject has a blood eosinophil count between about 200 cells/µL and about 299 cells/µL. In certain aspects, the subject has a blood eosinophil count of less than about 200 cells/µL.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the HCVR/LCVR sequence pair comprising SEQ ID NOs: 1/2. In certain aspects, the antibody or antigen-binding fragment thereof that specifically binds to IL-4R comprises three HCDR sequences comprising SEQ ID NOs: 3, 4, and 5, respectively, and three LCDR sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, the one or more maintenance doses are administered q2w. In certain aspects, the one or more maintenance doses are administered q4w.

An embodiment includes a method for treating persistent asthma in a subject in need thereof comprising administering to the subject a combination therapy comprising one or more maintenance doses of an inhaled corticosteroid (ICS), one or more maintenance doses of a long-acting beta$_2$-adrenergic agonist (LABA), a loading dose of about 400 to about 600 mg of an interleukin-4 receptor (IL-4R) antagonist, and one or more maintenance doses of about 200 to about 300 mg of the IL-4R antagonist, wherein the ICS and LABA are administered for the duration of administration of the IL-4R antagonist.

In certain aspects, the IL-4R antagonist is an antibody or an antigen-binding fragment thereof that specifically binds to IL-4R. In certain aspects, the antibody or antigen-binding fragment thereof that specifically binds to IL-4R comprises heavy and light chain CDR sequences from the Heavy Chain variable region (HCVR)/Light Chain Variable Region (LCVR) sequence pair comprising SEQ ID NOs: 1/2. In certain aspects, the antibody or antigen-binding fragment thereof that specifically binds to IL-4R comprises three Heavy chain Complementarity Determining Region (HCDR) sequences comprising SEQ ID NOs: 3, 4, and 5, respectively, and three Light chain Complementarity determining Region (LCDR) sequences comprising SEQ ID NOs: 6, 7, and 8, respectively. In certain aspects, the antibody or antigen-binding fragment thereof that specifically binds to IL-4R comprises an HCVR comprising the amino acid sequence of SEQ ID NO: 1 and an LCVR comprising the amino acid sequence of SEQ ID NO: 2. In certain aspects, the antibody is dupilumab.

In certain aspects, the one or more maintenance doses are administered every other week (q2w). In certain aspects, the one or more maintenance doses are administered every fourth week (q4w). In certain aspects, the antibody or antigen-binding fragment thereof is administered to the subject systemically, subcutaneously, intravenously, or intranasally.

In certain aspects, the subject has a blood eosinophil count selected from the group consisting of: greater than or equal to 300 cells/µL, 200 to 299 cells/µL; and less than 200 cells/µL.

In certain aspects, the ICS is selected from the group consisting of: mometasone furoate, budesonide, and fluticasone propionate. In certain aspects, the LABA is selected from the group consisting of: formoterol and salmeterol. In certain aspects, the ICS is mometasone furoate, and the LABA is formoterol. In certain aspects, the ICS is budesonide, and the LABA is formoterol. In certain aspects, the ICS is fluticasone propionate, and the LABA is salmeterol.

In certain aspects, the subject is selected from the group consisting of a subject about age 18 years or older, a subject about age 12 to about age 75 years old, a subject about age 12 to about age 18 years old, a subject about age 6 to about age 11 years old, and a subject about age 2 to about age 5 years old.

In certain aspects, the subject has persistent asthma for greater than or equal to 12 months, based on the Global Initiative for Asthma (GINA) 2009 Guidelines, and one or more of the following criteria: existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of IL-4R antagonist; Forced Expiratory Volume (FEV1) 40 to 80% predicted normal prior to administration of the loading dose of IL-4R antagonist; Juniper Asthma Control Questionnaire, 5-question version (ACQ-5) score greater than or equal to 1.5 prior to administration of the loading dose of IL-4R antagonist; reversibility of at least 12% and 200 mL in FEV1 after 200 µg to 400 µg (2 to 4 inhalations) of salbutamol/albuterol prior to administration of the loading dose of IL-4R antagonist; or has experienced, within 1 year prior to administration of the loading dose of IL-4R antagonist, any of the following events: treatment with greater than or equal to 1 systemic (oral or parenteral) steroid bursts for worsening asthma; or hospitalization or an emergency/urgent medical care visit for worsening asthma.

Other embodiments will become apparent from a review of the ensuing detailed description, drawings, tables and accompanying claims.

BRIEF DESCRIPTION OF THE FIGURES

The foregoing and other features and advantages of the present invention will be more fully understood from the following detailed description of illustrative embodiments taken in conjunction with the accompanying drawings. The file of this patent contains at least one drawing/photograph executed in color. Copies of this patent with color drawing(s)/photograph(s) will be provided by the Office upon request and payment of the necessary fee.

FIG. 24 is a table depicting demographic and disease baseline characteristics.

FIG. 48 is a table showing that the magnitude of TARC and IgE suppression was greater with dupilumab (patients with high Eos) than lebrikizumab after 12 weeks of treatment, even in patients retrospectively stratified by high periostin levels (mean % change).

FIG. 49 shows that TARC and IgE suppression was greater with dupilumab than lebrikizumab at week 12 (mean percent change).

FIG. 50 shows key efficacy results in moderate-to-severe asthma and high eosinophil/periostin subsets. Left column: exacerbations. Right column: FEV1 score.

FIG. 51 depicts subject accounting and disposition.

FIG. 52 depicts the randomized population of the study.

FIG. 53 depicts subject exposure to dupilumab.

FIG. 54 summarizes the change from baseline in FEV1(L) and annualized rate of severe exacerbation by baseline blood Eos.

FIG. 55 summarizes the percent change at week 12 among ITT, high Eos (greater than or equal to 300), and low Eos (less than 300) populations.

FIG. 56 depicts mean baseline biomarkers by eosinophil count subpopulation.

FIG. 57 depicts Asthma Control Questionnaire 5 (ACQ 5) data for an Intent To Treat (ITT) population.

FIG. 58 depicts ACQ 5 item analyses for an ITT population.

FIG. 59 depicts Asthma Quality of Life Questionnaire (AQLQ) data for an ITT population.

FIG. 60 depicts AQLQ ITT data by domain.

FIG. 61 depicts European Quality of Life-5 Dimensions-5L (EQSD-5L) data.

FIG. 62 depicts EQSD-5L data by item.

FIG. 63 depicts Hospital Anxiety and Depression Score (HADS) data by domain.

FIG. 64 depicts HADS data for an ITT population.

FIG. 65 depicts HADS data for an ITT High Eosinophil (HEos) population. *Derived from MMRM model with change from baseline score up to week 24 as dependent variables, factors (fixed effects) for treatment, pooled countries/regions, visit, treatment-by-visit interaction, baseline score value and baseline-by-visit interaction as covariates, unstructured correlation matrix. Score collected from systemic corticosteroid start date to systemic corticosteroid end date+30 days for each exacerbation episode are excluded in order to reduce the confounding effect of systemic corticosteroids.

FIG. 66 depicts HADS baseline data and change from baseline at week 12 for an ITT population. *Derived from MMRM model with change from baseline score up to week 24 as dependent variables, factors (fixed effects) for treatment, pooled countries/regions, visit, treatment-by-visit interaction, baseline score value and baseline-by-visit interaction as covariates, unstructured correlation matrix. Score collected from systemic corticosteroid start date to systemic corticosteroid end date+30 days for each exacerbation episode are excluded in order to reduce the confounding effect of systemic corticosteroids.

FIG. 67 depicts Sino Nasal Outcome Test 22 (SNOT 22) data for an ITT population.

FIG. 68 depicts SNOT 22 data by domain.

FIG. 69 depicts pruritus Numerical Rating Scale (NRS) results.

DETAILED DESCRIPTION

Figure 1:
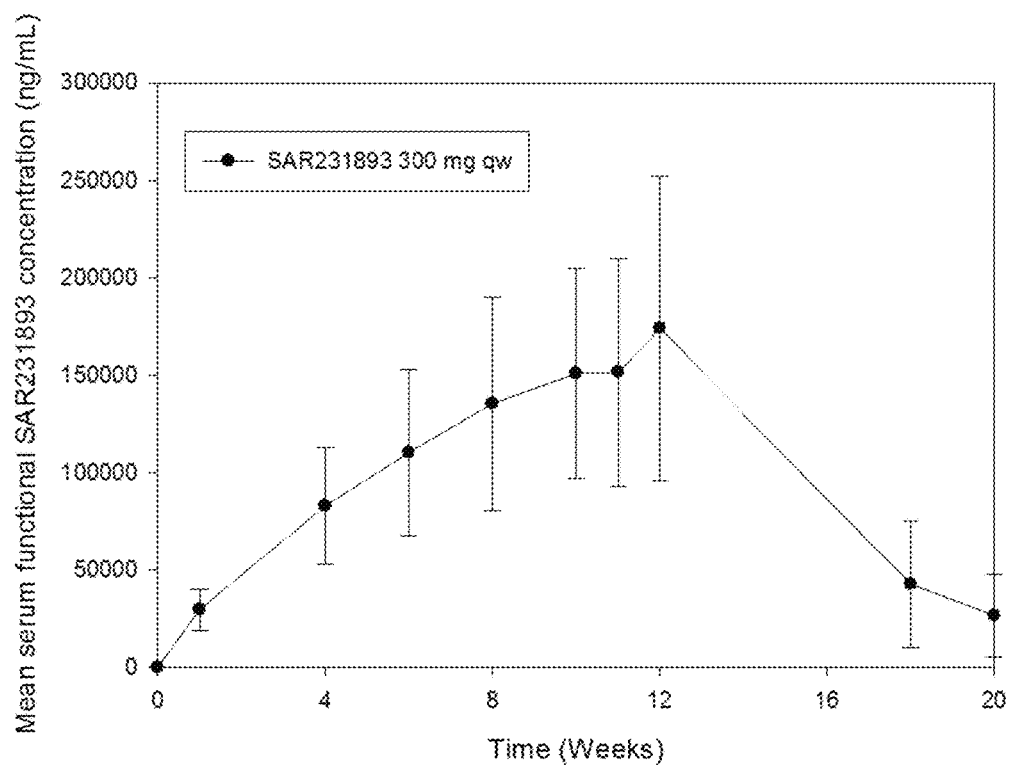
FIG. 1 graphically depicts the mean serum functional mAb1 concentration over time for mAb1 administered at 300 mg qw (once per week).

Before the invention is described, it is to be understood that this invention is not limited to particular methods and experimental conditions described, as such methods and conditions may vary. It is also to be understood that the terminology used herein is for the purpose of describing particular embodiments only, and is not intended to be limiting, because the scope of the invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the invention, the typical methods and materials are now described. All publications mentioned herein are incorporated herein by reference in their entirety.

Methods for Reducing the Incidence of Asthma Exacerbations

The invention includes methods for reducing the incidence of asthma exacerbations in a subject in need thereof comprising administering a pharmaceutical composition comprising an IL-4R antagonist to the subject. As used herein, the expression "asthma exacerbation" means an increase in the severity and/or frequency and/or duration of one or more symptoms or indicia of asthma. An "asthma exacerbation" also includes any deterioration in the respiratory health of a subject that requires and or is treatable by a therapeutic intervention for asthma (such as, e.g., steroid treatment, inhaled corticosteroid treatment, hospitalization, etc.). There are two types of asthma exacerbation events: a loss of asthma control (LOAC) event and a severe exacerbation event.

According to certain embodiments, a loss of asthma control (LOAC) event is defined as one or more of the following: (a) greater than or equal to 6 additional reliever puffs of salbutamol/albuterol or levosalbutamol/levalbuterol in a 24 hour period (compared to baseline) on 2 consecutive days; (b) an increase in ICS greater than or equal to 4 times the dose at visit 2; and (c) use of systemic corticosteroids for greater than or equal to 3 days; or (d) hospitalization or emergency room visit because of asthma, requiring systemic corticosteroids.

In certain instances, an asthma exacerbation may be categorized as a "severe asthma exacerbation event". A severe asthma exacerbation event means an incident requiring immediate intervention in the form of treatment with either systemic corticosteroids or with inhaled corticosteroids at four or more times the dose taken prior to the incident. According to certain embodiments, a severe asthma exacerbation event is defined as a deterioration of asthma requiring: use of systemic corticosteroids for greater than or equal to 3 days; or hospitalization or emergency room visit because of asthma, requiring systemic corticosteroids. The general expression "asthma exacerbation" therefore includes and encompasses the more specific subcategory of "severe asthma exacerbations." Accordingly, methods for reducing the incidence of severe asthma exacerbations in a patient in need thereof are included.

A "reduction in the incidence" of an asthma exacerbation means that a subject who has received a pharmaceutical composition comprising an IL-4R antagonist experiences fewer asthma exacerbations (i.e., at least one fewer exacerbation) after treatment than before treatment, or experiences no asthma exacerbations for at least 4 weeks (e.g., 4, 6, 8, 12, 14, or more weeks) following initiation of treatment with the pharmaceutical composition. A "reduction in the incidence" of an asthma exacerbation alternatively means that, following administration of the pharmaceutical composition, the likelihood that a subject experiences an asthma exacerbation is decreased by at least 10% (e.g., 10%, 15%, 20%, 25%, 30%, 35%, 40%, 45%, 50%, or more) as compared to a subject who has not received the pharmaceutical composition.

The invention includes methods for reducing the incidence of asthma exacerbations in a subject in need thereof comprising administering a pharmaceutical composition comprising an IL-4R antagonist to the subject as well as administering to the subject one or more maintenance doses of an inhaled corticosteroid (ICS) and/or one or more maintenance doses of a second controller, e.g., a Long-Acting Beta-Agonist (LABA) or a Leukotriene receptor Antagonist (LTA). Suitable ICSs include, but are not limited to, fluticasone (e.g., fluticasone propionate, e.g., Flovent™) budesonide, mometasone (e.g., mometasone furoate, e.g., Asmanex™), flunisolide (e.g., Aerobid™), dexamethasone acetate/phenobarbital/theophylline (e.g., Azmacort™), beclomethasone dipropionate HFA (Qvar™), and the like. Suitable LABAs include, but are not limited to, salmeterol (e.g., Serevent™), formoterol (e.g., Foradil™), and the like. Suitable LTAs include, but are not limited to, montelukast (e.g., Singulaire™), zafirlukast (e.g., Accolate™), and the like.

The invention includes methods for reducing the incidence of asthma exacerbations in a subject in need thereof comprising administering a pharmaceutical composition comprising an IL-4R antagonist to the subject as well as administering to the subject one or more reliever medications to eliminate or reduce one or more asthma-associated symptoms. Suitable reliever medications include, but are not limited to, quick-acting $beta_2$-adrenergic receptor agonists such as, e.g., albuterol (i.e., salbutamol, e.g., Proventil™, Ventolin™, Xopenex™ and the like), pirbuterol (e.g., Maxair™), metaproterenol (e.g., Alupent™) and the like.

Methods for Improving Asthma-Associated Parameters

The invention also includes methods for improving one or more asthma-associated parameters in a subject in need thereof, wherein the methods comprise administering a pharmaceutical composition comprising an IL-4R antagonist to the subject. A reduction in the incidence of an asthma exacerbation (as described above) may correlate with an improvement in one or more asthma-associated parameters; however, such a correlation is not necessarily observed in all cases.

Examples of "asthma-associated parameters" include: (1) relative percent change from baseline at week 12 in forced expiratory volume in 1 second (FEV1); (2) annualized rate of loss of asthma control events during the treatment period; (3) annualized rate of severe exacerbation events during the treatment period; (4) time to loss of asthma control events during the treatment period; (5) time to severe exacerbation events during the treatment period; (6) time to loss of asthma control events during overall study period; (7) time to severe exacerbation events during overall study period; (8) health care resource utilization; (9) change from baseline at week 12 in: i) morning and evening asthma symptom scores, ii) ACQ-5 score, iii) AQLQ score, iv) morning and evening PEF, v) number of inhalations/day of salbutamol/albuterol or levosalbutamol/levalbuterol for symptom relief, vi) nocturnal awakenings; (10) change from baseline at week 12 and week 24 in: i) 22-item Sino Nasal Outcome Test (SNOT-22), ii) Hospital Anxiety and Depression Score (HADS), iii) EuroQual questionnaire (EQ-5D-3L or EQ-5D-5L). An "improvement in an asthma-associated parameter" means an increase from baseline of one or more of FEV1, AM PEF or PM PEF, and/or a decrease from baseline of one or more of daily albuterol/levalbuterol use, ACQ5 score, average nighttime awakenings or SNOT-22 score. As used herein, the term "baseline," with regard to an asthma-associated parameter, means the numerical value of the asthma-associated parameter for a patient prior to or at the time of administration of a pharmaceutical composition comprising an IL-4R antagonist.

To determine whether an asthma-associated parameter has "improved," the parameter is quantified at baseline and at a time point after administration of the pharmaceutical composition described herein. For example, an asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the pharmaceutical composition. The difference between the value of the parameter at a particular time point following initiation of treatment and the value of the parameter at baseline is used to establish whether there has been an "improvement" in the asthma associated parameter (e.g., an increase or decrease, as the case may be, depending on the specific parameter being measured).

The terms "acquire" or "acquiring" as used herein, refer to obtaining possession of a physical entity, or a value, e.g., a numerical value, by "directly acquiring" or "indirectly acquiring" the physical entity or value, such as an asthma-associated parameter. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis").

Information that is acquired indirectly can be provided in the form of a report, e.g., supplied in paper or electronic form, such as from an online database or application (an "App"). The report or information can be provided by, for example, a healthcare institution, such as a hospital or clinic; or a healthcare provider, such as a doctor or nurse.

Forced Expiratory Volume in 1 Second (FEV1). According to certain embodiments, administration of an IL-4R antagonist to a patient results in an increase from baseline of forced expiratory volume in 1 second (FEV1). Methods for measuring FEV1 are known in the art. For example, a spirometer that meets the 2005 American Thoracic Society (ATS)/European Respiratory Society (ERS) recommendations can be used to measure FEV1 in a patient. The ATS/ERS Standardization of Spirometry may be used as a guideline. Spirometry is generally performed between 6 and 10 AM after an albuterol withhold of at least 6 hours. Pulmonary function tests are generally measured in the sitting position, and the highest measure is recorded for FEV1 (in liters).

The invention includes therapeutic methods that result in an increase of FEV1 from baseline of at least 0.05 L at week 12 following initiation of treatment with a pharmaceutical composition comprising an anti-IL-4R antagonist. For example, administration of an IL-4R antagonist to a subject in need thereof causes an increase of FEV1 from baseline of about 0.05 L, 0.10 L, 0.12 L, 0.14 L, 0.16 L, 0.18 L, 0.20 L, 0.22 L, 0.24 L, 0.26 L, 0.28 L, 0.30 L, 0.32 L, 0.34 L, 0.36 L, 0.38 L, 0.40 L, 0.42 L, 0.44 L, 0.46 L, 0.48 L, 0.50 L, or more at week 12.

Morning and Evening Peak Expiratory Flow (AM PEF and PM PEF). According to certain embodiments, administration of an IL-4R antagonist to a patient results in an increase from baseline of morning (AM) and/or evening (PM) peak expiratory flow (AM PEF and/or PM PEF). Methods for measuring PEF are known in the art. For example, according to one method for measuring PEF, patients are issued an electronic PEF meter for recording morning (AM) and evening (PM) PEF (as well as daily albuterol use, morning and evening asthma symptom scores, and number of nighttime awakenings due to asthma symptoms that require rescue medications). Patients are instructed on the use of the device, and written instructions on the use of the electronic PEF meter are provided to the patients. In addition, a medical professional may instruct the patients on how to record pertinent variables in the electronic PEF meter. AM PEF is generally performed within 15 minutes after arising (between 6 am and 10 am) prior to taking any albuterol. PM PEF is generally performed in the evening (between 6 pm and 10 pm) prior to taking any albuterol. Subjects should try to withhold albuterol for at least 6 hours prior to measuring their PEF. Three PEF efforts are performed by the patient and all 3 values are recorded by the electronic PEF meter. Usually the highest value is used for evaluation. Baseline AM PEF may be calculated as the mean AM measurement recorded for the 7 days prior to administration of the first dose of pharmaceutical composition comprising the IL-4R antagonist, and baseline PM PEF may be calculated as the mean PM measurement recorded for the 7 days prior to administration of the first dose of pharmaceutical composition comprising the IL-4R antagonist.

The invention includes therapeutic methods that result in an increase in AM PEF and/or PM PEF from baseline of at least 1.0 L/min at week 12 following initiation of treatment with a pharmaceutical composition comprising an anti-IL-4R antagonist. For example, according to the invention, administration of an IL-4R antagonist to a subject in need thereof causes an increase in PEF from baseline of about 0.5 L/min, 1.0 L/min, 1.5 L/min, 2.0 L/min, 2.5 L/min, 3.0 L/min, 3.5 L/min, 4.0 L/min, 4.5 L/min, 5.0 L/min, 5.5 L/min, 6.0 L/min, 6.5 L/min, 7.0 L/min, 7.5 L/min, 8.0 L/min, 8.5 L/min, 9.0 L/min, 9.5 L/min, 10.0 L/min, 10.5 L/min, 11.0 L/min, 12.0 L/min, 15 L/min, 20 L/min, or more at week 12.

Albuterol/Levalbuterol Use. According to certain embodiments, administration of an IL-4R antagonist to a patient results in a decrease from baseline of daily albuterol or levalbuterol use. The number of albuterol/levalbuterol inhalations can be recorded daily by the patients in a diary, PEF meter, or other recording device. During treatment with the pharmaceutical composition described herein, use of albuterol/levalbuterol typically may be on an as-needed basis for symptoms, not on a regular basis or prophylactically. The baseline number of albuterol/levalbuterol inhalations/day may be calculated based on the mean for the 7 days prior to administration of the first dose of pharmaceutical composition comprising the IL-4R antagonist.

The invention includes therapeutic methods that result in a decrease in albuterol/levalbuterol use from baseline of at least 0.25 puffs per day at week 12 following initiation of treatment with a pharmaceutical composition comprising an anti-IL-4R antagonist. For example, administration of an IL-4R antagonist to a subject in need thereof causes a decrease in albuterol/levalbuterol use from baseline of about 0.25 puffs per day, 0.50 puffs per day, 0.75 puffs per day, 1.00 puff per day, 1.25 puffs per day, 1.5 puffs per day, 1.75 puffs per day, 2.00 puffs per day, 2.25 puffs per day, 2.5 puffs per day, 2.75 puffs per day, 3.00 puffs per day, or more at week 12.

Prednisone Use. According to certain embodiments, administration of an IL-4R antagonist to a patient can be used in conjunction with oral prednisone. The number of prednisone administrations can be recorded daily by the patients in a diary, PEF meter, or other recording device. During treatment with the pharmaceutical composition described herein, occasional short term use of prednisone typically can be used to control acute asthmatic episodes, e.g., episodes in which bronchodilators and other anti-inflammatory agents fail to control symptoms. In other aspects, prednisone is used concurrent with or as a substitution for ICS. Oral prednisone may be administered in dosages of about 5 mg, 10 mg, 15 mg, 20 mg, 25 mg, 30 mg, 35 mg or 40 mg. Oral prednisone can optionally be administered once a day or multiple times a day (e.g., twice a day, three times a day, four times a day, etc.)

5-Item Asthma Control Questionnaire (ACQ) Score. According to certain embodiments, administration of an IL-4R antagonist to a patient results in a decrease from baseline of five-item Asthma Control Questionnaire (ACQ5) score. The ACQ5 is a validated questionnaire to evaluate asthma control.

The invention includes therapeutic methods that result in a decrease in ACQ5 score from baseline of at least 0.10 points at week 12 following initiation of treatment with a pharmaceutical composition comprising an anti-IL-4R antagonist. For example, administration of an IL-4R antagonist to a subject in need thereof causes a decrease in ACQ score from baseline of about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 12.

Night-Time Awakenings. According to certain embodiments, administration of an IL-4R antagonist to a patient results in a decrease from baseline of average number of nighttime awakenings.

In certain embodiments, the methods decrease the average number of nighttime awakenings from baseline by at least about 0.10 times per night at week 12 following initiation of treatment. For example, administration of an IL-4R antagonist to a subject in need thereof can cause a decrease in average number of nighttime awakenings from baseline of about 0.10 times per night, 0.15 times per night, 0.20 times per night, 0.25 times per night, 0.30 times per night, 0.35 times per night, 0.40 times per night, 0.45 times per night, 0.50 times per night, 0.55 times per night, 0.60 times per night, 0.65 times per night, 0.70 times per night, 0.75 times per night, 0.80 times per night, 0.85 times per night, 0.90 times per night, 0.95 times per night, 1.0 times per night, 2.0 times per night, or more at week 12.

22-Item Sinonasal Outcome Test (SNOT-22) Score. According to certain embodiments, administration of an IL-4R antagonist to a patient results in a decrease from baseline of 22-item Sinonasal Outcome Test (SNOT-22). The SNOT-22 is a validated questionnaire to assess the impact of chronic rhinosinusitis on quality of life (Hopkins et al 2009, Clin. Otolaryngol. 34: 447-454).

The invention includes therapeutic methods that result in a decrease in SNOT-22 score from baseline of at least 1 point at week 12 following initiation of treatment with a pharmaceutical composition comprising an anti-IL-4R antagonist. For example, administration of an IL-4R antagonist to a subject in need thereof can cause a decrease in SNOT-22 score from baseline of about 1, 2, 3, 4, 5, 6, 7, 8, 9, 10, 11, 12, 13 points, or more at week 12.

Methods for Treating Asthma

In some embodiments, the invention provides methods for treating asthma, including, e.g., moderate to severe uncontrolled asthma or inadequately controlled asthma, in a subject in need thereof, wherein the methods comprise administering a pharmaceutical composition comprising an IL-4R antagonist to the subject. In certain embodiments, the methods are useful for treating moderate to severe uncontrolled asthma in a subject.

As used herein, the term "asthma" can be used interchangeably with "intermittent asthma." "Asthma" and "intermittent asthma" refer to asthma in which one or any combination of the following are true: symptoms occur 2 or fewer days per week; symptoms do not interfere with normal activities; nighttime symptoms occur fewer than 2 days per month; or one or more lung function tests (e.g., forced expiratory volume in one second (FEV1) and/or peak expiratory flow (PEF) of greater than 80%) are normal when the subject is not suffering from an asthma attack.

As used herein, the term "persistent asthma" refers to asthma that is more severe than asthma/intermittent asthma. A subject suffering from persistent asthma experiences one or more of the following: symptoms more than 2 days per week; symptoms that interfere with normal activities; nighttime symptoms that occur more than 2 days per month; or one or more lung function tests (e.g., forced expiratory volume in one second (FEV1) and/or peak expiratory flow (PEF) of less than 80%) that are not normal when the subject is not suffering from an asthma attack; the subject relies on daily asthma control medication; the subject has taken a systemic steroid more than once in the last year after a severe asthma flare-up; or use of a short-acting beta-2 agonist more than two days per week for relief of asthma symptoms.

Asthma/intermittent asthma and persistent asthma can be categorized as "mild," "moderate," "severe" or "moderate-to-severe." "Mild intermittent asthma" is defined as having symptoms less than once a week, and having forced expiratory volume in one second (FEV1) or peak expiratory flow (PEF)≥80%. "Mild persistent asthma" differs in that symptoms frequency is greater than once per week but less than once per day, and variability in FEV1 or PEF is <20%-30%. "Moderate intermittent asthma" is defined as having symptoms less than once a week, and having forced expiratory volume in one second (FEV1) or peak expiratory flow (PEF) of 60-80% "Moderate persistent asthma" is defined as having daily symptoms, exacerbations that may affect activity and/or sleep, nocturnal symptoms more than once a week, daily use of inhaled short-acting beta-2 agonist and having forced expiratory volume in one second (FEV1) or peak expiratory flow (PEF) of 60-80%. "Severe intermittent asthma" is defined as having symptoms less than once a week, and having forced expiratory volume in one second (FEV1) or peak expiratory flow (PEF) of 60%. "Severe persistent asthma" is defined as having daily symptoms, frequent exacerbations that may affect activity and/or sleep, frequent nocturnal symptoms, limitation of physical activities, daily use of inhaled short-acting beta-2 agonist, and having forced expiratory volume in one second (FEV1) or peak expiratory flow (PEF) of 60%. "Moderate-to-severe intermittent asthma" is defined as having symptoms between those of moderate intermittent asthma and severe intermittent asthma. "Moderate-to-severe persistent asthma" is defined as having symptoms between those of moderate persistent asthma and severe persistent asthma.

As used herein, the term "inadequately controlled asthma" refers to patients whose asthma is either "not well controlled" or "very poorly controlled" as defined by the "Expert Panel Report 3: Guidelines for the Diagnosis and Management of Asthma," National Heart, Blood and Lung Institute, NIH, Aug. 28, 2007. "Not well controlled asthma" is defined as having symptoms greater than two days per week, nighttime awakenings one to three times per week, some limitations on normal activity, short-acting $beta_2$-agonist use for symptom control greater than two days per week, FEV1 of 60-80% of predicted and/or personal best, an ATAQ score of 1-2, an ACQ score of 1.5 or greater, and an ACT score of 16-19. "Very poorly controlled asthma" is defined as having symptoms throughout the day, nighttime awakenings four times or more per week, extreme limitations on normal activity, short-acting $beta_2$-agonist use for symptom control several times per day, FEV1 of less than 60% of predicted and/or personal best, an ATAQ score of 3-4, an ACQ score of N/A, and an ACT score of less than or equal to 15.

In some embodiments, a subject is identified as having moderate to severe uncontrolled asthma if the subject receives such a diagnosis from a physician, based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of IL-4R antagonist; ii) FEV1 40 to 80% predicted normal prior to administration of the loading dose of IL-4R antagonist; iii) ACQ-5 score greater than or equal to 1.5 prior to administration of the loading dose of IL-4R antagonist; iv) Reversibility of at least 12% and 200 mL in FEV1 after 200 µg to 400 µg (2 to 4 inhalations) of salbutamol/albuterol prior to administration of the loading dose of IL-4R antagonist; or v)

Has experienced, within 1 year prior to administration of the loading dose of IL-4R antagonist, any of the following events: a) treatment with greater than or equal to 1 systemic (oral or parenteral) steroid burst for worsening asthma, b) hospitalization or an emergency/urgent medical care visit for worsening asthma.

In one aspect, methods for treating asthma are provided comprising: (a) selecting a patient that exhibits a blood eosinophil level of at least 300 cells per microliter; and (b) administering to the patient a pharmaceutical composition comprising an IL-4R antagonist.

In another aspect, methods for treating asthma are provided comprising: (a) selecting a patient that exhibits a blood eosinophil level of 200-299 cells per microliter; and (b) administering to the patient a pharmaceutical composition comprising an IL-4R antagonist.

In another aspect, methods for treating asthma are provided comprising: (a) selecting a patient that exhibits a blood eosinophil level of less than 200 cells per microliter; and (b) administering to the patient a pharmaceutical composition comprising an IL-4R antagonist.

In a related aspect, methods for treating asthma comprising an add-on therapy to background therapy are provided. In certain embodiments, an IL-4R antagonist is administered as an add-on therapy to an asthma patient who is on background therapy for a certain period of time (e.g., 1 week, 2 weeks, 3 weeks, 1 month, 2 months, 5 months, 12 months, 18 months, 24 months, or longer) (also called the "stable phase"). In some embodiments, the background therapy comprises a ICS and/or a LABA.

In some embodiments, the invention includes a method for reducing an asthma patient's dependence on ICS and/or LABA for the treatment of one or more asthma exacerbations comprising: (a) selecting a patient who has moderate-to-severe asthma that is uncontrolled with a background asthma therapy comprising an ICS, a LABA, or a combination thereof; and administering to the patient a pharmaceutical composition comprising an IL-4R antagonist.

In some embodiments, the invention encompasses methods to treat or alleviate conditions or complications associated with asthma, such as chronic rhino sinusitis, allergic rhinitis, allergic fungal rhino sinusitis, allergic bronchopulmonary aspergillosis, unified airway disease, Churg-Strauss syndrome, vasculitis, chronic obstructive pulmonary disease (COPD), and exercise induced bronchospasm.

The invention also includes methods for treating persistent asthma. As used herein, the term "persistent asthma" means that the subject has symptoms at least once a week at day and/or at night, with the symptoms lasting a few hours to a few days. In certain alternative embodiments, the persistent asthma is "mildly persistent" (e.g., more than twice a week but less than daily with symptoms severe enough to interfere with daily activities or sleep and/or where pulmonary function is normal or reversible with inhalation of a bronchodilator), "moderately persistent" (e.g., symptoms occurring daily with sleep interrupted at least weekly and/or with pulmonary function moderately abnormal), or "severely persistent" (e.g., continuous symptoms despite the correct use of approved medications and/or where pulmonary function is severely affected).

Interleukin-4 Receptor Antagonists

The methods featured in the invention comprise administering to a subject in need thereof a therapeutic composition comprising an IL-4R antagonist. As used herein, an "IL-4R antagonist" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, anti-IL-4R aptamers, peptide-based IL-4R antagonists (e.g., "peptibody" molecules), and antibodies or antigen-binding fragments of antibodies that specifically bind human IL-4R.

The term "human IL4R" (hIL-4R) refers to a human cytokine receptor that specifically binds to interleukin-4 (IL-4), such as IL-4Rα.

The term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$, and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody" also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds to an antigen to form a complex. Antigen-binding fragments of an antibody may be derived, e.g., from full antibody molecules using any suitable standard techniques, such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment."

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody described herein include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$—$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids that result in a flexible or semi-flexible linkage between adjacent variable and/or constant domains in a single polypeptide molecule, typically the hinge region may consist of between 2 to 60 amino acids, typically between 5 to 50, or typically between 10 to 40 amino acids. Moreover, an antigen-binding fragment of an antibody described herein may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody described herein using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody" includes antibodies having variable and constant regions derived from human germline immunoglobulin sequences. The human antibodies featured in the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The invention encompasses antibodies having one or more mutations in the hinge, $C_H2$, or $C_H3$ region, which may be desirable, for example, in production, to improve the yield of the desired antibody form.

An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody". An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R, as featured in the invention, includes antibodies that bind IL-4R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods may comprise one or more amino acid substitutions, insertions, and/or deletions (e.g. 1, 2, 3, 4, 5, 6, 7, 8, 9, or 10 substitutions and/or 1, 2, 3, 4, 5, 6, 7, 8, 9, or 10 insertions and/or 1, 2, 3, 4, 5, 6, 7, 8, 9, or 10 deletions) in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The invention includes methods involving the use of antibodies, and antigen-binding fragments thereof, that are derived from any of the amino acid sequences disclosed herein, wherein one or more amino acids (e.g. 1, 2, 3, 4, 5, 6, 7, 8, 9, or 10 amino acids) within one or more framework and/or one or more (e.g. 1, 2, 3, 4, 5, 6, 7, 8, 9, 10, 11 or 12 with respect to the tetrameric antibody or 1, 2, 3, 4, 5 or 6 with respect to the HCVR and LCVR of an antibody) CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the invention.

The invention also includes methods involving the use of anti-IL-4R antibodies comprising variants of any of the HCVR, LCVR, and/or CDR amino acid sequences disclosed herein having one or more conservative substitutions. For example, the invention includes the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$" refers to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used to make human antibodies that specifically bind to human IL-4R.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate a fully human antibody featured in the invention, for example wild-type or modified IgG1 or IgG4. While the constant region selected may vary according to specific use, high affinity antigen-binding and target specificity characteristics reside in the variable region.

In general, the antibodies that can be used in the methods possess high affinities, as described above, when measured by binding to antigen either immobilized on solid phase or in solution phase. The mouse constant regions are replaced with desired human constant regions to generate the fully human antibodies featured in the invention. While the constant region selected may vary according to specific use, high affinity antigen-binding and target specificity characteristics reside in the variable region.

In one embodiment, human antibody or antigen-binding fragment thereof that specifically binds IL-4R that can be used in the context of the methods featured in the invention comprises the three heavy chain CDRs (HCDR1, HCDR2 and HCDR3) contained within a heavy chain variable region (HCVR) having an amino acid sequence of SEQ ID NO: 1. The antibody or antigen-binding fragment may comprise the three light chain CDRs (LCVR1, LCVR2, LCVR3) contained within a light chain variable region (LCVR) having an amino acid sequence of SEQ ID NO: 2. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) of SEQ ID NOs: 1/2.

In certain embodiments, the antibody or antigen-binding fragment thereof comprises six CDRs (HCDR1/HCDR2/HCDR3/LCDR1/LCDR2/LCDR3) having the amino acid sequences of SEQ ID NOs: 3/4/5/6/7/8.

In certain embodiments, the antibody or antigen-binding fragment thereof comprises HCVR/LCVR amino acid sequence pairs of SEQ ID NOs: 1/2.

In one embodiment, the antibody is dupilumab, which comprises the HCVR/LCVR amino acid sequence pairs of SEQ ID NOs: 1/2.

Pharmaceutical Compositions

The invention includes methods that comprise administering an IL-4R antagonist to a patient, wherein the IL-4R antagonist is contained within a pharmaceutical composition. The pharmaceutical compositions featured in the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical compositions featured in the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, intra-tracheal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition featured in the invention can be delivered subcutaneously or intravenously with a standard needle and syringe. In addition, with respect to subcutaneous delivery, a pen delivery device readily has applications in delivering a pharmaceutical composition featured in the invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition featured in the invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

For direct administration to the sinuses, the pharmaceutical compositions featured in the invention may be administered using, e.g., a microcatheter (e.g., an endoscope and microcatheter), an aerosolizer, a powder dispenser, a nebulizer or an inhaler. The methods include administration of an IL-4R antagonist to a subject in need thereof, in an aerosolized formulation. For example, aerosolized antibodies to IL-4R may be administered to treat asthma in a patient. Aerosolized antibodies can be prepared as described in, for example, U.S. Pat. No. 8,178,098, incorporated herein by reference in its entirety.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is typically filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the invention are disclosed, e.g., in US Patent Application Publication No. 2012/0097565.

Dosage

The amount of IL-4R antagonist (e.g., anti-IL-4R antibody) administered to a subject according to the methods featured in the invention is, generally, a therapeutically effective amount. As used herein, the phrase "therapeutically effective amount" means an amount of IL-4R antagonist that results in one or more of: (a) a reduction in the incidence of asthma exacerbations; (b) an improvement in one or more asthma-associated parameters (as defined elsewhere herein); and/or (c) a detectable improvement in one or more symptoms or indicia of an upper airway inflammatory condition. A "therapeutically effective amount" also includes an amount of IL-4R antagonist that inhibits, prevents, lessens, or delays the progression of asthma in a subject.

In the case of an anti-IL-4R antibody, a therapeutically effective amount can be from about 0.05 mg to about 700 mg, e.g., about 0.05 mg, about 0.1 mg, about 1.0 mg, about 1.5 mg, about 2.0 mg, about 3.0 mg, about 5.0 mg, about 7.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, or about 700 mg of the anti-IL-4R antibody. In certain embodiments, 300 mg of an anti-IL-4R antibody is administered.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight. For example, the IL-4R antagonist can be administered at a dose of 1 mg/kg, 2 mg/kg, 3 mg/kg, or 4 mg/kg.

In some embodiments, the dose of IL-4R antagonist may vary according to eosinophil count. For example, the subject may have a blood eosinophil count (high blood eosinophils) ≥300 cells/μL (HEos); a blood eosinophil count of 200 to 299 cells/μL; or a blood eosinophil count <200 cells/μL (low blood eosinophils).

In certain embodiments, the methods comprise a loading dose of about 400 to about 600 mg of an IL-4R antagonist.

In certain embodiments, the methods comprise one or more maintenance doses of about 200 to about 300 mg of the IL-4R antagonist.

In certain embodiments, the ICS and LABA are administered for the duration of administration of the IL-4R antagonist.

In certain embodiments, the loading dose comprises 600 mg of an anti-IL-4R antibody or antigen-binding fragment thereof, and the one or more maintenance doses comprises 300 mg of the antibody or antigen-binding fragment thereof administered every other week.

In certain embodiments, the loading dose comprises 400 mg of an anti-IL-4R antibody or antigen-binding fragment thereof, and the one or more maintenance dose comprises 200 mg of the antibody or antigen-binding fragment thereof administered every other week.

In other embodiments, the loading dose comprises 600 mg of an anti-IL-4R antibody or antigen-binding fragment thereof, and the one or more maintenance doses comprises 300 mg of the antibody or antigen-binding fragment thereof administered every fourth week.

In other embodiments, the loading dose comprises 400 mg of an anti-IL-4R antibody or antigen-binding fragment thereof, and the one or more maintenance doses comprises 200 mg of the antibody or antigen-binding fragment thereof administered every fourth week.

In other embodiments, the loading dose comprises 600 mg of an anti-IL-4R antibody or antigen-binding fragment thereof, and the one or more maintenance doses comprises 300 mg of the antibody or antigen-binding fragment thereof administered once a week.

In other embodiments, the loading dose comprises 400 mg of an anti-IL-4R antibody or antigen-binding fragment thereof, and the one or more maintenance doses comprises 200 mg of the antibody or antigen-binding fragment thereof administered once a week.

In other embodiments, the loading dose comprises 600 mg of an anti-IL-4R antibody or antigen-binding fragment thereof, and the one or more maintenance doses comprises 300 mg of the antibody or antigen-binding fragment thereof administered every third week.

In other embodiments, the loading dose comprises 400 mg of an anti-IL-4R antibody or antigen-binding fragment thereof, and the one or more maintenance doses comprises 200 mg of the antibody or antigen-binding fragment thereof administered every third week.

In one embodiment, the subject is 6 to <18 years old and the IL-4R antibody or antigen binding fragment thereof is administered at 2 mg/kg or 4 mg/kg.

In another embodiment, the subject is 2 to <6 years old and the IL-4R antibody or antigen binding fragment thereof is administered at 2 mg/kg or 4 mg/kg.

In yet another embodiment, the subject is <2 years old and the IL-4R antibody or antigen binding fragment thereof is administered at 2 mg/kg or 4 mg/kg.

Combination Therapies

Certain embodiments of the methods featured in the invention comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. In some embodiments, the term "in combination with" includes sequential or concomitant administration of an IL-4R antagonist and a second therapeutic agent. The invention includes methods to treat asthma or an associated condition or complication or to reduce at least one exacerbation, comprising administration of an IL-4R antagonist in combination with a second therapeutic agent for additive or synergistic activity.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes, or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, or about 72 hours after the administration of the pharmaceutical composition comprising the IL-4R antagonist. Administration "concurrent" with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), a TNF antagonist, an IL-8 antagonist, an IL-9 antagonist, an IL-17 antagonist, an IL-5 antagonist, an IgE antagonist, a CD48 antagonist, a leukotriene inhibitor, an anti-fungal agent, an NSAID, a long-acting $beta_2$ agonist (e.g., salmeterol or formoterol), an inhaled corticosteroid (e.g., fluticasone or budesonide), a systemic corticosteroid (e.g., oral or intravenous), methylxanthine, nedocromil sodium, cromolyn sodium, or combinations thereof. For example, in certain embodiments, the pharmaceutical composition comprising an IL-4R antagonist is administered in combination with a combination comprising a long-acting $beta_2$ agonist and an inhaled corticosteroid (e.g., fluticasone+salmeterol [e.g., Advair® (GlaxoSmithKline)]; or budesonide+formoterol [e.g., SYMBICORT® (Astra Zeneca)]).

Administration Regimens

According to certain embodiments, multiple doses of an IL-4R antagonist may be administered to a subject over a defined time course. Such methods comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks, or months). The invention includes methods that comprise sequentially administering to the patient a single initial dose of an IL-4R antagonist, followed by one or more secondary doses of the IL-4R antagonist, and optionally followed by one or more tertiary doses of the IL-4R antagonist.

The invention includes methods comprising administering to a subject a pharmaceutical composition comprising an IL-4R antagonist at a dosing frequency of about four times a week, twice a week, once a week, once every two weeks (bi-weekly), once every three weeks, once every four weeks (monthly), once every five weeks, once every six weeks, once every eight weeks, once every twelve weeks, or less frequently so long as a therapeutic response is achieved. In certain embodiments involving the administration of a pharmaceutical composition comprising an anti-IL-4R antibody, once a week dosing of an amount of about 75 mg, 100 mg, 150 mg, 200 mg, or 300 mg, can be employed. In other embodiments involving the administration of a pharmaceutical composition comprising an anti-IL-4R antibody, once every two weeks dosing (bi-weekly dosing) of an amount of about 75 mg, 100 mg, 150 mg, 200 mg, or 300 mg, can be employed. In other embodiments involving the administration of a pharmaceutical composition comprising an anti-IL-4R antibody, once every three weeks dosing of an amount of about 75 mg, 100 mg, 150 mg, 200 mg, or 300 mg, can be employed. In other embodiments involving the administration of a pharmaceutical composition comprising an anti-IL-4R antibody, once every four weeks dosing (monthly dosing) of an amount of about 75 mg, 100 mg, 150 mg, 200 mg, or 300 mg, can be employed. In other embodiments involving the administration of a pharmaceutical composition comprising an anti-IL-4R antibody, once every five weeks dosing of an amount of about 75 mg, 100 mg, 150 mg, 200 mg, or 300 mg, can be employed. In other embodiments involving the administration of a pharmaceutical composition comprising an anti-IL-4R antibody, once every six weeks dosing of an amount of about 75 mg, 100 mg, 150 mg, 200 mg, or 300 mg, can be employed. In other embodiments involving the administration of a pharmaceutical composition comprising an anti-IL-4R antibody, once every eight weeks dosing of an amount of about 75 mg, 100 mg, 150 mg, 200 mg, or 300 mg, can be employed. In other embodiments involving the administration of a pharmaceutical composition comprising an anti-IL-4R antibody, once every twelve weeks dosing of an amount of about 75 mg, 100 mg, 150 mg, 200 mg, or 300 mg, can be employed. In one embodiment, the route of administration is subcutaneous.

The term "week" or "weeks" refers to a period of (n×7 days) ±2 days, e.g. (n×7 days) ±1 day, or (n×7 days), wherein "n" designates the number of weeks, e.g. 1, 2, 3, 4, 5, 6, 8, 12 or more.

The terms "initial dose," "secondary doses," and "tertiary doses," refer to the temporal sequence of administration of the IL-4R antagonist. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses"). In one embodiment, the maintenance dose may be lower than the loading dose. For example, one or more loading doses of 600 mg of IL-4R antagonist may be administered followed by maintenance doses of about 75 mg to about 300 mg.

In certain embodiments, the loading dose is about 400 to about 600 mg of the IL-4R antagonist. In one embodiment, the loading dose is 400 mg of the IL-4R antagonist. In another embodiment, the loading dose is 600 mg of the IL-4R antagonist.

In certain embodiments, the maintenance dose is about 200 to about 300 mg of the IL-4R antagonist. In one embodiment, the maintenance dose is 200 mg of the IL-4R antagonist. In another embodiment, the maintenance dose is 300 mg of the IL-4R antagonist.

In certain embodiments, the loading dose is two times the maintenance dose.

In some embodiments, the loading dose comprises 600 mg of the antibody or antigen-binding fragment thereof, and the one or more maintenance doses comprises 300 mg of the antibody or antigen-binding fragment thereof administered every other week.

In some embodiments, the loading dose comprises 400 mg of the antibody or antigen-binding fragment thereof, and the one or more maintenance dose comprises 200 mg of the antibody or antigen-binding fragment thereof administered every other week.

In some embodiments, the loading dose comprises 600 mg of the antibody or antigen-binding fragment thereof, and the one or more maintenance doses comprises 300 mg of the antibody or antigen-binding fragment thereof administered every fourth week.

In some embodiments, the loading dose comprises 400 mg of the antibody or antigen-binding fragment thereof, and the one or more maintenance doses comprises 200 mg of the antibody or antigen-binding fragment thereof administered every fourth week.

In one exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose" means, in a sequence of multiple administrations, the dose of IL-4R antagonist that is administered to a patient prior to the administration of the very next dose in the sequence with no intervening doses.

The methods may include administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The invention includes methods comprising sequential administration of an IL-4R antagonist and a second therapeutic agent, to a patient to treat asthma or an associated condition. In some embodiments, the methods comprise administering one or more doses of an IL-4R antagonist followed by one or more doses (e.g., 2, 3, 4, 5, 6, 7, 8, or more) of a second therapeutic agent. For example, one or more doses of about 75 mg to about 300 mg of the IL-4R antagonist may be administered after which one or more doses (e.g., 2, 3, 4, 5, 6, 7, 8, or more) of a second therapeutic agent (e.g., an inhaled corticosteroid or a beta2-agonist or any other therapeutic agent, as described elsewhere herein) may be administered to treat, alleviate, reduce or ameliorate one or more symptoms of asthma. In some embodiments, the IL-4R antagonist is administered at one or more doses (e.g., 2, 3, 4, 5, 6, 7, 8, or more) resulting in an improvement in one or more asthma-associated parameters followed by the administration of a second therapeutic agent to prevent recurrence of at least one symptom of asthma. Alternative embodiments pertain to concomitant administration of an IL-4R antagonist and a second therapeutic agent. For example, one or more doses (e.g., 2, 3, 4, 5, 6, 7, 8, or more) of an IL-4R antagonist are administered and a second therapeutic agent is administered at a separate dosage at a similar or different frequency relative to the IL-4R antagonist. In some embodiments, the second therapeutic agent is administered before, after or concurrently with the IL-4R antagonist.

In certain embodiments, the IL-4R antagonist is administered every other week for 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks or more. In other embodiments, the IL-4R antagonist is administered every four weeks for 12 weeks, 16 weeks, 20 weeks, 24 weeks, 28 weeks, 32 weeks, 36 weeks, 40 weeks, 44 weeks, 48 weeks or more. In specific embodiments, the IL-4R antagonist is administered for at least 24 weeks.

Treatment Populations

The methods featured in the invention include administering to a subject in need thereof a therapeutic composition comprising an IL-4R antagonist. The expression "a subject in need thereof" means a human or non-human animal that exhibits one or more symptoms or indicia of asthma (e.g., moderate to severe uncontrolled asthma), or who has been diagnosed with asthma. For example, "a subject in need thereof" may include, e.g., subjects who, prior to treatment, exhibit (or have exhibited) one or more asthma-associated parameter, such as, e.g., impaired FEV1 (e.g., less than 2.0 L), impaired AM PEF (e.g., less than 400 L/min), impaired PM PEF (e.g., less than 400 L/min), an ACQ5 score of at least 2.5, at least 1 nighttime awakenings per night, and/or a SNOT-22 score of at least 20. In various embodiments, the methods may be used to treat mild, moderate-to-severe, and severe asthma in patients in need thereof.

In a related embodiment, a "subject in need thereof" may be a subject who, prior to receiving an IL-4R antagonist, has been prescribed or is currently taking a combination of ICS/LABA. Examples of ICS include mometasone furoate, budesonide, and fluticasone propionate. Examples of LABA include formoterol and salmeterol. Examples of ICS/LABA therapies include fluticasone/salmeterol combination therapy and budesonide/formoterol combination therapy. For example, the invention includes methods that comprise administering an IL-4R antagonist to a patient who has been taking a regular course of ICS/LABA for two or more weeks immediately preceding the administration of the IL-4R antagonist (such prior treatments are referred to herein as "background treatments"). The invention includes therapeutic methods in which background treatments are continued in combination with administration of the IL-4R antagonist. In yet other embodiments, the amount of the ICS component, the LABA component, or both, is gradually decreased prior to or after the start of IL-4R antagonist administration. In some embodiments, the invention includes methods to treat patients with persistent asthma for at least ≥12 months. In one embodiment, a patient with persistent asthma may be resistant to treatment by a therapeutic agent, such as a corticosteroid, and may be administered an IL-4R antagonist according to the present methods.

In some embodiments, a "subject in need thereof" may be a subject with elevated levels of an asthma-associated biomarker. Examples of asthma-associated biomarkers include, but are not limited to, IgE, *thymus* and activation regulated chemokine (TARC), eotaxin-3, CEA, YKL-40, and periostin. In some embodiments, a "subject in need thereof" may be a subject with blood eosinophils ≥300 cells/μL, 200-299 cells/μL, or <200 cells/μL. In one embodiment, a "subject in need thereof" may be a subject with elevated level of bronchial or airway inflammation as measured by the fraction of exhaled nitric oxide (FeNO).

In some embodiments, a "subject in need thereof" is selected from the group consisting of: a subject age 18 years of age or older, a subject age 12 to 17 years old (12 to <18 years old), a subject age 6 to 11 years old (6 to <12 years old), and a subject age 2 to 5 years old (2 to <6 years old). In some embodiments, a "subject in need thereof" is selected from the group consisting of: an adult, an adolescent, and a child. In some embodiments, a "subject in need thereof" is selected from the group consisting of: an adult age 18 years of age or older, an adolescent age 12 to 17 years old (12 to <18 years old), a child age 6 to 11 years old (6 to <12 years old), and a child age 2 to 5 years old (2 to <6 years old). The subject can be less than 2 years of age, e.g., 12 to 23 months, or 6 to 11 months.

A normal IgE level in healthy subjects is less than about 100 kU/L (e.g., as measured using the IMMUNOCAP® assay [Phadia, Inc. Portage, Mich.]). Thus, the invention includes methods comprising selecting a subject who exhibits an elevated serum IgE level, which is a serum IgE level greater than about 100 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L, and administering to the subject a pharmaceutical composition comprising a therapeutically effective amount of an IL-4R antagonist.

TARC levels in healthy subjects are in the range of 106 ng/L to 431 ng/L, with a mean of about 239 ng/L. (An exemplary assay system for measuring TARC level is the TARC quantitative ELISA kit offered as Cat. No. DDN00 by R&D Systems, Minneapolis, Minn.) Thus, the invention involves methods comprising selecting a subject who exhibits an elevated TARC level, which is a serum TARC level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L, and administering to the subject a pharmaceutical composition comprising a therapeutically effective amount of an IL-4R antagonist.

Eotaxin-3 belongs to a group of chemokines released by airway epithelial cells, which is up-regulated by the Th2 cytokines IL-4 and IL-13 (Lilly et al 1999, J. Allergy Clin.

Immunol. 104: 786-790). The invention includes methods comprising administering an IL-4R antagonist to treat patients with elevated levels of eotaxin-3, such as more than about 100 pg/ml, more than about 150 pg/ml, more than about 200 pg/ml, more than about 300 pg/ml, or more than about 350 pg/ml. Serum eotaxin-3 levels may be measured, for example, by ELISA.

Periostin is an extracellular matrix protein involved in the Th2-mediated inflammatory processes. Periostin levels are found to be up-regulated in patients with asthma (Jia et al 2012 J Allergy Clin Immunol. 130:647-654.e10. doi: 10.1016/j.jaci.2012.06.025. Epub 2012 Aug. 1). The invention includes methods comprising administering an IL-4R antagonist to treat patients with elevated levels of periostin.

Fractional exhaled NO (FeNO) is a biomarker of bronchial or airway inflammation. FeNO is produced by airway epithelial cells in response to inflammatory cytokines including IL-4 and IL-13 (Alwing et al 1993, Eur. Respir. J. 6: 1368-1370). FeNO levels in healthy adults range from 2 to 30 parts per billion (ppb). An exemplary assay for measuring FeNO is by using a NIOX instrument by Aerocrine AB, Solna, Sweden. The assessment may be conducted prior to spirometry and following a fast of at least an hour. The invention includes methods comprising administering an IL-4R antagonist to patients with elevated levels of exhaled NO (FeNO), such as more than about 30 ppb, more than about 31 ppb, more than about 32 ppb, more than about 33 ppb, more than about 34 ppb, or more than about 35 ppb.

Carcinoembryogenic antigen (CEA) (also known as CEA cell adhesion molecule 5 [CEACAMS]) is a tumor marker that is found correlated to non-neoplastic diseases of the lung (Marechal et al 1988, Anticancer Res. 8: 677-680). CEA levels in serum may be measured by ELISA. The invention includes methods comprising administering an IL-4R antagonist to patients with elevated levels of CEA, such as more than about 1.0 ng/ml, more than about 1.5 ng/ml, more than about 2.0 ng/ml, more than about 2.5 ng/ml, more than about 3.0 ng/ml, more than about 4.0 ng/ml, or more than about 5.0 ng/ml.

YKL-40 [named for its N-terminal amino acids tyrosine (Y), lysine (K) and leucine (L) and its molecular mass of 40 kD] is a chitinase-like protein found to be up regulated and correlated to asthma exacerbation, IgE, and eosinophils (Tang et al 2010 Eur. Respir. J. 35: 757-760). Serum YKL-40 levels are measured by, for example, ELISA. The invention includes methods comprising administering an IL-4R antagonist to patients with elevated levels of YKL-40, such as more than about 40 ng/ml, more than about 50 ng/ml, more than about 100 ng/ml, more than about 150 ng/ml, more than about 200 ng/ml, or more than about 250 ng/ml.

Periostin is a secreted matricellular protein associated with fibrosis, and its expression is upregulated by recombinant IL-4 and IL-13 in cultured bronchial epithelial cells and bronchial fibroblasts (Jia et al. (2012) J. Allergy Clin. Immunol.130:647). In human asthmatic patients periostin expression levels correlate with reticular basement membrane thickness, an indicator of subepithelial fibrosis. Id. The invention includes methods comprising administering an IL-4R antagonist to patients with elevated levels of periostin.

Induced sputum eosinophils and neutrophils are well-established direct markers of airway inflammation (Djukanovic et al 2002, Eur. Respire. J. 37: 1S-2S). Sputum is induced with inhalation of hypertonic saline solution and processed for cell counts according to methods known in the art, for example, the guidelines of European Respiratory Society.

In some embodiments, the subjects are stratified into the following groups: a blood eosinophil count (high blood eosinophils) ≥300 cells/µL (HEos), a blood eosinophil count of 200 to 299 cells/µL (moderate blood eosinophils), or a blood eosinophil count <200 cells/µL (low blood eosinophils), and are administered an anti-IL-4R antibody or antigen binding fragment thereof at a dose or dosing regimen based upon the eosinophil level.

Methods for Assessing Pharmacodynamic Asthma-Associated Parameters

The invention also includes methods for assessing one or more pharmacodynamic asthma-associated parameters a subject in need thereof, caused by administration of a pharmaceutical composition comprising an IL-4R antagonist. A reduction in the incidence of an asthma exacerbation (as described above) or an improvement in one or more asthma-associated parameters (as described above) may correlate with an improvement in one or more pharmacodynamic asthma-associated parameters; however, such a correlation is not necessarily observed in all cases.

Examples of "pharmacodynamic asthma-associated parameters" include, for example, the following: (a) biomarker expression levels; (b) serum protein and RNA analysis; (c) induced sputum eosinophils and neutrophil levels; (d) exhaled nitric oxide (FeNO); and (e) blood eosinophil count. An "improvement in a pharmacodynamic asthma-associated parameter" means, for example, a decrease from baseline of one or more biomarkers, such as TARC, eotaxin-3 or IgE, a decrease in sputum eosinophils or neutrophils, FeNO, periostin or blood eosinophil count. As used herein, the term "baseline," with regard to a pharmacodynamic asthma-associated parameter, means the numerical value of the pharmacodynamic asthma-associated parameter for a patient prior to or at the time of administration of a pharmaceutical composition described herein.

To assess a pharmacodynamic asthma-associated parameter, the parameter is quantified at baseline and at a time point after administration of the pharmaceutical composition. For example, a pharmacodynamic asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the pharmaceutical composition. The difference between the value of the parameter at a particular time point following initiation of treatment and the value of the parameter at baseline is used to establish whether there has been change, such as an "improvement," in the pharmacodynamic asthma-associated parameter (e.g., an increase or decrease, as the case may be, depending on the specific parameter being measured).

In certain embodiments, administration of an IL-4R antagonist to a patient causes a change, such as a decrease or increase, in expression of a particular biomarker. Asthma-associated biomarkers include, but are not limited to, the following: (a) total IgE; (b) *thymus* and activation-regulated chemokine (TARC); (c) YKL-40; (d) carcinoembryonic antigen in serum; (e) eotaxin-3 in plasma; and (f) periostin in serum. For example, administration of an IL-4R antagonist to an asthma patient can cause one or more of a decrease in TARC or eotaxin-3 levels, or a decrease in total serum IgE levels. The decrease can be detected at week 1, week 2, week 3, week 4, week 5, or longer following administration of the IL-4R antagonist. Biomarker expression can be assayed by methods known in the art. For example, protein levels can be measured by ELISA (Enzyme Linked Immunosorbent Assay). RNA levels can be measured, for example, by reverse transcription coupled to polymerase chain reaction (RT-PCR).

Biomarker expression, as discussed above, can be assayed by detection of protein or RNA in serum. The serum samples can also be used to monitor additional protein or RNA biomarkers related to response to treatment with an IL-4R antagonist, IL-4/IL-13 signaling, asthma, atopy or eosinophilic diseases (e.g., by measuring soluble IL-4Rα, IL-4, IL-13, periostin). In some embodiments, RNA samples are used to determine RNA levels (non-genetic analysis), e.g., RNA levels of biomarkers; and in other embodiments, RNA samples are used for transcriptome sequencing (e.g., genetic analysis).

Formulations

In some embodiments, the antibody or antigen binding fragment thereof is formulated in a composition comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, wherein the pH of the formulation is about 5.9, and wherein the viscosity of the formulation is about 8.5 cPoise.

In alternative embodiments, the antibody or antigen binding fragment thereof is formulated in a composition comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, wherein the pH of the formulation is about 5.9, and wherein the viscosity of the formulation is about 8.5 cPoise.

In specific embodiments, the antibody or antigen-binding fragment thereof comprises an HCVR comprising the amino acid sequence of SEQ ID NO: 1 and an LCVR comprising the amino acid sequence of SEQ ID NO: 2.

The present invention is further illustrated by the following examples which should not be construed as further limiting. The contents of the figures and all references, patents and published patent applications cited throughout this application are expressly incorporated herein by reference for all purposes.

Furthermore, in accordance with the present invention there may be employed conventional molecular biology, microbiology, and recombinant DNA techniques within the skill of the art. Such techniques are explained fully in the literature. See, e.g., Green & Sambrook, *Molecular Cloning: A Laboratory Manual*, Fourth Edition (2012) Cold Spring Harbor Laboratory Press, Cold Spring Harbor, N.Y.; *DNA Cloning: A Practical Approach*, Volumes I and II (D. N. Glover ed. 1985); *Oligonucleotide Synthesis* (M. J. Gait ed. 1984); Nucleic Acid Hybridization [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary IL-4R antagonist used in the following Examples is the human anti-IL-4R antibody named dupilumab (also referred to herein as "mAb1").

Example 1 mAb1 Pharmacokinetics in Asthma Patients

A pharmacokinetic study in asthma patients was conducted. 300 mg of mAb1 was administered to each patient every week for 12 weeks. Various pharmacokinetic parameters were measured, including $C_{max}$, AUC, $t_{last}$, $C_{last}$, and $t_{1/2}$, the results of which are shown in Table 1 below.

TABLE 1

| PK parameters | Serum mAb1 |
| --- | --- |
| $C_{max}$ (N = 9) (ng/mL) | 173000 ± 75300 (156000)[43.6] |
| $AUC_{0-168}$ (N = 8) (ng*h/mL) | 24400000 ± 9610000 (22500000)[39.4] |
| $t_{last}$ (N = 10)$^a$ (h) | 1180 (314-1370) |
| $C_{last}$ (N = 10) (h) | 51600 ± 46600 (34400)[90.2] |
| $t_{1/2}$ (N = 8) (h) | 458 ± 233 (415)[50.9] |

$^a$Median(Min-Max)

The mean $t_{1/2}$ of 458 hours (19.1 days) is consistent with the half-life of IgG molecules, further providing support that at the concentrations observed during the study, target-mediated clearance was not the dominant elimination pathway of mAb1.

A graph of the mean serum functional mAb1 concentration over time is shown in FIG. 1. As shown in FIG. 1, following 12 weekly doses of mAb1 at the doses of 300 mg/week to asthma patients, $C_{trough}$ concentrations appeared to have reached a plateau between Week 10 and Week 12. Accumulation as assessed by $C_{trough}$ following the 12$^{th}$ dose as compared to after the first dose was 5.88 at the 300 mg once-weekly dose. In a majority of patients, there were still detectable levels of mAb1 in the serum at the last PK sample time point (7 to 9 weeks after last drug administration). The results of this study suggest benefits that may be derived from a loading dose.

Figure 2:
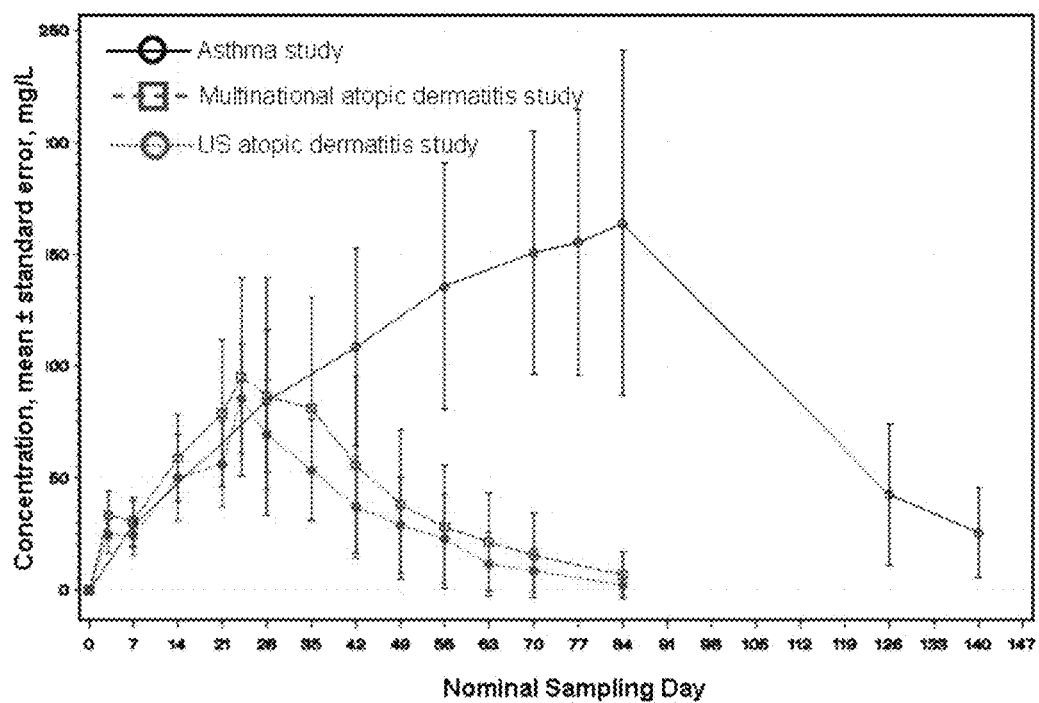
FIG. 2 graphically depicts the mean serum concentrations over time for various studies in which mAb1 was administered at 300 mg once weekly. The asthma study is indicated by a solid line with circles. The multinational atopic dermatitis study is indicated by a dashed line with squares. The U.S. atopic dermatitis study is indicated by a dashed line with circles.

The serum concentrations of mAb1 during 300 mg once weekly dosing regimens in patients with atopic dermatitis or asthma were measured. As shown in FIG. 2, mAb1 systemic exposure was similar in atopic dermatitis and asthma patients during the first 4 weeks of 300 mg weekly dosing.

Example 2

A Randomized, Double-Blind, Placebo-Controlled, Dose-Ranging Study to Evaluate the Anti-IL-4R Antibody Dupilumab in Patients with Moderate to Severe Uncontrolled Asthma A. Study Objectives and Overview A randomized, double-blind, placebo-controlled, dose-ranging study was conducted to evaluate mAb1 (dupilumab)

in patients with moderate to severe uncontrolled asthma. The primary objective of the study was to evaluate the efficacy of different doses and regimens of mAb1 in patients with moderate to severe, uncontrolled asthma. The secondary objectives of the study were to evaluate different doses and regimens of mAb1 in patients with moderate to severe, uncontrolled asthma, with regards to: safety and tolerability, mAb1 systemic exposure and anti-drug antibodies, and patient-reported outcomes (PROs); to evaluate baseline biomarkers for their potential value to predict treatment response; to evaluate on-treatment biomarkers for their potential value to associate with treatment response; and to evaluate genetic profiles for their potential value to predict treatment response.

B. Study Design

This study is a multinational, multicenter, randomized, double-blind, placebo-controlled, dose-ranging, parallel group study comparing different doses and regimens of mAb1 administered subcutaneously (SC) for 24 weeks in patients with moderate to severe, uncontrolled asthma. Approximately 770 patients were randomized into 5 treatment groups of 150 patients per group.

The clinical trial consisted of three periods, using an add-on therapy approach to inhaled corticosteroid/long-acting beta agonist combination therapy (ICS/LABA): a Screening Period (14 to 21 days) to determine whether patients met entry criteria and to establish level of asthma control before the Randomized Treatment Period; a Randomized Treatment Period (24 weeks); and a Post-treatment Period (16 weeks) to monitor patients after treatment.

C. Selection of Patients

Patients 18-65 years old with a physician diagnosis of moderate to severe, uncontrolled asthma for ≥12 months, based on the Global Initiative for Asthma (GINA) 2009 Guidelines, and the following criteria were eligible for inclusion in the study: (1) Existing treatment with moderate- or high-dose ICS/LABA (2 fluticasone propionate 250 μg twice daily or equipotent ICS daily dosage) with a stable dose of ICS/LABA for ≥1 month prior to Visit 1; (2) FEV1 40 to 80% predicted normal at Visit 1 and at Visit 2 prior to the first dose of investigational product; (3) ACQ-5 score ≥1.5 at Visit 1 and Visit 2; (4) Reversibility of at least 12% and 200 mL in FEV1 after 200 μg to 400 μg (2 to 4 inhalations) of salbutamol/albuterol at Visit 1; and (5) Has experienced, within 1 year prior to Visit 1, any of the following events: Treatment with ≥1 systemic (oral or parenteral) steroid bursts for worsening asthma, or Hospitalization or an emergency/urgent medical care visit for worsening asthma.

Patients who met all the above inclusion criteria were screened for the following exclusion criteria: (1) Patients <18 years; (2) Chronic obstructive pulmonary disease (COPD) or other lung diseases (e.g., emphysema, idiopathic pulmonary fibrosis, Churg-Strauss syndrome, allergic bronchopulmonary aspergillosis) which impair pulmonary function tests; (3) Chest X-ray within 12 months of screening visit or at screening visit with clinically significant findings of lung disease(s) other than asthma; (4) Current smoker or cessation of smoking within 6 months prior to Visit 1; (5) Previous smoker with a smoking history >10 pack-years; (6) Comorbid disease that might interfere with the evaluation of IMP (mAb1); (7) Known or suspected non-compliance, alcohol abuse or drug abuse; (8) Inability to follow the procedures of the study (e.g., due to language problems or psychological disorders); (9) Reversal of sleep pattern (e.g., night shift workers); (10) Patients requiring beta-adrenergic receptor blockers (beta blockers) for any reason; (11) Anti-immunoglobulin E (IgE) therapy (omalizumab) within 130 days prior to Visit 1; biologic therapy within 6 months of Visit 1; (12) Initiation of allergen immunotherapy within 3 months prior to Visit 1 or a plan to begin therapy or change dose during the Screening Period or the Randomized Treatment Period; (13) Exposure to another investigative antibody within a time period prior to Visit 1 that is less than 5 half-lives of the antibody (if known). In case the half-life is not known, then the minimum interval since exposure to the prior investigative antibody is 6 months. The minimum interval since exposure to any other (non-antibody) investigative study medication is 30 days prior to Visit 1; (14) Patients receiving medications that are prohibited as concomitant medications; (15) Previous enrollment into the current study or another mAb1 study; (16) Patient is the Investigator or any Sub-Investigator, research assistant, pharmacist, study coordinator, other staff or relative thereof directly involved in the conduct of the protocol; (17) Non-compliance with use of the mandatory background therapy, ICS/LABA combination product during the screening period, as defined as: <80% of total number of prescribed "stable dose" puffs taken during the screening period. Compliance is verified based ICS/LABA use recorded on the patient electronic diary during the screening period; (18) Concomitant severe diseases or diseases for which the use of ICS (e.g., active and inactive pulmonary tuberculosis) or LABA (e.g., diagnosis of a history of significant cardiovascular disease, insulin-dependent diabetes mellitus, uncontrolled hypertension, hyperthyroidism, thyrotoxicosis, pheochromocytoma, hypokalemia, prolonged QTc interval (male >450 msec, female >470 msec) or tachyarrhythmia) are contraindicated; (19) Treatment with drugs associated with clinically significant QTc interval prolongation/Torsades de Pointes ventricular tachycardia; (20) Women of childbearing potential (pre-menopausal female biologically capable of becoming pregnant) who: Do not have a confirmed negative serum β-hCG test at Visit 1, or Who are not protected by one of the following acceptable forms of effective contraception during the study: Established use of oral, injected or implanted hormonal contraceptive; Intrauterine device (IUD) with copper or intrauterine system (IUS) with progestogen; Barrier contraceptive (condom, diaphragm or cervical/vault caps) used with spermicide (foam, gel, film, cream or suppository); Female sterilization (e.g., tubal occlusion, hysterectomy or bilateral salpingectomy); Male sterilization with post-vasectomy documentation of the absence of sperm in the ejaculate; for female patients the study, the vasectomized male partner should be the sole partner for that patient; True abstinence; periodic abstinence (e.g., calendar, ovulation, symptothermal, post-ovulation methods) is not an acceptable method of contraception; or Menopausal women (defined as at least 12 consecutive months without menses) are not required to use additional contraception; (21) Diagnosed active parasitic infection; suspected or high risk of parasitic infection, unless clinical and (if necessary) laboratory assessments have ruled out active infection before randomization; (22) History of human immunodeficiency virus (HIV) infection or positive HIV screen (Anti-HIV-1 and HIV-2 antibodies) at Visit 1; (23) Known or suspected history of immunosuppression, including history of invasive opportunistic infections (e.g., tuberculosis, histoplasmosis, listeriosis, coccidioidomycosis, pneumocystosis, aspergillosis), despite infection resolution; or unusually frequent, recurrent, or prolonged infections, per Investigator judgment; (24) Evidence of acute or chronic infection requiring treatment with antibacterials, antivirals, antifungals, antiparasitics or antiprotozoals within 4 weeks before Visit 1; significant viral infections within 4 weeks before Visit 1 that may not have received antiviral treatment (e.g., influenza receiving only symptomatic treatment); (25) Live, attenuated vaccinations within 12 weeks prior to Visit 1 or planned live, attenuated vaccinations during the study—the prohibited live, attenuated vaccines are *Bacillus* Calmette-Guérin (BCG) anti-tuberculosis vaccine; Chickenpox (Varicella); Intranasal influenza (FluMist-Influenza); inactive influenza vaccine delivered by injection is permitted; Measles (Rubeola); Measles-mumps-rubella (MMR) combination; Measles-mumps-rubella-varicella (MMRV) combination; Mumps; Oral polio (Sabin); Oral typhoid; Rotavirus; Rubella; Smallpox (Vaccinia); Varicella Zoster (shingles); and Yellow fever; (26) Patients with active autoimmune disease or patients using immunosuppressive therapy for autoimmune disease (e.g. Hashimito's thyroiditis, Graves' disease, inflammatory bowel disease, primary biliary cirrhosis, systemic lupus erythematosus, multiple sclerosis, psoriasis *vulgaris*); and (27) Patients with positive or indeterminate hepatitis B surface antigen (HBsAg), hepatitis B core antibody (HBcAb), or hepatitis C antibody at Visit 1.

Only patients who met all of the inclusion criteria, and none of the exclusion criteria were included in the study.

D. Study Treatments

Sterile mAb1 of various concentrations was provided in 5 mL glass vials; each vial contained a deliverable volume of 2 mL: 150 mg/mL solution (300 mg dose/2 mL) or 100 mg/mL solution (200 mg dose/2 mL).

Patients were randomized to one of the following treatments for 24 weeks, receiving every other week (q2w) subcutaneous (SC) administrations of mAb1 or placebo according to one of the following doses and regimens:

mAb1 300 mg q 2 weeks (D) with 600 mg loading dose (LD);

mAb1 200 mg q 2 weeks (D) with 400 mg loading dose (LD);

mAb1 300 mg q 4 weeks (D) with 600 mg loading dose (LD);

mAb1 200 mg q 4 weeks (D) with 400 mg loading dose (LD); or

Placebo q 2 week (P) with placebo loading dose.

Dosing every other week is also known as bi-weekly dosing. Dosing every four weeks is also known as monthly dosing.

Prior to screening, patients had been on a stable dose of moderate- or high-dose ICS/LABA (≥fluticasone propionate 250 µg twice daily or equipotent ICS dosage) for ≥1 month prior to Visit 1. The allowable combination products in the study during the treatment period were the following: Mometasone furoate/formoterol; Budesonide/formoterol; and Fluticasone propionate/salmeterol. If the patient was using an alternative combination product (e g., fluticasone/formoterol) prior to the randomization visit, then at the randomization Visit 2 (Day 1), the Investigator switched the patient to an equivalent dosage of 1 of the 3 allowable treatment period combination products above.

During the Randomized Treatment Period, patients continued the stable dose of ICS/LABA of equivalent dosage used during the Screening Period. See Table 2 for allowable ICS/LABA combination products and acceptable dosage form, strength and schedule required during the treatment period to meet the background therapy requirement for moderate to high dose ICS daily dose.

TABLE 2

Allowable Inhaled Glucocorticosteroid/Long-Acting Beta2 Agonist Combination Products and Acceptable Dosage Form, Strength and Dosage Schedule

| Generic Name | Brand Name | Acceptable Product | Acceptable Dosage Form, Strength and Dosage Schedule |
|---|---|---|---|
| Fluticasone propionate and salmeterol | Advair ® Seretide ® | /DPI (250/50 or 500/50) MDI (115/21 or 230/21) | DPI: 1 puff twice daily (500/50) DPI: 1 puffs twice daily (250/50) MDI: 2 puffs twice daily (115/21) MDI: 2 puffs twice daily (230/21) |
| Budesonide and formoterol | Symbicort ® | DPI (200/6 or 400/12 MDI (160/4.5) | DPI: 1 puff twice daily (400/12) DPI: 2 puffs twice daily (200/6) MDI: 2 puffs twice daily (160/4.5) MDI: 2 puffs twice daily (200/5) |
| Mometasone furoate and formoterol | Dulera ® | MDI (100/5 or 200/5) | |

Upon completing the Randomized Treatment Period (or following early discontinuation of investigational product), patients continued treatment with the stable dose of ICS/LABA maintained over the randomized treatment period (or modify treatment based on medical judgment).

Patients were allowed to administer salbutamol/albuterol hydrofluoroalkane pressurized MDI or levosalbutamol/levalbuterol hydrofluoroalkane pressurized MDI as reliever medication as needed during the study. Nebulizer solutions may be used as an alternative delivery method.

The following concomitant treatments are not permitted during the Screening Period or the Randomized Treatment Period: Systemic (oral or injectable) corticosteroids, except if used to treat an asthma exacerbation; Methylxanthines (e.g., theophylline, aminophyllines); Lipoxygenase inhibitors (e.g., azelastine, zileuton); Cromones; Anti-immunoglobulin E (IgE) therapy (e.g., omalizumab); Biologic therapy; Methotrexate; Initiation of allergen immunotherapy (allergen immunotherapy in place for three or more months prior to Visit 1 is permitted); and Intravenous immunoglobulin (IVIG) therapy.

Permitted concomitant medications include: Leukotriene antagonists/modifiers are permitted during the study, but patients must be on a stable dose 30 days or more prior to Visit 1; Allergen immunotherapy in place for three or more months prior to Visit 1 is permitted. Antihistamines are permitted as concomitant medication; and Ocular or intranasal corticosteroids are permitted during the study, but patients must be on a stable dose 30 days or more prior to Visit 1.

Patients were randomized using a 1:1:1:1:1 randomization ratio for mAb1 300 mg q 2 weeks, mAb1 200 mg q 2 weeks, mAb1 300 mg q 4 weeks, mAb1 200 mg q 4 weeks, and placebo. Randomization was stratified by Visit 1 central laboratory blood eosinophil count (high blood eosinophils ≥300 cells/µL (HEos); blood eosinophils 200 to 299 cells/µL; blood eosinophils <200 cells/µL) and country.

About 40 percent of patients had high eosinophils across the dose groups, and about 77 percent of randomized patients had a history of atopic disease, which includes atopic dermatitis, allergic conjunctivitis, allergic rhinitis, chronic rhinosinusitis, nasal polyposis, food allergy and/or a history of hives.

E. Efficacy of Treatment

The primary endpoint of the study was the change from baseline at Week 12 in $FEV_1$. A spirometer was used to make such measurement. Spirometry was performed between 6 and 10 AM after withholding the last dose of salbutamol/albuterol or levosalbutamol/levalbuterol for 6 hours and withholding the last dose of ICS/LABA for 12 hours. Pulmonary function tests were measured in the sitting position and the highest measure was recorded in liters for FEV1.

The secondary efficacy endpoints assessed the: (1) Relative change (%) from baseline at Week 12 in FEV1; (2) Annualized rate of loss of asthma control events during the treatment period; (3) Annualized rate of severe exacerbation events during the treatment period; (4) Time to loss of asthma control events during the treatment period; (5) Time to severe exacerbation events during the treatment period; (6) Time to loss of asthma control events during overall study period; (7) Time to severe exacerbation events during overall study period; (8) Health care resource utilization; (9) Change from baseline at Week 12 in: Morning and evening asthma symptom scores, ACQ-5 score, AQLQ score, Morning and evening PEF, Number of inhalations/day of salbutamol/albuterol or levosalbutamol/levalbuterol for symptom relief, and Nocturnal awakenings; (10) Change from baseline at Week 12 and Week 24: SNOT-22, Hospital Anxiety and Depression Scale (HADS), and EuroQual questionnaire (EQ-5D-3L or EQ-5D-5L). For the above measurements, change from baseline at other time points (e.g., 24 weeks) were also analyzed.

Two types of asthma exacerbation events were defined: a loss of asthma control (LOAC) event and a severe exacerbation event. A loss of asthma control (LOAC) event during the study was defined as any of the following: 6 or more additional reliever puffs of salbutamol/albuterol or levosalbutamol/levalbuterol in a 24 hour period (compared to baseline) on 2 consecutive days; or Increase in ICS 4 times or more the dose at Visit 2; or Use of systemic corticosteroids for three or more days; or Hospitalization or emergency room visit because of asthma, requiring systemic corticosteroids. A severe exacerbation event during the study was defined as a deterioration of asthma requiring: Use of systemic corticosteroids for three or more days; or Hospitalization or emergency room visit because of asthma, requiring systemic corticosteroids.

Three disease-specific efficacy measures were used in the study: the ACQ-5 (Asthma Control Questionnaire, 5-question version), the AQLQ (Asthma Quality of Life Questionnaire), and the 22-item Sinonasal Outcome Test.

The ACQ-5 was designed to measure both the adequacy of asthma control and change in asthma control which occurs either spontaneously or as a result of treatment. The ACQ-5 has 5 questions, reflecting the top-scoring five asthma symptoms: woken at night by symptoms, wake in the mornings with symptoms, limitation of daily activities, shortness of breath and wheeze. Patients are asked to recall how their asthma has been during the previous week and to respond to the symptom questions on a 7-point scale (0=no impairment, 6=maximum impairment). A global score is calculated: the questions are equally weighted and the ACQ-5 score is the mean of the 5 questions and, therefore, between 0 (totally controlled) and 6 (severely uncontrolled). A higher score indicates lower asthma control. Patients with a score below 1.0 will have adequately controlled asthma, and above 1.0 their asthma will not be well controlled. On the 7-point scale of the ACQ-5, a change or difference in score of 0.5 is the smallest that can be considered clinically important.

The AQLQ was designed to measure the functional impairments that are most troublesome to adults (17 to 70 years) as a result of their asthma. The instrument is comprised of 32 items, each rated on a 7-point Likert scales from 1 to 7. The AQLQ has 4 domains. The domains and the number of items in each domain are as follows: Symptoms (12 items), Activity limitation (11 items), Emotional function (5 items), and Environmental Stimuli (4 items). A global score is calculated ranging from 0 to 7, and a score by domain. Higher scores indicate better quality of life.

The SNOT-22 is a validated questionnaire to assess the impact of chronic rhino sinusitis on quality of life.

Three disease-specific, daily efficacy assessments were used in the study: Peak expiratory flow, Asthma Symptom Score, and Reliever use. On a daily basis throughout the study, the patient uses an electronic diary/PEF meter to: Measure morning and evening PEF, Respond to the morning and evening asthma symptom scale questions, Indicate the number of inhalations/day of salbutamol/albuterol or levosalbutamol/levalbuterol for symptom relief, Record the number of inhalations/day of background combination ICS/LABA product used, and Record the number of nocturnal awakenings.

At screening (Visit 1), patients were issued an electronic PEF meter for recording morning (AM) and evening (PM) PEF, daily salbutamol/albuterol or levosalbutamol/levalbuterol, morning and evening asthma symptom scores, and number of nighttime awakenings due to asthma symptoms that require reliever medications. In addition, the investigator instructed the patients on how to record the following variables in the electronic PEF meter: AM PEF performed within 15 minutes after arising (between 6 AM and 10 AM) prior to taking any albuterol or levalbuterol; PM PEF performed in the evening (between 6 PM and 10 PM) prior to taking any albuterol or levalbuterol; Patients should try to withhold albuterol or levalbuterol for at least 6 hours prior to measuring their PEF; and Three PEF efforts will be performed by the patient; all 3 values will be recorded by the electronic PEF meter, and the highest value will be used for evaluation. Baseline AM PEF will be the mean AM measurement recorded for the 7 days prior to the first dose of investigational product, and baseline PM PEF will be the mean PM measurement recorded for the 7 days prior to the first dose of investigational product.

Patients recorded overall symptom scores twice a day prior to measuring PEF. The patient's overall asthma symptoms experienced during the waking hours were recorded in the evening (PM symptom score). Symptoms experienced during the night were recorded upon arising (AM symptom score). Baseline symptom scores were the mean AM and mean PM scores recorded for the 7 days prior to randomization. Patients were instructed to record the severity of symptoms as follows. The AM symptom score: 0=No asthma symptoms, slept through the night; 1=Slept well, but some complaints in the morning. No nighttime awakenings; 2=Woke up once because of asthma (including early awakening); 3=Woke up several times because of asthma (including early awakening), and 4=Bad night, awake most of the night because of asthma. The PM symptom score: 0=Very well, no asthma symptoms; 1=One episode of wheezing, cough, or breathlessness; 2=More than one episode of wheezing, cough, or breathlessness without interference of normal activities; 3=Wheezing, cough, or breathlessness most of the day, which interfered to some extent with normal activities; and 4=Asthma very bad, unable to carry out daily activities as usual.

The number of salbutamol/albuterol or levosalbutamol/levalbuterol inhalations were recorded daily by the patients in an electronic diary/PEF meter. Each patient was reminded that salbutamol/albuterol or levosalbutamol/levalbuterol should be used only as needed for symptoms, and not on a regular basis or prophylactically. The baseline number of salbutamol/albuterol or levosalbutamol/levalbuterol inhalations/day were based on the mean of the 7 days prior to randomization.

The same safety assessments will be applied across all arms, including adverse events, vital signs, physical examination, electrocardiogram variables, laboratory safety variables, and pregnancy test.

Adverse events for each patient were monitored and documented from the time the subject gave informed consent at Visit 1 until the End-of Study Visit, except for: SAEs, and AEs that are ongoing at database lock. Adverse events (Aes), adverse events with special interest (AESI), and serious adverse events (SAEs) were reported.

Vital signs, including blood pressure (mmHg), heart rate (beats per minute), respiratory rate (breaths per minute), body temperature (degrees Celsius), and body weight (kg) were measured at every visit. Height (cm) was measured at screening (Visit 1) only. Vital signs were measured in the sitting position using the same arm at each visit, and were measured prior to receiving investigational product at the clinic visits.

Pharmacokinetic and anti-drug antibody endpoints were tested. Pre-dose blood samples were collected for determination of serum functional dupilumab and anti-dupilumab antibodies. Pre-dose serum mAb1 concentrations at Visit 2 (Day 1), mAb1 trough levels at Week 2, Week 4, Week 8, Week 12, Week 16, Week 20, Week 24, and follow-up serum mAb1 at Week 28, Week 32, Week 36, Week 40 were provided. Anti-mAb1 antibody status (negative or titer value) at Visit 2 (Day 1), Week 2, Week 4, Week 8, Week 12, Week 16, Week 20, Week 24, and Week 40 were provided. Patients with ADA titers ≥240 at the end of study visit were scheduled to return approximately 6 months later for an additional assessment of ADA titer. Further follow-up was considered based on the overall assessment of antibody titers and clinical presentation.

Several biomarkers (whole blood biomarkers, plasma biomarkers, serum biomarkers, and exhaled nitric oxide) related to asthmatic inflammation and Th2 polarization were assessed for their value in predicting therapeutic response and/or in documenting the time course of drug response.

Blood eosinophil count was measured as part of the standard 5-part WBC differential cell count on a hematology autoanalyzer.

Eotaxin-3 was measured in heparinized plasma with a validated enzyme immunoassay (Human Eotaxin-3 Quantikine ELISA kit; R&D Systems).

Concentrations of eosinophil cationic protein (ECP) and Staphylococcal *aureus* enterotoxin IgE were measured using quantitative ImmunoCAP assays (Phadia). Antigen-specific IgE was detected using panels of antigens appropriate to the location of the clinical site (Phadiatop test; Phadia). Total IgE was measured with a quantitative method (e.g., ImmunoCAP) approved for diagnostic testing. *Thymus* and activation-regulated chemokine (TARC) was assayed with a validated enzyme immunoassay (Human TARC Quantikine ELISA kit; R&D Systems). Periostin was measured with a validated immunoassay (Human Periostin DuoSet ELISA Development kit; R&D Systems).

Exhaled nitric oxide was analyzed using a NIOX instrument (Aerocrine AB, Solna, Sweden), or similar analyzer using a flow rate of 50 mL/s, and reported in parts per billion (ppb). This assessment was conducted prior to spirometry and following a fast of at least 1 hour.

Pharmacogenetic testing was optional and voluntary. Participants donated a blood sample at the study visit, and this sample was stored for future analysis. For DNA and RNA, blood was collected. DNA and RNA samples may be used to determine a possible relationship between genes and response to treatment with mAb1 and possible side effects to mAb1. Genes that may be studied include those for the IL4R receptor, IL-4, IL-13 and STATE and additional genes that may potentially be part of the IL4R signaling pathway or asthma.

Patient-reported outcomes and health care resource utilization were assessed using the HADS (Hospital Anxiety and Depression Scale), EQ-5D-3L or EQ-5D-5L, and Health care resource utilization.

The HADS is a general scale to detect states of anxiety and depression already used and validated in asthma. The instrument is comprised of 14 items: 7 related to anxiety and 7 to depression. Each item on the questionnaire is scored from 0-3; one can score between 0 and 21 for either anxiety or depression. Scores of 11 or more on either subscale are considered to be a significant 'case' of psychological morbidity, while scores of 8 to 10 represent 'borderline' and 0 to 7 'normal'.

The EQ-5D-3L or EQ-5D-5L is a standardized health-related quality of life questionnaire developed by the Euro-Qol Group in order to provide a simple, generic measure of health for clinical and economic appraisal. The EQ-5D is designed for self-completion by patients. The EQ-5D essentially consists of 2 pages—the EQ-5D descriptive system and the EQ VAS. The EQ-5D descriptive system comprises 5 dimensions: mobility, self-care, usual activities, pain/discomfort and anxiety/depression. Each dimension has 3 levels: no problem, some problems, severe problems. The EQ Visual Analogue Scale (VAS) records the respondent's self-rated health on a vertical visual analogue scale. The EQ VAS 'thermometer' has endpoints of 100 (Best imaginable health state) at the top and 0 (Worst imaginable health state) at the bottom.

A questionnaire of health care resource utilization (reliever medication, specialist visit, hospitalization, emergency or urgent medical care facility visit, outcome, sick leaves, etc.) was administered at Visit 2 and monthly thereafter.

F. Study Procedures

The clinical trial consists of three periods, using an add-on therapy approach to inhaled corticosteroid/long-acting beta agonist combination therapy (ICS/LABA): a Screening Period (14 to 21 days; Visit 1), a Randomized Treatment Period (24 weeks; Visits 2-11), and a Post-treatment Period (16 weeks; Visits 12-15).

The following procedures were performed at Visit 1: (1) Interviewed to collect patient demographic information, asthma history (including smoking habits), other medical history and surgical history, and prior and concomitant medications; (2) Reviewed entry criteria to assess eligibility, with special attention to verify the following: (a) Prescribed combination product ICS/LABA dosage meets the pre-protocol definition of medium to high dose ICS requirement (i.e., fluticasone propionate 250 µg twice daily or equipotent ICS daily dosage) with a stable dose of ICS/LABA for 1 month prior to Visit 1; and (b) Patient had experienced, within 1 year prior to Visit 1: 1) Treatment with 1 systemic (oral or parenteral) steroids bursts for worsening asthma and/or 2) Hospitalization or an emergency/urgent medical care visit for worsening asthma; (3) Measured vital signs [blood pressure, heart rate, respiration rate, body temperature, weight (kg), height (cm)]; (4) Performed physical examination; (5) Administered ACQ-5 and Verify ACQ-5 score is 1.5; (6) Measured exhaled nitric oxide, Exhaled nitric oxide assessment was conducted prior to spirometry and following a fast of 1 hour; (7) Performed spirometry. Entry criteria at Visit 1 included the requirement of a specific FEV1 and demonstration of reversibility. Spirometry was performed first, between 6 and 10 AM after withholding the last dose of salbutamol/albuterol or levosalbutamol/levalbuterol for 6 hours and withholding the last dose of ICS/LABA for 12 hours. FEV1 must be 40 to 80% predicted normal, and three attempts may be made during the Screening Period to meet the qualifying criteria for spirometry; (8) Established reversibility, Reversibility must be at least 12% and 200 mL in FEV1 after 200 µg to 400 µg (2 to 4 inhalations) of salbutamol/albuterol; (9) Performed 12-lead electrocardiography (ECG); (10) Performed chest X-ray if none available within the previous 12 months; (11) Obtained (fasting) blood samples for screening clinical laboratory determinations: a) Hematology: included hemoglobin, hematocrit, platelet count, total white blood cell count with five-part differential count, and total red blood cell count; b) Obtained a separate hematology sample for local analysis, and c) Serum chemistry: included: creatinine, blood urea nitrogen, glucose, uric acid, total cholesterol, total protein, albumin, total bilirubin, alanine aminotransferase, aspartate aminotransferase, alkaline phosphatase, electrolytes (sodium, potassium, chloride), bicarbonate, and creatine phosphokinase; (12) Obtained blood samples for hepatitis screen (hepatitis B surface antigen (HBsAg), Hepatitis B IgM core antibody (HBcAb-IgM), hepatitis C antibodies (HC Ab), HIV screen (Anti-HIV-1 and HIV-2 antibodies), anti-nuclear antibody (ANA); (13) Obtained blood sample for serum immunoglobulin electrophoresis (IgG, IgG subclasses1-4, IgM, and IgA); (14) Obtained serum β-HCG pregnancy test if female of childbearing potential; (15) Obtained urine for urinalysis (dipstick); (16) Obtained blood sampling for biomarker set A, and serum total IgE; (17) For those patients who have signed the specific informed consent form; perform optional blood RNA sampling; (18) Dispensed electronic diary/PEF meter, provided instructions for daily use, and reminded patient to bring the device to the next visit; (19) Reminded patient to continue their stable dose of ICS/LABA and instructed patient to record daily usage in the electronic diary; (20) Dispensed and resupplied salbutamol/albuterol or levosalbutamol/levalbuterol for use as reliever medication throughout the study. Instructed patient to record usage in the electronic diary; (21) Reminded patient to withhold last dose of salbutamol/albuterol or levosalbutamol/levalbuterol for 6 hours and withhold last dose of ICS/LABA for 12 hours prior to next visit; and (22) Commenced AE reporting.

The following procedures were performed at Visit 2 (Week 0): (1) Recorded all medication use with start date and dose in eCRF; inquired about AEs/SAEs and background asthma therapy tolerability; (2) Reviewed entry criteria and reconfirmed eligibility based on review of Inclusion/Exclusion Criteria; (3) Administered ACQ-5 and AQLQ; (4) Verified the following: a) Visit 2 ACQ-5 score is 21.5, and b) Compliance with use of the mandatory background therapy, ICS/LABA combination product, as defined as: 80% of total number of prescribed "stable dose" puffs taken during the screening period. Compliance was verified based on ICS/LABA use recorded on the patient electronic diary during the screening period; (5) Measured vital signs (blood pressure, heart rate, respiration rate, body temperature, weight); (6) Performed spirometry: Entry criteria at Visit 1 included the requirement of a specific $FEV_1$ and demonstration of reversibility, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product, FEV1 must be 40 to 80% predicted normal, and Patients must also meet the criteria for spirometry at Visit 2 prior to randomization.

If the patient met all inclusion and did not meet any exclusion criteria, then the following procedures were also performed at Visit 2: (1) Called IVRS/IWRS to register visit, randomized the patient if entry criteria were met, and received the first treatment kit number assignment. Referred to the Visit 1 central laboratory blood eosinophil count at this IVRS/IWRS call to stratify to patient into the correct high (≥300 cells/µL), middle (200 to 299 cells/µL) or low blood eosinophil stratum (<200 cells/µL); (2) Switched the patient to an equivalent dosage of 1 of the 3 allowable treatment period combination products listed below if the patient's background combination product ICS/LABA prior to Visit 2 was an alternative combination product (e g., fluticasone/formoterol): fluticasone propionate/salmeterol, or budesonide/formoterol, or mometasone furoate/formoterol. Note that the allowable ICS/LABA combination products and acceptable dosage form, strength and schedule required during the treatment period to meet the background therapy requirement for moderate to high dose ICS daily dose were discussed above; (3) Administered SNOT-22; (4) Administered HADS and EQ-5D-3L or EQ-5D-5L questionnaire; (5) Administered health care resource utilization questionnaire; (6) Performed urine pregnancy test (for women of childbearing potential); (7) Performed blood sampling (prior to administration of IMP (mAb1)) for clinical laboratories. Note that Clinical laboratory testing at Visit 2 was limited to hematology (including a separate hematology sample obtained for local analysis), pharmacokinetics, anti-drug antibodies, biomarker set A, periostin, serum total IgE, biomarker set B and archival serum sample; (8) For those patients who signed a specific informed consent form, collected blood sample for DNA and RNA sampling (prior to administration of investigational product during the Randomized Treatment Period); (9) Downloaded electronic diary/PEF meter and reminded patient to bring the device to the next visit; (10) Dispensed and administered IMP (mAb1); (11) Reminded patient to continue the stable dose of ICS/LABA and record daily usage in the electronic diary; and (12) Scheduled appointment for next visit and reminded patient to withhold last dose of salbutamol/albuterol or levosalbutamol/levalbuterol for 6 hours and withhold last dose of ICS/LABA for 12 hours prior to next visit.

The following procedures were performed at Visit 3 (Week 2): (1) Recorded all concomitant medication used; inquired about AEs/SAEs and background asthma therapy tolerability; (2) Measured vital signs (blood pressure, heart rate, respiration rate, body temperature, weight); (3) Administered ACQ-5; (4) Measured exhaled nitric oxide, Exhaled nitric oxide assessment was conducted prior to spirometry and following a fast of ≥1 hour; (5) Performed spirometry, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product; (6) Performed 12-lead electrocardiography (ECG); (7) Performed blood sampling (prior to administration of IMP (mAb1)) for pharmacokinetics, anti-drug antibodies, and biomarker set A; (8) Performed optional blood RNA sampling; (9) Downloaded electronic diary/PEF meter and reminded patient to bring the device to the next visit; (10) Dispensed and administered IMP (mAb1); and (11) Scheduled appointment for next visit and reminded patient to withhold last dose of salbutamol/albuterol or levosalbutamol/levalbuterol for 6 hours and withhold last dose of ICS/LABA for 12 hours prior to next visit.

These same procedures were performed at Visit 4 (Week 4). In addition, patient was administered a health care resource utilization questionnaire.

The following procedures were performed at Visit 5 (Week 6): (1) Recorded all concomitant medication used; inquired about AEs/SAEs and background asthma therapy tolerability; (2) Measured vital signs (blood pressure, heart rate, respiration rate, body temperature, weight); (3) Downloaded electronic diary/PEF meter and reminded patient to bring the device to the next visit; (4) Dispensed and administered IMP (mAb1); (5) Reminded patient to continue the stable dose of ICS/LABA and record daily usage in the electronic diary; and (6) Scheduled appointment for next visit and reminded patient to withhold last dose of salbutamol/albuterol or levosalbutamol/levalbuterol for 6 hours and withhold last dose of ICS/LABA for 12 hours prior to next visit.

The following procedures were performed at Visit 6 (Week 8): (1) Recorded all concomitant medication use; inquired about AEs/SAEs and background asthma therapy tolerability; (2) Measured vital signs (blood pressure, heart rate, respiration rate, body temperature, weight); (3) Administered ACQ-5; (4) Administered health care resource utilization questionnaire; (5) Measured exhaled nitric oxide, Exhaled nitric oxide assessment was conducted prior to spirometry and following a fast of ≥1 hour; (6) Performed spirometry, Spirometry was performed between 6 and 10 AM after withholding the last dose of ICS/LABA for 12 hours and prior to administration of investigational product; (7) Performed blood sampling for clinical laboratories, pharmacokinetics, anti-drug antibodies, biomarker set A, and serum total IgE; (8) Downloaded electronic diary/PEF meter and reminded patient to bring the device to the next visit and record daily usage in the electronic diary; and (9) Dispensed and administered IMP (mAb1).

The following procedures were performed at Visit 7 (Week 10): (1) Recorded all concomitant medication use; inquired about AEs/SAEs and background asthma therapy tolerability; (2) Measured vital signs (blood pressure, heart rate, respiration rate, body temperature, weight); (3) Downloaded electronic diary/PEF meter and reminded patient to bring the device to the next visit; (4) Dispensed and administered IMP (mAb1); (5) Scheduled appointment for next visit and reminded patient: To continue the stable dose of ICS/LABA and record daily usage in the electronic diary, To come for next visit in fasting state, and To withhold last dose of salbutamol/albuterol or levosalbutamol/levalbuterol for 6 hours and withhold last dose of ICS/LABA for 12 hours prior to next visit.

The following procedures were performed at Visit 8 (Week 12): (1) Recorded all concomitant medication used; inquired about AEs/SAEs and background asthma therapy tolerability; (2) Measured vital signs (blood pressure, heart rate, respiration rate, body temperature, weight); (3) Performed physical examination; (4) Administered ACQ-5 and AQLQ; (5) Administered SNOT-22; (6) Administered HADS and EQ-5D-3L or EQ-5D-5L questionnaire; (7) Administered health care resource utilization questionnaire; (8) Measured exhaled nitric oxide, Exhaled nitric oxide assessment was conducted prior to spirometry and following a fast of ≥1 hour; (9) Performed spirometry, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product; (10) Performed 12-lead electrocardiography (ECG); (11) Performed blood sampling (fasting) for clinical laboratories, pharmacokinetics, anti-drug antibodies, biomarker set A, periostin, archival serum sample, and serum total IgE; (12) Obtained blood sample for serum immunoglobulin electrophoresis (IgG, IgG subclasses1-4, IgM, and IgA); (13) Obtained urine for urinalysis (dipstick); (14) Downloaded electronic diary/PEF meter and reminded patient to bring the device to the next visit and record daily usage in the electronic diary; (15) Dispensed and administered IMP (mAb1); (16) Dispensed patient (self-injection) Home Dosing Diary; (17) Reminded patient to continue the stable dose of ICS/LABA and record daily usage in the electronic diary; and (18) Scheduled appointment for next visit and remind patient to withhold last dose of salbutamol/albuterol or levosalbutamol/levalbuterol for 6 hours and withhold last dose of ICS/LABA for 12 hours prior to next visit.

The following procedures were performed at Visit 9 (Week 16): (1) Checked compliance to IMP (mAb1); recorded all concomitant medication use; inquired about AEs/SAEs and background asthma therapy tolerability; (2) Reviewed patient Home Dosing Diary for content and completeness; (3) Measured vital signs (blood pressure, heart rate, respiration rate, body temperature, weight); (4) Administered ACQ-5; (5) Administered health care resource utilization questionnaire; (6) Measured exhaled nitric oxide, Exhaled nitric oxide assessment was conducted prior to spirometry and following a fast of ≥1 hour; (7) Performed spirometry, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product; (8) Performed blood sampling for clinical laboratories, pharmacokinetics, anti-drug antibodies, biomarker set A, and serum total IgE; (9) Downloaded electronic diary/PEF meter and reminded patient to bring the device to the next visit; (10) Reviewed instructions on self-injection and dosing and dispensed patient (self-injection) Home Dosing Diary; (11) Dispensed and administered IMP (mAb1); (12) Reminded patient to continue the stable dose of ICS/LABA and record daily usage in the electronic diary; and (13) Scheduled appointment for next visit and reminded patient to withhold last dose of salbutamol/albuterol or levosalbutamol/levalbuterol for 6 hours and withhold last dose of ICS/LABA for 12 hours prior to next visit.

The same procedures were conducted at Visit 10 (Week 20), except that for the next visit, the patient was reminded to continue the stable dose of ICS/LABA used during the screening period, to come for next visit in fasting state, and to withhold last dose of salbutamol/albuterol or levosalbutamol/levalbuterol for 6 hours and withhold last dose of ICS/LABA for 12 hours prior to next visit.

The following procedures were performed at Visit 11 (Week 24/end-of-treatment visit): (1) Checked compliance to IMP (mAb1); recorded all concomitant medication use; inquired about AEs/SAEs and background asthma therapy tolerability; (2) Reviewed patient Home Dosing Diary for content and completeness; (3) Measured vital signs (blood pressure, heart rate, respiration rate, body temperature, weight); (4) Performed physical examination; (5) Administered ACQ-5 and AQLQ; (6) Administered SNOT-22; (7) Administered HADS and EQ-5D-3L or EQ-5D-5L questionnaire; (8) Administered health care resource utilization questionnaire; (9) Measured exhaled nitric oxide, Exhaled nitric oxide assessment was conducted prior to spirometry and following a fast of ≥1 hour; (10) Performed spirometry, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product; (11) Performed 12-lead electrocardiography (ECG); (13) Performed blood sampling (fasting) for clinical laboratories, pharmacokinetics, anti-drug antibodies, biomarker set A, periostin, biomarker set B, archival serum sample, and serum total IgE; (14) Obtained blood sample for serum immunoglobulin electrophoresis (IgG, IgG subclasses1-4, IgM, and IgA); (15) Obtained urine for urinalysis (dipstick); (16) Downloaded electronic diary/PEF meter and reminded patient to bring the device to the next visit and record daily usage in the electronic diary; (17) Reminded patient to continue the stable dose of ICS/LABA and record daily usage in the electronic diary; (18) Scheduled appointment for next visit and reminded patient to withhold last dose of salbutamol/albuterol or levosalbutamol/levalbuterol for 6 hours and withhold last dose of ICS/LABA for 12 hours prior to next visit; and (19) Called IVRS/IWRS to register the EOT (end of treatment) date.

The following were performed at each of Visits 12, 13, and 14 (Weeks, 28, 32, and 36 Post Treatment Period): (1) Recorded all concomitant medication use; inquired about AEs/SAEs and background asthma therapy tolerability; (2) Measured vital signs (blood pressure, heart rate, respiration rate, body temperature, weight); (3) Administered ACQ-5; (4) Administered health care resource utilization questionnaire; (5) Measured exhaled nitric oxide, Exhaled nitric oxide assessment was conducted prior to spirometry and following a fast of ≥1 hour; (6) Performed spirometry, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product; (7) Performed blood sampling for pharmacokinetics, biomarker set A; (8) For Visit 13, performed serum total IgE; (9) Downloaded electronic diary/PEF meter and reminded patient to bring the device to the next visit; (10) Reminded patient to continue the stable dose of ICS/LABA maintained over the randomized treatment period (unless treatment modified based on medical judgment) and record daily usage in the electronic diary; (11) Scheduled appointment for next visit and reminded patient to withhold last dose of salbutamol/albuterol or levosalbutamol/levalbuterol for 6 hours and withhold last dose of ICS/LABA for 12 hours prior to next visit; and (12) For Visit 14, reminded patient to come for visit in fasting state.

The following were performed at visit 15 (Week 40 End-of-Study Visit): (1) Recorded all concomitant medication use; inquired about AEs/SAEs and background asthma therapy tolerability; (2) Measured vital signs (blood pressure, heart rate, respiration rate, body temperature, weight); (3) Performed physical examination; (4) Administered ACQ-5; (5) Administered SNOT-22; (6) Administered health care resource utilization questionnaire; (7) Measured exhaled nitric oxide, Exhaled nitric oxide assessment was conducted prior to spirometry and following a fast of ≥1 hour; (8) Perform spirometry, Spirometry was performed between 6 and 10 AM after withholding the last dose of salbutamol/albuterol or levosalbutamol/levalbuterol for 6 hours and withholding the last dose of ICS/LABA for 12 hours and prior to administration of investigational product; (9) Performed 12-lead electrocardiography (ECG); (10) Perform blood sampling for (fasting) clinical laboratories, pharmacokinetics, anti-drug antibodies, biomarker set A, serum total IgE, periostin, and biomarker set B; (11) Obtained blood sample for serum immunoglobulin electrophoresis (IgG, IgG subclasses1-4, IgM, and IgA); (12) Downloaded electronic diary/PEF meter; and (13) Called IVRS/IWRS to register the EOS (end of study) date.

Study participant baseline biomarker values were as follows (Table 3):

TABLE 3

Summary of baseline biomarkers-descriptive statistics in a randomized population.

| | Placebo (N = 158) | Dupilumab | | | | All (N = 776) |
| --- | --- | --- | --- | --- | --- | --- |
| | | 200 mg q4w (N = 154) | 300 mg q4w (N = 157) | 200 mg q2w (N = 150) | 300 mg q2w (N = 157) | |
| Baseline eosinophil (GIGA/L) | | | | | | |
| Number | 158 | 154 | 157 | 150 | 157 | 776 |
| Mean SD | 0.34 (0.30) | 0.38 (0.76) | 0.33 (0.27) | 0.36 (0.35) | 0.32 (0.25) | 0.35 (0.43) |
| Median | 0.26 | 0.26 | 0.27 | 0.25 | 0.26 | 0.26 |
| Q1:Q3 | 0.16:0.43 | 0.14:0.39 | 0.14:0.42 | 0.16:0.45 | 0.16:0.39 | 0.15:0.42 |
| Min:Max | 0.0:2.1 | 0.0:8.8 | 0.0:1.9 | 0.0:2.7 | 0.1:1.8 | 0.0:8.8 |
| Baseline eosinophil group (GIGA/L) | | | | | | |
| <0.2 | 52 (32.9%) | 60 (39.0%) | 55 (35.0%) | 51 (34.0%) | 53 (33.8%) | 271 (34.9%) |
| 0.2-0.299 | 38 (24.1%) | 32 (20.8%) | 36 (22.9%) | 34 (22.7%) | 40 (25.5%) | 180 (23.2%) |
| >=0.3 | 68 (43.0%) | 62 (40.3%) | 66 (42.0%) | 65 (43.3%) | 64 (40.8%) | 325 (41.9%) |
| Baseline total IgE (IU/ML) | | | | | | |
| Number | 157 | 154 | 157 | 150 | 157 | 775 |
| Mean (SD) | 419.31 (736.31) | 454.36 (817.46) | 517.07 (974.39) | 416.21 (607.07) | 367.83 (555.50) | 435.05 (753.88) |
| Median | 200.00 | 184.50 | 166.00 | 176.50 | 158.00 | 181.00 |
| Q1:Q3 | 87.00:448.00 | 72.00:475.00 | 80.00:464.00 | 51.00:490.00 | 73.00:405.00 | 76.00:436.00 |
| Min:Max | 9.0:5000.0 | 5.0:5000.0 | 4.0:5000.0 | 5.0:3821.0 | 1.0:3413.0 | 1.0:5000.0 |

TABLE 3-continued

Summary of baseline biomarkers-descriptive statistics in a randomized population.

| | Placebo (N = 158) | Dupilumab 200 mg q4w (N = 154) | 300 mg q4w (N = 157) | 200 mg q2w (N = 150) | 300 mg q2w (N = 157) | All (N = 776) |
|---|---|---|---|---|---|---|
| Baseline total eosinophil (CIGA/L) and IgE (IU/ML) | | | | | | |
| IgE > 100 and EOS > 0.14 | 90 (57.3%) | 80 (51.9%) | 83 (52.9%) | 89 (59.3%) | 82 (52.2%) | 424 (54.7%) |
| IgE <= 100 or EOS <= 0.14 | 67 (42.7%) | 74 (48.1%) | 74 (47.1%) | 61 (40.7%) | 75 (47.8%) | 351 (45.3%) |
| Baseline ECP (NG/ML) | | | | | | |
| Number | 156 | 152 | 157 | 149 | 155 | 769 |
| Mean SD | 22.04 (29.06) | 25.20 (35.85) | 21.34 (24.24) | 24.00 (26.55) | 24.97 (27.87) | 23.49 (28.92) |
| Median | 13.00 | 12.50 | 15.00 | 14.00 | 16.00 | 14.00 |
| Q1:Q3 | 6.00:27.00 | 7.00:29.50 | 6.00:25.00 | 7.00:30.00 | 9.00:30.00 | 7.00:27.00 |
| Min:Max | 1.0:196.0 | 2.0:200.0 | 1.0:162.0 | 1.0:133.0 | 1.0:200.0 | 1.0:200.0 |
| Baseline periostin (PG/ML) | | | | | | |
| Number | 143 | 130 | 144 | 129 | 137 | 683 |
| Mean (SD) | 50074.83 (18401.04) | 52086.92 (21308.44) | 51684.72 (20077.88) | 60510.85 (77310.99) | 49837.23 (19712.27) | 52720.64 (38145.73) |
| Median | 46100.00 | 48700.00 | 46400.00 | 50800.00 | 46100.00 | 47400.00 |
| Q1:Q3 | 38400.00: 57700.00 | 37200.00: 59100.00 | 38600.00: 58800.00 | 39400.00: 63600.00 | 37800.00: 56600.00 | 38500.00: 5900.00 |
| Min:Max | 25600.0: 139000.0 | 24400.0: 144000.0 | 24000.0: 146000.0 | 26100.0: 902000.0 | 24400.0: 194000.0 | 24000.0: 902000.0 |
| Baseline eofaxin (PG/ML) | | | | | | |
| Number | 157 | 152 | 157 | 148 | 156 | 770 |
| Mean (SD) | 83.49 (300.40) | 65.23 (63.98) | 63.91 (56.02) | 59.01 (46.60) | 58.42 (43.29) | 66.11 (143.61) |
| Median | 47.30 | 49.75 | 50.90 | 49.20 | 48.65 | 46.90 |
| Q1:Q3 | 29.50:71.90 | 32.50:81.50 | 31.90:79.90 | 31.70:75.95 | 31.25:70.20 | 31.60:76.00 |
| Min:Max | 3.9:3774.1 | 3.9:615.7 | 3.9:397.1 | 3.9:349.3 | 3.9:246.8 | 3.9:3774.1 |
| Baseline TARC (PG/ML) | | | | | | |
| Number | 158 | 154 | 157 | 150 | 157 | 776 |
| Mean (SD) | 602.27 (1399.52) | 694.43 (2608.08) | 565.18 (484.19) | 616.41 (1074.74) | 471.93 (315.91) | 589.42 (1426.28) |
| Median | 359.24 | 415.16 | 419.03 | 445.75 | 390.22 | 404.01 |
| Q1:Q3 | 259.53:550.17 | 262.66:680.08 | 283.78:652.10 | 302.61:632.50 | 274.29:598.68 | 279.66:620.59 |
| Min:Max | 58.9:15419.0 | 63.7:32651.0 | 101.1:3686.6 | 84.0:12453.0 | 54.4:2119.5 | 54.4:32651.0 |
| Baseline FeNO (ppb) | | | | | | |
| Number | 144 | 139 | 139 | 136 | 141 | 699 |
| Mean (SD) | 38.95 (34.79) | 42.03 (38.85) | 38.13 (35.11) | 39.25 (36.67) | 37.16 (29.86) | 39.10 (35.09) |
| Median | 28.00 | 31.00 | 24.00 | 29.00 | 29.00 | 28.00 |
| Q1:Q3 | 16.00:45.50 | 18.00:54.00 | 16.00:47.00 | 17.00:47.00 | 14.00:51.00 | 16.00:48.00 |
| Min:Max | 3.0:186.0 | 3.0:294.0 | 5.0:222.0 | 6.0:224.0 | 3.0:175.0 | 3.0:294.0 |

Abbreviations: ECP = eosinophil cationic protein; FeNO = fractional exhaled nitric oxide; max = maximum; min = minimum; q2w = once every 2 weeks; q4w = once every 4 weeks; SD = standard deviation; TARC = thymus and activation-regulated chemokine.

G. Dosage and Duration

The summary of treatment exposure is presented in Table 4. The cumulative treatment exposure to treatment was 61.4 to 65.3 patient-years, across the placebo and Dupilumab treatment arms. The mean duration of study treatment ranged from 146.4 days to 151.7 days in the 5 treatment groups.

change in FEV1 from baseline at week 12 was 0.18 L in the placebo group, and ranged from 0.26 L (200 mg q4w dose) to 0.43 L (200 mg q2w dose) in the 4 dupilumab treatment arms (Table 5). The LS mean differences between dupilumab and placebo were 0.08 L (200 mg q4w), 0.017 L (300 mg q4w), 0.25 L (200 mg q2w) and 0.20 L (300 mg q2w).

TABLE 4

Exposure to investigational product in a safety population.

| | Placebo (N = 158) | Dupilumab | | | |
|---|---|---|---|---|---|
| | | 200 mg q4w (N = 150) | 300 mg q4w (N = 157) | 200 mg q2w (N = 148) | 300 mg q2w (N = 156) |
| Cumulative exposure to treatment (patient years) | 65.3 | 61.4 | 62.9 | 61.5 | 64.4 |
| Duration of study treatment (Day) | | | | | |
| Number | 158 | 150 | 157 | 148 | 156 |
| Mean (SD) | 151.0 (30.2) | 149.5 (32.6) | 146.4 (36.0) | 151.7 (31.6) | 150.9 (33.5) |
| Median | 167.0 | 167.0 | 167.0 | 167.0 | 168.0 |
| Min:Max | 14:174 | 14:188 | 14:197 | 14:176 | 14:176 |
| Duration of study treatment by category [n (%)] | | | | | |
| >0 and <=2 weeks | 2 (1.3%) | 3 (2.0%) | 1 (0.6%) | 1 (0.7%) | 3 (1.9%) |
| >2 and <=4 weeks | 2 (1.3%) | 1 (0.7%) | 2 (1.3%) | 1 (0.7%) | 0 |
| >4 and <=8 weeks | 0 | 0 | 5 (3.2%) | 4 (2.7%) | 4 (2.6%) |
| >8 and <=12 weeks | 1 (0.6%) | 2 (1.3%) | 3 (1.9%) | 1 (0.7%) | 0 |
| >12 and <=16 weeks | 11 (7.0%) | 17 (11.3%) | 14 (8.9%) | 7 (4.7%) | 9 (5.8%) |
| >16 and <=20 weeks | 23 (14.8%) | 17 (11.3%) | 22 (14.0%) | 17 (11.5%) | 23 (14.7%) |
| >20 and <=24 weeks | 86 (54.4%) | 80 (53.3%) | 76 (48.4%) | 89 (60.1%) | 89 (57.1%) |
| >24 weeks | 33 (20.9%) | 30 (20.0%) | 34 (21.7%) | 28 (18.9%) | 28 (17.9%) |
| Number of patients with duration of study treatment by category [n (%)] | | | | | |
| >0 week | 156 (100%) | 150 (100%) | 157 (100%) | 148 (100%) | 156 (100%) |
| >2 week | 156 (98.7%) | 147 (98.0%) | 156 (99.4%) | 147 (99.3%) | 153 (98.1%) |
| >4 weeks | 154 (97.5%) | 146 (97.3%) | 154 (98.1%) | 146 (98.6%) | 153 (98.1%) |
| >8 weeks | 154 (97.5%) | 146 (97.3%) | 149 (94.9%) | 142 (95.9%) | 149 (95.5%) |
| >12 weeks | 153 (96.8%) | 144 (96.0%) | 146 (93.0%) | 141 (95.3%) | 149 (95.5%) |
| >16 weeks | 142 (89.9%) | 127 (84.7%) | 132 (64.1%) | 134 (90.5%) | 140 (89.7%) |
| >20 weeks | 119 (75.3%) | 110 (73.3%) | 110 (70.1%) | 117 (79.1%) | 117 (75.0%) |
| >24 weeks | 33 (20.9%) | 30 (20.0%) | 34 (21.7%) | 28 (18.9%) | 28 (17.9%) |
| Number of injections [n (%)] | | | | | |
| 1 injection | 0 | 0 | 0 | 0 | 0 |
| 2 injection | 2 (1.3%) | 3 (2.0%) | 1 (0.6%) | 1 (0.7%) | 3 (1.9%) |
| 3 injection | 2 (1.3%) | 1 (0.7%) | 3 (1.9%) | 1 (0.7%) | 1 (0.6%) |
| 4 injection | 0 | 0 | 2 (1.3%) | 2 (1.4%) | 2 (1.3%) |
| 5 injection | 0 | 0 | 2 (1.3%) | 3 (2.0%) | 1 (0.6%) |
| 6 injection | 0 | 1 (0.7%) | 3 (1.9%) | 0 | 0 |
| 7 injection | 2 (1.3%) | 2 (1.3%) | 2 (1.3%) | 1 (0.7%) | 1 (0.6%) |
| 8 injection | 2 (1.3%) | 7 (4.7%) | 6 (3.8%) | 3 (2.0%) | 3 (1.9%) |
| 9 injection | 8 (5.1%) | 12 (8.0%) | 13 (8.3%) | 6 (4.1%) | 9 (5.8%) |
| 10 injection | 18 (11.4%) | 9 (6.0%) | 9 (5.7%) | 10 (6.8%) | 13 (8.3%) |
| 11 injection | 7 (4.4%) | 11 (7.3%) | 9 (5.7%) | 7 (4.7%) | 12 (7.7%) |
| 12 injection | 23 (14.6%) | 24 (16.0%) | 22 (14.0%) | 21 (14.2%) | 5 (3.2%) |
| 13 injection | 94 (59.5%) | 80 (53.3%) | 85 (54.1%) | 92 (62.2%) | 105 (67.3%) |
| 14 injection | 0 | 0 | 0 | 1 (0.7%) | 0 |
| 15 injection | 0 | 0 | 0 | 0 | 1 (0.6%) |

Abbreviations: min = minimum; max = maximum; n = number of patients; N = sample/treatment group size; q2w = once every 2 weeks; q4w = once every 4 weeks; SD = standard deviation.
Patients were considered in the treatment group they actually received. The loading dose was counted as 2 injections.

H. Efficacy

Primary Efficacy Endpoint

The primary analysis compared the dupilumab treatment groups to the placebo group. The primary efficacy endpoint was the change in FEV1 from baseline to week 12 in the HEos ITT population. The primary efficacy variable was analyzed using a mixed-effect model with repeated measures (MMRM) approach. The assessment of absolute change in FEV1 from baseline at week 12 performed during the interim analysis was the final analysis of the primary endpoint.

Figure 3:
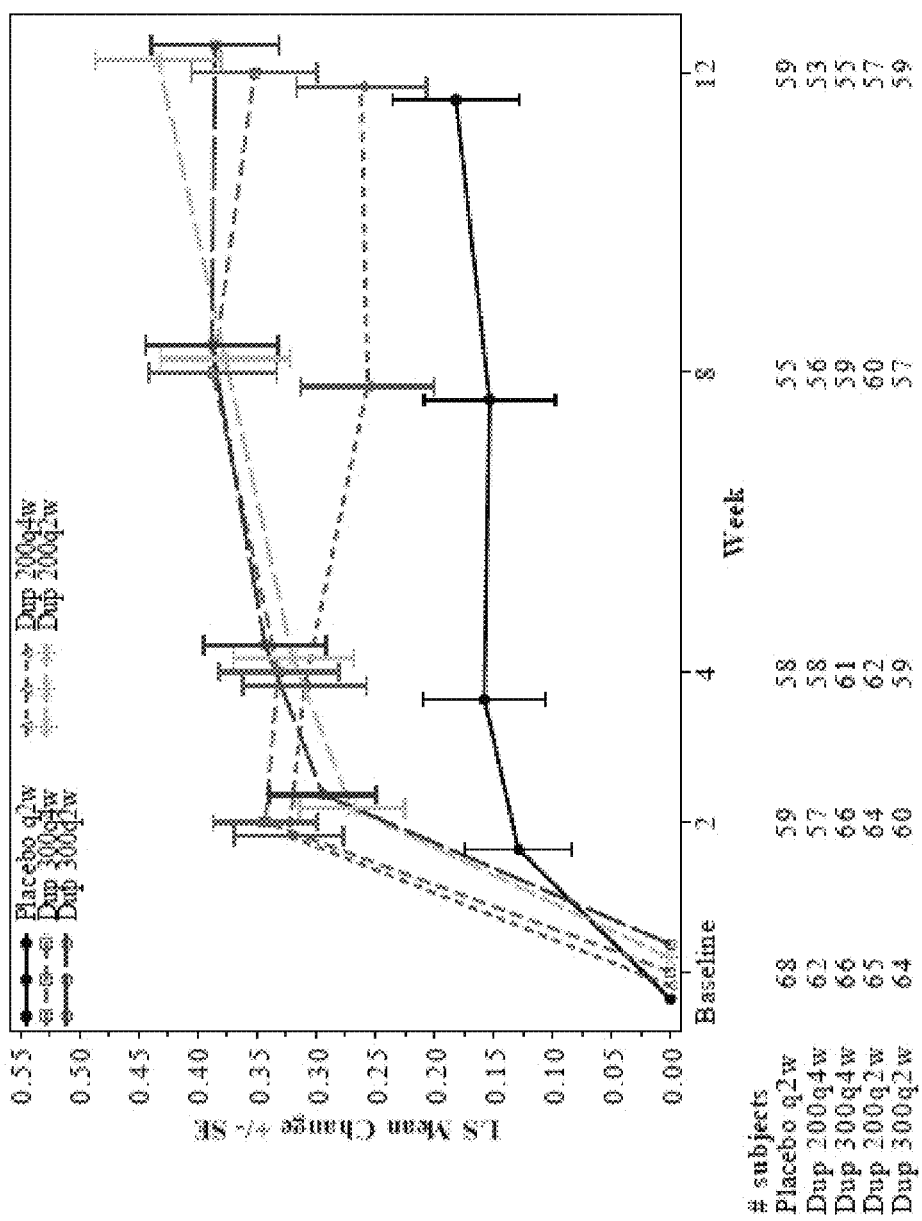
FIG. 3 graphically depicts the least squares mean change from baseline in FEV1 (L) over time (mixed-effect model with repeated measures (MMRM) including measurements up to week 12) in a High Eosinophil (HEos) Intent-To-Treat (ITT) population. Abbreviations: Dup=Dupilumab; FEV1=forced expiratory volume in 1 second; LS=least squares; q2w=once every 2 weeks; q4w=once every 4 weeks; SE=standard error of the mean. FEV1 (L) collected from systemic corticosteroid start date to systemic corticosteroid end date+30 days for each severe exacerbation episode are excluded in order to reduce the confounding effect of systemic corticosteroids.

FIG. 3 presents the least squares (LS) mean change in FEV1 over time for the HEos ITT population. The LS mean The LS mean differences were statistically significant when compared with placebo for the 300 mg q4w (p=0.024), 200 mg q2w (p=0.0009), 300 mg q2w doses (p=0.0073). Statistical significance was not achieved for the lowest dose (200 mg q4 w; p=0.2966). The change in FEV1 from baseline to week 12 in the ITT population was analyzed to determine the treatment effect of dupilumab on FEV1 for the entire study population.

Figure 4:
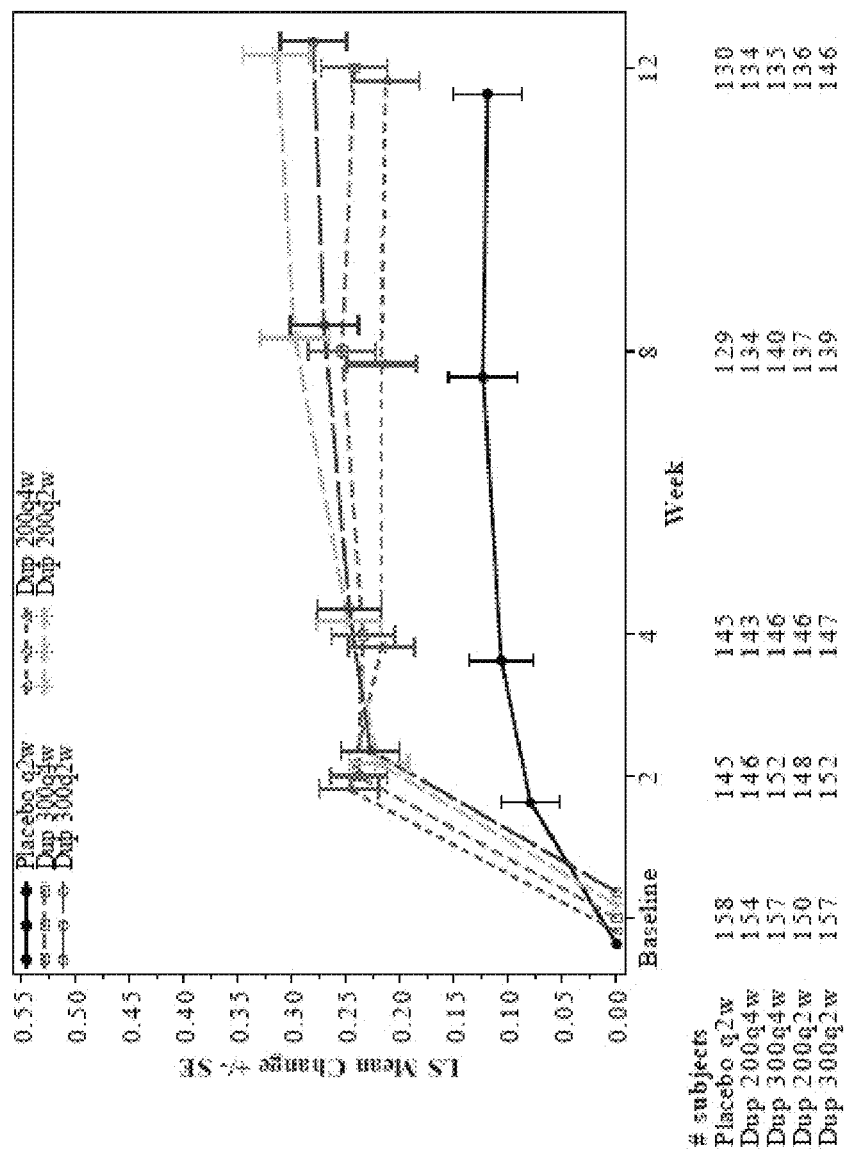
FIG. 4 graphically depicts the least squares mean change from baseline in FEV1 (L) over time (MMRM including measurements up to week 12) in an ITT population. FEV1 (L) collected from systemic corticosteroid start date to systemic corticosteroid end date+30 days for each severe exacerbation episode are excluded in order to reduce the confounding effect of systemic corticosteroids.

FIG. 4 presents the LS mean change in FEV1 over time for the ITT population. The LS mean change in FEV1 from baseline to week 12 for the ITT population was 0.12 L in the placebo group, and ranged from 0.21 L (200 mg q4w dose)

to 0.31 L (200 mg q2w dose) in the 4 dupilumab treatment arms (Table 6). The LS mean differences between dupilumab and placebo were 0.09 L (200 mg q4w), 0.012 L (300 mg q4w), 0.19 L (200 mg q2w) and 0.16 L (300 mg q2w). The LS mean differences were statistically significant when compared with placebo for all dupilumab doses.

TABLE 5

Primary analysis: Change from baseline in FEV1 (L) at week 12 in a HEos ITT population.

| FEV$_1$ | Placebo (N = 68) | Dupilumab 200 mg q4w (N = 62) | 300 mg q4w (N = 66) | 200 mg q2w (N = 65) | 300 mg q2w (N = 64) |
|---|---|---|---|---|---|
| Baseline | | | | | |
| Number | 68 | 62 | 66 | 65 | 64 |
| Mean (SD) | 1.86 (0.68) | 1.80 (0.49) | 1.87 (0.60) | 1.80 (0.52) | 1.77 (0.50) |
| Median | 1.65 | 1.75 | 1.72 | 1.75 | 1.71 |
| Q1:Q3 | 1.33:2.40 | 1.40:2.11 | 1.47:2.13 | 1.45:2.09 | 1.31:2.09 |
| Min:Max | 0.9:3.6 | 0.9:3.4 | 1.0:4.2 | 0.9:3.4 | 1.0:3.1 |
| Week 12 | | | | | |
| Number | 59 | 53 | 55 | 57 | 59 |
| Mean (SD) | 2.13 (0.77) | 2.09 (0.54) | 2.26 (0.70) | 2.26 (0.68) | 2.12 (0.54) |
| Median | 2.08 | 2.01 | 2.16 | 2.12 | 2.20 |
| Q1:Q3 | 1.50:2.86 | 1.76:2.37 | 1.74:2.52 | 1.77:2.51 | 1.77:2.46 |
| Min:Max | 0.9:3.6 | 1.1:3.7 | 1.3:4.2 | 1.0:4.6 | 0.8:3.3 |
| Change from baseline | | | | | |
| Number | 59 | 53 | 55 | 57 | 59 |
| Mean (SD) | 0.19 (3.7) | 0.26 (0.47) | 0.35 (0.43) | 0.45 (0.40) | 0.36 (0.46) |
| Median | 0.15 | 0.20 | 0.25 | 0.35 | 0.28 |
| Q1:Q3 | −0.02:0.37 | −0.02:0.49 | 0.07:0.66 | 0.16:0.58 | 0.06:0.58 |
| Min:Max | −0.7:1.2 | −1.5:1.3 | −0.4:1.4 | −0.4:1.8 | −0.5:1.6 |
| LS Mean (SE) a | 0.18 (0.05) | 0.26 (0.06) | 0.35 (0.05) | 0.43 (0.05) | 0.39 (0.05) |
| LS Mean Diff, 95% CI a | | 0.08 (−0.07, 0.23) | 0.17 (0.02, 0.32) | 0.25 (0.10, 0.40) | 0.20 (0.06, 0.35) |
| P-value vs placebo a | | 0.2966 | 0.240 | 0.0009 | 0.0073 |

Abbreviations: CI = confidence interval; FEV1 = forced expiratory volume in 1 second; HEos = high eosinophil; LS = least squares; q2w = once every 2 weeks; q4w = once every 4 weeks; SD = standard deviation; SE = standard error of the mean.
a Derived from MMRM model with a change in FEV1 from baseline up to week 12 as dependent variables, factors (fixed effects) for treatment, pooled countries/regions, visit, treatment-by-visit interaction, FEV1 baseline value and baseline-by-visit interaction as covariates, unstructured correlation matrix. FEV1 was collected from systemic corticosteroid start date to systemic corticosteroid end date + 30 days for each severe exacerbation episode are excluded in order to reduce the confounding effect of systemic corticosteroids.

TABLE 6

Change from baseline in FEV1 (L) at week 12 in in ITT population.

| FEV$_1$ | Placebo (N = 158) | Dupilumab 200 mg q4w (N = 154) | 300 mg q4w (N = 157) | 200 mg q2w (N = 150) | 300 mg q2w (N = 157) |
|---|---|---|---|---|---|
| Baseline | | | | | |
| Number | 158 | 154 | 157 | 150 | 157 |
| Mean (SD) | 1.82 (0.55) | 1.88 (0.54) | 186 (0.57) | 1.79 (0.52) | 1.85 (0.53) |
| Median | 1.74 | 1.80 | 1.74 | 1.72 | 1.75 |
| Q1:Q3 | 1.44:2.16 | 1.49:2.19 | 1.45:2.15 | 1.42:2.04 | 1.46:2.18 |
| Min:Max | 0.9:3.6 | 0.9:3.9 | 0.8:4.2 | 0.8:3.4 | 0.8:3.8 |
| Week 12 | | | | | |
| Number | 130 | 134 | 135 | 136 | 146 |
| Mean (SD) | 2.01 (0.69) | 20.7 (0.63) | 2.14 (0.69) | 2.12 (0.68) | 2.12 (0.59) |
| Median | 1.86 | 1.99 | 2.08 | 1.99 | 2.10 |
| Q1:Q3 | 1.52:2.39 | 1.62:2.41 | 1.66:2.56 | 1.57:2.48 | 1.72:2.55 |
| Min:Max | 0.9:4.0 | 0.8:4.0 | 0.9:4.2 | 1.0:4.6 | 0.8:4.4 |
| Change from baseline | | | | | |
| Number | 130 | 134 | 135 | 136 | 146 |
| Mean (SD) | 0.14 (0.37) | 0.20 (0.41) | 0.24 (0.40) | 0.32 (0.38) | 0.26 (0.39) |
| Median | 0.09 | 0.18 | 0.19 | 0.24 | 0.21 |
| Q1:Q3 | −0.10:0.29 | −0.03:0.40 | −0.03:0.42 | 0.08:0.53 | 0.00:0.46 |
| Min:Max | −0.7:1.5 | −1.5:1.3 | −0.7:1.4 | −0.4:1.8 | −0.5:1.6 |
| LS Mean (SE) a | 0.12 (0.03) | 0.21 (0.03) | 0.24 (0.03) | 0.31 (0.03) | 0.28 (0.03) |

TABLE 6-continued

Change from baseline in FEV1 (L) at week 12 in in ITT population.

| FEV$_1$ | Placebo (N = 158) | Dupilumab | | | |
|---|---|---|---|---|---|
| | | 200 mg q4w (N = 154) | 300 mg q4w (N = 157) | 200 mg q2w (N = 150) | 300 mg q2w (N = 157) |
| LS Mean Diff, 95% CI a | | 0.09 (0.01, 0.18) | 0.12 (0.04, 0.21) | 0.19 (0.11, 0.28) | 0.16 (0.08, 0.25) |
| P-value vs placebo a | | 0.0343 | 0.0052 | <.0001 | 0.0002 |

Abbreviations: CI = confidence interval; FEV1 = forced expiratory volume in 1 second; HEos = high eosinophil; LS = least squares; q2w = once every 2 weeks; q4w = once every 4 weeks; SD = standard deviation; SE = standard error of the mean.
a Derived from MMRM model with change in FEV1 (L) from baseline up to week 12 as dependent variables, factors (fixed effects) for treatment, baseline eosinophil strata, pooled countries/regions, visit, treatment-by-visit interaction, FEV1 (L) baseline value and baseline-by-visit interaction as covariates, unstructured correlation matrix. FEV1 (L) was collected from systemic corticosteroid start date to systemic corticosteroid end date + 30 days for each severe exacerbation episode are excluded in order to reduce the confounding effect of systemic corticosteroids.

Two sets of sensitivity analyses were performed for the primary endpoint, i.e., change in FEV1 from baseline to week 12 in the HEos ITT population: 1) Sensitivity Analysis 1 was the same as the main statistical model, but included all FEV1 measurements (i.e., no FEV1 measurements were censored+30 days from the systemic corticosteroid start date as was done for the primary endpoint analysis); and 2) Sensitivity Analysis 2 was the same as the main statistical model, but excluded all FEV1 measurements collected on and after first day of systemic corticosteroid use. Both sensitivity analyses (Table 7 and Table 8) compared favorably with the primary endpoint analysis presented above.

TABLE 7

Sensitivity Analysis 1: Change from baseline in FEV1 (L) over time (MMRM including measurements up to week 12) in a HEos ITT population.

| FEV$_1$ | Placebo (N = 68) | Dupilumab | | | |
|---|---|---|---|---|---|
| | | 200 mg q4w (N = 62) | 300 mg q4w (N = 66) | 200 mg q2w (N = 65) | 300 mg q2w (N = 54) |
| Baseline | | | | | |
| Number | 68 | 62 | 66 | 65 | 64 |
| Mean (SD) | 1.86 (0.68) | 1.80 (0.49) | 1.87 (0.60) | 1.80 (0.52) | 1.77 (0.50) |
| Median | 1.65 | 1.75 | 1.72 | 1.75 | 1.71 |
| Q1:Q3 | 1.33:2.40 | 1.40:2.11 | 1.47:2.13 | 1.45:2.09 | 1.31:2.09 |
| Min:Max | 0.9:3.6 | 0.9:3.4 | 1.0:4.2 | 0.9:3.4 | 1.0:3.1 |
| Week 2 Change from baseline | | | | | |
| Number | 65 | 57 | 66 | 64 | 61 |
| LS Mean (SE) a | 0.12 (0.04) | 0.32 (0.05) | 0.34 (0.04) | 0.27 (0.04) | 0.30 (0.05) |
| LS Mean Diff, 95% CI a | | 0.20 (0.08, 0.33) | 0.22 (0.10, 0.34) | 0.15 (0.03, 0.27) | 0.17 (0.05, 0.30) |
| P-value vs placebo a | | 0.0016 | 0.0004 | 0.0165 | 0.0055 |
| Week 4 Change from baseline | | | | | |
| Number | 67 | 58 | 64 | 64 | 62 |
| LS Mean (SE) a | 0.17 (0.50) | 0.31 (0.05) | 0.32 (0.05) | 0.33 (0.05) | 0.33 (0.05) |
| LS Mean Diff, 95% CI a | | 0.14 (−0.01, 0.29) | 0.15 (0.01, 0.29) | 0.16 (0.01, 0.30) | 0.16 (0.02, 0.30) |
| P-value vs placebo a | | 0.0588 | 0.0380 | 0.0320 | 0.0268 |
| Week 8 Change from baseline | | | | | |
| Number | 66 | 58 | 63 | 63 | 60 |
| LS Mean (SE) a | 0.16 (0.05) | 0.26 (0.06) | 0.40 (0.05) | 0.37 (0.05) | 0.37 (0.05) |
| LS Mean Diff, 95% CI a | | 0.10 (−0.05, 0.25) | 0.24 (0.10, 0.39) | 0.22 (0.07, 0.36) | 0.21 (0.06, 0.36) |
| P-value vs placebo a | | 0.1762 | 0.0012 | 0.0039 | 0.0049 |
| Week 12 Change from baseline | | | | | |
| Number | 66 | 55 | 63 | 60 | 60 |
| LS Mean (SE) a | 0.22 (0.05) | 0.27 (0.06) | 0.31 (0.05) | 0.42 (0.06) | 0.39 (0.06) |
| LS Mean Diff, 95% CI a | | 0.05 (−0.10, 0.20) | 0.10 (−0.05, 0.25) | 0.20 (0.06, 0.35) | 0.17 (0.02, 0.33) |
| P-value vs placebo a | | 0.5182 | 0.1950 | 0.0073 | 0.0229 |

Abbreviations: CI = confidence interval; FEV1 = forced expiratory volume in 1 second; HEos = high eosinophil; LS = least squares; q2w = once every 2 weeks; q4w = once every 4 weeks; SD = standard deviation; SE = standard error of the mean.
a Derived from MMRM model with change in FEV1 (L) from baseline up to week 12 as dependent variables, factors (fixed effects) for treatment, pooled countries/regions, visit, treatment-by-visit interaction, FEV1 baseline value and baseline-by-visit interaction as covariates, unstructured correlation matrix.

TABLE 8

Sensitivity Analysis 2: Change from baseline in FEV1 (L) over time
(MMRM including measurements up to Week 12) - HEos ITT population.

| | | Dupilumab | | | |
|---|---|---|---|---|---|
| FEV$_1$ | Placebo (N = 68) | 200 mg q4w (N = 62) | 300 mg q4w (N = 66) | 200 mg q2w (N = 65) | 300 mg q2w (N = 64) |
| Baseline | | | | | |
| Number | 68 | 62 | 66 | 65 | 64 |
| Mean (SD) | 1.86 (0.68) | 1.80 (0.49) | 1.87 (0.60) | 1.80 (0.52) | 1.77 (0.50) |
| Median | 1.65 | 1.72 | 1.72 | 1.75 | 1.71 |
| Q1:Q3 | 1.33:2.40 | 1.40:2.11 | 1.47:2.13 | 1.45:2.09 | 1.31:2.09 |
| Min:Max | 0.9:3.6 | 0.9:3.4 | 1.0:4.2 | 0.9:3.4 | 1.0:3.1 |
| Week 2 Change from baseline | | | | | |
| Number | 59 | 57 | 66 | 64 | 60 |
| LS Mean (SE) a | 0.13 (0.05) | 0.32 (0.05) | 0.35 (0.04) | 0.27 (0.04) | 0.29 (0.05) |
| LS Mean Diff, 95% CI a | | 0.19 (0.06, 0.32) | 0.21 (0.09, 0.34) | 0.14 (0.02, 0.26) | 0.15 (0.03, 0.28) |
| P-value vs placebo a | | 0.0032 | 0.0008 | 0.0277 | 0.0159 |
| Week 4 Change from baseline | | | | | |
| Number | 58 | 58 | 61 | 62 | 59 |
| LS Mean (SE) a | 0.16 (0.05) | 0.31 (0.05) | 0.34 (0.05) | 0.32 (0.05) | 0.34 (0.05) |
| LS Mean Diff, 95% CI a | | 0.15 (0.00, 0.29) | 0.18 (0.03, 0.32) | 0.16 (0.02, 0.30) | 0.17 (0.03, 0.32) |
| P-value vs placebo a | | 0.0435 | 0.0149 | 0.0275 | 0.0186 |
| Week 8 Change from baseline | | | | | |
| Number | 52 | 56 | 59 | 60 | 55 |
| LS Mean (SE) a | 0.16 (0.06) | 0.26 (0.06) | 0.40 (0.05) | 0.38 (0.05) | 0.38 (0.06) |
| LS Mean Diff, 95% CI a | | 0.10 (−0.06, 0.25) | 0.23 (0.08, 0.39) | 0.22 (0.06, 0.37) | 0.21 (0.06, 0.37) |
| P-value vs placebo a | | 0.2207 | 0.0030 | 0.0058 | 0.0078 |
| Week 12 Change from baseline | | | | | |
| Number | 52 | 52 | 54 | 55 | 55 |
| LS Mean (SE) a | 0.19 (0.06) | 0.27 (0.06) | 0.37 (0.05) | 0.44 (0.05) | 0.37 (0.05) |
| LS Mean Diff, 95% CI a | | 0.08 (−0.07, 0.23) | 0.18 (0.03, 0.33) | 0.25 (0.10, 0.40) | 0.18 (0.03, 0.33) |
| P-value vs placebo a | | 0.2913 | 0.0196 | 0.0011 | 0.0177 |

Abbreviations: CI = confidence interval; FEV1 = forced expiratory volume in 1 second; LS = least squares; q2w = once every 2 weeks; q4w = once every 4 weeks; SD = standard deviation; SE = standard error of the mean.
a Derived from MMRM model with change in FEV1 (L) from baseline up to week 12 as dependent variables, factors (fixed effects) for treatment, pooled countries/regions, visit, treatment-by-visit interaction, FEV1 baseline value and baseline-by-visit interaction as covariates, unstructured correlation matrix. FEV1 measurements collected on and after the start date of systemic corticosteroid used for severe exacerbation will be excluded.

Figure 5:
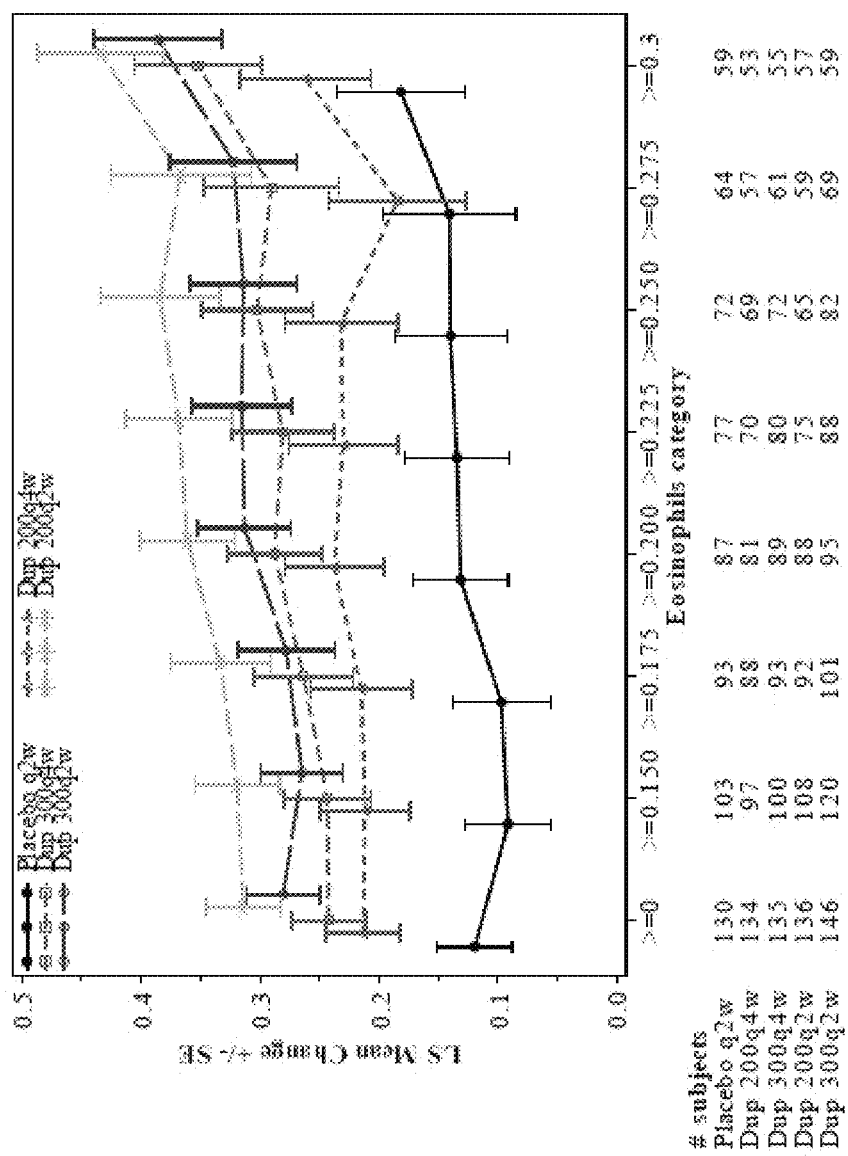
FIG. 5 graphically depicts the least squares mean change from baseline in FEV1 (L) at week 12 by eosinophil category in an ITT population. FEV1 (L) collected from systemic corticosteroid start date to systemic corticosteroid end date+30 days for each severe exacerbation episode are excluded in order to reduce the confounding effect of systemic corticosteroids.

The change in FEV1 from baseline to week 12 was analyzed by the eosinophil category in the ITT population to determine the treatment effect of dupilumab on FEV1 across the spectrum of patients with low to high baseline peripheral blood eosinophil counts (Table 9). As the patient category of peripheral blood eosinophil count increased from ≥0 to ≥0.300, in general, the change from baseline in FEV1 response increased modestly in all treatment groups, including placebo (FIG. 5).

TABLE 9

Least squares mean change from baseline in FEV1 (L) at week 12 by subgroups defined by baseline blood eosinophil count.

| | | Dupilumab | | | |
|---|---|---|---|---|---|
| | Placebo (N = 158) | 200 mg q4w (N = 154) | 300 mg q4w (N = 157) | 200 mg q2w (N = 150) | 300 mg q2w (N = 157) |
| Patients with eosinophil count >=300 | | | | | |
| Baseline | | | | | |
| Number | 68 | 62 | 66 | 65 | 64 |
| Mean (SD) | 1.86 (0.68) | 1.80 (0.49) | 1.87 (0.60) | 1.80 (0.52) | 1.77 (0.50) |
| Median | 1.65 | 1.75 | 1.72 | 1.75 | 1.71 |
| Q1:Q3 | 1.33:2.40 | 1.40:2.11 | 1.47:2.13 | 1.45:2.09 | 1.31:2.09 |
| Min:Max | 0.9:3.6 | 0.9:3.4 | 1.0:4.2 | 0.9:3.4 | 1.0:3.1 |
| Change from baseline at Week 12 | | | | | |
| Number | 59 | 53 | 55 | 57 | 59 |
| Mean (SD) | 0.19 (0.37) | 0.26 (0.47) | 0.35 (0.43) | 0.45 (0.40) | 0.36 (0.46) |
| Median | 0.15 | 0.20 | 0.25 | 0.35 | 0.28 |
| Q1:Q3 | −0.02:0.37 | −0.02:0.49 | 0.07:0.66 | 0.16:0.58 | 0.06:0.58 |

TABLE 9-continued

Least squares mean change from baseline in FEV1 (L) at week 12 by subgroups defined by baseline blood eosinophil count.

|  | Placebo (N = 158) | Dupilumab | | | |
|---|---|---|---|---|---|
|  |  | 200 mg q4w (N = 154) | 300 mg q4w (N = 157) | 200 mg q2w (N = 150) | 300 mg q2w (N = 157) |
| Min:Max | −0.7:1.2 | −1.5:1.3 | −0.4:1.4 | −0.4:1.8 | −0.5:1.6 |
| LS Mean (SE) a | 0.18 (0.05) | 0.26 (0.06) | 0.35 (0.05) | 0.43 (0.05) | 0.39 (0.05) |
| LS Mean Diff, 95% CI a |  | 0.08 (−0.07, 0.23) | 0.17 (0.02, 0.32) | 0.25 (0.10, 0.40) | 0.20 (0.05, 0.35) |
| P-value vs placebo a |  | 0.2966 | 0.240 | 0.0009 | 0.0073 |
| Patients with eosinophil count <300 Baseline |  |  |  |  |  |
| Number | 90 | 92 | 91 | 85 | 93 |
| Mean (SD) | 1.79 (0.42) | 1.94 (0.56) | 1.85 (0.56) | 1.79 (0.53) | 1.90 (0.55) |
| Median | 1.75 | 1.91 | 1.75 | 1.71 | 1.82 |
| Q1:Q3 | 1.51:2.04 | 1.51:2.22 | 1.43:2.21 | 1.41:2.01 | 1.53:2.26 |
| Min:Max | 0.9:2.9 | 0.9:3.9 | 0.8:3.3 | 0.8:3.3 | 0.8:3.8 |
| Change from baseline at Week 12 |  |  |  |  |  |
| Number | 71 | 81 | 80 | 79 | 87 |
| Mean (SD) | 0.09 (0.36) | 0.17 (0.36) | 0.16 (0.36) | 0.23 (0.33) | 0.19 (0.31) |
| Median | 0.03 | 0.16 | 0.10 | 0.18 | 0.13 |
| Q1:Q3 | −0.12:0.26 | −0.03:0.34 | −0.08:0.30 | 0.03:0.40 | −0.03:0.38 |
| Q1:Q3 | −0.12:0.23 | −0.03:0.34 | −0.07:0.30 | 0.04:0.40 | −0.03:0.38 |
| Min:Max | −0.7:1.5 | −1.0:1.3 | −0.7:1.2 | −0.4:1.1 | −0.5:1.0 |
| LS Mean (SE) a | 0.10 (0.04) | 0.22 (0.04) | 0.19 (0.04) | 0.26 (0.04) | 0.22 (0.04) |
| LS Mean Diff, 95% CI a |  | 0.12 (0.02, 0.23) | 0.09 (−0.02, 0.20) | 0.16 (0.05, 0.27) | 0.12 (0.01, 0.23) |
| P-value vs placebo a |  | 0.0255 | 0.1019 | 0.0034 | 0.0289 |
| Patients with eosinophil count >=250 Baseline |  |  |  |  |  |
| Number | 86 | 82 | 84 | 75 | 88 |
| Mean (SD) | 1.84 (0.64) | 1.88 (0.53) | 1.88 (0.59) | 1.81 (0.52) | 1.81 (0.48) |
| Median | 1.69 | 1.77 | 1.73 | 1.75 | 1.82 |
| Q1:Q3 | 1.39:2.34 | 1.52:2.17 | 1.47:2.15 | 1.45:2.09 | 1.42:2.11 |
| Min:Max | 0.9:3.6 | 0.9:3.4 | 1.0:4.2 | 0.8:3.4 | 1.0:3.1 |
| Change from baseline at Week 12 |  |  |  |  |  |
| Number | 72 | 69 | 72 | 65 | 82 |
| Mean (SD) | 0:19 (0.36) | 0.25 (0.47) | 0.32 (0.40) | 0.44 (0.38) | 0.31 (0.43) |
| Median | 0.15 | 0.20 | 0.24 | 0.35 | 0.25 |
| Q1:Q3 | −0.03:0.37 | −0.04:0.49 | 0.07:0.53 | 0.18:0.58 | 0.02:0.51 |
| Min:Max | −0.7:1.2 | −1.5:1.3 | −0.4:1.4 | −0.4:1.8 | −0.5:1.8 |
| LS Mean (SE) a | 0.14 (0.05) | 0.23 (0.05) | 0.30 (0.05) | 0.38 (0.05) | 0.31 (0.05) |
| LS Mean Diff, 95% CI a |  | 0.09 (−0.04, 0.22) | 0.16 (0.04, 0.29) | 0.24 (0.11, 0.37) | 0.17 (0.05, 0.30) |
| P-value vs placebo a |  | 0.1597 | 0.0117 | 0.0003 | 0.0062 |
| Patients with eosinophil count <250 Baseline |  |  |  |  |  |
| Number | 72 | 72 | 73 | 75 | 69 |
| Mean (SD) | 1.80 (0.42) | 1.89 (0.55) | 1.83 (0.55) | 1.78 (0.54) | 1.89 (0.59) |
| Median | 1.79 | 1.86 | 1.76 | 1.70 | 1.71 |
| Q1:Q3 | 1.50:2.06 | 1.49:2.20 | 1.39:2.15 | 1.38:1.99 | 1.48:2.29 |
| Min:Max | 1.1:2.9 | 0.9:3.9 | 0.8:3.2 | 1.0:3.3 | 0.8:3.8 |
| Change from baseline at Week 12 |  |  |  |  |  |
| Number | 58 | 65 | 63 | 71 | 64 |
| Mean (SD) | 0.07 (0.37) | 0.16 (0.32) | 0.14 (0.37) | 0.22 (0.33) | 0.20 (0.32) |
| Median | 0.02 | 0.16 | 0.07 | 0.17 | 0.14 |
| Q1:Q3 | −0.12:0.23 | −0.03:0.34 | −0.07:0.29 | 0.00:0.37 | 0.00:0.37 |
| Min:Max | −0.7:1.5 | −1.0:1.0 | −0.7:1.2 | −0.4:1.1 | −0.5:1.0 |
| LS Mean (SE) a | 0.10 (0.04) | 0.19 (0.04) | 0.18 (0.04) | 0.24 (0.04) | 0.23 (0.04) |
| LS Mean Diff, 95% CI a |  | 0.09 (−0.03, 0.20) | 0.08 (−0.04, 0.19) | 0.14 (0.03, 0.26) | 0.13 (0.01, 0.24) |
| P-value vs placebo a |  | 0.1270 | 0.1932 | 0.0133 | 0.0331 |
| Patients with eosinophil count >=225 Baseline |  |  |  |  |  |
| Number | 95 | 83 | 93 | 86 | 94 |
| Mean (SD) | 1.83 (0.62) | 1.88 (0.53) | 1.86 (0.58) | 1.82 (0.53) | 1.83 (0.48) |
| Median | 1.73 | 1.77 | 1.72 | 1.75 | 1.84 |
| Q1:Q3 | 1.39:2.32 | 1.52:2.17 | 1.47:2.13 | 1.46:2.09 | 1.42:2.17 |
| Min:Max | 0.9:3.6 | 0.9:3.4 | 1.0:4.2 | 0.8:3.4 | 1.0:3.1 |
| Change from baseline at Week 12 |  |  |  |  |  |
| Number | 77 | 70 | 80 | 75 | 88 |
| Mean (SD) | 0.17 (0.36) | 0.25 (0.47) | 0.30 (0.40) | 0.41 (0.37) | 0.30 (0.42) |
| Median | 0.15 | 0.19 | 0.21 | 0.30 | 0.27 |
| Q1:Q3 | −0.04:0.31 | −0.04:0.49 | 0.06:0.45 | 0.17:0.57 | 0.02:0.51 |

TABLE 9-continued

Least squares mean change from baseline in FEV1 (L) at week 12 by subgroups defined by baseline blood eosinophil count.

|  | Placebo (N = 158) | Dupilumab | | | |
|---|---|---|---|---|---|
|  |  | 200 mg q4w (N = 154) | 300 mg q4w (N = 157) | 200 mg q2w (N = 150) | 300 mg q2w (N = 157) |
| Min:Max | −0.7:1.2 | −1.5:1.3 | −0.4:1.4 | −0.4:1.8 | −0.5:1.6 |
| LS Mean (SE) a | 0.13 (0.04) | 0.23 (0.05) | 0.28 (0.04) | 0.37 (0.04) | 0.32 (0.04) |
| LS Mean Diff, 95% CI a |  | 0.10 (−0.03, 0.22) | 0.15 (0.03, 0.26) | 0.23 (0.11, 0.35) | 0.18 (0.06, 0.30) |
| P-value vs placebo a |  | 0.1263 | 0.0150 | 0.0001 | 0.0025 |
| Patients with eosinophil count <225 Baseline |  |  |  |  |  |
| Number | 63 | 71 | 64 | 64 | 63 |
| Mean (SD) | 1.80 (0.42) | 1.89 (0.56) | 1.86 (0.57) | 1.75 (0.52) | 1.87 (0.60) |
| Median | 1.78 | 1.85 | 1.81 | 1.67 | 1.71 |
| Q1:Q3 | 1.49:2.11 | 1.49:2.20 | 1.41:2.25 | 1.37:1.99 | 1.47:2.29 |
| Min:Max | 1.1:2.9 | 0.9:3.9 | 0.8:3.2 | 1.0:3.3 | 0.8:3.8 |
| Change from baseline at Week 12 |  |  |  |  |  |
| Number | 53 | 64 | 55 | 61 | 58 |
| Mean (SD) | 0.08 (0.38) | 0.16 (0.32) | 0.15 (0.37) | 0.21 (0.36) | 0.20 (0.32) |
| Median | 0.01 | 0.16 | 0.08 | 0.14 | 0.12 |
| Q1:Q3 | −0.12:0.23 | −0.03:0.34 | −0.07:0.33 | −0.02:0.41 | 0.00:0.32 |
| Min:Max | −0.7:1.5 | −1.0:1.0 | −0.7:1.2 | −0.4:1.1 | −0.5:1.0 |
| LS Mean (SE) a | 0.11 (0.05) | 0.19 (0.05) | 0.19 (0.05) | 0.25 (0.05) | 0.23 (0.05) |
| LS Mean Diff, 95% CI a |  | 0.08 (−0.04, 0.21) | 0.08 (−0.04, 0.21) | 0.14 (0.02, 0.26) | 0.12 (−0.01, 0.24) |
| P-value vs placebo a |  | 0.1711 | 0.1893 | 0.0266 | 0.0695 |
| Patients with eosinophil count >=200 Baseline |  |  |  |  |  |
| Number | 106 | 94 | 102 | 99 | 104 |
| Mean (SD) | 1.81 (0.60) | 1.86 (0.51) | 1.87 (0.58) | 1.80 (0.51) | 1.83 (0.49) |
| Median | 1.69 | 1.77 | 1.74 | 1.73 | 1.81 |
| Q1:Q3 | 1.39:2.26 | 1.52:2.15 | 1.46:2.15 | 1.45:2.07 | 1.44:2.18 |
| Min:Max | 0.9:3.6 | 0.9:3.4 | 1.0:4.2 | 0.8:3.4 | 1.0:3.2 |
| Change from baseline at Week 12 |  |  |  |  |  |
| Number | 87 | 81 | 89 | 88 | 95 |
| Mean (SD) | 0.16 (0.35) | 0.24 (0.45) | 0.29 (0.40) | 0.39 (0.37) | 0.29 (0.41) |
| Median | 0.13 | 0.20 | 0.19 | 0.29 | 0.25 |
| Q1:Q3 | −0.08:0.31 | −0.02:0.47 | 0.06:0.45 | 0.41:0.56 | 0.03:0.51 |
| Min:Max | −0.7:1.2 | −1.5:1.3 | −0.4:1.4 | −0.4:1.8 | −0.5:1.6 |
| LS Mean (SE) a | 0.13 (0.04) | 0.24 (0.04) | 0.29 (0.04) | 0.36 (0.04) | 0.31 (0.04) |
| LS Mean Diff, 95% CI a |  | 0.11 (−0.01, 0.22) | 0.16 (0.05, 0.27) | 0.23 (0.12, 0.34) | 0.18 (0.07, 0.29) |
| P-value vs placebo a |  | 0.0650 | 0.0054 | <.0001 | 0.0012 |
| Patients with eosinophil count <200 Baseline |  |  |  |  |  |
| Number | 52 | 60 | 55 | 51 | 53 |
| Mean (SD) | 1.83 (0.42) | 1.92 (0.58) | 1.83 (0.57) | 1.79 (0.56) | 1.87 (0.60) |
| Median | 1.84 | 1.88 | 1.76 | 1.67 | 1.71 |
| Q1:Q3 | 1.57:2.16 | 1.49:2.29 | 1.37:2.15 | 1.37:2.04 | 1.47:2.19 |
| Min:Max | 1.1:2.9 | 0.9:3.9 | 0.8:3.2 | 1.0:3.3 | 0.8:3.8 |
| Change from baseline at Week 12 |  |  |  |  |  |
| Number | 43 | 53 | 46 | 48 | 51 |
| Mean (SD) | 0.09 (0.40) | 0.14 (0.32) | 0.14 (0.37) | 0.21 (0.35) | 0.20 (0.34) |
| Median | 0.01 | 0.16 | 0.08 | 0.12 | 0.12 |
| Q1:Q3 | −0.12:0.21 | −0.03:0.34 | −0.07:0.29 | −0.01:0.42 | −0.02:0.44 |
| Min:Max | −0.7:1.5 | −1.0:0.9 | −0.7:1.2 | −0.4:1.0 | −0.5:1.0 |
| LS Mean (SE) a | 0.10 (0.05) | 0.16 (0.05) | 0.16 (0.05) | 0.23 (0.05) | 0.21 (0.05) |
| LS Mean Diff, 95% CI a |  | 0.07 (−0.07, 0.20) | 0.07 (−0.07, 0.20) | 0.13 (−0.01, 0.27) | 0.11 (−0.02, 0.25) |
| P-value vs placebo a |  | 0.3377 | 0.3512 | 0.0674 | 0.1029 |
| Patients with eosinophil count >=175 Baseline |  |  |  |  |  |
| Number | 114 | 101 | 107 | 104 | 110 |
| Mean (SD) | 1.81 (0.59) | 1.85 (0.52) | 1.87 (0.58) | 1.81 (0.52) | 1.82 (0.49) |
| Median | 1.69 | 1.76 | 1.72 | 1.75 | 1.80 |
| Q1:Q3 | 1.39:2.11 | 1.49:2.15 | 1.45:2.15 | 1.46:2.09 | 1.42:2.14 |
| Min:Max | 0.9:3.6 | 0.9:3.4 | 1.0:4.2 | 0.8:3.4 | 1.0:3.2 |
| Change from baseline at Week 12 |  |  |  |  |  |
| Number | 93 | 88 | 93 | 92 | 101 |
| Mean (SD) | 0.15 (0.35) | 0.24 (0.44) | 0.29 (0.40) | 0.38 (0.37) | 0.28 (0.41) |
| Median | 0.12 | 0.20 | 0.19 | 0.29 | 0.24 |
| Q1:Q3 | −0.08:0.30 | −0.02:0.47 | 0.06:0.45 | 0.14:0.56 | 0.02:0.46 |
| Min:Max | −0.7:1.2 | −1.5:1.3 | −0.4:1.4 | −0.4:1.8 | −0.5:1.6 |

TABLE 9-continued

Least squares mean change from baseline in FEV1 (L) at week 12 by subgroups defined by baseline blood eosinophil count.

| | | Dupilumab | | | |
|---|---|---|---|---|---|
| | Placebo (N = 158) | 200 mg q4w (N = 154) | 300 mg q4w (N = 157) | 200 mg q2w (N = 150) | 300 mg q2w (N = 157) |
| LS Mean (SE) a | 0.10 (0.04) | 0.21 (0.04) | 0.26 (0.04) | 0.33 (0.04) | 0.28 (0.04) |
| LS Mean Diff, 95% CI a | | 0.12 (0.01, 0.22) | 0.17 (0.06, 0.27) | 0.24 (0.13, 0.34) | 0.18 (0.08, 0.29) |
| P-value vs placebo a | | 0.0319 | 0.0020 | <.0001 | 0.0007 |
| Patients with eosinophil count <175 | | | | | |
| Baseline | | | | | |
| Number | 44 | 53 | 50 | 46 | 47 |
| Mean (SD) | 1.86 (0.44) | 1.95 (0.57) | 1.84 (0.56) | 1.75 (0.53) | 1.90 (0.61) |
| Median | 1.85 | 1.88 | 1.81 | 1.65 | 1.71 |
| Q1:Q3 | 1.60:2.17 | 1.50:2.29 | 1.44:2.15 | 1.37:1.99 | 1.47:2.41 |
| Min:Max | 1.1:2.9 | 0.9:3.9 | 0.8:3.2 | 1.0:3.3 | 0.8:3.8 |
| Change from baseline at Week 12 | | | | | |
| Number | 37 | 46 | 42 | 44 | 45 |
| Mean (SD) | 0.11 (0.42) | 0.13 (0.33) | 0.12 (0.35) | 0.21 (0.37) | 0.21 (0.34) |
| Median | 0.02 | 0.14 | 0.08 | 0.10 | 0.14 |
| Q1:Q3 | −0.10:0.21 | −0.07:0.34 | −0.11:0.29 | −0.04:0.46 | 0.00:0.44 |
| Min:Max | −0.7:1.5 | −1.0:0.9 | −0.7:1.1 | −0.4:1.0 | −0.5:1.0 |
| LS Mean (SE) a | 0.12 (0.06) | 0.15 (0.05) | 0.15 (0.05) | 0.23 (0.05) | 0.22 (0.05) |
| LS Mean Diff, 95% CI a | | 0.03 (−0.12, 0.17) | 0.03 (−0.12, 0.18) | 0.11 (−0.04, 0.26) | 0.10 (−0.05, 0.25) |
| P-value vs placebo a | | 0.7203 | 0.6921 | 0.1646 | 0.1825 |
| Patients with eosinophil count >=150 | | | | | |
| Baseline | | | | | |
| Number | 127 | 112 | 116 | 120 | 129 |
| Mean (SD) | 1.80 (0.57) | 1.85 (0.52) | 1.87 (0.58) | 1.81 (0.51) | 1.84 (0.50) |
| Median | 1.68 | 1.77 | 1.74 | 1.75 | 1.79 |
| Q1:Q3 | 1.39:2.17 | 1.50:2.15 | 1.46:2.15 | 1.45:2.07 | 1.49:2.18 |
| Min:Max | 0.9:3.6 | 0.9:3.4 | 1.0:4.2 | 0.6:3.4 | 1.0:3.2 |
| Change from baseline at Week 12 | | | | | |
| Number | 103 | 97 | 100 | 108 | 120 |
| Mean (SD) | 0.13 (0.35) | 0.24 (1.42) | 0.27 (0.40) | 0.35 (0.38) | 0.26 (0.40) |
| Median | 0.12 | 0.20 | 0.19 | 0.27 | 0.20 |
| Q1:Q3 | −0.10:0.29 | −0.02:0.45 | 0.05:0.45 | 0.12:0.54 | −0.01:0.45 |
| Min:Max | −0.7:1.2 | −1.5:1.3 | −0.4:1.4 | −0.4:1.8 | −0.5:1.6 |
| LS Mean (SE) a | 0.09 (0.04) | 0.21 (0.04) | 0.24 (0.04) | 0.32 (0.04) | 0.26 (0.03) |
| LS Mean Diff, 95% CI a | | 0.12 (0.02, 0.22) | 0.15 (0.05, 0.25) | 0.23 (0.31, 0.33) | 0.17 (0.08, 0.27) |
| P-value vs placebo a | | 0.0192 | 0.0028 | <.0001 | 0.0004 |
| Patients with eosinophil count <=150 | | | | | |
| Baseline | | | | | |
| Number | 31 | 42 | 41 | 30 | 28 |
| Mean (SD) | 1.90 (0.42) | 1.97 (0.59) | 1.83 (0.56) | 1.74 (0.59) | 1.90 (0.68) |
| Median | 1.92 | 1.90 | 1.80 | 1.64 | 1.72 |
| Q1:Q3 | 1.63:2.15 | 1.49:2.34 | 1.44:2.12 | 1.23:1.96 | 1.44:2.30 |
| Min:Max | 1.1:2.9 | 0.9:3.9 | 0.8:2.9 | 1.0:3.3 | 0.8:3.8 |
| Change from baseline at Week 12 | | | | | |
| Number | 27 | 37 | 35 | 28 | 26 |
| Mean (SD) | 0.14 (0.44) | 0.12 (0.36) | 0.15 (0.37) | 0.21 (0.34) | 0.27 (0.36) |
| Median | 0.01 | 0.14 | 0.11 | 0.09 | 0.26 |
| Q1:Q3 | −0.10:0.28 | −0.07:0.30 | −0.11:0.34 | 0.02:0.42 | 0.01:0.50 |
| Min:Max | −0.6:1.5 | −1.0:0.8 | −0.7:1.1 | −0.4:1.0 | −0.5:1.0 |
| LS Mean (SE) a | 0.15 (0.07) | 0.16 (0.06) | 0.19 (0.06) | 0.24 (0.07) | 0.27 (0.07) |
| LS Mean Diff, 95% CI a | | 0.00 (−0.17, 0.18) | 0.04 (−0.14, 0.21) | 0.09 (−0.11, 0.28) | 0.11 (−0.08, 0.31) |
| P-value vs placebo a | | 0.9700 | 0.6868 | 0.3777 | 0.2397 |

Abbreviations: CI = confidence interval; FEV1 = forced expiratory volume in 1 second; LS = least squares; max = maximum; min = minimum; q2w = once every 2 weeks; q4w = once every 4 weeks; SD = standard deviation; SE = standard error of the mean.
a Derived from MMRM model with change in FEV1 (L) from baseline up to week 12 as dependent variables, factors (fixed effects) for treatment, baseline eosinophil strata, pooled countries/regions, visit, treatment-by-visit interaction, FEV1 baseline value and baseline-by-visit interaction as covariates, unstructured correlation matrix. FEV1 was collected from systemic corticosteroid start date to systemic corticosteroid end date + 30 days for each severe exacerbation episode are excluded in order to reduce the confounding effect of systemic corticosteroids.

I. Annualized Rate of Severe Exacerbation Events during the Treatment Period

Figure 6:
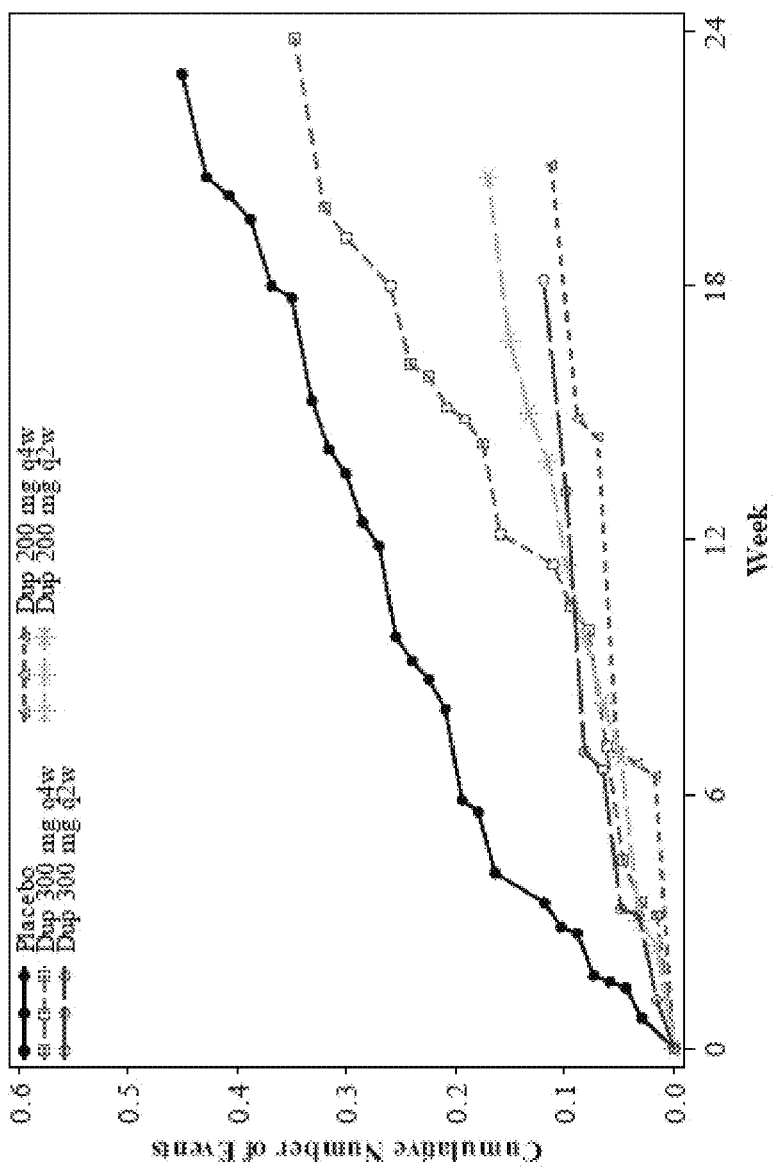
FIG. 6 graphically depicts the cumulative mean functions for the number of severe exacerbation events-treatment period in a HEos ITT population. FEV1 (L) collected from systemic corticosteroid start date to systemic corticosteroid end date+30 days for each severe exacerbation episode are excluded in order to reduce the confounding effect of systemic corticosteroids.

The cumulative number of severe exacerbation events in the HEos ITT population during the treatment period (including all events up to the data cutoff date) is shown by treatment arm in FIG. 6. The annualized rate of severe asthma exacerbation events was analyzed using a negative binomial regression model. During the 24-week treatment period, the number of patients in the HEos ITT population with ≥1 severe exacerbation event(s) was 16 patients in the placebo group, and 5, 5, 7, and 10 patients in the dupilumab 200 mg q4w, 200 mg q2w, 300 mg q2w and 300 mg q2w groups, respectively (Table 10). The relative risks for a severe asthma exacerbation, based on the adjusted annualized severe exacerbation event rate, compared with placebo, were 0.257 (200 mg q4w), 0.739 (300 mg q4w), 0.356 (200 mg q2w), and 0.254 (300 mg q2w). Statistical significance (not adjusted for multiplicity) was demonstrated for all dupilumab doses with the exception of the 300 mg q4w dose.

Figure 7:
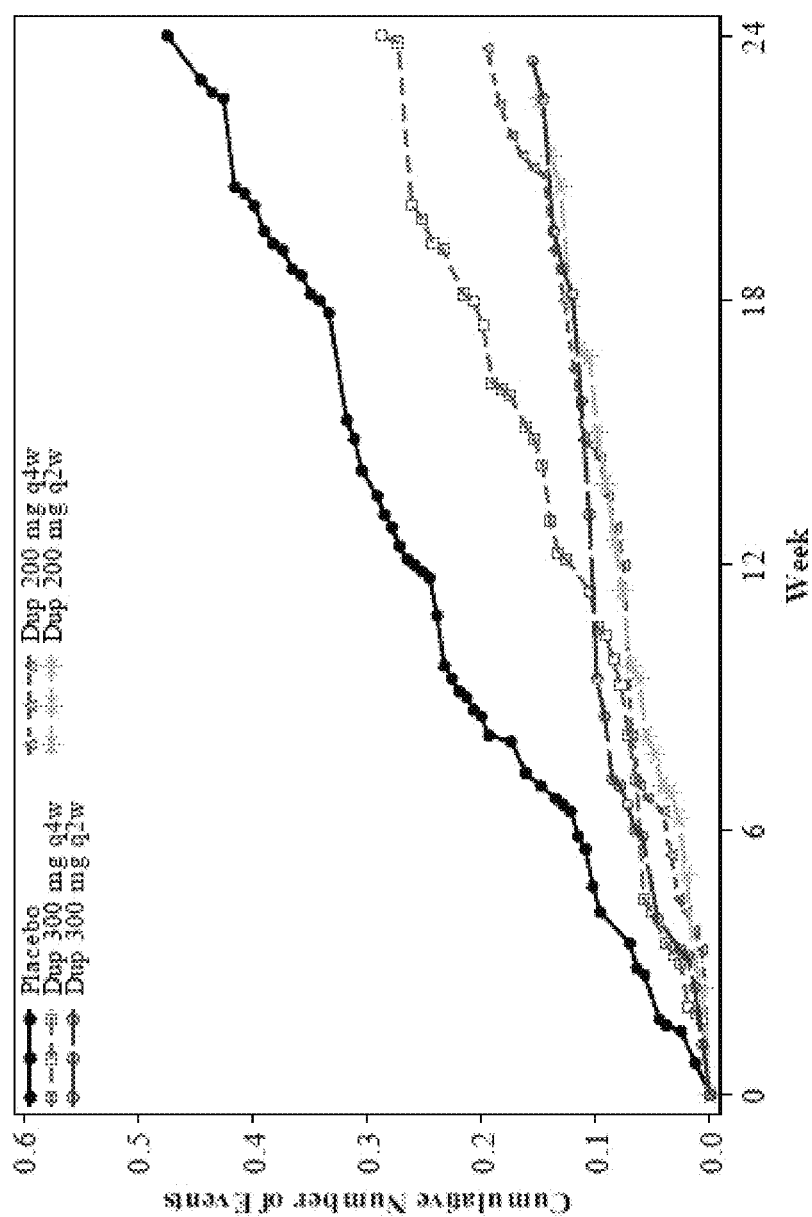
FIG. 7 graphically depicts the cumulative mean functions for the number of severe exacerbation events-treatment period in an ITT population. FEV1 (L) collected from systemic corticosteroid start date to systemic corticosteroid end date+30 days for each severe exacerbation episode are excluded in order to reduce the confounding effect of systemic corticosteroids.
Figure 8:
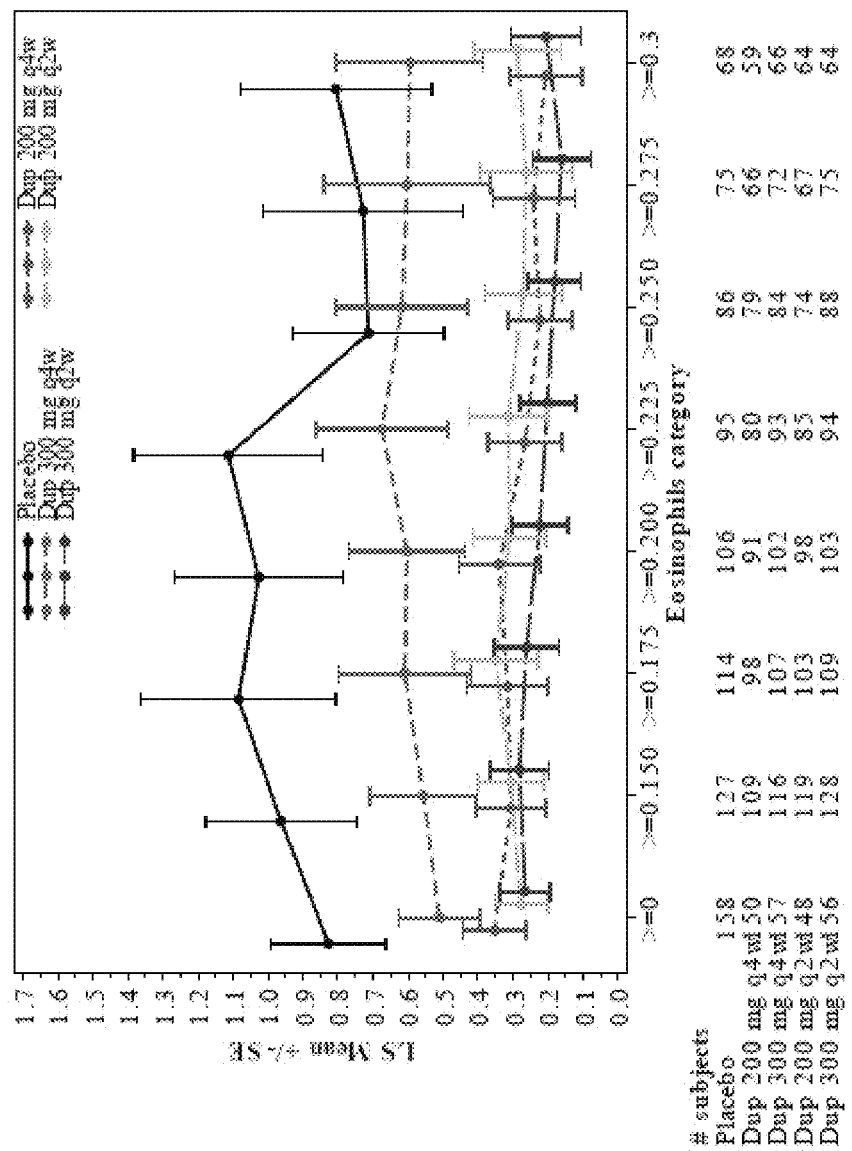
FIG. 8 graphically depicts the annualized event rate of severe exacerbation events during the treatment period by baseline blood eosinophil (GIGA/L) category for the treatment period in an ITT population. Note: SE of the annualized event rate estimate was calculated from the SE of the log annualized event rate estimate by delta method.

The annualized rate of severe asthma exacerbation events was analyzed in the ITT population. The cumulative number of severe exacerbation events in the ITT population during the treatment period are shown by treatment arms in FIG. 7. Similar to the HEos ITT population analysis, during the 24-week treatment period, fewer number of patients on dupilumab experienced severe exacerbations (Table 11), and the relative risks for a severe asthma exacerbation, based on adjusted annualized severe exacerbation event rate, compared with placebo, were reduced. Statistical significance was demonstrated for all dupilumab doses with the exception of the 300 mg q4w dose. The annualized rate of severe asthma exacerbation events was analyzed by eosinophil category in the ITT population to determine the treatment effect of dupilumab on severe exacerbation rate across the spectrum of patients with low to high baseline peripheral blood eosinophil counts (Table 12). As shown in FIG. 8, as the patient category of peripheral blood eosinophil count increased from ≥0 to ≥0.300, the adjusted annualized severe exacerbation event rates, compared with placebo, were reduced in dupilumab-treated patients irrespective of eosinophil category. In the placebo group, patients with eosinophil counts below 0.250 experienced higher severe exacerbation rates, compared with placebo patients with eosinophil counts ≥0.250.

TABLE 10

Annualized event rate of severe exacerbation events during the treatment period-
HEos-ITT population.

|  | Placebo (N = 68) | Dupilumab | | | |
|---|---|---|---|---|---|
|  |  | 200 mg q4w (N = 62) | 300 mg q4w (N = 63) | 200 mg q2w (N = 65) | 300 mg q2w (N = 64) |
| Number of patients with >=1 severe exacerbation event |  |  |  |  |  |
| Number | 68 | 59 | 65 | 64 | 64 |
| No | 52 (76.5%) | 54 (91.5%) | 56 (84.8%) | 56 (82.2%) | 57 (89.1%) |
| Yes | 16 (23.5%) | 5 (8.5%) | 10 (15.2%) | 5 (7.8%) | 7 (10.9%) |
| Number of severe exacerbation events |  |  |  |  |  |
| 0 | 52 (76.5%) | 54 (81.5%) | 56 (84.8%) | 59 (82.2%) | 57 (89.1%) |
| 1 | 7 (10.3%) | 4 (6.8%) | 4 (6.1%) | 3 (4.7%) | 7 (10.9%) |
| 2 | 6 (8.8%) | 1 (1.7%) | 2 (3.0%) | 1 (1.6%) | 0 |
| 3 | 3 (4.4%) | 0 | 4 (6.1%) | 0 | 0 |
| >=4 | 0 | 0 | 0 | 1 (1.6%) | 0 |
| Total number of severe exacerbation events | 28 | 6 | 20 | 10 | 7 |
| Total patient-years followed | 28.0 | 24.0 | 27.0 | 26.4 | 25.6 |
| Unadjusted annualized severe exacerbation event rate a | 1.000 | 0.250 | 0.741 | 0.379 | 0.273 |
| Adjusted annualized severe exacerbation event rate b |  |  |  |  |  |
| Estimate (95% CI) | 0.806 (0.413, 1.571) | 0.207 (0.076, 0.580) | 0.595 (0.296, 1.195) | 0.287 (0.122, 0.674) | 0.205 (0.077, 0.545) |
| Relative risk (95% CI) |  | 0.257 (0.082, 0.603) | 0.739 (0.299, 1.827) | 0.358 (0.128, 0.982) | 0.254 (0.084, 0.789) |
| P-value |  | 0.0194 | 0.5120 | 0.0460 | 0.0153 |
| Individual patient annualized severe exacerbation event rate c |  |  |  |  |  |
| Number | 68 | 59 | 68 | 64 | 64 |
| Mean (SD) | 1.01 (2.10) | 0.26 (0.36) | 0.69 (1.85) | 0.35 (1.62) | 0.27 (0.50) |
| Median | 0.00 | 0.00 | 0.00 | 0.00 | 0.00 |
| Min:Max | 0.0:3.9 | 0.0:5.8 | 0.0:8.2 | 0.0:11.9 | 0.0:3.1 |

Abbreviations:
CI = confidence interval;
HEos = high eosinophil;
max = maximum;
min = minimum;
q2w = once every 2 weeks;
q4w = once every 4 weeks;
SD = standard deviation.

[a]The total number of event that occurred during the treatment period divided by the total number of patient-years followed in the treatment period.

[b]Derived using negative binomial model with the total number of events onset between first dose date and last dose date + 14 days as the response variable, treatment, pooled countries/regions and number of asthma event prior to the study as covariates, and log-transformed standardized treatment duration as an offset variable.

[c]The number of severe exacerbation events for each patient divided by the number of years followed in the treatment period for that patient.

TABLE 11

Annualized event rate of severe exacerbation events during the treatment period-ITT population.

|  | Placebo (N = 156) | Dupilumab | | | |
|---|---|---|---|---|---|
|  |  | 200 mg q4w (N = 154) | 300 mg q4w (N = 157) | 200 mg q2w (N = 150) | 300 mg q2w (N = 157) |
| Number of patients with >=1 severe exacerbation event |  |  |  |  |  |
| Number | 158 | 150 | 157 | 148 | 156 |
| No | 121 (76.6%) | 130 (66.7%) | 133 (84.7%) | 135 (91.2%) | 139 (89.1%) |
| Yes | 37 (23.4%) | 20 (13.3%) | 24 (15.3%) | 13 (8.8%) | 17 (10.9%) |
| Number of severe exacerbation events |  |  |  |  |  |
| 0 | 121 (76.6%) | 130 (86.7%) | 133 (841%) | 135 (91.2%) | 139 (89.1%) |
| 1 | 21 (13.3%) | 16 (10.7%) | 15 (9.6%) | 9 (6.1%) | 13 (8.3%) |
| 2 | 9 (5.7%) | 3 (2.0%) | 4 (2.5%) | 3 (2.0%) | 3 (1.9%) |
| 3 | 5 (3.2%) | 1 (0.7%) | 5 (3.2%) | 0 | 1 (0.6%) |
| >=4 | 2 (1.3%) | 0 | 0 | 1 (0.7%) | 0 |
| Total number of severe exacerbation events | 65 | 25 | 38 | 20 | 22 |
| Total patient-years followed | 65.3 | 61.4 | 62.9 | 61.5 | 64.4 |
| Unadjusted aannualized severe exacerbation event rate a | 0.995 | 0.407 | 0.604 | 0.325 | 0.342 |
| Adjusted annualized severe exacerbation event rate b |  |  |  |  |  |
| Estimate (95% CI) | 0.827 (0.580, 1.221) | 0.353 (0.212, 0.589) | 0.510 (0.324, 0.801) | 0.276 (0.159, 0.479) | 0.285 (0.155, 0.455) |
| Relative risk (95% CI) |  | 0.427 (0.229, 0.794) | 0.616 (0.348, 1.091) | 0.334 (0.174, 0.641) | 0.321 (0.169, 0.608) |
| P-value |  | 0.0072 | 0.0966 | 0.0010 | 0.0005 |
| Individual patient annualized severe exacerbation events rate c |  |  |  |  |  |
| Number | 158 | 150 | 157 | 148 | 155 |
| Mean (SD) | 0.98 (2.20) | 0.43 (1.18) | 0.56 (1.51) | 0.31 (1.25) | 0.34 (1.05) |
| Median | 0.00 | 0.00 | 0.00 | 0.00 | 0.00 |
| Min:Max | 0.0:15.2 | 0.0:6.5 | 0.0:8.2 | 0.0:11.9 | 0.0:6.6 |

Abbreviations:
CI = confidence interval;
HEos = high eosinophil;
max = maximum;
min = minimum;
q2w = once every 2 weeks;
q4w = once every 4 weeks;
SD = standard deviation.
[a]The total number of event that occurred during the treatment period divided by the total number of patient-years followed in the treatment period.
[b]Derived using negative binomial model with the total number of events onset between first dose date and last dose date + 14 days as the response variable, treatment, baseline eosinophil strata, pooled countries/regions and number of asthma event prior to the study as covariates, and log-transformed standardized treatment duration as an offset variable.
[c]The number of severe exacerbation events for each patient divided by the number of years followed in the treatment period for that patient.

TABLE 12

Annualized event rate of severe exacerbation by subgroups defined by baseline blood eosinophil (GIGA/L) during the treatment period in an ITT population.

| n (%) | Placebo (N = 158) | Dupilumab | | | |
|---|---|---|---|---|---|
|  |  | 200 mg q4w (N = 154) | 300 mg q4w (N = 157) | 200 mg q2w (N = 150) | 300 mg q2w (N = 157) |
| Subgroup: All patients |  |  |  |  |  |
| Number of patients with >=1 severe exacerbation event |  |  |  |  |  |
| Number | 158 | 150 | 157 | 148 | 156 |
| No | 121 (76.6%) | 130 (86.7%) | 133 (84.7%) | 135 (91.2%) | 139 (89.1%) |
| Yes | 37 (23.4%) | 20 (13.3%) | 24 (15.3%) | 13 (8.8%) | 17 (10.9%) |
| Total number of severe exacerbation events | 65 | 25 | 38 | 20 | 22 |
| Total patient-years followed | 65.3 | 61.4 | 62.9 | 61.5 | 64.4 |
| Unadjusted annualized severe exacerbation event rate a | 0.995 | 0.407 | 0.604 | 0.325 | 0.342 |

TABLE 12-continued

Annualized event rate of severe exacerbation by subgroups defined by baseline
blood eosinophil (GIGA/L) during the treatment period in an ITT population.

| | | Dupilumab | | | |
|---|---|---|---|---|---|
| n (%) | Placebo (N = 158) | 200 mg q4w (N = 154) | 300 mg q4w (N = 157) | 200 mg q2w (N = 150) | 300 mg q2w (N = 157) |
| Adjusted annualized severe exacerbation event rate b | | | | | |
| Estimate (95% CI) | 0.827 (0.560, 1.221) | 0.353 (0.212, 0.589) | 0.510 (0.324, 0.801) | 0.276 (0.159, 0.479) | 0.265 (0.155, 0.455) |
| Relative Risk (95% CI) | | 0.427 (0.229, 0.794) | 0.616 (0.348, 1.091) | 0.334 (0.174, 0.641) | 0.321 (0.169, 0.608) |
| P-value | | 0.0072 | 0.0966 | 0.0010 | 0.0005 |
| Subgroup: Patients with eosinophil count >=300 | | | | | |
| Number of patients with >=1 severe exacerbation event | | | | | |
| Number | 68 | 59 | 66 | 64 | 64 |
| No | 52 (76.5%) | 54 (91.5%) | 56 (84.8%) | 58 (92.2%) | 57 (89.1%) |
| Yes | 16 (23.5%) | 5 (8.5%) | 10 (15.2%) | 5 (7.8%) | 7 (10.9%) |
| Total number of severe exacerbation events | 28 | 6 | 20 | 10 | 7 |
| Total patient-years followed | 28.0 | 24.0 | 27.0 | 26.4 | 25.6 |
| Unadjusted annualized severe exacerbation event rate a | 1.000 | 0.250 | 0.741 | 0.379 | 0.273 |
| Adjusted annualized severe exacerbation event rate b | | | | | |
| Estimate (95% CI) | 0.806 (0.413, 1.571) | 0.207 (0.076, 0.560) | 0.595 (0.296, 1.195) | 0.267 (0.122, 0.674) | 0.205 (0.077, 0.545) |
| Relative risk (95% CI) | | 0.257 (0.082, 0.803) | 0.739 (0.299, 1.827) | 0.356 (0.129, 0.982) | 0.254 (0.084, 0.769) |
| P-value | | 0.0194 | 0.5120 | 0.0460 | 0.0153 |
| Subgroup: Patients with eosinophil count <300 | | | | | |
| Number of patients with >=1 severe exacerbation event | | | | | |
| Number | 90 | 91 | 91 | 84 | 92 |
| No | 69 (76.7%) | 76 (83.5%) | 77 (84.6%) | 76 (90.5%) | 82 (89.1%) |
| Yes | 21 (23.3%) | 15 (16.5%) | 14 (15.4%) | 8 (9.5%) | 10 (10.9%) |
| Total number of severe exacerbation events | 37 | 19 | 18 | 10 | 15 |
| Total patient-years followed | 37.3 | 37.4 | 35.9 | 35.0 | 38.8 |
| Unadjusted annualized severe exacerbation event rate a | 0.992 | 0.508 | 0.501 | 0.288 | 0.387 |
| Adjusted annualized severe exacerbation event rate b | | | | | |
| Estimate (95% CI) | 0.805 (0.502, 1.290) | 0.437 (0.241, 0.791) | 0.392 (0.214, 0.718) | 0.260 (0.126, 0.538) | 0.307 (0.162, 0.582) |
| Relative risk (95% CI) | | 0.543 (0.261, 1.129) | 0.486 (0.232, 1.019) | 0.323 (0.138, 0.755) | 0.382 (0.177, 0.821) |
| P-value | | 0.1020 | 0.0561 | 0.0091 | 0.0137 |
| Subgroup: Patients with eosinophil count >=275 | | | | | |
| Number of patients with >=1 severe exacerbation event | | | | | |
| Number | 75 | 66 | 72 | 67 | 75 |
| No | 57 (76.0%) | 59 (89.4%) | 60 (83.3%) | 62 (92.5%) | 68 (90.7%) |
| Yes | 18 (24.0%) | 7 (10.6%) | 12 (16.7%) | 5 (7.5%) | 7 (9.3%) |
| Tota number of severe exacerbation events | 30 | 8 | 23 | 10 | 7 |
| Total patient-years followed | 31.1 | 26.2 | 29.3 | 27.3 | 30.1 |
| Unadjusted annualized severe exacerbation event rate a | 0.965 | 0.305 | 0.785 | 0.366 | 0.233 |
| Adjusted annualized severe exacerbation event rate b | | | | | |
| Estimate (95% CI) | 0.728 (0.335, 1.582) | 0.241 (0.091, 0.634) | 0.602 (0.278, 1.305) | 0.263 (0.098, 0.710) | 0.160 (0.057, 0.449) |

TABLE 12-continued

Annualized event rate of severe exacerbation by subgroups defined by baseline
blood eosinophil (GIGA/L) during the treatment period in an ITT population.

|  |  | Dupilumab | | | |
|---|---|---|---|---|---|
| n (%) | Placebo (N = 158) | 200 mg q4w (N = 154) | 300 mg q4w (N = 157) | 200 mg q2w (N = 150) | 300 mg q2w (N = 157) |
| Relative risk (95% CI) |  | 0.331 (0.120, 0.912) | 0.827 (0.362, 1.892) | 0.362 (0.138, 0.948) | 0.220 (0.077, 0.633) |
| P-value |  | 0.0324 | 0.6536 | 0.0387 | 0.0050 |
| Subgroup: Patients with eosinophil count <275 |  |  |  |  |  |
| Number of patients with >=1 severe exacerbation event |  |  |  |  |  |
| Number | 83 | 84 | 85 | 81 | 81 |
| No | 64 (77.1%) | 71 (84.5%) | 73 (85.9%) | 73 (90.1%) | 71 (87.7%) |
| Yes | 19 (22.9%) | 13 (15.5%) | 12 (14.1%) | 8 (9.9%) | 10 (12.3%) |
| Total number of severe exacerbation events | 35 | 17 | 15 | 10 | 15 |
| Total patient-years followed | 34.2 | 35.2 | 33.6 | 34.1 | 34.4 |
| Unadjusted annualized severe exacerbation event rate a | 1.023 | 0.483 | 0.448 | 0.293 | 0.436 |
| Adjusted annualized severe exacerbation event rate b |  |  |  |  |  |
| Estimate (95% CI) | 0.844 (0.512, 1.390) | 0.440 (0.234, 0.827) | 0.366 (0.191, 0.709) | 0.274 (0.131, 0.573) | 0.352 (0.182, 0.883) |
| Relative risk (95% CI) |  | 0.521 (0.238, 1.140) | 0.436 (0.196, 0.969) | 0.325 (0.135, 0.780) | 0.418 (0.187, 0.932) |
| P-value |  | 0.1027 | 0.0416 | 0.0118 | 0.0330 |
| Subgroup: Patients with eosinophil count >=250 |  |  |  |  |  |
| Number of patients with >=1 severe exacerbation event |  |  |  |  |  |
| Number | 86 | 79 | 84 | 74 | 88 |
| No | 65 (75.6%) | 71 (89.9%) | 70 (83.3%) | 68 (91.9%) | 79 (89.8%) |
| Yes | 21 (24.4%) | 8 (10.1%) | 14 (16.7%) | 6 (8.1%) | 9 (10.2%) |
| Total number of severe exacerbation events | 33 | 9 | 27 | 11 | 9 |
| Total patient-years followed | 36.0 | 31.8 | 33.8 | 30.4 | 35.6 |
| Unadjusted annualized severe exacerbation event rate a | 0.917 | 0.283 | 0.799 | 0.362 | 0.253 |
| Adjusted annualized severe exacerbation event rate b |  |  |  |  |  |
| Estimate (95% CI) | 0.713 (0.393 1.291) | 0.224 (0.099, 0.506) | 0.616 (0.336, 1.131) | 0.271 (0.120, 0.609) | 0.181 (0.079, 0.417) |
| Relative risk (95% CI) |  | 0.314 (0.125, 0.791) | 0.865 (0.410, 1.824) | 0.380 (0.156, 0.924) | 0.254 (0.100, 0.646) |
| P-value |  | 0.0141 | 0.7036 | 0.0328 | 0.0040 |
| Subgroup: Patients with eosinophil count <250 |  |  |  |  |  |
| Number of patients with >=1 severe exacerbation event |  |  |  |  |  |
| Number | 72 | 71 | 73 | 74 | 68 |
| No | 56 (77.8%) | 59 (83.1%) | 83 (86.3%) | 67 (90.5%) | 60 (88.2%) |
| Yes | 16 (22.2%) | 12 (16.9%) | 10 (13.7%) | 7 (9.5%) | 8 (11.8%) |
| Total number of severe exacerbation events | 32 | 16 | 11 | 9 | 13 |
| Total patient-years followed | 29.4 | 29.6 | 29.1 | 31.1 | 28.8 |
| Unadjusted annualized severe exacerbation event rate a | 1.088 | 0.541 | 0.378 | 0.289 | 0.451 |
| Adjusted annualized severe exacerbation event rate b |  |  |  |  |  |
| Estimate (95% CI) | 0.906 (0.525, 1.563) | 0.523 (0.263, 1.040) | 0.336 (0.156, 0.722) | 0.269 (0.122, 0.594) | 0.386 (0.184, 0.808) |

TABLE 12-continued

Annualized event rate of severe exacerbation by subgroups defined by baseline
blood eosinophil (GIGA/L) during the treatment period in an ITT population.

|  |  | Dupilumab | | | |
|---|---|---|---|---|---|
| n (%) | Placebo (N = 158) | 200 mg q4w (N = 154) | 300 mg q4w (N = 157) | 200 mg q2w (N = 150) | 300 mg q2w (N = 157) |
| Relative risk (95% CI) |  | 0.577 (0.249, 1.341) | 0.371 (0.150, 0.915) | 0.297 (0.116, 0.757) | 0.426 (0.176, 1.028) |
| P-value |  | 0.2013 | 0.0314 | 0.0110 | 0.0576 |
| Subgroup: Patients with eosinophil count >=225 |  |  |  |  |  |
| Number of patients with >=1 severe exacerbation event |  |  |  |  |  |
| Number | 95 | 80 | 93 | 85 | 94 |
| No | 69 (72.6%) | 72 (90.0%) | 78 (83.9%) | 78 (91.8%) | 85 (90.4%) |
| Yes | 26 (27.4%) | 8 (10.0%) | 15 (16.1%) | 7 (8.2%) | 9 (9.6%) |
| Total number of severe exacerbation events | 47 | 9 | 28 | 12 | 9 |
| Total patient-years followed | 39.8 | 32.3 | 37.7 | 35.1 | 38.4 |
| Unadjusted annualized severe exacerbation event rate a | 1.181 | 0.279 | 0.743 | 0.342 | 0.234 |
| Adjusted annualized severe exacerbation event rate b |  |  |  |  |  |
| Estimate (95% CI) | 1.113 (0.690, 1.795) | 0.265 (0.120, 0.584) | 0.674 (0.386, 1.176) | 0.313 (0.152, 0.645) | 0.201 (0.091, 0.444) |
| Relative risk (95% CI) |  | 0.238 (0.096, 0.558) | 0.606 (0.298, 1.231) | 0.261 (0.121, 0.651) | 0.181 (0.073, 0.446) |
| P-value |  | 0.0019 | 0.1657 | 0.0031 | 0.0002 |
| Subgroup: Patients with eosinophil count <225 |  |  |  |  |  |
| Number of patients with >=1 severe exacerbation event |  |  |  |  |  |
| Number | 63 | 70 | 64 | 63 | 62 |
| No | 52 (82.5%) | 58 (82.9%) | 55 (85.9%) | 57 (90.5%) | 54 (87.1%) |
| Yes | 11 (17.5%) | 12 (17.1%) | 9 (14.1%) | 6 (9.5%) | 8 (12.9%) |
| Total number of severe exacerbation events | 18 | 16 | 10 | 8 | 13 |
| Total patient-years followed | 25.6 | 29.1 | 25.2 | 26.3 | 26.1 |
| Unadjusted annualized severe exacerbation event rate a | 0.703 | 0.550 | 0.397 | 0.304 | 0.498 |
| Adjusted annualized severe exacerbation event rate b |  |  |  |  |  |
| Estimate (95% CI) | 0.388 (0.169, 0.891) | 0.339 (0.148, 0.778) | 0.236 (0.092, 0.605) | 0.201 (0.077, 0.525) | 0.281 (0.116, 0.680) |
| Relative risk (95% CI) |  | 0.873 (0.362, 2.108) | 0.607 (0.232, 1.590) | 0.517 (0.187, 1.429) | 0.725 (0.288, 1.822) |
| P-value |  | 0.7626 | 0.3098 | 0.2034 | 0.4937 |
| Subgroup: Patients with eosinophil count >=200 |  |  |  |  |  |
| Number of patients with >=1 severe exacerbation event |  |  |  |  |  |
| Number | 106 | 91 | 102 | 98 | 103 |
| No | 79 (74.5%) | 79 (86.8%) | 87 (85.3%) | 90 (91.8%) | 92 (89.3%) |
| Yes | 27 (25.5%) | 12 (13.2%) | 15 (14.7%) | 8 (8.2%) | 11 (10.7%) |
| Total number of severe exacerbation events | 50 | 13 | 28 | 14 | 11 |
| Total patient-years followed | 44.2 | 36.8 | 41.7 | 40.3 | 41.8 |
| Unadjusted annualized severe exacerbation event rate a | 1.131 | 0.353 | 0.671 | 0.347 | 0.263 |
| Adjusted annualized severe exacerbation event rate b |  |  |  |  |  |
| Estimate (95% CI) | 1.026 (0.649, 1.622) | 0.339 (0.171, 0.669) | 0.603 (0.350, 1.039) | 0.311 (0.160, 0.605) | 0.223 (0.108, 0.462) |

TABLE 12-continued

Annualized event rate of severe exacerbation by subgroups defined by baseline
blood eosinophil (GIGA/L) during the treatment period in an ITT population.

|  |  | Dupilumab | | | |
| --- | --- | --- | --- | --- | --- |
| n (%) | Placebo (N = 158) | 200 mg q4w (N = 154) | 300 mg q4w (N = 157) | 200 mg q2w (N = 150) | 300 mg q2w (N = 157) |
| Relative risk (95% CI) |  | 0.330 (0.147, 0.740) | 0.587 (0.294, 1.174) | 0.303 (0.138, 0.668) | 0.218 (0.094, 0.504) |
| P-value |  | 0.0071 | 0.1319 | 0.0031 | 0.0004 |
| Subgroup: Patients with eosinophil count <200 |  |  |  |  |  |
| Number of patients with >=1 severe exacerbation event |  |  |  |  |  |
| Number | 52 | 59 | 55 | 50 | 53 |
| No | 42 (80.8%) | 51 (86.4%) | 46 (83.6%) | 45 (90.0%) | 47 (88.7%) |
| Yes | 10 (19.2%) | 8 (13.6%) | 9 (16.4%) | 5 (10.0%) | 6 (11.3%) |
| Total number of severe exacerbation events | 15 | 12 | 10 | 6 | 11 |
| Total patient-years followed | 21.1 | 24.6 | 21.2 | 21.2 | 22.6 |
| Unadjusted annualized severe exacerbation event rate a | 0.711 | 0.488 | 0.472 | 0.283 | 0.487 |
| Subgroup: Patients with eosinophil count >=175 |  |  |  |  |  |
| Number of patients with >=1 severe exacerbation event |  |  |  |  |  |
| Number | 114 | 98 | 107 | 103 | 109 |
| No | 84 (73.7%) | 86 (87.8%) | 92 (86.0%) | 93 (90.3%) | 97 (89.0%) |
| Yes | 30 (26.3%) | 12 (12.2%) | 15 (14.0%) | 10 (9.7%) | 12 (11.0%) |
| Total number of severe exacerbation events | 55 | 13 | 28 | 16 | 13 |
| Total patient-years followed | 47.5 | 39.8 | 43.6 | 42.2 | 44.4 |
| Unadjusted annualized severe exacerbation event rate a | 1.158 | 0.327 | 0.642 | 0.379 | 0.293 |
| Adjusted annualized severe exacerbation event rate b |  |  |  |  |  |
| Estimate (95% CI) | 1.084 (0.655, 1.794) | 0.316 (0.153, 0.655) | 0.609 (0.330, 1.124) | 0.348 (0.176, 0.688) | 0.262 (0.128, 0.533) |
| Relative risk (95% CI) |  | 0.292 (0.133, 0.639) | 0.562 (0.289, 1.095) | 0.321 (0.153, 0.676) | 0.241 (0.111, 0.524) |
| P-value |  | 0.0021 | 0.0905 | 0.0027 | 0.0003 |
| Subgroup: Patients with eosinophil count <175 |  |  |  |  |  |
| Number of patients with >=1 severe exacerbation event |  |  |  |  |  |
| Number | 44 | 52 | 50 | 45 | 47 |
| No | 37 (84.1%) | 44 (84.6%) | 41 (82.0%) | 42 (93.3%) | 42 (89.4%) |
| Yes | 7 (15.9%) | 8 (15.4%) | 9 (18.0%) | 3 (6.7%) | 5 (10.6%) |
| Total number of severe exacerbation events | 10 | 12 | 10 | 4 | 9 |
| Total patient-years followed | 17.9 | 21.6 | 19.3 | 19.3 | 20.0 |
| Unadjusted annualized severe exacerbation event rate a | 0.559 | 0.556 | 0.518 | 0.207 | 0.450 |
| Subgroup: Patients with eosinophil count >=150 |  |  |  |  |  |
| Number of patients with >=1 severe exacerbation event |  |  |  |  |  |
| Number | 127 | 109 | 116 | 119 | 128 |
| No | 95 (74.8%) | 95 (87.2%) | 100 (86.2%) | 108 (90.8%) | 113 (88.3%) |
| Yes | 32 (25.2%) | 14 (12.8%) | 16 (13.8%) | 11 (9.2%) | 15 (11.7%) |
| Total number of severe exacerbation events | 60 | 15 | 29 | 17 | 19 |
| Total patient-years followed | 52.9 | 44.0 | 46.7 | 49.0 | 52.9 |
| Unadjusted annualized severe exacerbation event rate a | 1.134 | 0.341 | 0.621 | 0.347 | 0.359 |
| Adjusted annualized severe exacerbation event rate b |  |  |  |  |  |
| Estimate (95% CI) | 0.962 (0.621, 1.492) | 0.306 (0.160, 0.584) | 0.556 (0.321, 0.961) | 0.306 (0.165, 0.565) | 0.281 (0.155, 0.510) |

TABLE 12-continued

Annualized event rate of severe exacerbation by subgroups defined by baseline blood eosinophil (GIGA/L) during the treatment period in an ITT population.

|  | Placebo (N = 158) | Dupilumab | | | |
|---|---|---|---|---|---|
| n (%) | | 200 mg q4w (N = 154) | 300 mg q4w (N = 157) | 200 mg q2w (N = 150) | 300 mg q2w (N = 157) |
| Relative risk (95% CI) | | 0.318 (0.151, 0.668) | 0.577 (0.301, 1.108) | 0.318 (0.155, 0.650) | 0.293 (0.145, 0.591) |
| P-value | | 0.0025 | 0.0984 | 0.0017 | 0.0006 |
| Subgroup: Patients with eosinophil count <150 | | | | | |
| Number of patients with >=1 severe exacerbation event | | | | | |
| Number | 31 | 41 | 41 | 29 | 28 |
| No | 26 (83.9%) | 35 (85.4%) | 32 (80.5%) | 27 (93.1%) | 26 (92.9%) |
| Yes | 5 (16.1%) | 6 (14.6%) | 8 (19.5%) | 2 (6.9%) | 2 (7.1%) |
| Total number of severe exacerbation events | 5 | 10 | 9 | 3 | 3 |
| Total patient-years followed | 12.4 | 17.4 | 16.2 | 12.5 | 11.5 |
| Unadjusted annualized severe exacerbation event rate a | 0.403 | 0.575 | 0.556 | 0.240 | 0.261 |

Abbreviations:
CI = confidence interval;
q2w = once every 2 weeks;
q4w = once every 4 weeks.
[a]The total number of event that occurred during the treatment period divided by the total number of patient-years followed in the treatment period.
[b]Derived using negative binomial model with the total number of confirmed events with onset between first dose date and last dose date + 14 days as the response variable, treatment, baseline eosinophil strata, pooled countries/regions and number of asthma event prior to the study as covariates, and log-transformed standardized treatment duration as an offset variable.

J. Relative Change (%) in FEV1 from Baseline to Week 12

Figure 9:
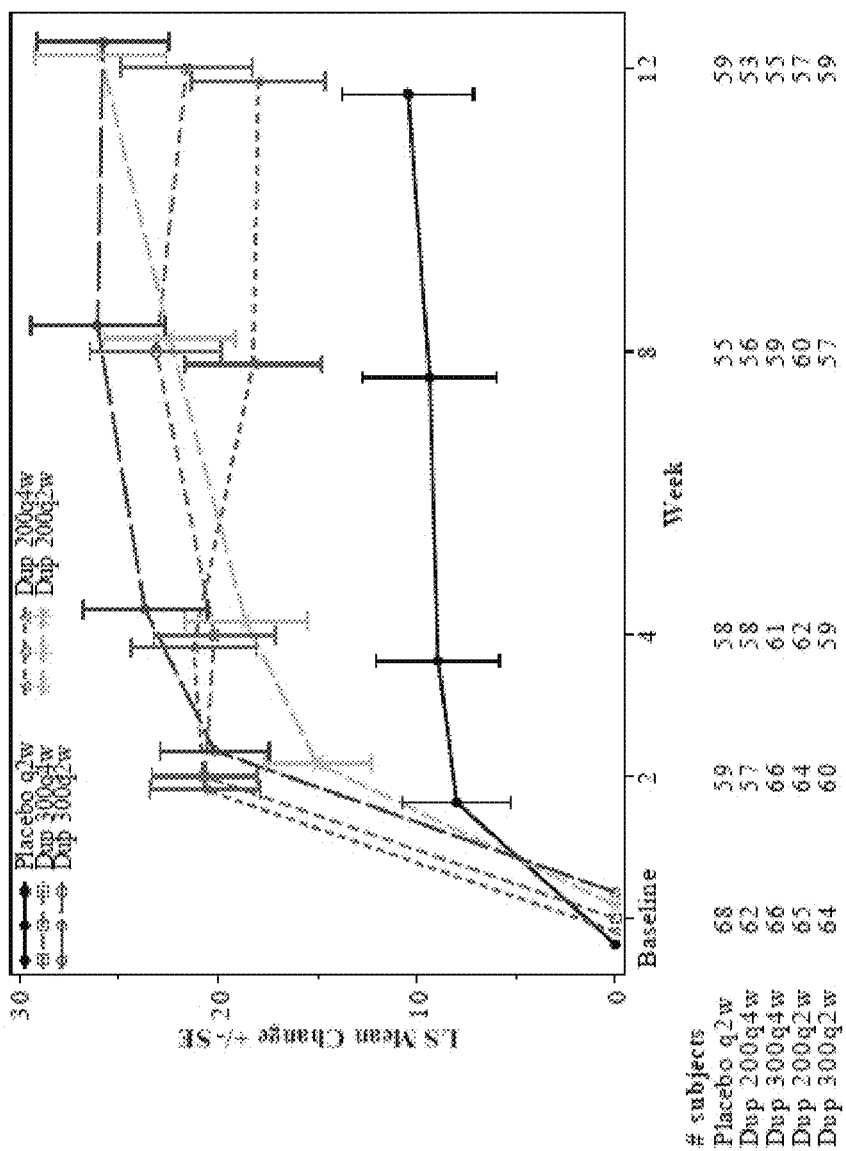
FIG. 9 graphically depicts the least squares mean percent change from baseline in FEV1 at week 12 in a HEos ITT population. FEV1 (L) collected from systemic corticosteroid start date to systemic corticosteroid end date+30 days for each severe exacerbation episode are excluded in order to reduce the confounding effect of systemic corticosteroids.

The percent change from baseline in FEV1 in the HEos ITT population was analyzed at week 12. FIG. 9 depicts the LS mean percent change from baseline in FEV1 through Week 12. The LS mean percent change in FEV1 from baseline to week 12 was 10.44% in the placebo group, and ranged from 17.98% (200 mg q4w dose) to 25.92% (200 mg q2w dose) in the 4 dupilumab treatment arms (Table 13). The LS mean differences between dupilumab and placebo were 7.54% (200 mg q4w), 11.14% (300 mg q4w), 15.48% (200 mg q2w), and 15.37% (300 mg q2w). The LS mean differences were statistically significant when compared with placebo for the 300 mg q4w, 200 mg q2w, and 300 mg q2w doses. Statistical significance was not shown for the lowest dose (200 mg q4w).

TABLE 13

Percent change from baseline in FEV1 at week 12 in a HEos ITT population.

| FEV$_1$ | Placebo (N = 68) | Dupilumab | | | |
|---|---|---|---|---|---|
| | | 200 mg q4w (N = 62) | 300 mg q4w (N = 66) | 200 mg q2w (N = 65) | 300 mg q2w (N = 64) |
| Baseline | | | | | |
| Number | 68 | 62 | 66 | 85 | 64 |
| Mean (SD) | 1.86 (0.68) | 1.80 (0.49) | 1.97 (0.60) | 1.80 (0.52) | 1.77 (0.50) |
| Median | 1.65 | 1.75 | 1.72 | 1.75 | 1.71 |
| Q1:Q3 | 1.33:2.40 | 1.40:2.11 | 1.47:2.13 | 1.45:2.09 | 1.31:2.09 |
| Min:Max | 0.9:3.6 | 0.9:3.4 | 1.0:4.2 | 0.9:3.4 | 1.0:3.1 |
| Week 12 | | | | | |
| Number | 59 | 53 | 55 | 57 | 59 |
| Mean (SD) | 2.13 (0.77) | 2.09 (0.54) | 2.26 (0.70) | 2.26 (0.68) | 2.12 (0.54) |
| Median | 2.08 | 20.1 | 2.16 | 2.12 | 2.20 |
| Q1:Q3 | 1.50:2.86 | 1.76:2.37 | 1.74:2.52 | 1.77:2.51 | 1.77:2.46 |
| Min:Max | 0.9:3.6 | 1.1:3.7 | 1.3:4.2 | 1.0:4.6 | 0.8:3.3 |
| Percent change from baseline | | | | | |
| Number | 59 | 53 | 55 | 57 | 59 |
| Mean (SD) | 10.46 (19.70) | 18.07 (29.18) | 20.68 (24.86) | 27.42 (25.68) | 25.29 (36.15) |
| Median | 7.77 | 9.18 | 12.89 | 17.78 | 14.57 |
| Q1:Q3 | −1.18:20.32 | −1.02:37.41 | 3.57:35.78 | 9.93:39.37 | 2.35:35.29 |
| Min:Max | −41.0:55.3 | −57.6:92.2 | −23.8:95.5 | −18.2:139.8 | −38.1:138.3 |
| LS Mean (SE) a | 10.44 (3.31) | 17.98 (3.43) | 21.58 (3.32) | 25.92 (3.32) | 25.81 (3.35) |

TABLE 13-continued

Percent change from baseline in FEV1 at week 12 in a HEos ITT population.

| FEV$_1$ | Placebo (N = 68) | Dupilumab | | | |
|---|---|---|---|---|---|
| | | 200 mg q4w (N = 62) | 300 mg q4w (N = 66) | 200 mg q2w (N = 65) | 300 mg q2w (N = 64) |
| LS Mean Diff, 95% CI a | | 7.54 (−1.77, 16.84) | 11.14 (2.03, 20.26) | 15.48 (6.36, 24.60) | 15.37 (6.21, 24.53) |
| P-value vs placebo a | | 0.1119 | 0.0168 | 0.0009 | 0.0011 |

Abbreviations:
CI = confidence interval;
Diff = difference;
FEV1 = forced expiratory volume in 1 second;
HEos = high eosinophil;
max = maximum;
min = minimum;
q2w = once every 2 weeks;
q4w = 2once every 4 weeks;
SD = standard deviation;
SE = standard error of the mean.
a Derived from MMRM model with percent change in FEV1 from baseline up to week 12 as dependent variables, factors (fixed effects) for treatment, pooled countries/regions, visit, treatment-by-visit interaction, FEV1 baseline value and baseline-by-visit interaction as covariates, unstructured correlation matrix. FEV1 collected from systemic corticosteroid start date to systemic corticosteroid end date + 30 days for each exacerbation episode are excluded in order to reduce the confounding effect of systemic corticosteroids.

Figure 10:
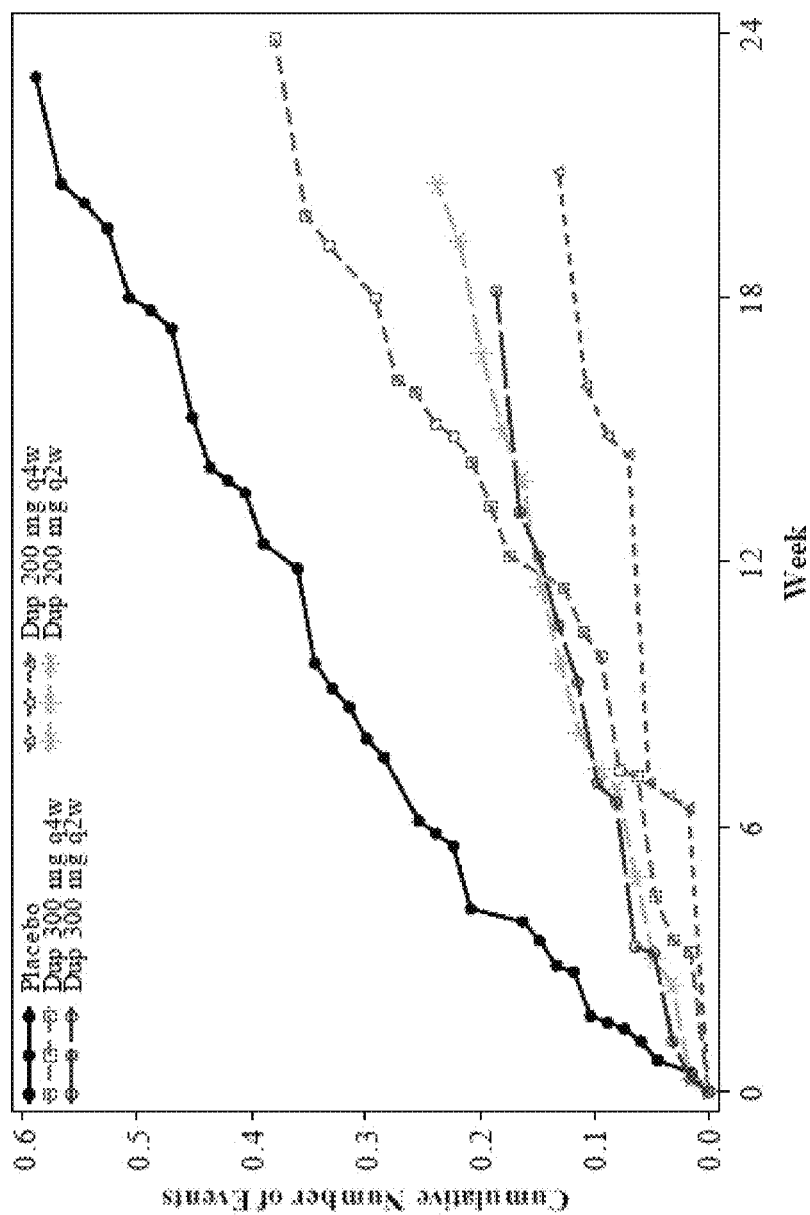
FIG. 10 graphically depicts the cumulative mean functions for the number of loss of asthma control events for the treatment period in a HEos ITT population.

K. Annualized Rate of Loss of Asthma Control (LOAC) Events during the Treatment Period FIG. 10 presents changes in the cumulative mean function for the number of LOAC events by treatment arm through 24-weeks. During the 24-week treatment period, the number of patients in the HEos ITT population with ≥1 LOAC event(s) were 23 patients in the placebo group, and 6, 12, 7, and 10 patients in the dupilumab 200 mg q4w, 300 mg q4w, 200 mg q2w and 300 mg q2w groups, respectively (Table 14). The relative risks for a LOAC, based on adjusted annualized LOAC event rate, compared to placebo, were 0.232 (200 mg q4w), 0.626 (300 mg q4w), 0.413 (200 mg q2w), and 0.311 (300 mg q2w). Statistical significance was demonstrated for all dupilumab doses with the exception of the 300 mg q4w dose.

TABLE 14

Annualized event rate of loss of asthma control during the treatment period in a HEos ITT.

| | Placebo (N = 68) | Dupilumab | | | |
|---|---|---|---|---|---|
| | | 200 mg q4w (N = 62) | 300 mg q4w (N = 66) | 200 mg q2w (N = 65) | 300 mg q2w (N = 64) |
| Number of patients with >=1 LOAC event | | | | | |
| Number | 68 | 59 | 66 | 64 | 64 |
| No | 45 (66.2%) | 53 (89.8%) | 54 (81.8%) | 57 (89.1%) | 54 (84.4%) |
| Yes | 23 (33.8%) | 6 (10.2%) | 12 (18.2%) | 7 (10.9%) | 10 (15.6%) |
| Number of LOAC events | | | | | |
| 0 | 45 (66.2%) | 53 (89.8%) | 54 (81.8%) | 57 (89.1%) | 54 (84.4%) |
| 1 | 13 (19.1%) | 5 (8.5%) | 6 (9.1%) | 3 (4.7%) | 9 (14.1%) |
| 2 | 6 (8.8%) | 1 (1.7%) | 2 (3.0%) | 3 (4.7%) | 1 (1.6%) |
| 3 | 4 (5.9%) | 0 | 4 (6.1%) | 0 | 0 |
| >=4 | 0 | 0 | 0 | 1 (1.6%) | 0 |
| Total number of LOAC events | 37 | 7 | 22 | 14 | 11 |
| Total patient-years followed | 28.0 | 24.0 | 27.0 | 26.4 | 25.6 |
| Unadjusted annualized LOAC event rate a | 1.321 | 0.292 | 0.815 | 0.530 | 0.430 |
| Adjusted annualized LOAC event rate b | | | | | |
| Estimate (95% CI) | 1.098 (0.650, 1.853) | 0.255 (0.108, 0.601) | 0.688 (0.385, 1.228) | 0.454 (0.231, 0.892) | 0.341 (0.160, 0.725) |
| Relative risk (95% CI) | | 0.232 (0.088, 0.610) | 0.626 (0.299, 1.310) | 0.413 (0.184, 0.927) | 0.311 (0.131, 0.735) |
| P-value | | 0.0030 | 0.2138 | 0.320 | 0.0078 |
| Individual patient annualized LOAC events rate c | | | | | |
| Number | 68 | 59 | 66 | 64 | 64 |
| Mean (SD) | 1.30 (2.19) | 0.30 (0.99) | 0.77 (1.88) | 0.53 (1.89) | 0.41 (1.00) |

TABLE 14-continued

Annualized event rate of loss of asthma control during the treatment period in a HEos ITT.

|  | Placebo (N = 68) | Dupilumab | | | |
|---|---|---|---|---|---|
|  |  | 200 mg q4w (N = 62) | 300 mg q4w (N = 66) | 200 mg q2w (N = 65) | 300 mg q2w (N = 64) |
| Median | 0.00 | 0.00 | 0.00 | 0.00 | 0.00 |
| Min:Max | 0.0:9.9 | 0.0:5.8 | 0.0:8.2 | 0.0:11.9 | 0.0:4.3 |

Abbreviations:
CI = confidence interval;
HEos = high eosinophil;
max = maximum;
min = minimum;
q2w = once every 2 weeks;
q4w = once every 4 weeks.
a The total number of event that occurred during the treatment period divided by the total number of patient-years followed in the treatment period.
b Derived using negative binomial model with the total number of events onset between first dose date and last dose date + 14 days as the response variable, treatment, pooled countries/regions and number of asthma event prior to the study as covariates, and log-transformed standardized treatment duration as an offset variable.

Figure 11:
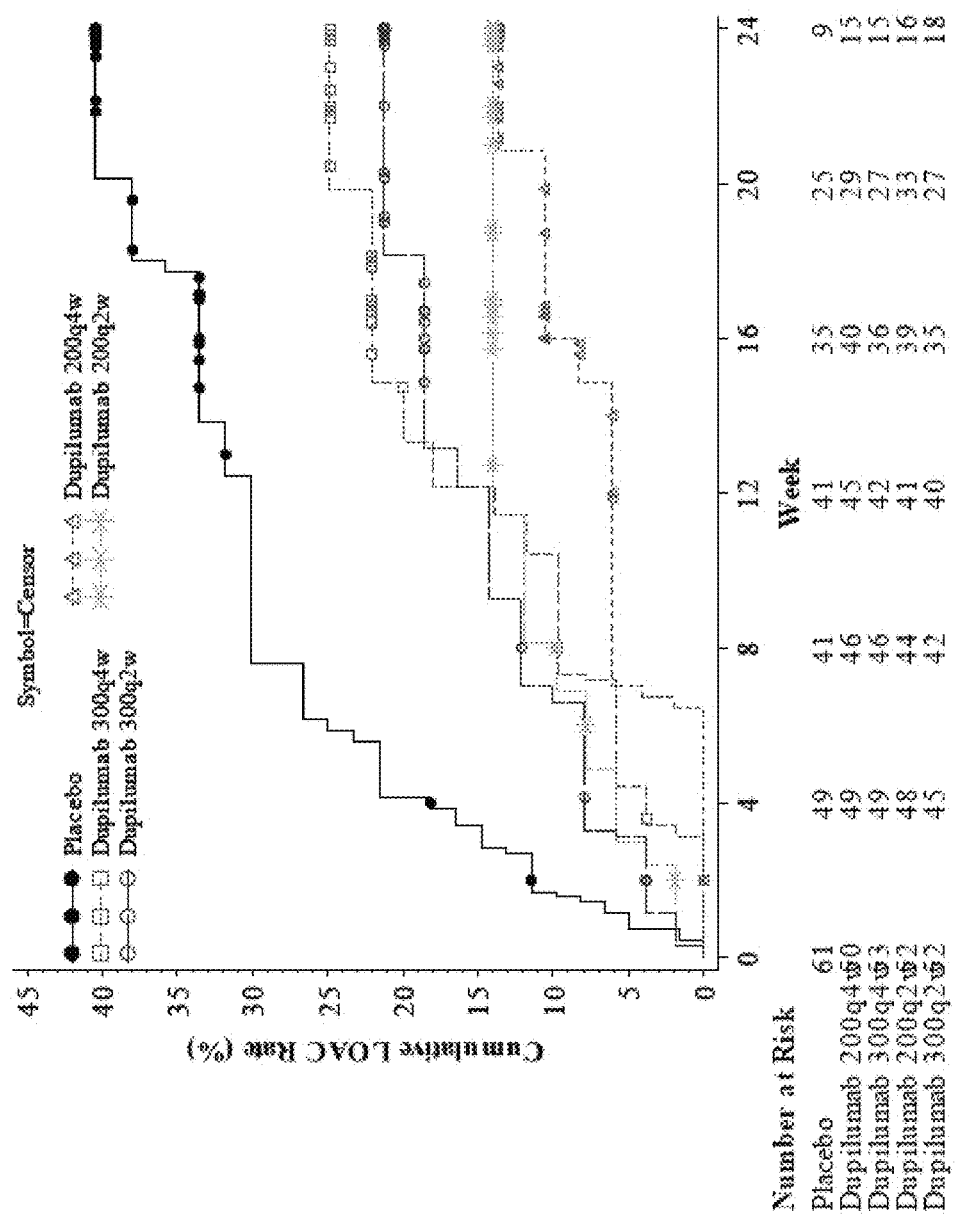
FIG. 11 depicts a Kaplan-Meier plot of time to first loss of asthma control event during the treatment period in a HEos ITT population.
Figure 12:
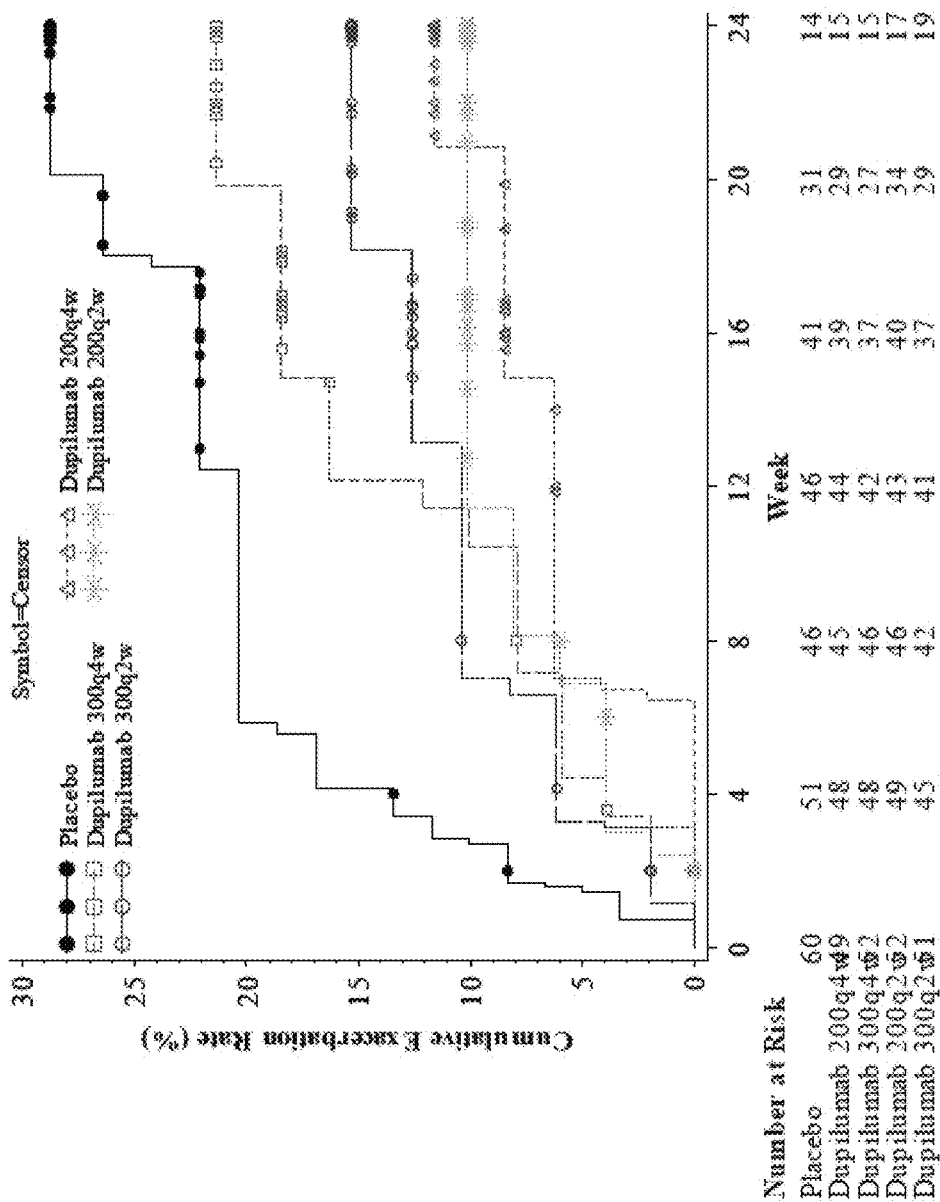
FIG. 12 depicts a Kaplan-Meier plot of time to first severe exacerbation event during the treatment period in a HEos ITT population.

L. Time to Loss of Asthma Control and Severe Exacerbation Events during the Treatment Period The time to the first LOAC event and time to the first severe exacerbation event in the HEos ITT population during the treatment period are shown by treatment arms in FIG. 11 and FIG. 12, respectively. These two Kaplan-Meier plots show comparable results for time to first severe exacerbation event and time to first LOAC event. All dupilumab groups demonstrated a delayed onset to an event.

M. Serum *Thymus* and Activation-regulated Chemokine

Figure 13:
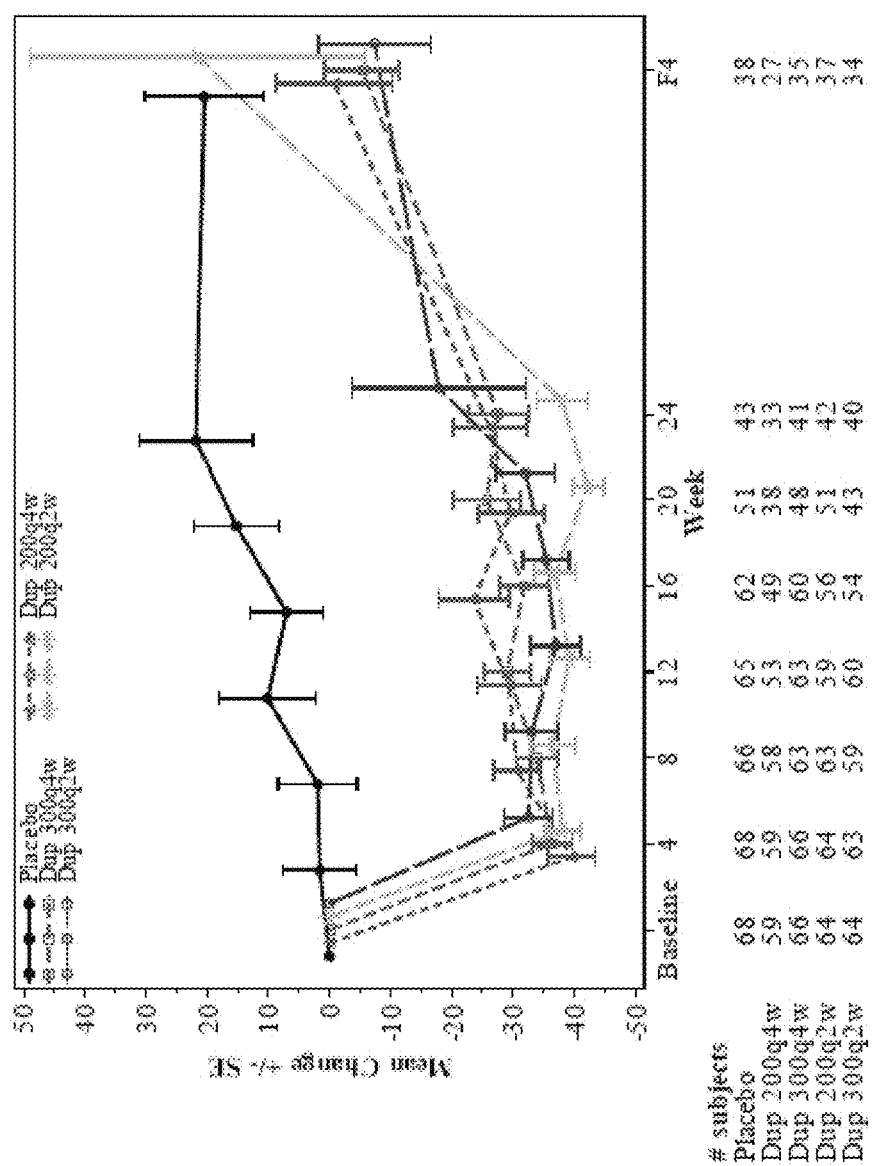
FIG. 13 graphically depicts the mean percent change from baseline TARC in a HEos ITT population. TARC=*thymus and activation-regulated chemokine*.
Figure 14:
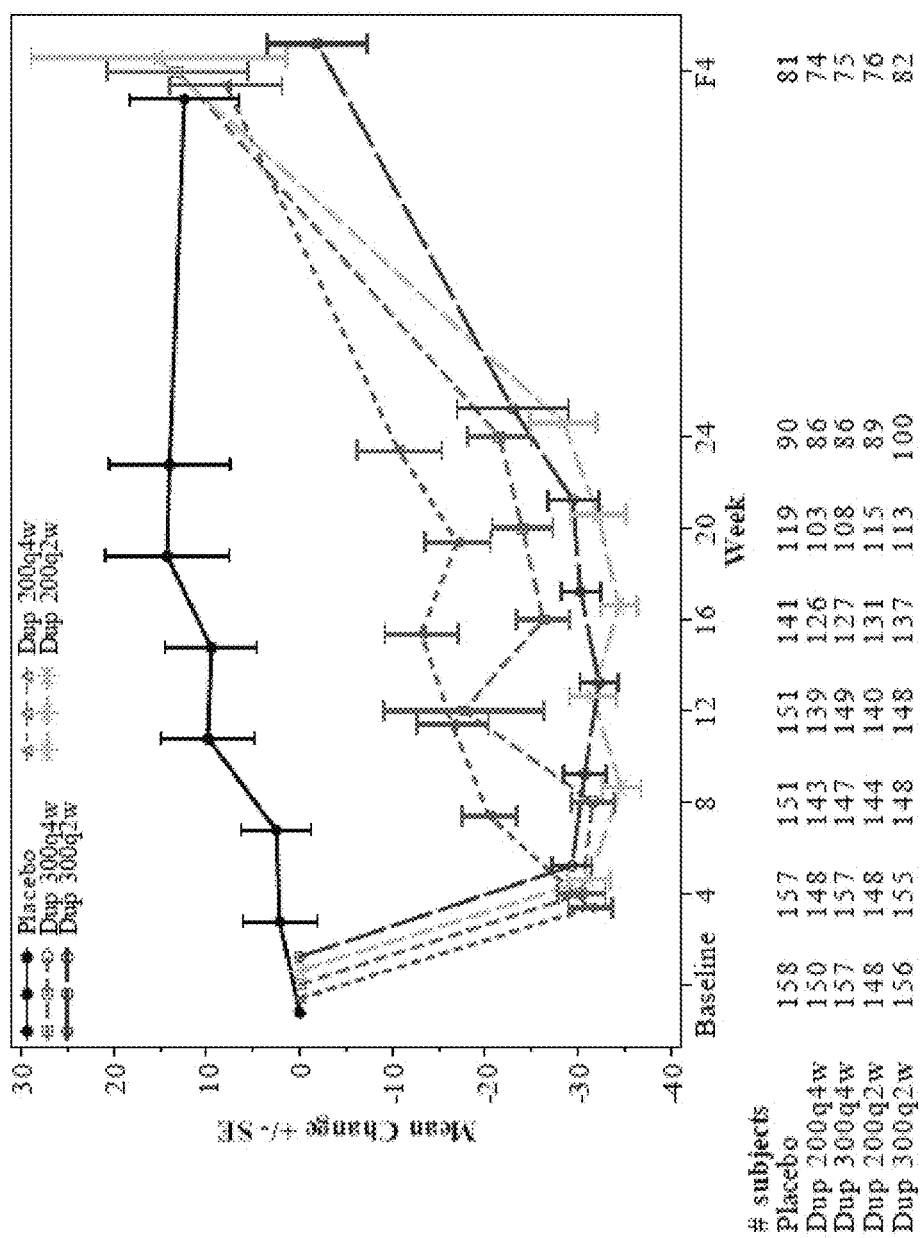
FIG. 14 graphically depicts the mean percent change from baseline TARC in an ITT population.

Dupilumab treatment was associated with a marked decline (compared with baseline) in mean serum TARC concentration (FIG. 13 and FIG. 14). The near-maximal effect was approached by week 4 and was similar for all 4 dose regimens. This effect was sustained, except for a partial loss of effect in the HEos ITT population treated with the two q4w regimens. Serum TARC gradually increased over time in the placebo group.

N. Plasma Eotaxin-3

Figure 15:
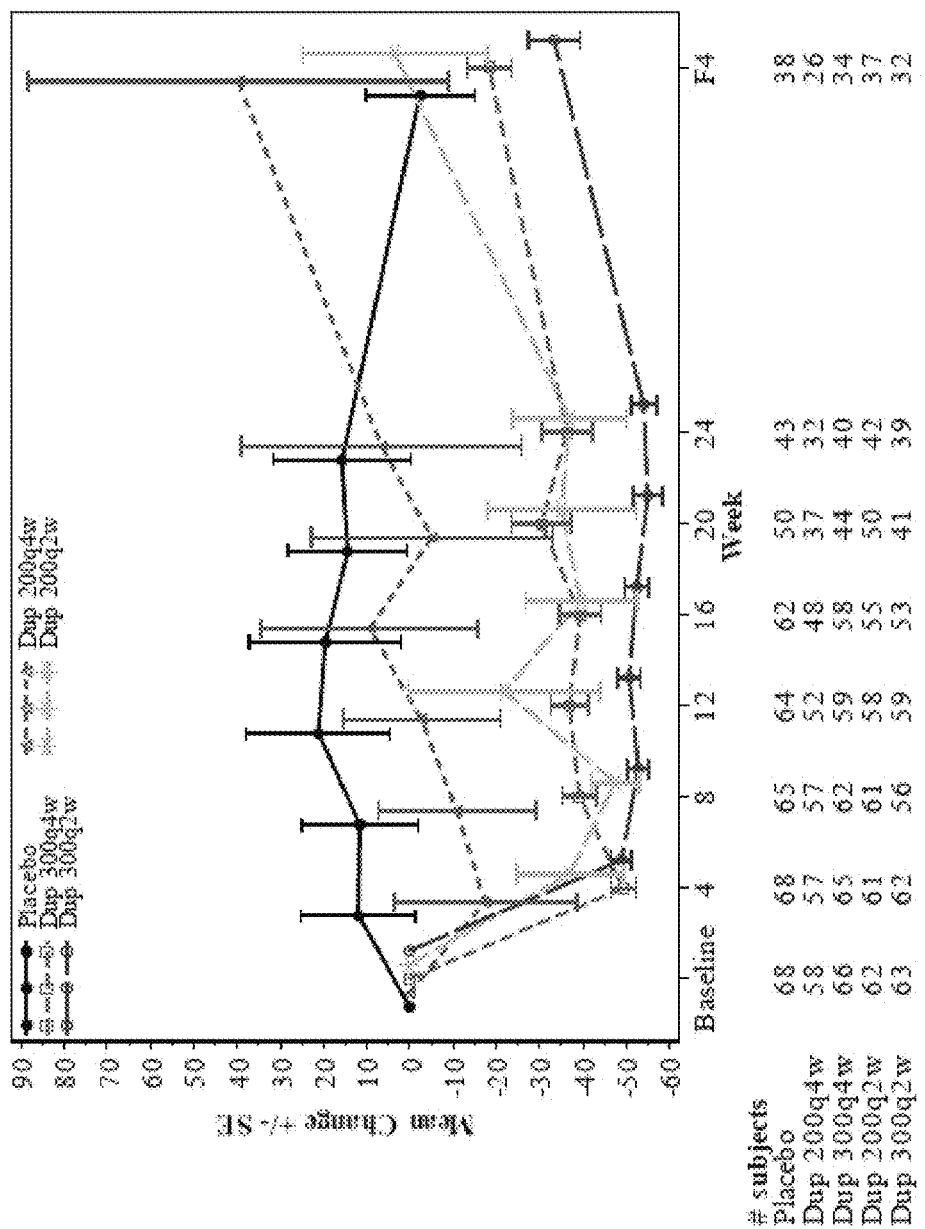
FIG. 15 graphically depicts the mean percent change from baseline eotaxin-3 in a HEos ITT population.
Figure 16:
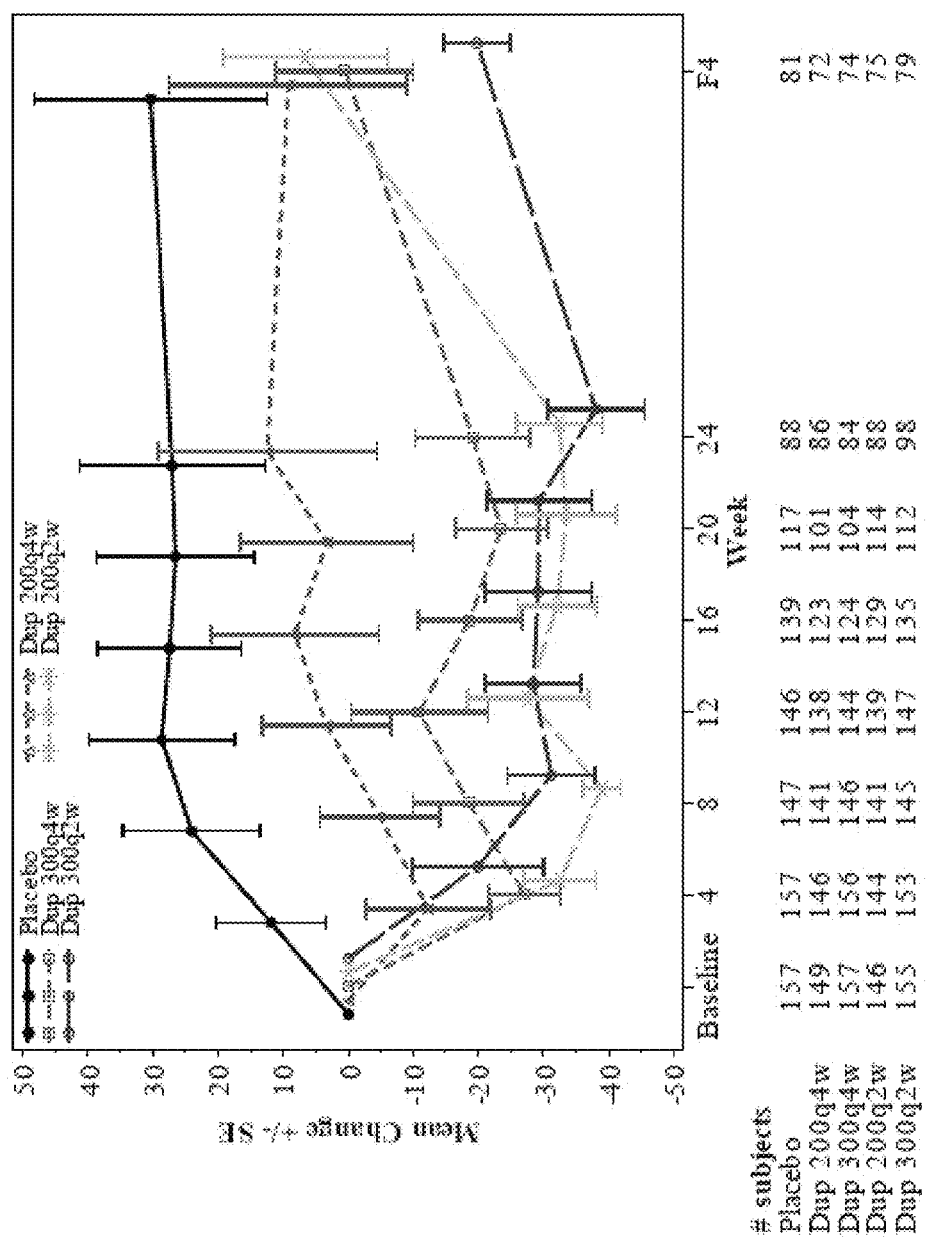
FIG. 16 graphically depicts the mean percent change from baseline eotaxin-3 in an ITT population.

The mean concentration of plasma eotaxin-3 declined with all 4 dupilumab regimens with a near-maximal effect observed by 4 to 8 weeks of treatment, whereas an increase in plasma eotaxin-3 was observed in patients receiving placebo (FIG. 15 and FIG. 16). Mean percent decreases in plasma eotaxin-3 showed dose-dependency, with a lesser effect in the 200 mg q4w group. Differentiation among the 3 higher dose regimens was less clear. The group mean percent decreases in eotaxin-3 were generally greater in the HEos ITT population than those observed in the ITT population.

O. Fractional Exhaled Nitric Oxide

Figure 17:
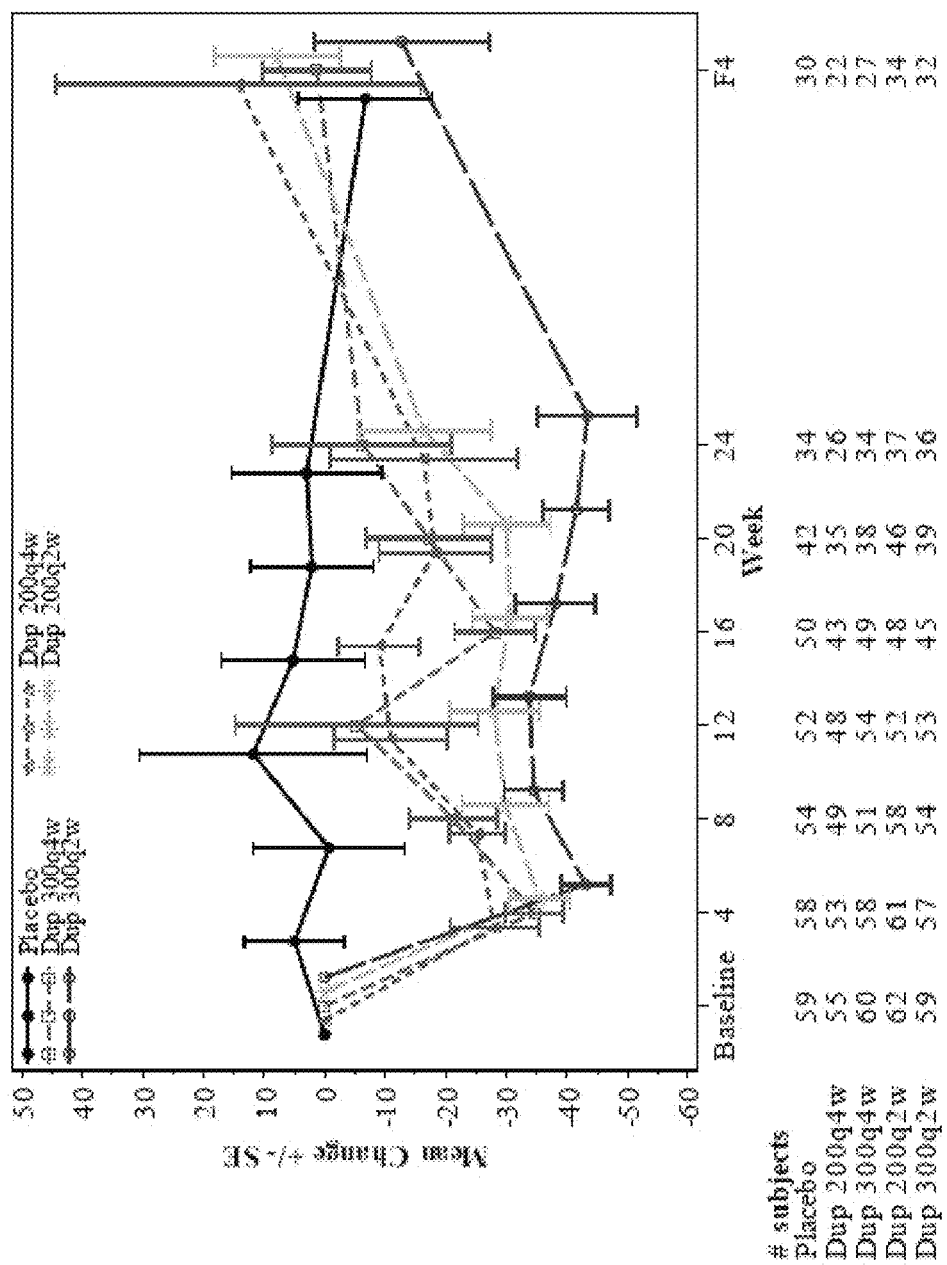
FIG. 17 graphically depicts the mean percent change from baseline FeNO in a HEos ITT population. FeNO=fractional exhaled nitric oxide.
Figure 18:
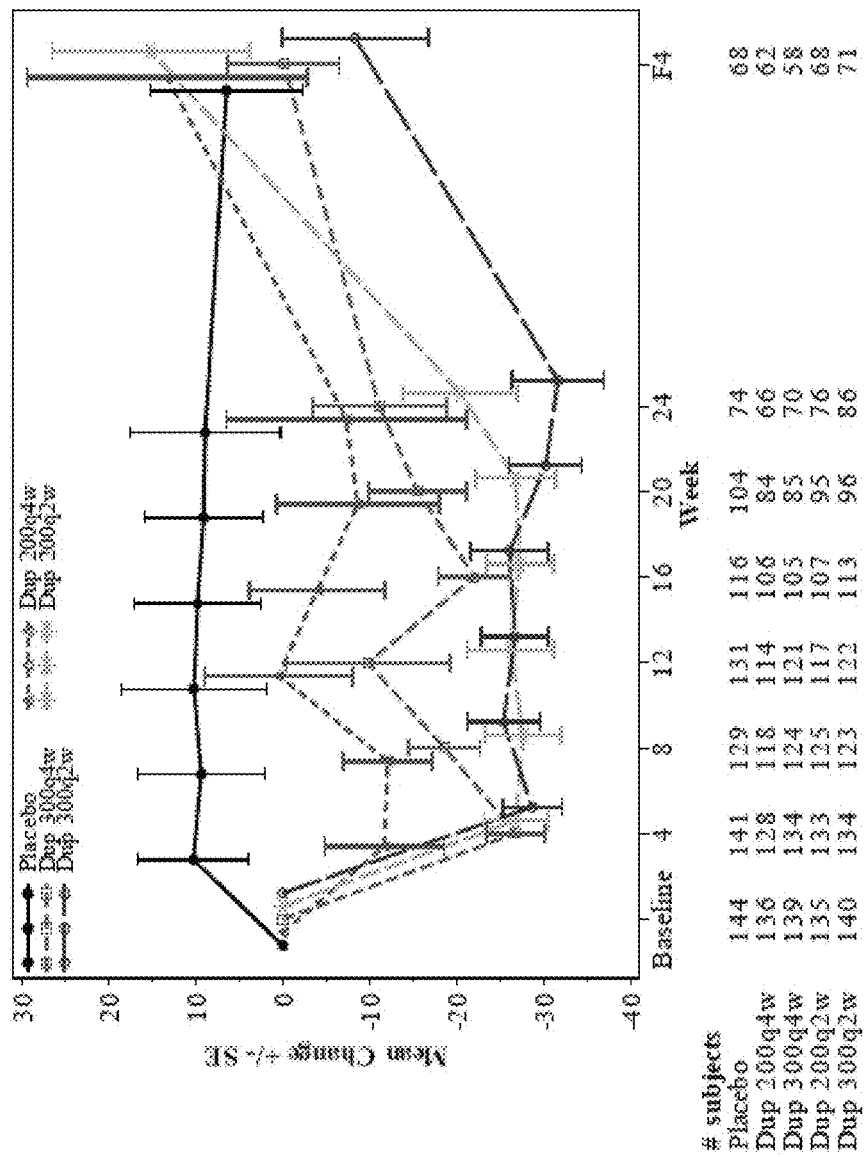
FIG. 18 graphically depicts the mean percent change from baseline FeNO-ITT population.

Fractional exhaled nitric oxide values were elevated at baseline in about half of the patients (median 28 ppb relative to a healthy upper norm of 25 ppb) and were higher in the HEos ITT population (median 40 ppb). The group mean FeNO values declined with all dupilumab dose regimens in a roughly dose-dependent manner, with the maximal effect achieved by 4 weeks of treatment (FIG. 17 and FIG. 18). The greater effect observed in the two q2w dose regimens was sustained throughout dupilumab treatment.

Example 3

Subgroup Analyses

Figure 19:
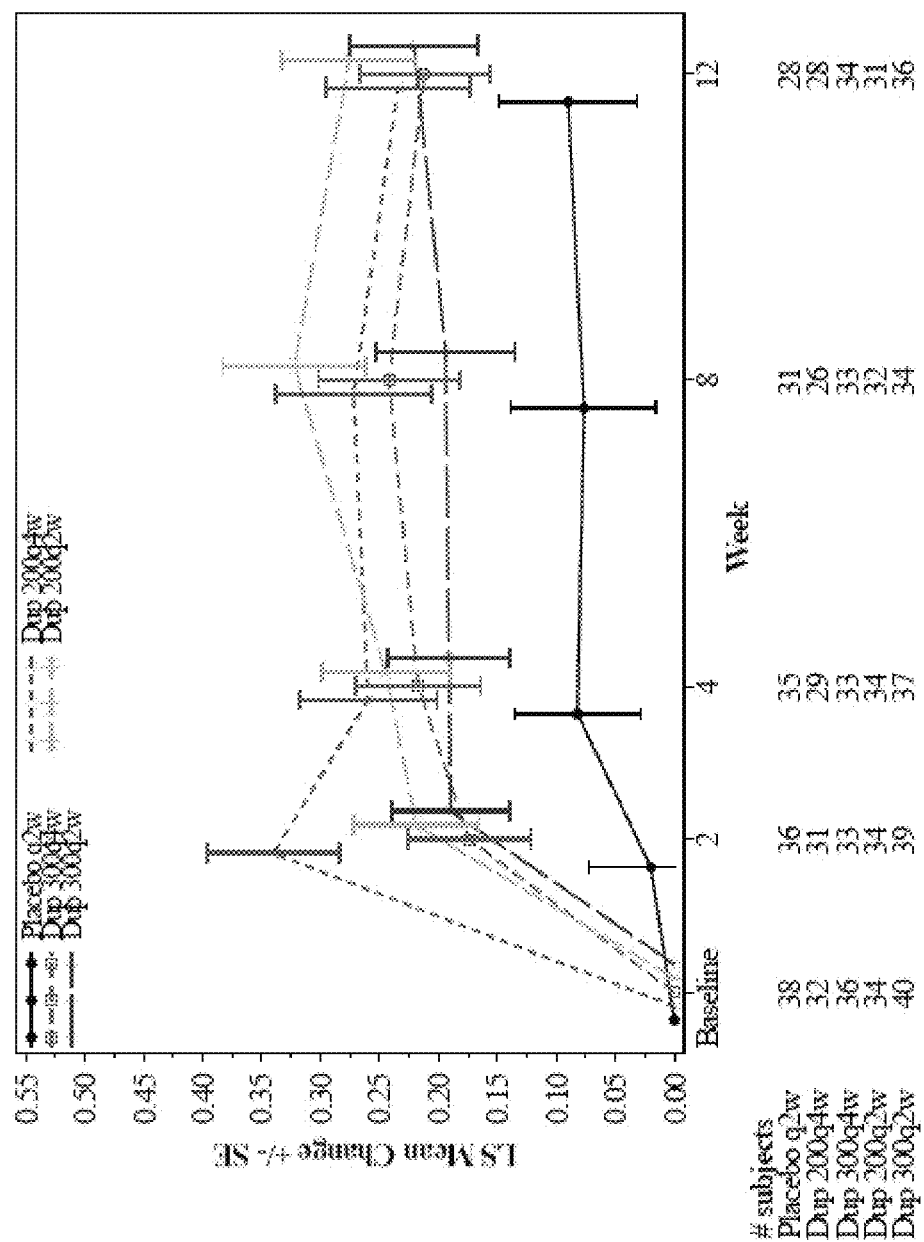
FIG. 19 graphically depicts the least squares (LS) mean change from baseline in FEV1 (L) over time (MMRM including measurements up to Week 12) in an ITT population with medium blood eosinophil (0.2-0.299 GIGA/L). FEV1 (L) collected from systemic corticosteroid start date to systemic corticosteroid end date+30 days for each severe exacerbation episode are excluded in order to reduce the confounding effect of systemic corticosteroids.

FEV1 values were determined for a population having medium blood Eos (Table 15). FIG. 19 graphically depicts these results.

TABLE 15

Change from baseline in FEV1 (L) at week 12 in an ITT population with medium blood eosinophil (0.2-0.299 GIGA/L).

| FEV1 | Placebo (N = 38) | Dupilumab | | | |
|---|---|---|---|---|---|
|  |  | 200 mg q4w (N = 32) | 300 mg q4w (N = 36) | 200 mg q2w (N = 34) | 300 mg q2w (N = 40) |
| Baseline | | | | | |
| Number | 38 | 32 | 36 | 34 | 40 |
| Mean (SD) | 1.73 (0.42) | 1.98 (0.53) | 1.88 (0.54) | 1.80 (0.50) | 1.94 (0.47) |
| Median | 1.74 | 1.92 | 1.75 | 1.73 | 1.96 |
| Q1:Q3 | 1.44:1.90 | 1.62:2.17 | 1.44:2.25 | 1.49:1.98 | 1.57:2.30 |
| Min:Max | 0.9:2.8 | 1.0:3.3 | 1.1:3.3 | 0.8:3.2 | 1.1:3.2 |
| Week 12 | | | | | |
| Number | 28 | 28 | 34 | 31 | 36 |
| Mean (SD) | 1.86 (0.53) | 2.12 (0.63) | 2.10 (0.67) | 2.10 (0.59) | 2.14 (0.55) |
| Median | 1.84 | 2.10 | 2.09 | 1.98 | 2.09 |
| Q1:Q3 | 1.51:2.23 | 1.62:2.37 | 1.58:2.70 | 1.59:2.51 | 1.71:2.55 |
| Min:Max | 1.0:3.1 | 1.2:4.0 | 0.9:3.2 | 1.1:3.4 | 1.3:3.5 |

TABLE 15-continued

Change from baseline in FEV1 (L) at week 12 in an ITT population with medium blood eosinophil (0.2-0.299 GIGA/L).

| | | Dupilumab | | | |
| --- | --- | --- | --- | --- | --- |
| FEV1 | Placebo (N = 38) | 200 mg q4w (N = 32) | 300 mg q4w (N = 36) | 200 mg q2w (N = 34) | 300 mg q2w (N = 40) |
| Change from baseline | | | | | |
| Number | 28 | 28 | 34 | 31 | 36 |
| Mean (SD) | 0.10 (0.30) | 0.22 (0.44) | 0.19 (0.33) | 0.26 (0.29) | 0.17 (0.27) |
| Median | 0.08 | 0.15 | 0.14 | 0.24 | 0.17 |
| Q1:Q3 | −0.15:0.27 | −0.03:0.27 | −0.03:0.30 | 0.10:0.40 | −0.05:0.37 |
| Min:Max | −0.5:0.7 | −0.5:1.3 | −0.3:1.1 | −0.3:1.1 | −0.3:0.7 |
| LS Mean (SE)[a] | 0.09 (0.06) | 0.23 (0.06) | 0.21 (0.06) | 0.28 (0.06) | 0.22 (0.05) |
| LS Mean Diff, 95% CI[a] | | 0.14 (−0.02, 0.31) | 0.12 (−0.04, 0.28) | 0.19 (0.02, 0.35) | 0.13 (−0.03, 0.29) |
| P-value vs placebo[a] | | 0.0870 | 0.1322 | 0.0239 | 0.1011 |

[a] Derived from MMRM model with change in FEV1 (L) from baseline up to week 12 as dependent variables, factors (fixed effects) for treatment, pooled countries/regions, visit, treatment-by-visit interaction, FEV1 (L) baseline value and baseline-by-visit interaction as covariates, unstructured correlation matrix. FEV1 (L) collected from systemic corticosteroid start date to systemic corticosteroid end date + 30 days for each severe exacerbation episode are excluded in order to reduce the confounding effect of systemic corticosteroids.

Figure 20:
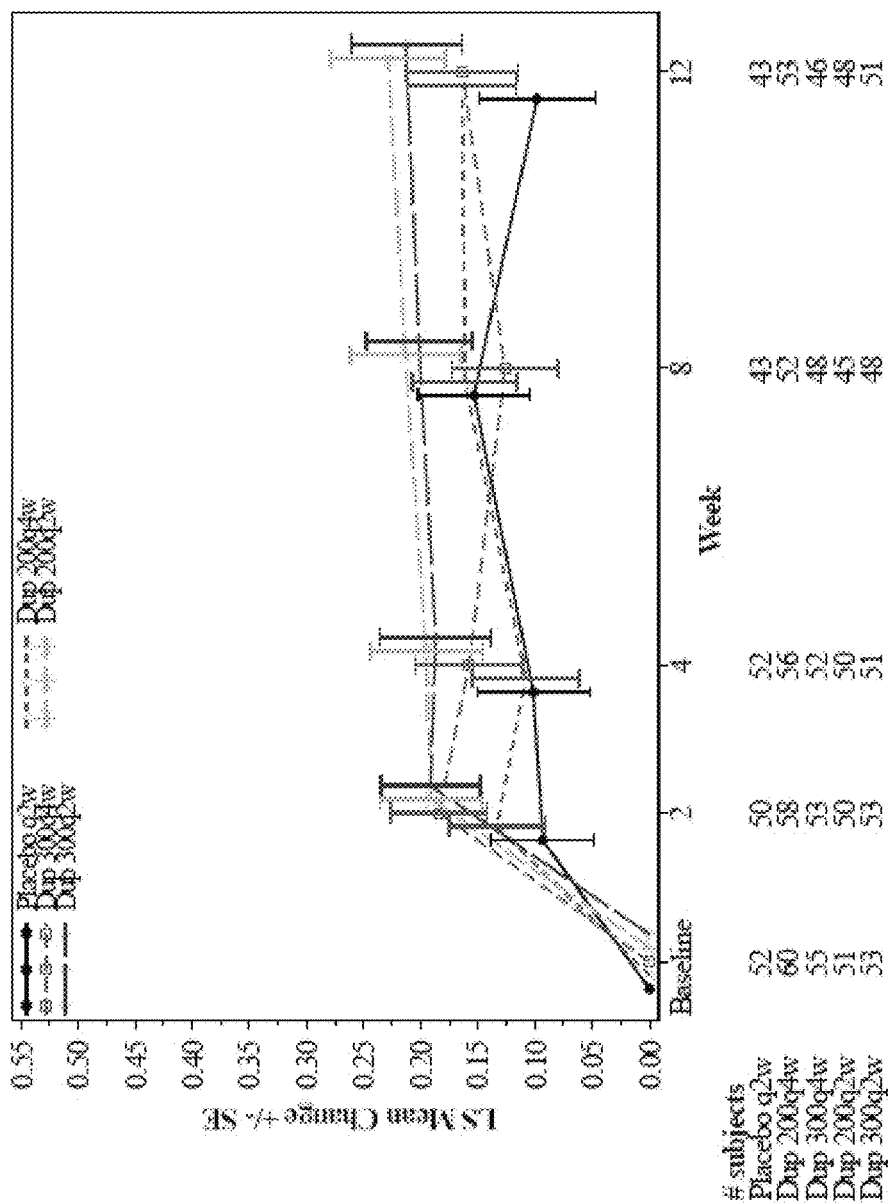
FIG. 20 graphically depicts the LS mean change from baseline in FEV1 (L) over time (MMRM including measurements up to Week 12) in an ITT population with low blood eosinophil (<0.2 GIGA/L). FEV1 (L) collected from systemic corticosteroid start date to systemic corticosteroid end date+30 days for each severe exacerbation episode are excluded in order to reduce the confounding effect of systemic corticosteroids.

FEV1 values were determined for a population having low blood Eos (Table 16). FIG. 20 graphically depicts these results.

TABLE 16

Change from baseline in FEV1 (L) at week 12 in an ITT population with low blood eosinophil (<0.2 GIGA/L).

| | | Dupilumab | | | |
| --- | --- | --- | --- | --- | --- |
| FEV1 | Placebo (N = 52) | 200 mg q4w (N = 60) | 300 mg q4w (N = 55) | 200 mg q2w (N = 51) | 300 mg q2w (N = 53) |
| Baseline | | | | | |
| Number | 52 | 60 | 55 | 51 | 53 |
| Mean (SD) | 1.83 (0.42) | 1.92 (0.58) | 1.83 (0.57) | 1.79 (0.56) | 1.87 (0.60) |
| Median | 1.84 | 1.88 | 1.76 | 1.67 | 1.71 |
| Q1:Q3 | 1.57:2.16 | 1.49:2.29 | 1.37:2.15 | 1.37:2.04 | 1.47:2.19 |
| Min:Max | 1.1:2.9 | 0.9:3.9 | 0.8:3.2 | 1.0:3.3 | 0.8:3.8 |
| Week 12 | | | | | |
| Number | 43 | 53 | 46 | 48 | 51 |
| Mean (SD) | 1.95 (0.65) | 2.04 (0.71) | 2.01 (0.68) | 1.97 (0.72) | 2.11 (0.69) |
| Median | 1.81 | 1.96 | 1.93 | 1.83 | 2.08 |
| Q1:Q3 | 1.60:2.20 | 1.51:2.42 | 1.57:2.45 | 1.44:2.21 | 1.59:2.59 |
| Min:Max | 1.0:4.0 | 0.8:3.8 | 0.9:3.6 | 1.0:3.9 | 1.0:4.4 |
| Change from baseline | | | | | |
| Number | 43 | 53 | 46 | 48 | 51 |
| Mean (SD) | 0.09 (0.40) | 0.14 (0.32) | 0.14 (0.37) | 0.21 (0.35) | 0.20 (0.34) |
| Median | 0.01 | 0.16 | 0.08 | 0.12 | 0.12 |
| Q1:Q3 | −0.12:0.21 | −0.03:0.34 | −0.07:0.29 | −0.01:0.42 | −0.02:0.44 |
| Min:Max | −0.7:1.5 | −1.0:0.9 | −0.7:1.2 | −0.4:1.0 | −0.5:1.0 |
| LS Mean (SE)[a] | 0.10 (0.05) | 0.16 (0.05) | 0.16 (0.05) | 0.23 (0.95) | 0.21 (0.05) |
| LS Mean Diff, 95% CI[a] | | 0.07 (−0.07, 0.20) | 0.07 (−0.07, 0.20) | 0.13 (−0.01, 0.27) | 0.11 (−0.02, 0.25) |
| P-value vs placebo[a] | | 0.3377 | 0.3512 | 0.0674 | 0.1029 |

[a] Derived from MMRM model with change in FEV1 (L) from baseline up to week 12 as dependent variables, factors (fixed effects) for treatment, pooled countries/regions, visit, treatment-by-visit interaction, FEV1 (L) baseline value and baseline-by-visit interaction as covariates, unstructured correlation matrix. FEV1 (L) collected from systemic corticosteroid start date to systemic corticosteroid end date + 30 days for each severe exacerbation episode are excluded in order to reduce the confounding effect of systemic corticosteroids.

An analysis of the change in baseline FEV1 values over time was performed for an ITT population (Table 17).

TABLE 17

Change from baseline in FEV1 (L) over time (MMRM including measurements up to week 12) in an ITT population.

| | | Dupilumab | | | |
|---|---|---|---|---|---|
| FEV1 | Placebo (N = 158) | 200 mg q4w (N = 154) | 300 mg q4w (N = 157) | 200 mg q2w (N = 150) | 300 mg q2w (N = 157) |
| Baseline | | | | | |
| Number | 158 | 154 | 157 | 150 | 157 |
| Mean (SD) | 1.82 (0.55) | 1.88 (0.54) | 1.86 (0.57) | 1.79 (0.52) | 1.85 (0.53) |
| Median | 1.74 | 1.80 | 1.74 | 1.72 | 1.75 |
| Q1:Q3 | 1.44:2.16 | 1.49:2.19 | 1.45:2.15 | 1.42:2.04 | 1.46:2.18 |
| Min:Max | 0.9:3.6 | 0.9:3.9 | 0.8:4.2 | 0.8:3.4 | 0.8:3.8 |
| Week 2 Change from baseline | | | | | |
| Number | 145 | 146 | 152 | 148 | 152 |
| LS Mean (SE)[a] | 0.08 (0.03) | 0.25 (0.03) | 0.24 (0.03) | 0.22 (0.03) | 0.23 (0.03) |
| LS Mean Diff, 95% CI[a] | | 0.17 (0.09, 0.24) | 0.16 (0.08, 0.23) | 0.14 (0.07, 0.22) | 0.15 (0.07, 0.22) |
| P-value vs placebo[a] | | <.0001 | <.0001 | 0.0003 | 0.0001 |
| Week 4 Change from baseline | | | | | |
| Number | 145 | 143 | 146 | 146 | 147 |
| LS Mean (SE)[a] | 0.11 (0.03) | 0.22 (0.03) | 0.23 (0.03) | 0.25 (0.03) | 0.25 (0.03) |
| LS Mean Diff, 95% CI[a] | | 0.11 (0.03, 0.19) | 0.13 (0.05, 0.21) | 0.14 (0.06, 0.22) | 0.14 (0.06, 0.22) |
| P-value vs placebo[a] | | 0.0091 | 0.0024 | 0.0009 | 0.0009 |
| Week 8 Change from baseline | | | | | |
| Number | 129 | 134 | 140 | 137 | 139 |
| LS Mean (SE)[a] | 0.12 (0.03) | 0.22 (0.03) | 0.25 (0.03) | 0.30 (0.03) | 0.27 (0.03) |
| LS Mean Diff, 95% CI[a] | | 0.09 (0.01, 0.18) | 0.13 (0.04, 0.22) | 0.17 (0.09, 0.26) | 0.15 (0.06, 0.23) |
| P-value vs placebo[a] | | 0.0380 | 0.0036 | 0.0001 | 0.0011 |
| Week 12 Change from baseline | | | | | |
| Number | 130 | 134 | 135 | 136 | 146 |
| LS Mean (SE)[a] | 0.12 (0.03) | 0.21 (0.03) | 0.24 (0.03) | 0.31 (0.03) | 0.28 (0.03) |
| LS Mean Diff, 95% CI[a] | | 0.09 (0.01, 0.18) | 0.12 (0.04, 0.21) | 0.19 (0.11, 0.28) | 0.16 (0.08, 0.25) |
| P-value vs placebo[a] | | 0.0343 | 0.0052 | <.0001 | 0.0002 |

[a]Derived from MMRM model with change in FEV1 (L) from baseline up to week 12 as dependent variables, factors (fixed effects) for treatment, baseline eosinophil strata, pooled countries/regions, visit, treatment-by-visit interaction, FEV1 (L) baseline value and baseline-by-visit interaction as covariates, unstructured correlation matrix. FEV1 (L) collected from systemic corticosteroid start date to systemic corticosteroid end date + 30 days for each severe exacerbation episode are excluded in order to reduce the confounding effect of systemic corticosteroids.

Figure 21:
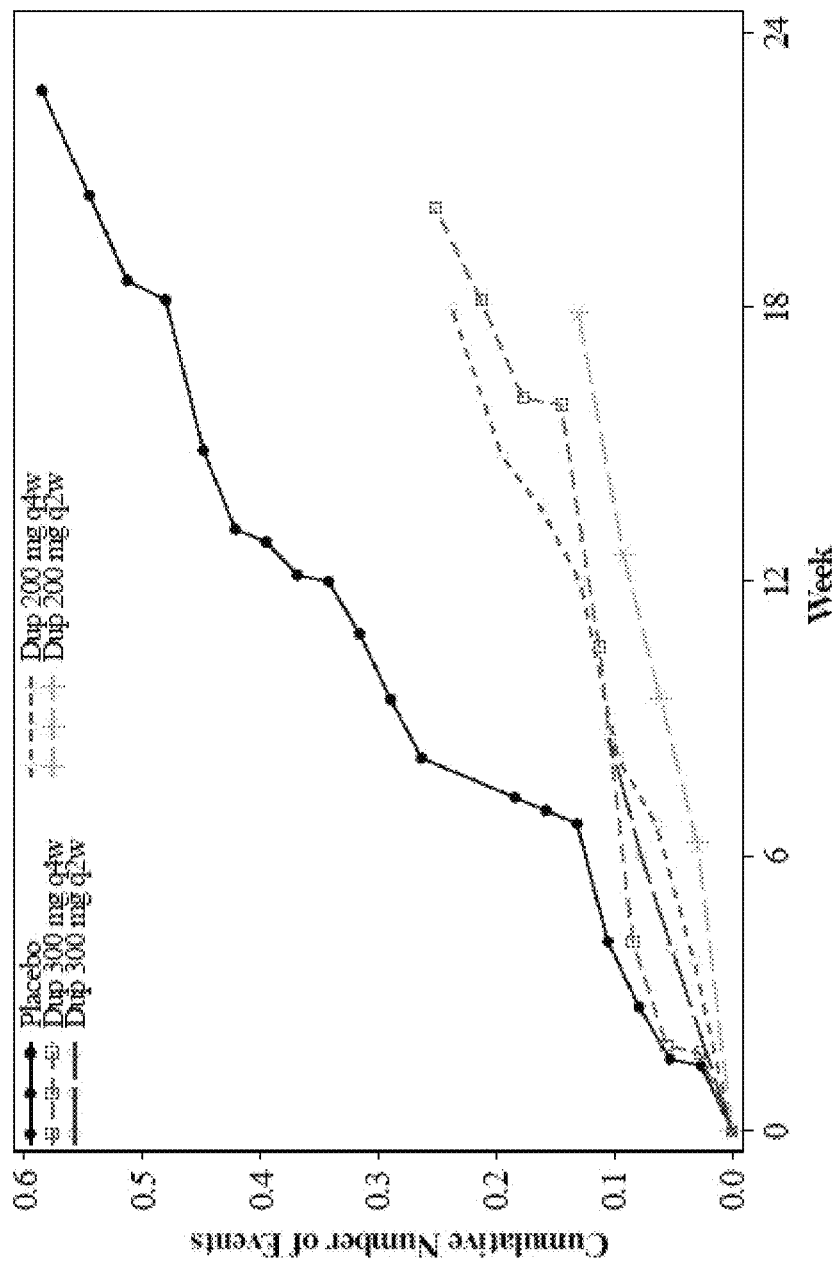
FIG. 21 graphically depicts the cumulative mean functions for the number of severe exacerbation events over the treatment period in an ITT population with medium blood eosinophil (0.2-0.299 GIGA/L).

An analysis of the number of severe exacerbation events in an ITT population having medium blood Eos was performed (Table 18). FIG. 21 graphically depicts these results.

TABLE 18

Analysis of annualized event rate of severe exacerbation during the treatment period in an ITT population with medium blood eosinophil (0.2-0.299 GIGA/L).

| | | Dupilumab | | | |
|---|---|---|---|---|---|
| | Placebo (N = 38) | 200 mg q4w (N = 32) | 300 mg q4w (N = 36) | 200 mg q2w (N = 34) | 300 mg q2w (N = 40) |
| Number of patients with >=1 severe exacerbation event | | | | | |
| Number | 38 | 32 | 36 | 34 | 39 |
| No | 27 (71.1%) | 25 (78.1%) | 31 (86.1%) | 31 (91.2%) | 35 (89.7%) |
| Yes | 11 (28.9%) | 7 (21.9%) | 5 (13.9%) | 3 (8.8%) | 4 (10.3%) |
| Number of severe exacerbation events | | | | | |
| 0 | 27 (71.1%) | 25 (78.1%) | 31 (86.1%) | 31 (91.2%) | 35 (89.7%) |
| 1 | 7 (18.4%) | 7 (21.9%) | 3 (8.3%) | 2 (5.9%) | 4 (10.3%) |
| 2 | 1 (2.6%) | 0 | 1 (2.8%) | 1 (2.9%) | 0 |

TABLE 18-continued

Analysis of annualized event rate of severe exacerbation during the treatment period in an ITT population with medium blood eosinophil (0.2-0.299 GIGA/L).

|  | Placebo (N = 38) | Dupilumab | | | |
|---|---|---|---|---|---|
|  |  | 200 mg q4w (N = 32) | 300 mg q4w (N = 36) | 200 mg q2w (N = 34) | 300 mg q2w (N = 40) |
| 3 | 2 (5.3%) | 0 | 1 (2.8%) | 0 | 0 |
| >=4 | 1 (2.6%) | 0 | 0 | 0 | 0 |
| Total number of severe exacerbation events | 22 | 7 | 8 | 4 | 4 |
| Total patient-years followed | 16.2 | 12.8 | 14.7 | 13.8 | 16.2 |
| Unadjusted annualized severe exacerbation event rate[a] | 1.358 | 0.547 | 0.544 | 0.290 | 0.247 |
| Adjusted annualized severe exacerbation event rate[b] |  |  |  |  |  |
| Estimate (95% CI) | 1.086 (0.570, 2.067) | 0.506 (0.197, 1.303) | 0.339 (0.132, 0.866) | 0.242 (0.077, 0.754) | 0.198 (0.063, 0.621) |
| Relative risk (95% CI) |  | 0.466 (0.151, 1.438) | 0.312 (0.103, 0.941) | 0.222 (0.061, 0.809) | 0.183 (0.050, 0.662) |
| P-value |  | 0.1843 | 0.0386 | 0.0226 | 0.0097 |
| Individual patient annualized severe exacerbation event rate[c] |  |  |  |  |  |
| Number | 38 | 32 | 36 | 34 | 39 |
| Mean (SD) | 1.29 (2.90) | 0.62 (1.22) | 0.51 (1.44) | 0.26 (0.89) | 0.29 (0.88) |
| Median | 0.00 | 0.00 | 0.00 | 0.00 | 0.00 |
| Min:Max | 0.0:15.2 | 0.0:3.7 | 0.0:6.6 | 0.0:4.3 | 0.0:3.4 |

[a]The total number of event that occurred during the treatment period divided by the total number of patient-years followed in the treatment period.
[b]Derived using negative binomial model with the total number of events onset between first dose date and last dose date + 14 days as the response variable, treatment, pooled countries/regions and number of asthma event prior to the study as covariates, and log-transformed standardized treatment duration as an offset variable.
[c]The number of severe exacerbation events for each patient divided by the number of years followed in the treatment period for that patient.

Figure 22:
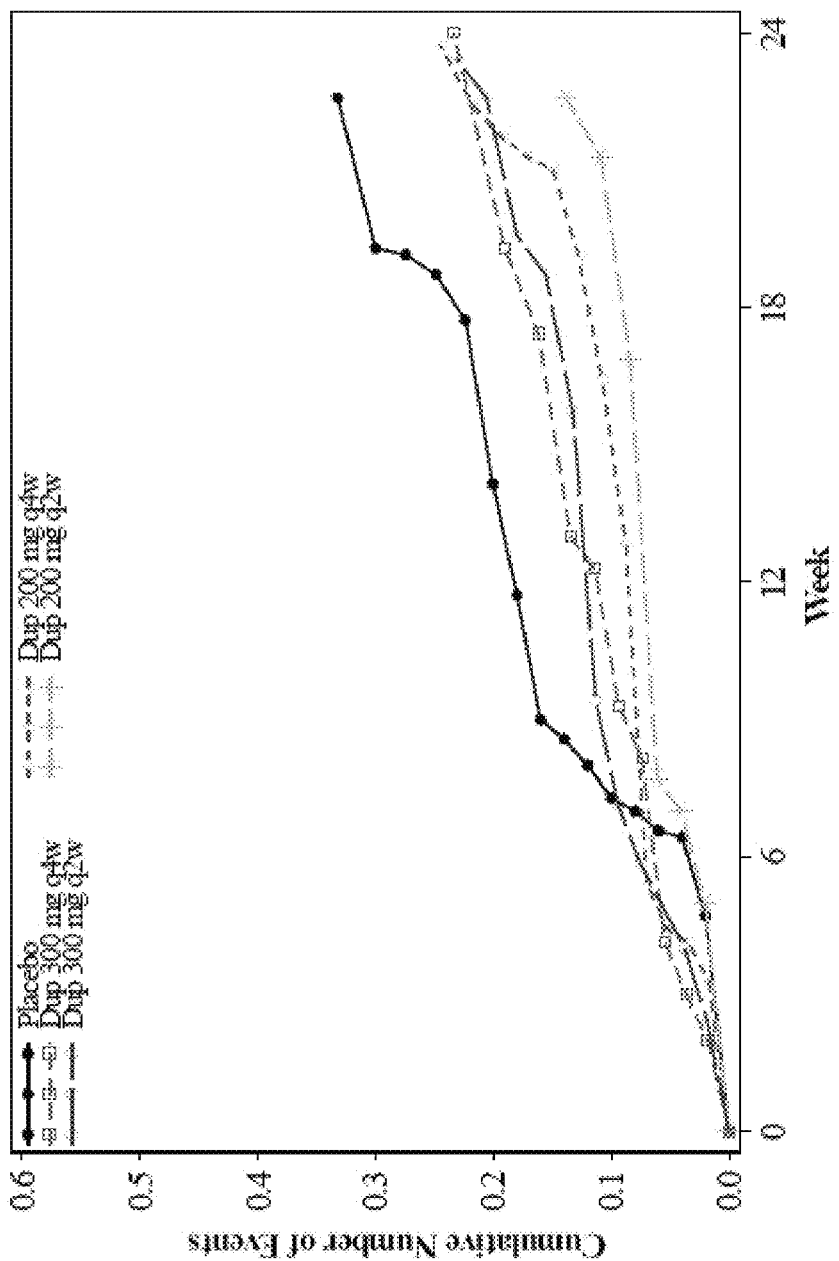
FIG. 22 graphically depicts the cumulative mean functions for the number of severe exacerbation events over the treatment period in an ITT population with low blood eosinophil (<0.2 GIGA/L).
Figure 23:
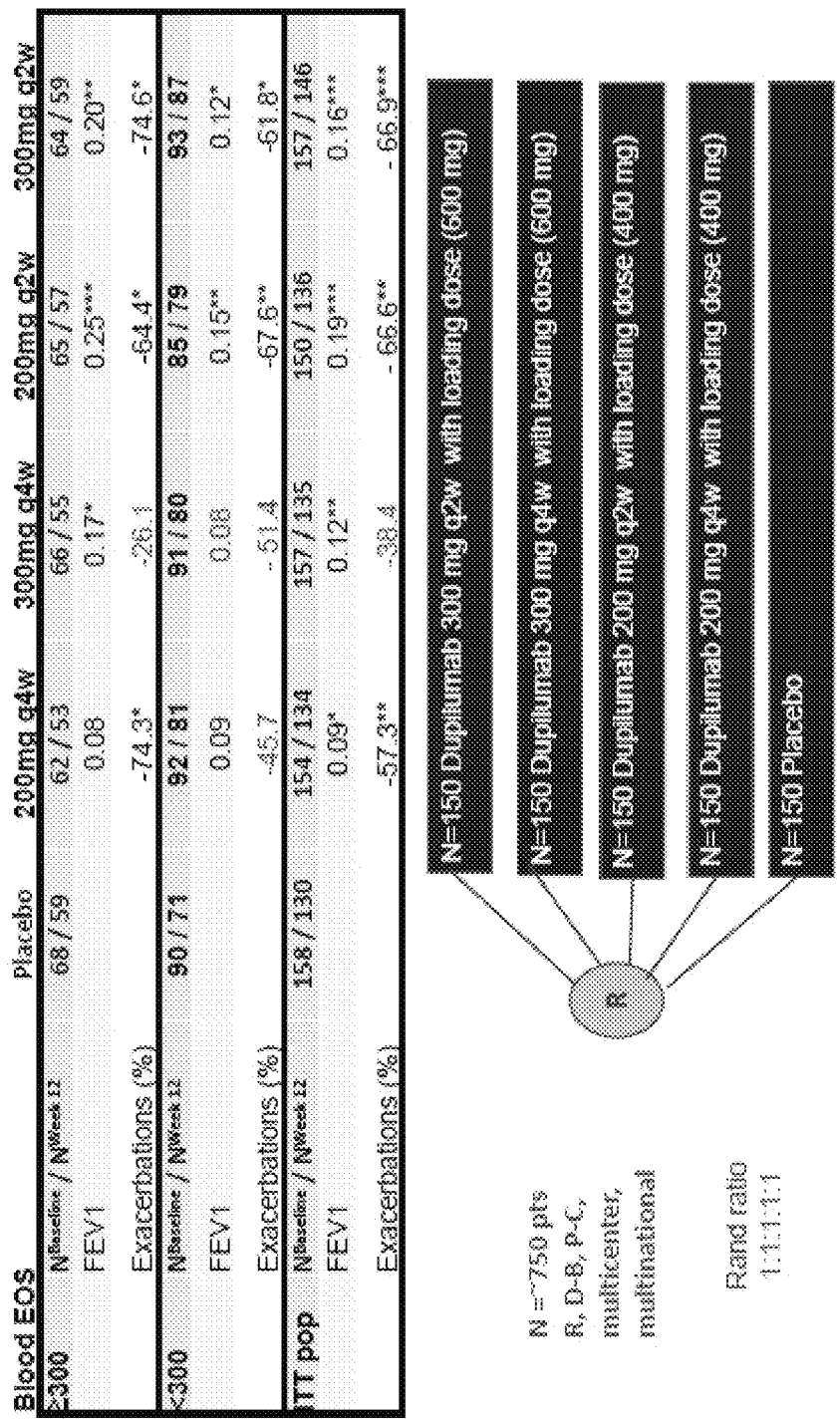
FIG. 23 depicts the asthma interim analysis summary disclosed herein.
Figure 25:
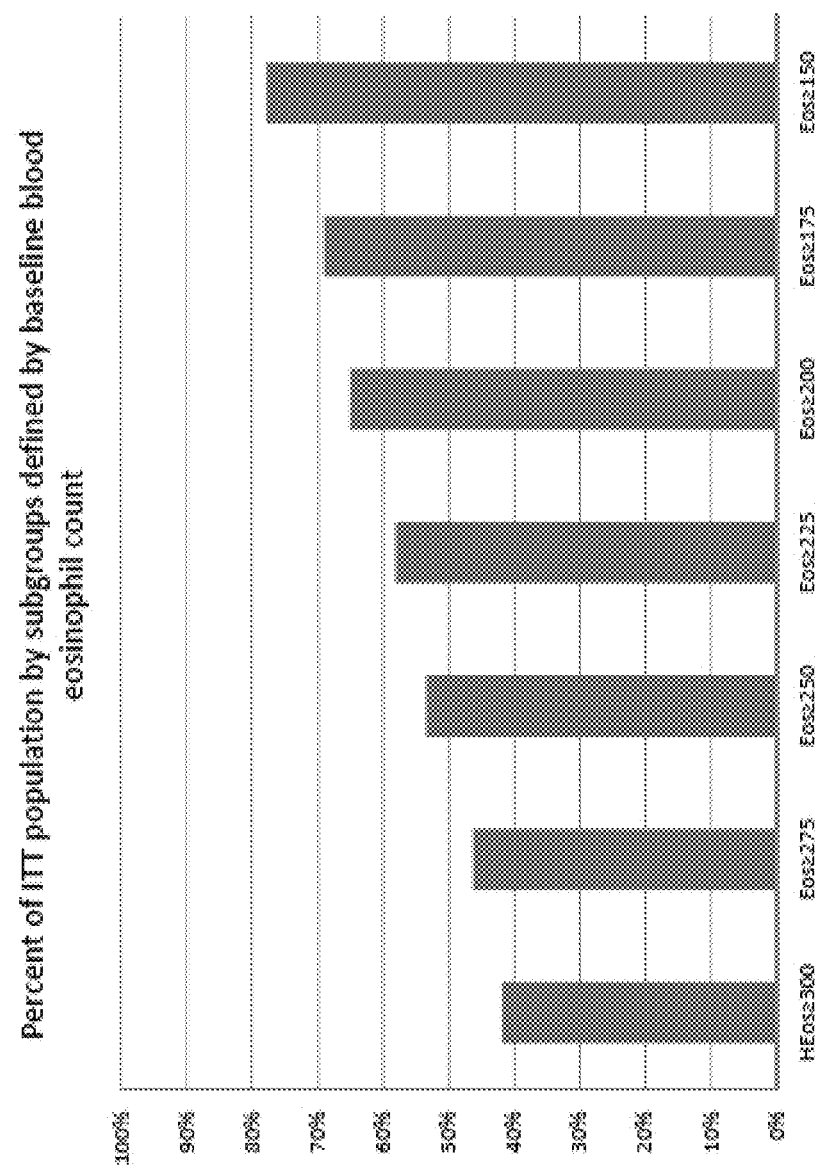
FIG. 25 graphically depicts percent of ITT population by subgroups defined by baseline blood eosinophil count.
Figure 26:
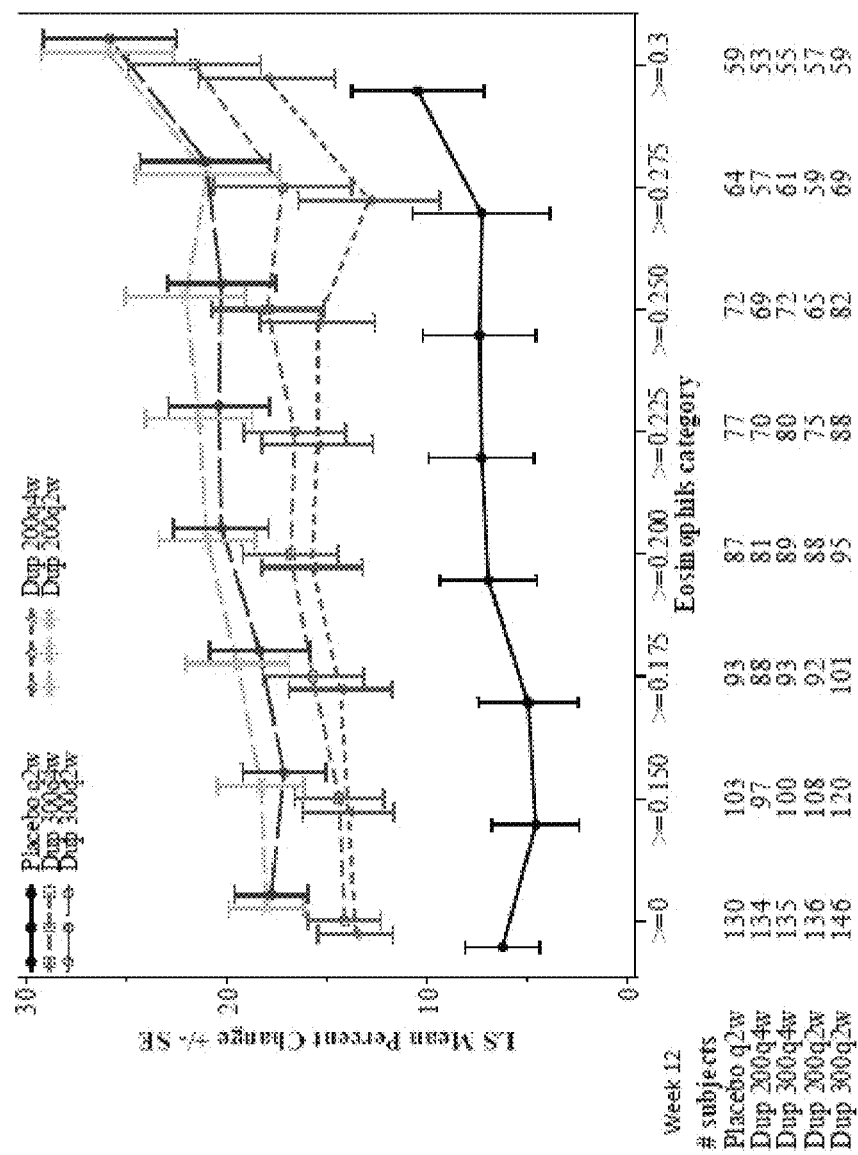
FIG. 26 graphically depicts LS mean percent change from baseline in FEV1(L) at week 12 by eosinophil subgroups defined by baseline blood eosinophil count (GIGA/L).
Figure 27:
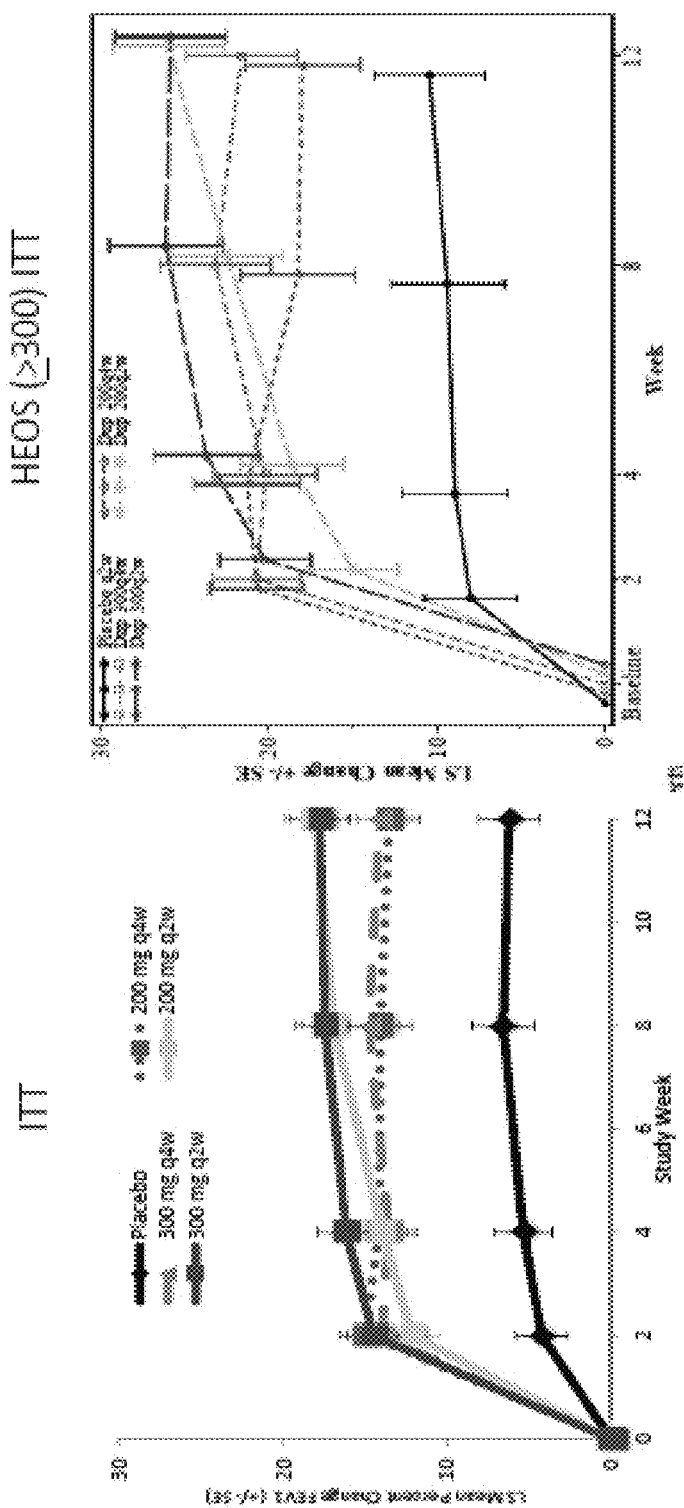
FIG. 27 graphically depicts LS mean percent change in FEV1 showing a comparison between an ITT population and a HEos population.
Figure 28:
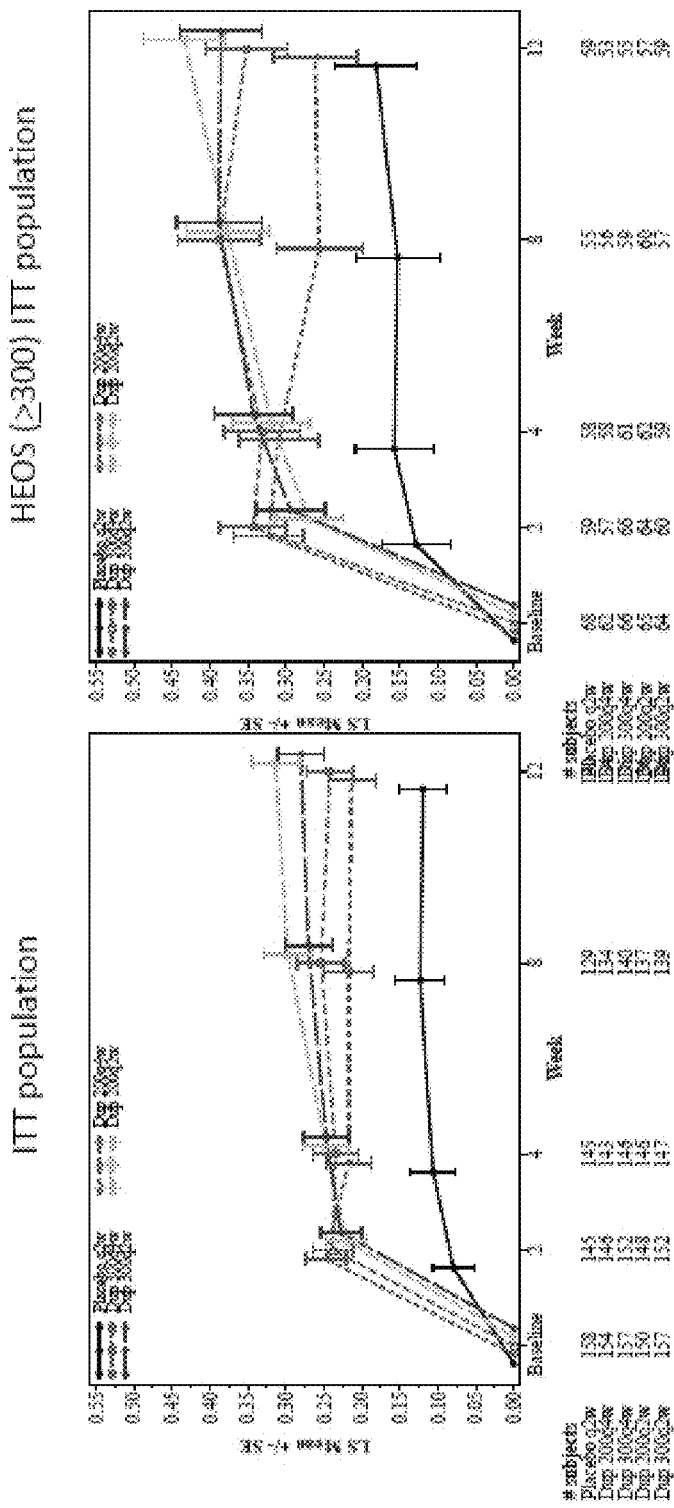
FIG. 28 graphically depicts LS mean change from baseline in FEV1 (L) over time (MMRM) including measurements up to week 12.
Figure 29:
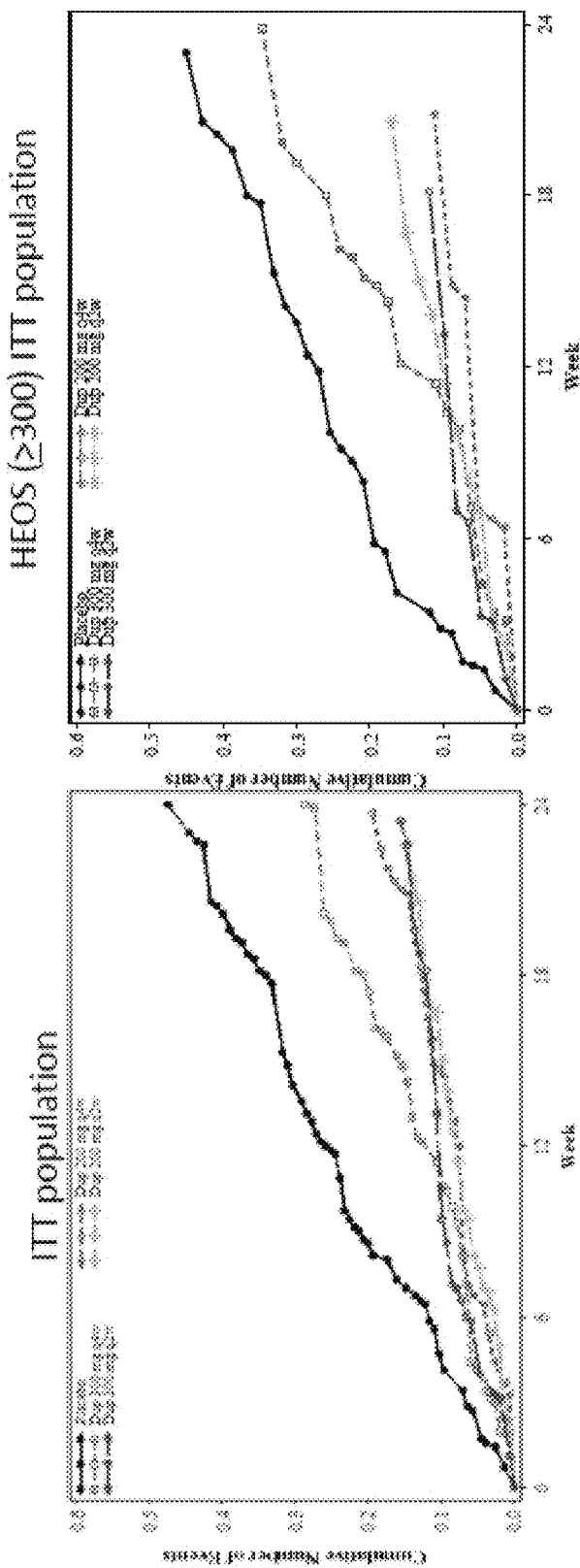
FIG. 29 graphically depicts cumulative mean functions for the number of severe exacerbation events for the available data.
Figure 30:
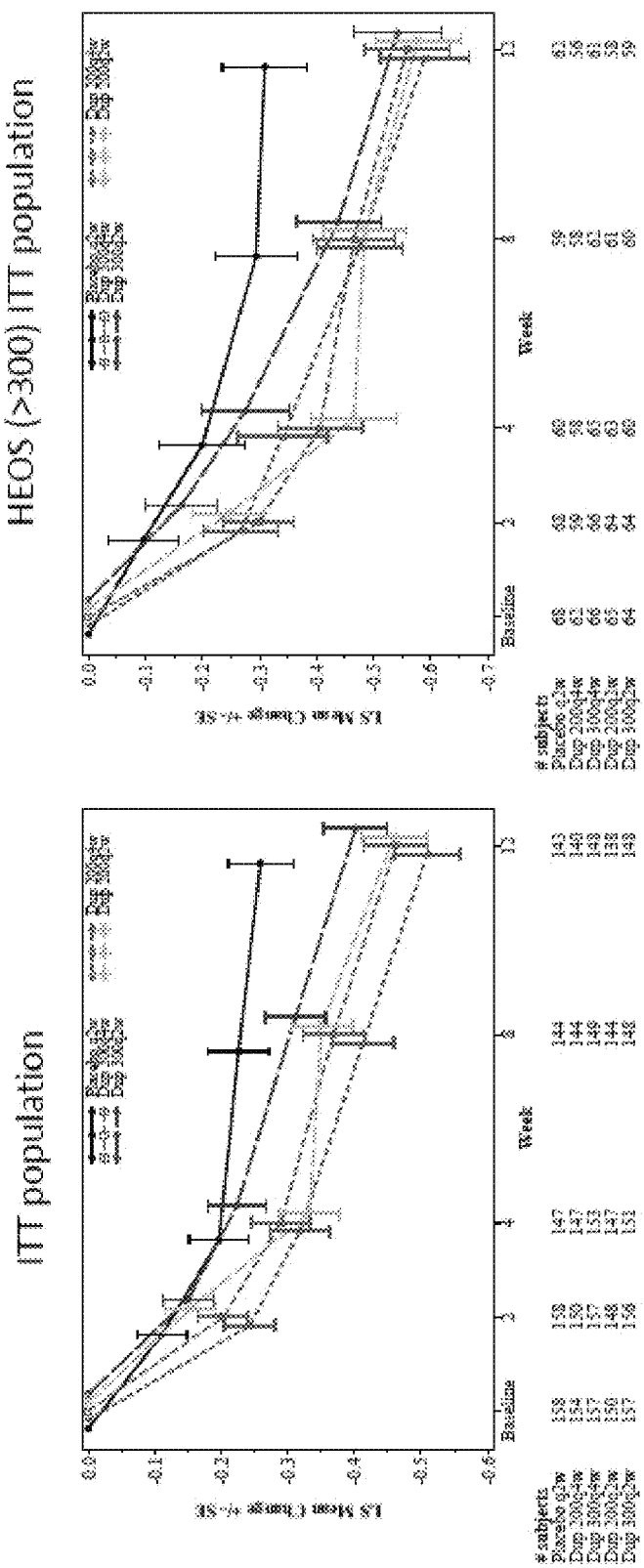
FIG. 30 graphically depicts LS mean change from baseline in AM asthma symptoms score over time (MMRM including measurements up to week 12).
Figure 31:
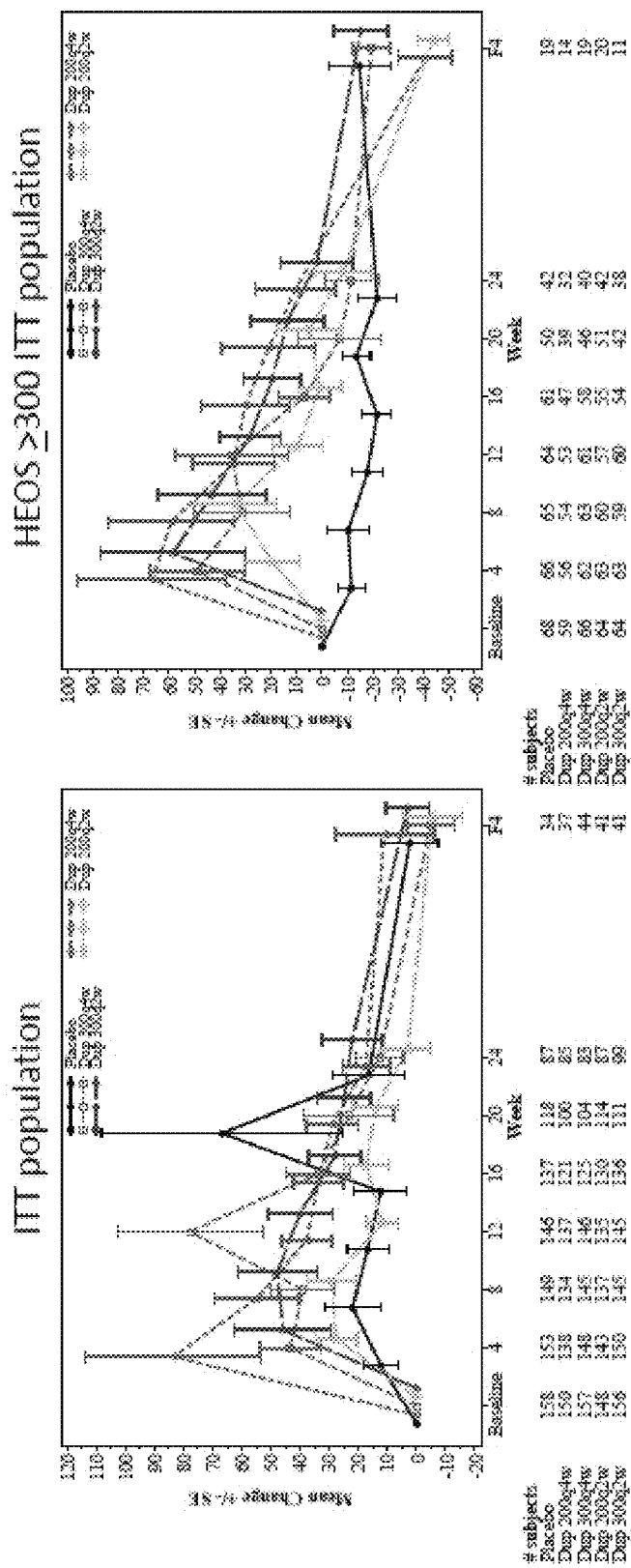
FIG. 31 graphically depicts the mean percent change from baseline in blood eosinophils over time.
Figure 32:
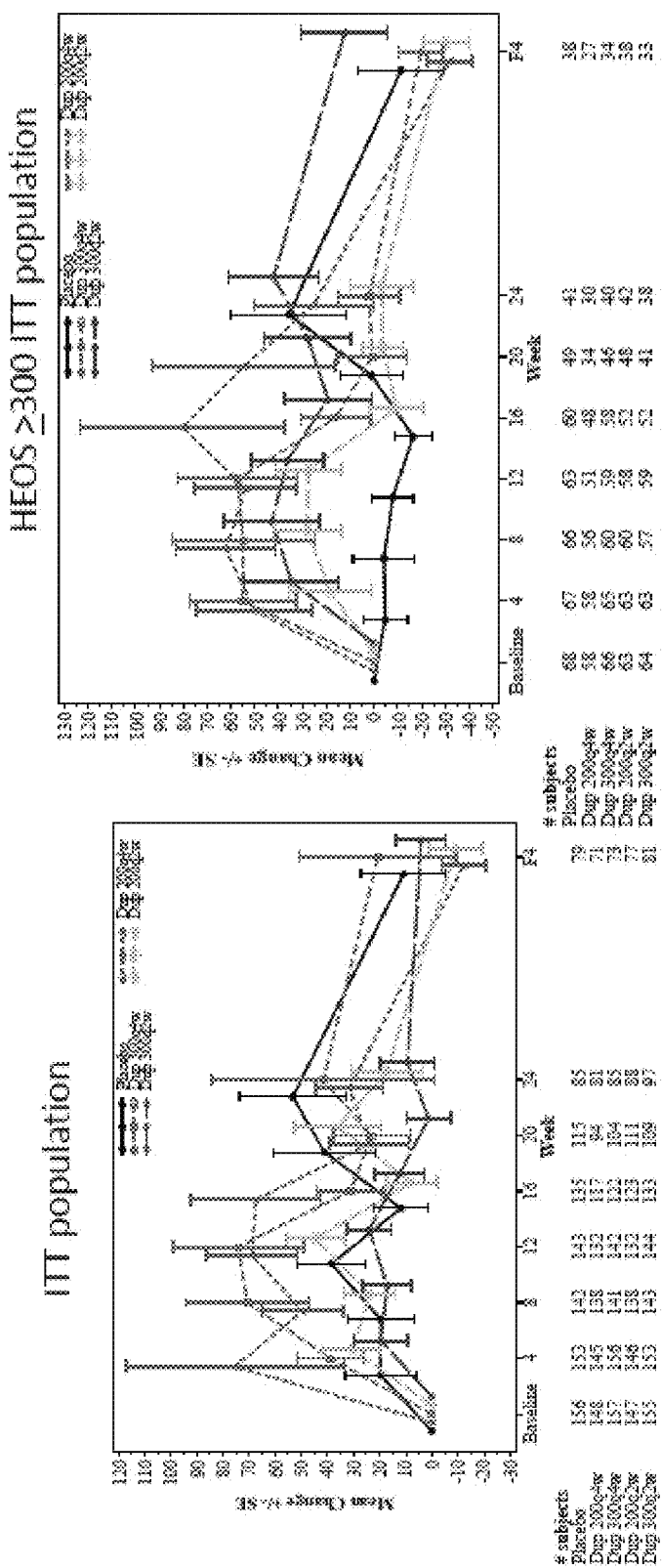
FIG. 32 graphically depicts the mean percent change from baseline in Eosinophil Cationic Protein (ECP).
Figure 33:
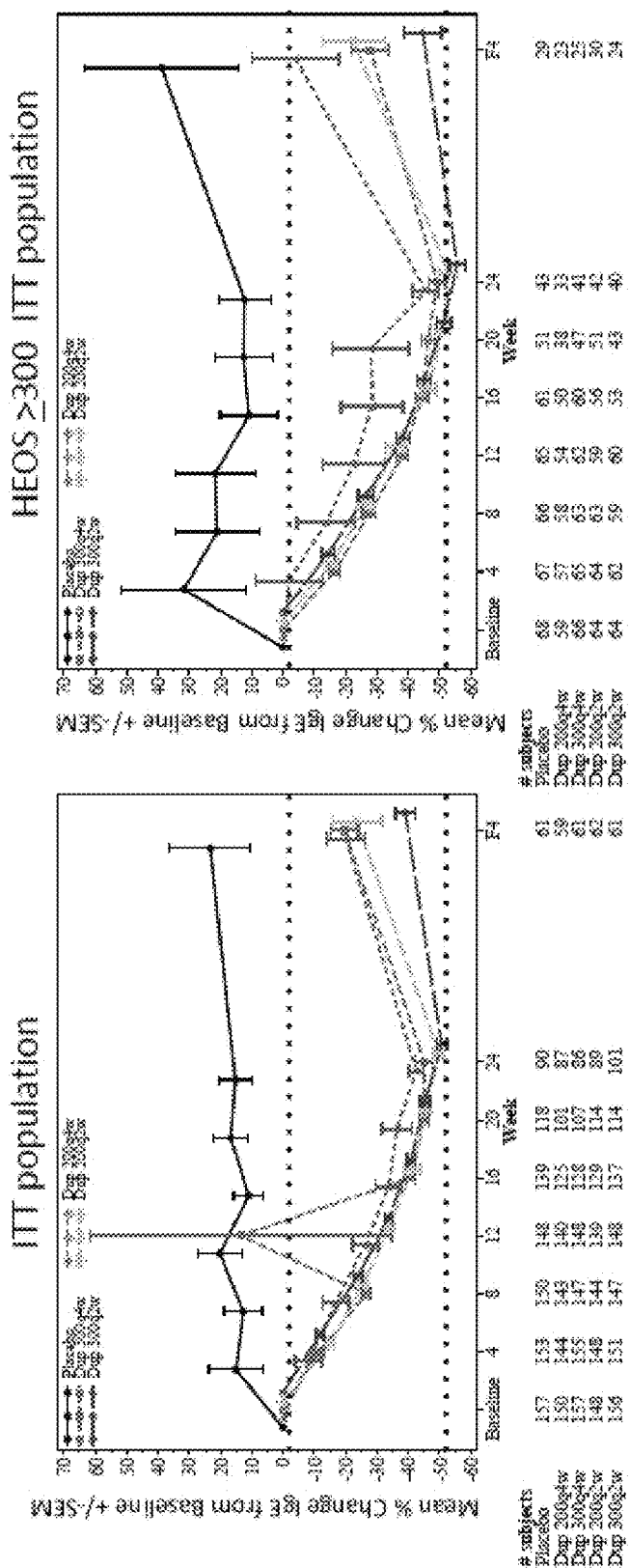
FIG. 33 graphically depicts that the suppression of total IgE was comparable between the ITT and HEos ITT populations.
Figure 34:
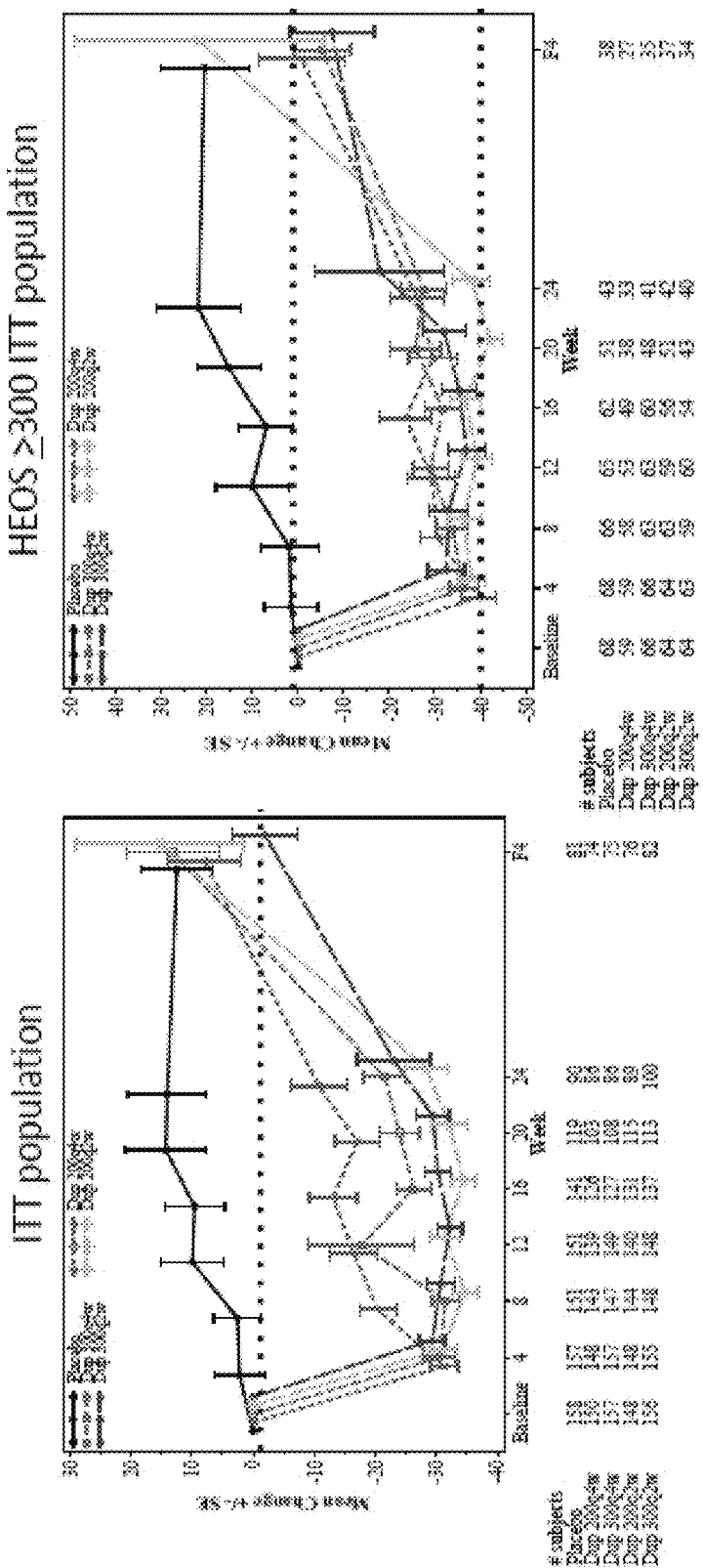
FIG. 34 graphically depicts the mean percent change from baseline TARC.
Figure 35:
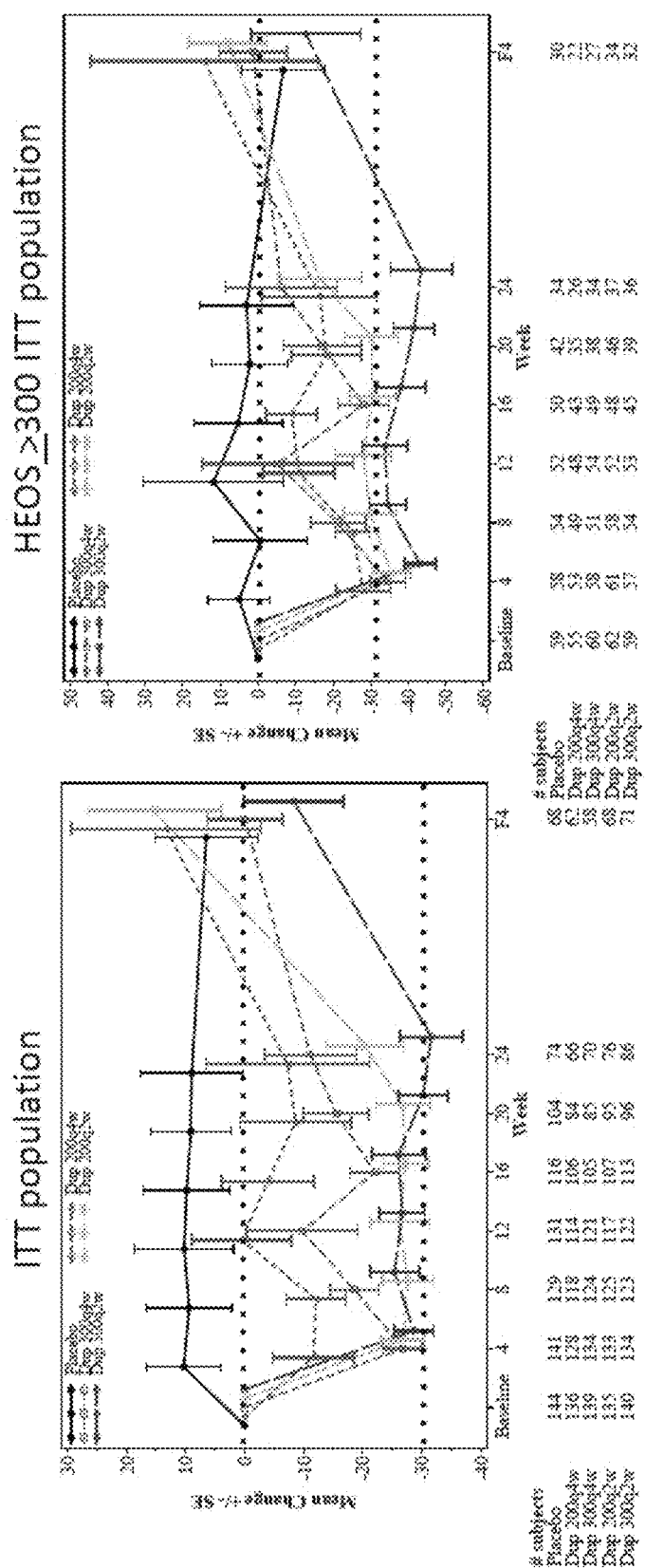
FIG. 35 graphically depicts the mean percent change from baseline FeNO.
Figure 36:
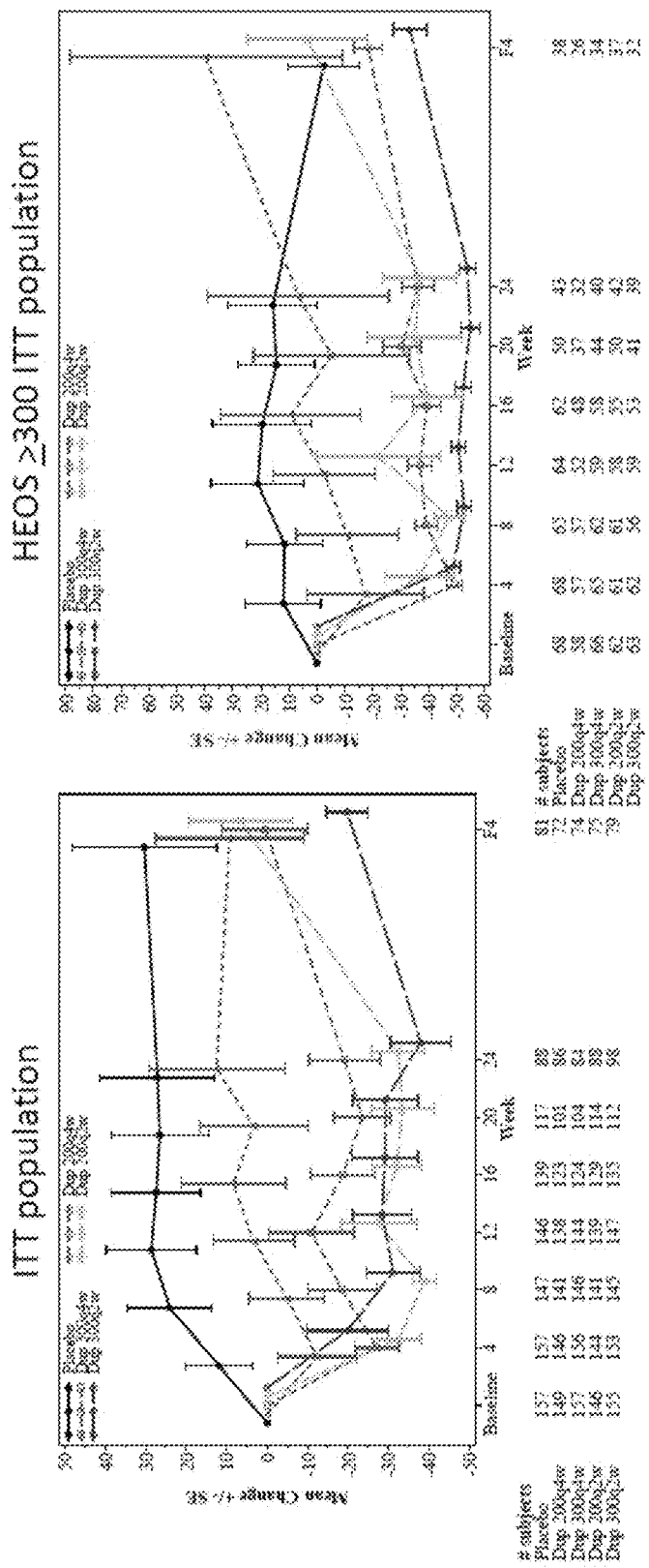
FIG. 36 graphically depicts the mean percent change from baseline Eotaxin-3.
Figure 37:
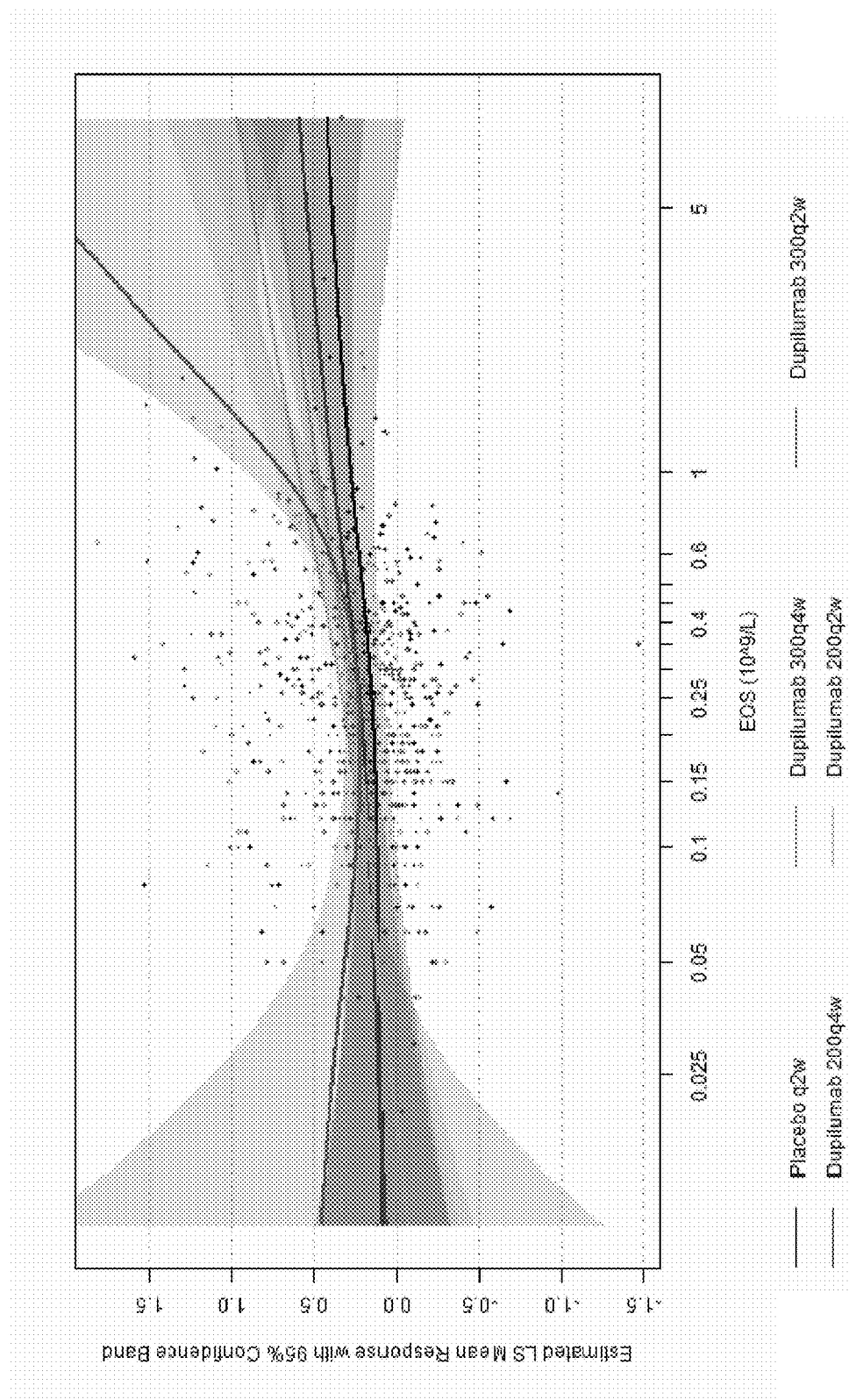
FIG. 37 depicts a scatter plot analysis showing absolute FEV1.
Figure 38:
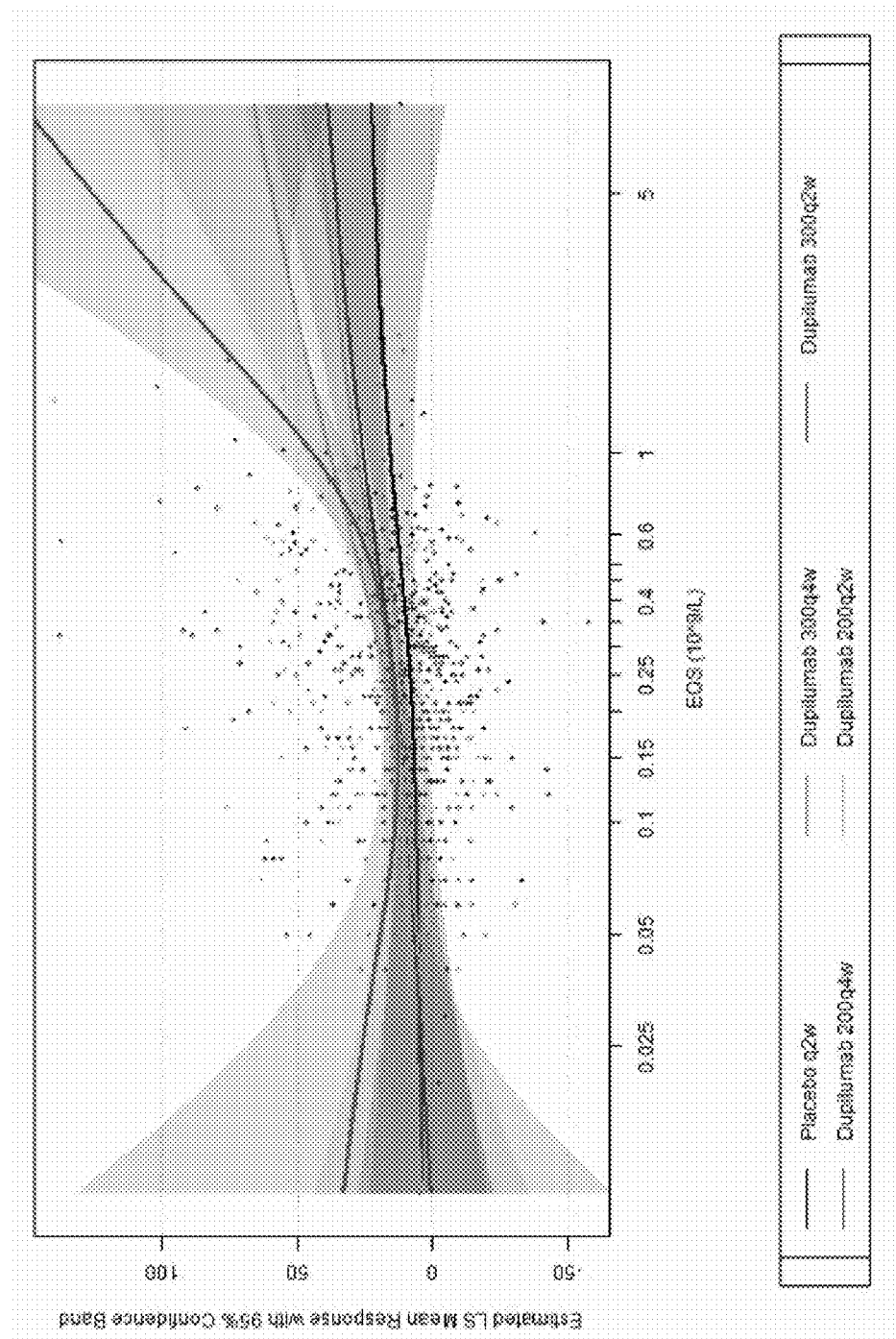
FIG. 38 depicts a scatter plot analysis showing percent change of FEV1.
Figure 39:
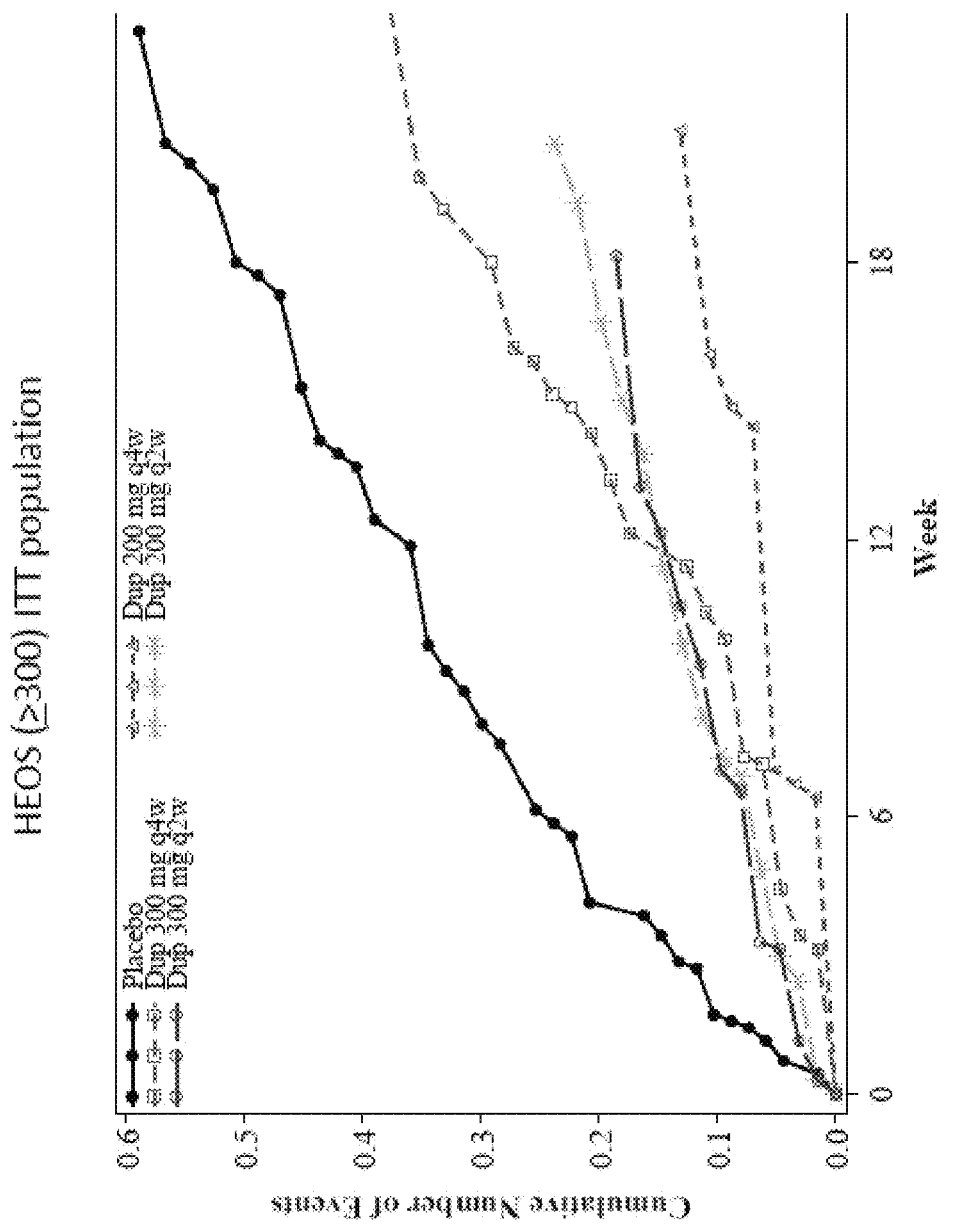
FIG. 39 graphically depicts the cumulative mean functions for the number of LOAC events for the available data.
Figure 40:
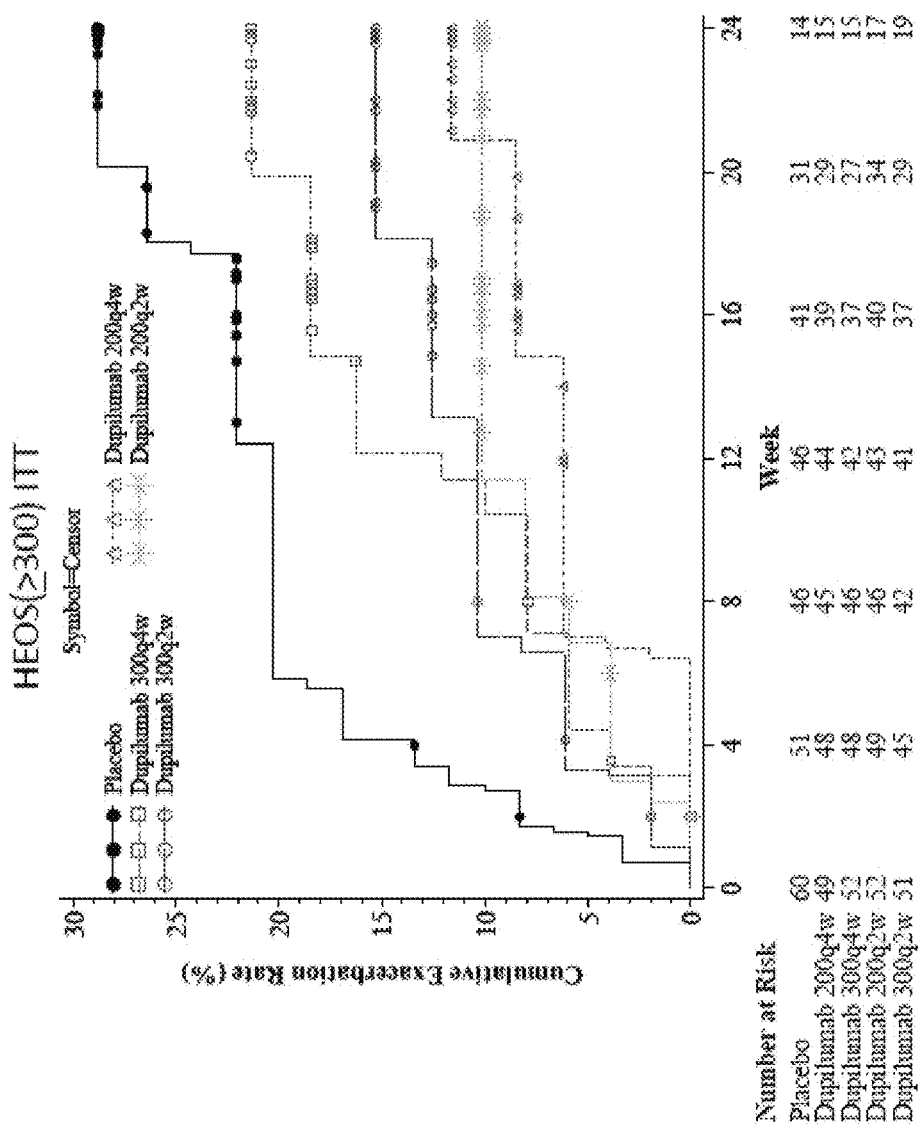
FIG. 40 depicts a Kaplan-Meier Plot of time to first severe exacerbation event over the treatment period.
Figure 41:
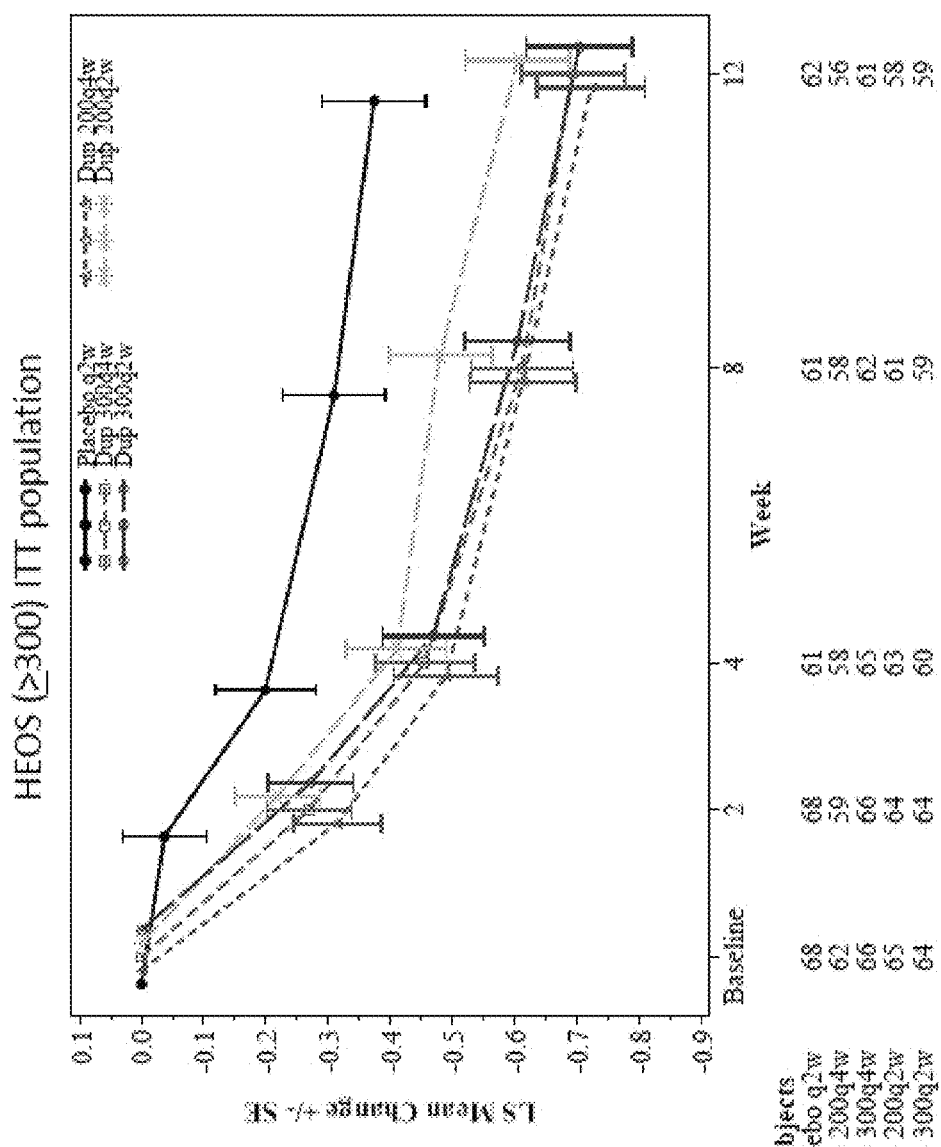
FIG. 41 graphically depicts LS mean change from baseline in PM asthma symptoms over score time (MMRM) including measurements up to week 12.
Figure 42:
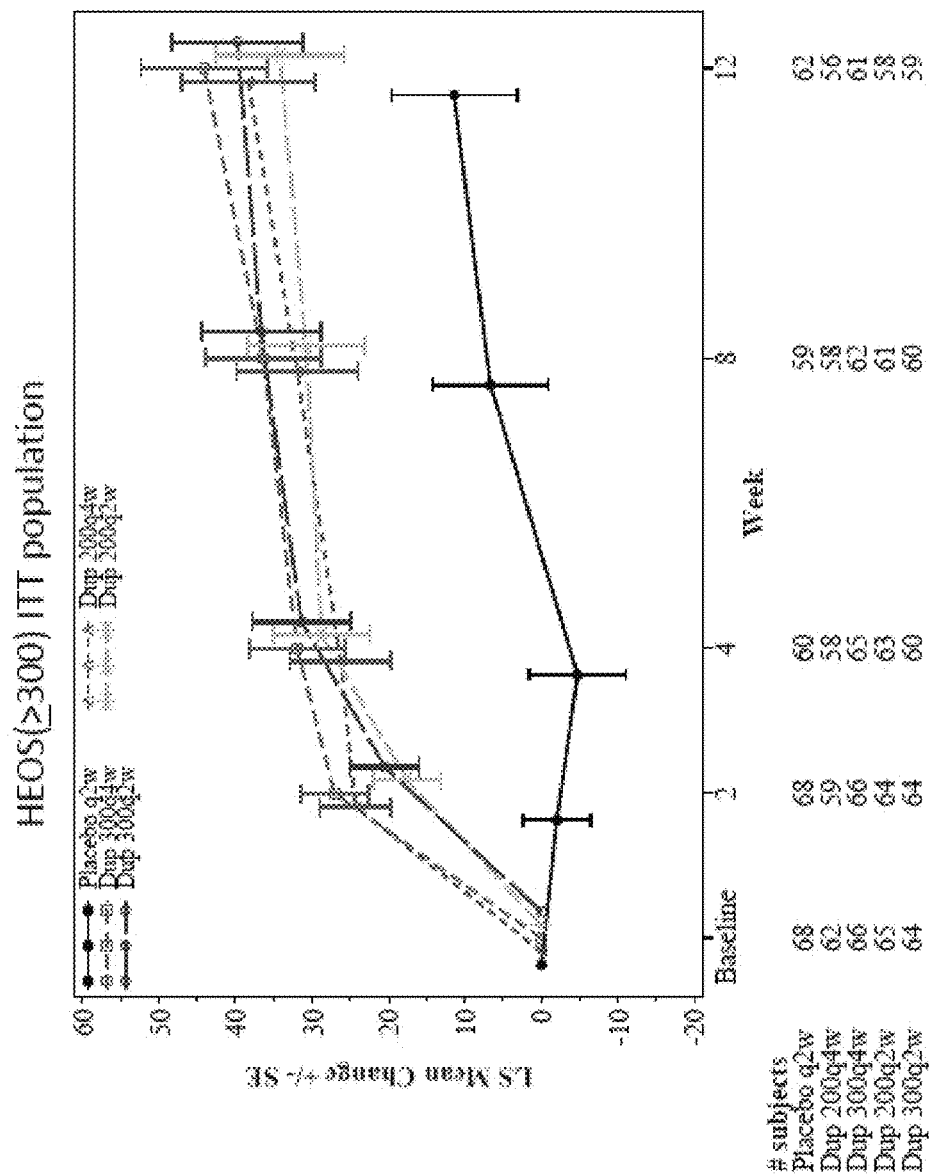
FIG. 42 graphically depicts LS mean change from baseline in AM PEF (L/minute) over time (MMRM including measurements up to week 12).
Figure 43:
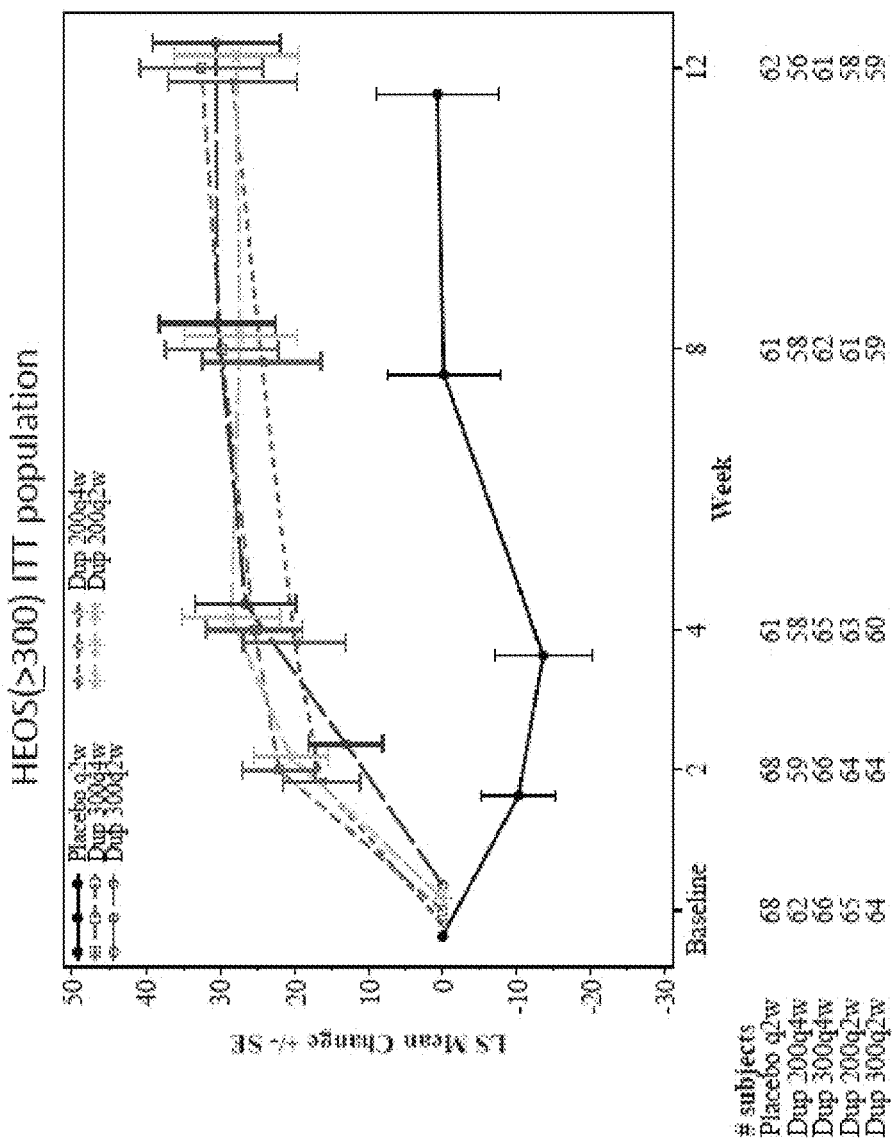
FIG. 43 graphically depicts LS mean change from baseline in PM PEF (L/minute) over time (MMRM including measurements up to week 12).
Figure 44:
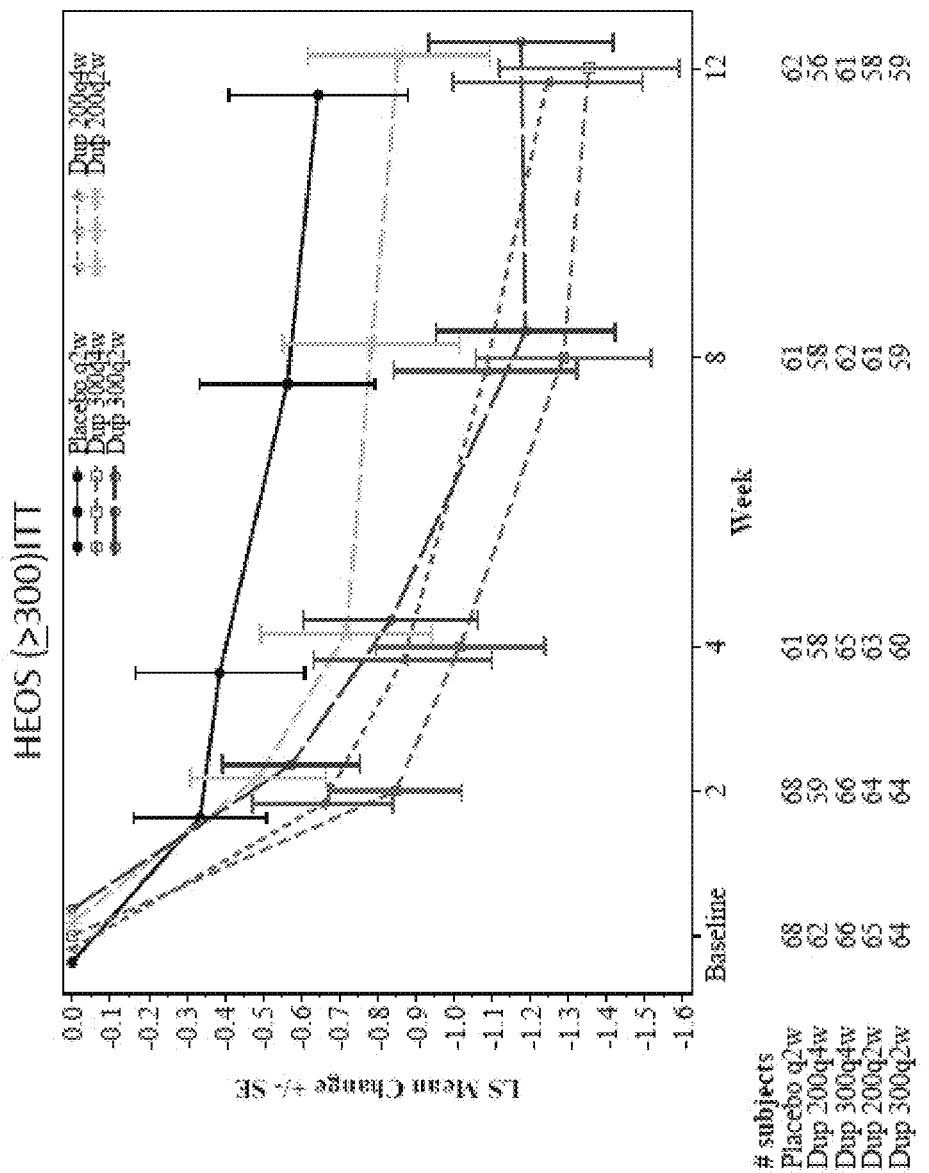
FIG. 44 graphically depicts LS mean change from baseline in the number of inhalations per day of salbutamol/albuterol or levosalbutamol/levalbuterol for symptom relief over time (MMRM including measurements up to week 12).
Figure 45:
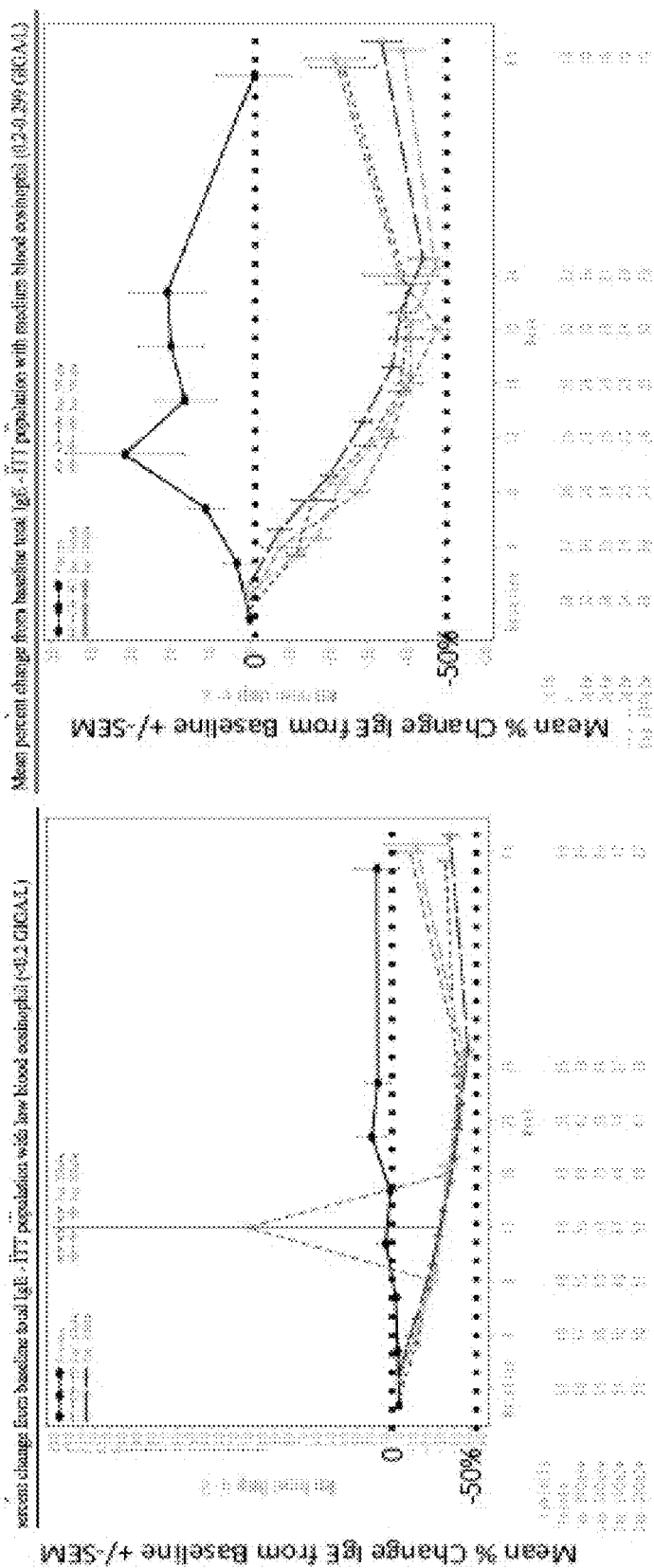
FIG. 45 illustrates that suppression of total IgE was comparable between the low Eos (<0.2 GI/L) and medium Eos (0.200-0.299 GI/L) in ITT populations.
Figure 46:
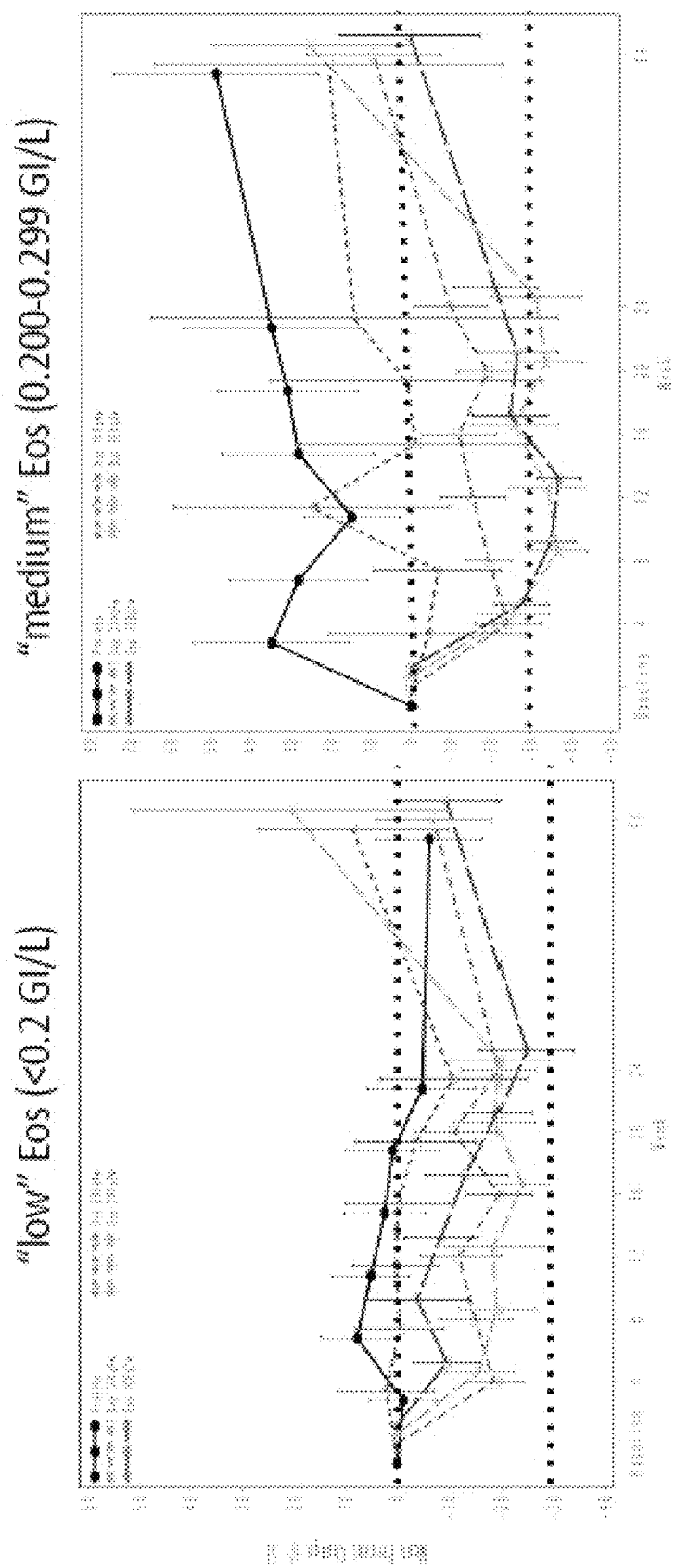
FIG. 46 illustrates mean percent change from baseline FeNO.
Figure 47:
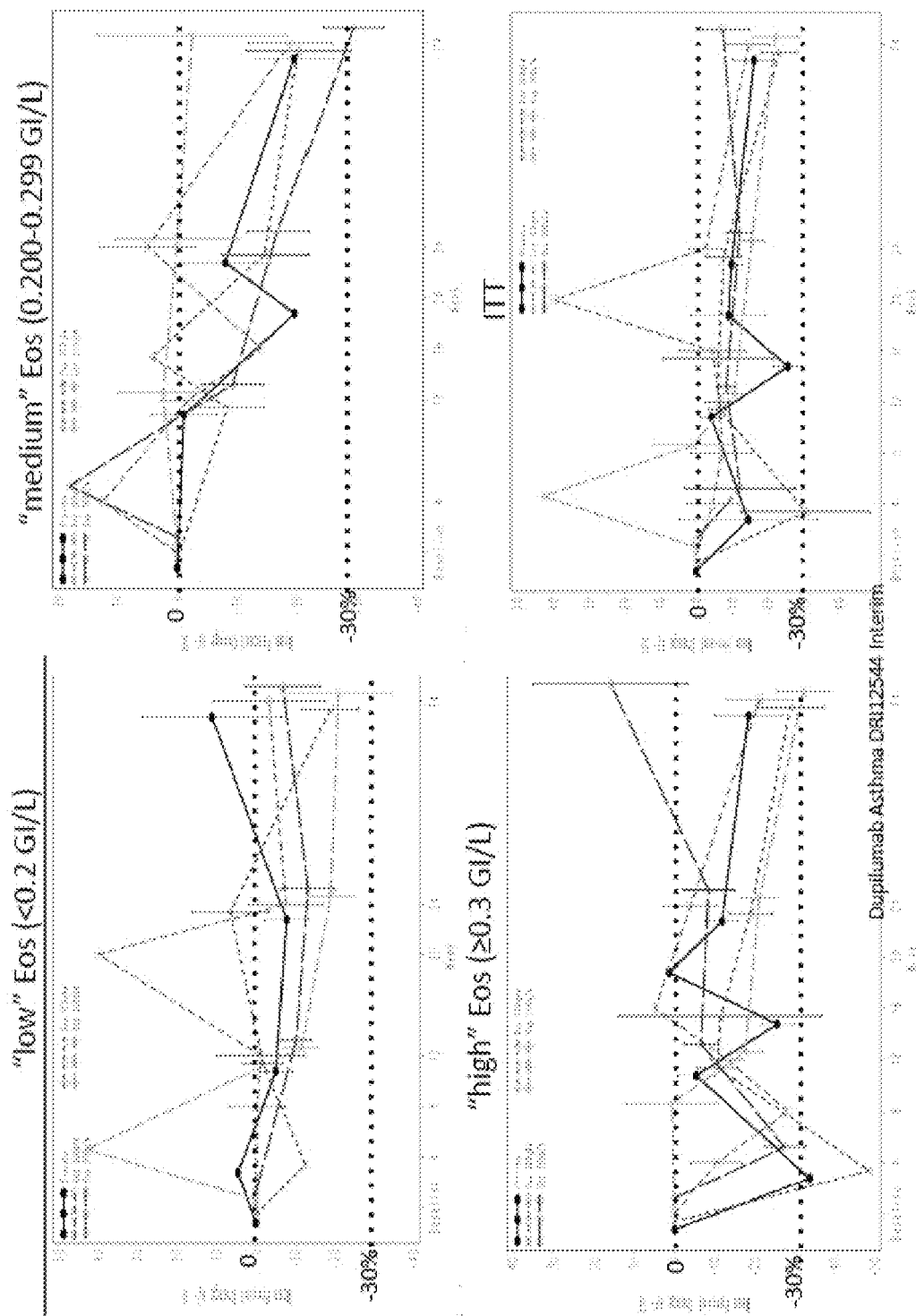
FIG. 47 illustrates periostin levels (pg/mL) in low Eos, medium Eos, high Eos and ITT populations.

An analysis of the number of severe exacerbation events in an ITT population having low blood Eos was performed (Table 19). FIG. 22 graphically depicts these results.

The most common adverse event was injection site reaction, which was more frequent in the four dupilumab dose groups (13 to 25 percent) compared to placebo (12 percent).

TABLE 19

Analysis of annualized event rate of severe exacerbation during the treatment period in an ITT population with low blood eosinophil (<0.2 GIGA/L).

|  | Placebo (N = 52) | Dupilumab | | | |
|---|---|---|---|---|---|
|  |  | 200 mg q4w (N = 60) | 300 mg q4w (N = 55) | 200 mg q2w (N = 51) | 300 mg q2w (N = 53) |
| Number of patients with >=1 severe exacerbation event |  |  |  |  |  |
| Number | 52 | 59 | 55 | 50 | 53 |
| No | 42 (80.8%) | 51 (86.4%) | 46 (83.6%) | 45 (90.0%) | 47 (88.7%) |
| Yes | 10 (19.2%) | 8 (13.6%) | 9 (16.4%) | 5 (10.0) | 6 (11.3%) |
| Number of severe exacerbation events |  |  |  |  |  |
| 0 | 42 (80.8%) | 51 (86.4%) | 46 (83.6%) | 45 (90.0%) | 47 (88.7%) |
| 1 | 7 (13.5%) | 5 (8.5%) | 8 (14.5%) | 4 (8.0%) | 2 (3.8%) |
| 2 | 2 (3.8%) | 2 (3.4%) | 1 (1.8%) | 1 (2.0%) | 3 (5.7%) |
| 3 | 0 | 1 (1.7%) | 0 | 0 | 1 (1.9%) |
| >=4 | 1 (1.9%) | 0 | 0 | 0 | 0 |
| Total number of severe exacerbation events | 15 | 12 | 10 | 6 | 11 |
| Total patient-years followed | 21.1 | 24.6 | 21.2 | 21.2 | 22.6 |
| Unadjusted annualized severe exacerbation event rate[a] | 0.711 | 0.488 | 0.472 | 0.283 | 0.487 |
| Individual patient annualized severe exacerbation events rate[c] |  |  |  |  |  |
| Number | 52 | 59 | 55 | 50 | 53 |
| Mean (SD) | 0.71 (1.69) | 0.49 (1.35) | 0.43 (1.02) | 0.28 (0.89) | 0.45 (1.38) |
| Median | 0.00 | 0.00 | 0.00 | 0.00 | 0.00 |
| Min:Max | 0.0:8.6 | 0.0:6.5 | 0.0:4.3 | 0.0:4.3 | 0.0:6.6 |

[a]The total number of event that occurred during the treatment period divided by the total number of patient-years followed in the treatment period.
[b]Derived using negative binomial model with the total number of events onset between first dose date and last dose date + 14 days as the response variable, treatment, pooled countries/regions and number of asthma event prior to the study as covariates, and log-transformed standardized treatment duration as an offset variable.
[c]The number of severe exacerbation events for each patient divided by the number of years followed in the treatment period for that patient.

Other common adverse events in the study included upper respiratory tract infection (10 to 13 percent dupilumab; 13 percent placebo), headache (5 to 10 percent dupilumab; 8 percent placebo), nasopharyngitis (3 to 10 percent dupilumab; 6 percent placebo) and bronchitis (5 to 8 percent dupilumab; 8 percent placebo). The incidence of infections was balanced across treatment groups (42 to 45 percent dupilumab; 46 percent placebo), as was the incidence of serious adverse events (3 to 7 percent dupilumab; 5 percent placebo).

P. Patient Reported Outcome Interim Analysis

ACQ

Patient Reported Outcome (PRO) data was obtained. FIGS. 57 and 58 depict results of an Asthma Control Questionnaire (ACQ). The effect was not stabilized at 12 weeks. A higher treatment effect was observed for a High Eosinophil (HEos) population as compared with an ITT population (−0.46 (−0.79, −0.12)) (FIG. 57). The first two domains (awoken, morning symptoms) were significantly significant versus placebo (PBO).

AQLQ

Asthma Quality of Life Questionnaire (AQLQ) data was obtained (FIGS. 59 and 60). The results indicated that Dupilumab (DUPI) was superior to placebo (PBO) in all domains.

EQ5D—5L

European Quality of Life 5 Dimensions—5L (EQSD—5L) data was obtained (FIGS. 61 and 62). A significant effect was observed in a HEos population (0.10 (0.04, 0.16)).

HADS

Hospital Anxiety and Depression Score (HADS) data was obtained (FIGS. 63-66). A statistically significant effect in a HEos population was observed both for anxiety (−1.54 (−2.58, −0.50)) and depression (−1.88 (−2.88, −0.88)). Anxiety was more impacted at baseline than depression. A higher treatment effect was observed for depression relative to anxiety. For HADS total, a significant improvement was observed in a HEos population (−3.47 (−5.29, −1.65))

At baseline, the 300mgq2w arm was more deteriorated compared to the other treatment arms. Patients were more deteriorated in depression environment than in anxiety domain. At week 12, 200mgq4w, 200mgq2w and 300mgq2w arms demonstrated a high significant compared to placebo and were improved between the different treatment arms. The same trends were observed in each sub-score. HADS anxiety demonstrated the same trend for change, but arm 1 demonstrated the highest risk of response compared to placebo (based on analysis on responders profile). HADS depression demonstrated the same trend for change, but arm 1 demonstrated the highest risk of response compared to placebo (based on analysis on responders profile). Responders: OR demonstrated a significant risk of treatment (arm 1, 3, 4) versus placebo on the response. This risk was improved in arm 3 (OR 200mgq2w=4.61) Responders (%): placebo (39.7%) versus 200mgq2w (66.2%) (FIG. 65.)

At baseline, 300mgq2w arm was more deteriorated compared to the other treatment arms (except for depression). Patients were more deteriorated in depression environment than in anxiety domain. At week 12, only 200mgq2w demonstrated a significant effect compared to placebo, which effect was improved between the different treatment arms. Different trends were observed in each sub-score: HADS anxiety—no significant impact was observed versus placebo; HADS depression—arm 3 and 4 were significant. (FIG. 66.)

SNOT-22

Sino Nasal Outcome Test-22 (SNOT-22) data was obtained (FIGS. 67 and 68). The results indicated that Dupilumab (DUPI) was superior to placebo (PBO) (FIG. 67), that nasal score droves treatment effect, and that DUPI was superior to PBO in nasal score, sleep score and general score.

NRS

Pruritus Numerical Rating Scale (NRS) data was obtained (FIG. 69).

Example 3

Summary of Results

Overall, high efficacy was demonstrated with dupilumab, resulting in a reduction in exacerbations, improvement in lung function, and improvement in asthma control. Dupilumab was very well tolerated (Table 20). Dupilumab was superior to placebo in nasal score, sleep score and general score. The safety profile was consistent with observations in previous studies. A dose response was observed, with bi-weekly regimens being superior. Although there was a dose-dependent imbalance between dupilumab and placebo for injection site reactions, there was no imbalance in nasopharyngitis, as has been previously observed with other therapies. Efficacy was observed across the entire population, indicating that a biomarker may not be needed to differentiate among one or more subpopulations that will respond to the therapy. Importantly, outstanding efficacy was demonstrated in ITT populations relative to the efficacy of other therapies known in the art at the time of filing. Comparable or superior efficacy was observed in biomarker-enriched populations relative to the efficacy of other therapies for biomarker-enriched populations known in the art at the time of filing.

TABLE 20

Summary of Treatment Emergent Adverse Events

| n(%) | Placebo (N = 158) | Dupilumab | | | | |
|---|---|---|---|---|---|---|
| | | 200 mg q4w (N = 150) | 300 mg q4w (N = 157) | 200 mg q2w (N = 148) | 300 mg q2w (N = 156) | Combined (N = 611) |
| Patients with any TEAE | 105 (66.5%) | 106 (70.7%) | 116 (73.9%) | 106 (71.6%) | 109 (69.9%) | 437 (71.5%) |
| Patients with any treatment emergent SAE | 8 (5.1%) | 5 (3.3%) | 11 (7.0%) | 7 (4.7%) | 10 (6.4%) | 33 (5.4%) |
| Patients with any TEAE leading to death | 0 | 0 | 1 (0.6%) | 0 | 0 | 1 (0.2%) |

TABLE 20-continued

Summary of Treatment Emergent Adverse Events

| n(%) | Placebo (N = 158) | Dupilumab 200 mg q4w (N = 150) | 300 mg q4w (N = 157) | 200 mg q2w (N = 148) | 300 mg q2w (N = 156) | Combined (N = 611) |
|---|---|---|---|---|---|---|
| Patients with any TEAE leading to permanent treatment discontinuation | 6 (3.8%) | 6 (4.0%) | 10 (6.4%) | 5 (3.4%) | 3 (1.9%) | 24 (3.9%) |

Treated patients (N = 769), interim analysis. TEAE: Treatment-emergent adverse event; SAE: Serious Adverse Event; n(%) = number and percentage of patients with TEAE.

The three highest doses of dupilumab in combination with standard-of-care therapy met the primary endpoint of a statistically significant improvement from baseline in FEV1 at week 12 in patients with high blood eosinophils (greater than or equal to 300 cells/µL), as compared to placebo in combination with standard-of-care therapy. In addition, the two highest doses of dupilumab showed a statistically significant improvement in mean percent change in FEV1, as well as a reduction in severe exacerbations, in both the high eosinophils and overall study population.

In the High Eosinophils Patient Group:
Mean improvements from baseline in FEV1 (and mean percent change in FEV1) at 12 weeks, the primary (and a secondary) endpoint of the study were: 390 ml (26 percent) dupilumab 300 mg Q2W; 430 ml (26 percent) dupilumab 200 mg Q2W; 180 ml (10 percent) placebo. (p less than 0.01.)

In the Overall Population:
Mean improvements from baseline in FEV1 at 12 weeks (and mean percent change in FEV1) were: 280 ml (18 percent) dupilumab 300 mg Q2W; 310 ml (18 percent) dupilumab 200 mg Q2W; 120 ml (6 percent) placebo. (p less than 0.001.)

In Both the High Eosinophils Patient Group and Overall Patient Group:
Dupilumab showed a reduction in adjusted annualized rate of severe exacerbations compared to placebo (64 to 75 percent reduction, p less than 0.05 for high eosinophils group and p less than 0.01 for the overall population).

These results were based on a pre-specified interim analysis, which occurred when all patients had reached week 12 of the 24-week treatment period. The average treatment duration at the time of the analysis was 21.5 weeks.

Label

Dupilumab is indicated in adults and adolescents (12 years of age and above) for the treatment of persistent asthma as add-on treatment to medium-to-high dose inhaled corticosteroid (ICS) and a second controller medication.

What is claimed is:

1. A method for treating persistent asthma in a subject in need thereof comprising administering to the subject a combination therapy comprising:
   i) one or more maintenance doses of an inhaled corticosteroid (ICS),
   ii) one or more maintenance doses of a long-acting beta$_2$-adrenergic agonist (LABA),
   iii) a loading dose of about 600 mg of an antibody or an antigen-binding fragment thereof that specifically binds to interleukin-4 receptor (IL-4R) comprising three Heavy chain Complementarity Determining Region (HCDR) sequences comprising SEQ ID NOs: 3, 4, and 5, and three Light chain Complementarity Determining Region (LCDR) sequences comprising SEQ ID NOs: 6, 7, and 8, and
   iv) one or more maintenance doses of about 300 mg of the antibody or the antigen-binding fragment thereof,
   wherein the ICS and LABA are administered for the duration of administration of the antibody or the antigen-binding fragment thereof.

2. The method of claim 1, wherein the antibody or antigen-binding fragment thereof that specifically binds to IL-4R comprises a Heavy Chain Variable Region (HCVR) comprising the amino acid sequence of SEQ ID NO: 1 and a Light Chain Variable Region (LCVR) comprising the amino acid sequence of SEQ ID NO: 2.

3. The method of claim 2, wherein the antibody is dupilumab.

4. The method of claim 1, wherein the one or more maintenance doses are administered every other week (q2w).

5. The method of claim 4, wherein the maintenance doses of the antibody or antigen-binding fragment thereof are administered for at least 24 weeks.

6. The method of claim 1, wherein the one or more maintenance doses are administered every fourth week (q4w).

7. The method of claim 6, wherein the maintenance doses of the antibody or antigen-binding fragment thereof are administered for at least 24 weeks.

8. The method of claim 1, wherein the antibody or antigen-binding fragment thereof is administered to the subject systemically, subcutaneously, intravenously, or intranasally.

9. The method of claim 1, wherein the subject has a blood eosinophil count selected from the group consisting of: greater than or equal to 300 cells/μL, 200 to 299 cells/μL; and less than 200 cells/μL.

10. The method of claim 1, wherein the ICS is selected from the group consisting of: mometasone furoate, budesonide, and fluticasone propionate.

11. The method of claim 1, wherein the LABA is selected from the group consisting of: formoterol and salmeterol.

12. The method of claim 1, wherein the subject is 12 years of age and above.

13. A method for increasing Forced Expiratory Volume in 1 second (FEV1) in liters to treat persistent asthma in a subject in need thereof comprising administering to the subject a combination therapy comprising:
   i) one or more maintenance doses of an ICS,
   ii) one or more maintenance doses of a LABA,
   iii) a loading dose of about 600 mg of an antibody or an antigen-binding fragment thereof that specifically binds to IL-4R comprising three HCDR sequences comprising SEQ ID NOs: 3, 4, and 5, and three LCDR sequences comprising SEQ ID NOs: 6, 7, and 8, and iv) one or more maintenance doses of about 300 mg of the antibody or the antigen-binding fragment thereof, wherein the ICS and LABA are administered for the duration of administration of the antibody or the antigen-binding fragment thereof.

14. A method for improving one or more persistent asthma-associated parameter(s) in a subject in need thereof comprising administering to the subject a combination therapy comprising:
   i) one or more maintenance doses of an ICS,
   ii) one or more maintenance doses of a LABA,
   iii) a loading dose of about 600 mg of an antibody or an antigen-binding fragment thereof that specifically binds to IL-4R comprising three HCDR sequences comprising SEQ ID NOs: 3, 4, and 5, and three LCDR sequences comprising SEQ ID NOs: 6, 7, and 8, and
   iv) one or more maintenance doses of about 300 mg of the antibody or the antigen-binding fragment thereof,
   wherein the ICS and LABA are administered for the duration of administration of the antibody or the antigen-binding fragment thereof.

15. A method for reducing an asthma patient's dependence on ICS and/or LABA for the treatment of one or more exacerbations of persistent asthma comprising:
   (a) selecting a patient who has moderate-to-severe asthma that is uncontrolled with a background asthma therapy comprising an ICS, a LABA, or a combination thereof; and
   (b) administering to the patient a combination therapy comprising:
      i) one or more maintenance doses of an ICS,
      ii) one or more maintenance doses of a LABA,
      iii) a loading dose of about 600 mg of an antibody or an antigen-binding fragment thereof that specifically binds to IL-4R comprising three HCDR sequences comprising SEQ ID NOs: 3, 4, and 5, and three LCDR sequences comprising SEQ ID NOs: 6, 7, and 8, and
      iv) one or more maintenance doses of about 300 mg of the antibody or the antigen-binding fragment thereof,
   wherein the ICS and LABA are administered for the duration of administration of the antibody or the antigen-binding fragment thereof.

16. A method for treating persistent asthma in a subject in need thereof comprising administering to the subject a combination therapy comprising:
   i) one or more maintenance doses of an inhaled corticosteroid (ICS),
   ii) one or more maintenance doses of a long-acting beta$_2$-adrenergic agonist (LABA),
   iii) a loading dose of about 400 mg of an antibody or an antigen-binding fragment thereof that specifically binds to interleukin-4 receptor (IL-4R) comprising three Heavy chain Complementarity Determining Region (HCDR) sequences comprising SEQ ID NOs: 3, 4, and 5, and three Light chain Complementarity Determining Region (LCDR) sequences comprising SEQ ID NOs: 6, 7, and 8, and
   iv) one or more maintenance doses of about 200 mg of the antibody or the antigen-binding fragment thereof,
   wherein the ICS and LABA are administered for the duration of administration of the antibody or the antigen-binding fragment thereof.

17. The method of claim 16, wherein the antibody or antigen-binding fragment thereof that specifically binds to IL-4R comprises a Heavy Chain Variable Region (HCVR) comprising the amino acid sequence of SEQ ID NO: 1 and a Light Chain Variable Region (LCVR) comprising the amino acid sequence of SEQ ID NO: 2.

18. The method of claim 17, wherein the antibody is dupilumab.

19. The method of claim 16, wherein the one or more maintenance doses are administered every other week (q2w).

20. The method of claim 19, wherein the maintenance doses of the antibody or antigen-binding fragment thereof are administered for at least 24 weeks.

21. The method of claim 16, wherein the one or more maintenance doses are administered every fourth week (q4w).

22. The method of claim 21, wherein the maintenance doses of the antibody or antigen-binding fragment thereof are administered for at least 24 weeks.

23. The method of claim 16, wherein the antibody or antigen-binding fragment thereof is administered to the subject systemically, subcutaneously, intravenously, or intranasally.

24. The method of claim 16, wherein the subject has a blood eosinophil count selected from the group consisting of: greater than or equal to 300 cells/µL, 200 to 299 cells/µL; and less than 200 cells/µL.

25. The method of claim 16, wherein the ICS is selected from the group consisting of: mometasone furoate, budesonide, and fluticasone propionate.

26. The method of claim 16, wherein the LABA is selected from the group consisting of: formoterol and salmeterol.

27. The method of claim 16, wherein the subject is 12 years of age and above.

28. A method for increasing Forced Expiratory Volume in 1 second (FEV1) in liters to treat persistent asthma in a subject in need thereof comprising administering to the subject a combination therapy comprising:
   i) one or more maintenance doses of an ICS,
   ii) one or more maintenance doses of a LABA,
   iii) a loading dose of about 400 mg of an antibody or an antigen-binding fragment thereof that specifically binds to IL-4R comprising three HCDR sequences comprising SEQ ID NOs: 3, 4, and 5, and three LCDR sequences comprising SEQ ID NOs: 6, 7, and 8, and
   iv) one or more maintenance doses of about 200 mg of the antibody or the antigen-binding fragment thereof,
   wherein the ICS and LABA are administered for the duration of administration of the antibody or the antigen-binding fragment thereof.

29. A method for improving one or more persistent asthma-associated parameter(s) in a subject in need thereof comprising administering to the subject a combination therapy comprising:
   i) one or more maintenance doses of an ICS,
   ii) one or more maintenance doses of a LABA,
   iii) a loading dose of about 400 mg of an antibody or an antigen-binding fragment thereof that specifically binds to IL-4R comprising three HCDR sequences comprising SEQ ID NOs: 3, 4, and 5, and three LCDR sequences comprising SEQ ID NOs: 6, 7, and 8, and
   iv) one or more maintenance doses of about 200 mg of the antibody or the antigen-binding fragment thereof,
   wherein the ICS and LABA are administered for the duration of administration of the antibody or the antigen-binding fragment thereof.

30. A method for reducing an asthma patient's dependence on ICS and/or LABA for the treatment of one or more exacerbations of persistent asthma comprising:
  (a) selecting a patient who has moderate-to-severe asthma that is uncontrolled with a background asthma therapy comprising an ICS, a LABA, or a combination thereof; and
  (b) administering to the patient a combination therapy comprising:
    i) one or more maintenance doses of an ICS,
    ii) one or more maintenance doses of a LABA,
    iii) a loading dose of about 400 mg of an antibody or an antigen-binding fragment thereof that specifically binds to IL-4R comprising three HCDR sequences comprising SEQ ID NOs: 3, 4, and 5, and three LCDR sequences comprising SEQ ID NOs: 6, 7, and 8, and
    iv) one or more maintenance doses of about 200 mg of the antibody or the antigen-binding fragment thereof,
  wherein the ICS and LABA are administered for the duration of administration of the antibody or the antigen-binding fragment thereof.

* * * * *

UNITED STATES PATENT AND TRADEMARK OFFICE
CERTIFICATE OF CORRECTION

PATENT NO. : 10,137,193 B2
APPLICATION NO. : 14/627728
DATED : November 27, 2018
INVENTOR(S) : Pirozzi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this
Seventeenth Day of September, 2019

Andrei Iancu
*Director of the United States Patent and Trademark Office*